US010940201B2

(12) United States Patent
Kugimiya et al.

(10) Patent No.: US 10,940,201 B2
(45) Date of Patent: Mar. 9, 2021

(54) NUCLEIC ACID DERIVATIVE HAVING IMMUNOSTIMULATORY ACTIVITY

(71) Applicant: Shionogi & Co., Ltd., Osaka (JP)

(72) Inventors: Akira Kugimiya, Toyonaka (JP);
Tetsuya Tanino, Toyonaka (JP);
Mitsuaki Sekiguchi, Toyonaka (JP);
Yasunori Mitsuoka, Toyonaka (JP);
Norikazu Kuroda, Toyonaka (JP); Jun Nakamura, Toyonaka (JP)

(73) Assignee: SHIONOGI & CO., LTD., Osaka (JP)

( * ) Notice: Subject to any disclaimer, the term of this patent is extended or adjusted under 35 U.S.C. 154(b) by 373 days.

(21) Appl. No.: 15/907,920

(22) Filed: Feb. 28, 2018

(65) Prior Publication Data

US 2018/0264105 A1  Sep. 20, 2018

Related U.S. Application Data

(63) Continuation of application No. PCT/JP2016/078765, filed on Sep. 29, 2016, and a continuation of application No. PCT/JP2017/013025, filed on Mar. 29, 2017.

(30) Foreign Application Priority Data

Sep. 30, 2015 (JP) .............................. JP2015-192565

(51) Int. Cl.
| | |
|---|---|
| *A61K 39/39* | (2006.01) |
| *A61P 35/00* | (2006.01) |
| *A61K 39/00* | (2006.01) |
| *A61K 39/104* | (2006.01) |
| *A61P 31/04* | (2006.01) |

(52) U.S. Cl.
CPC .......... *A61K 39/39* (2013.01); *A61K 39/0011* (2013.01); *A61K 39/001156* (2018.08); *A61K 39/104* (2013.01); *A61P 31/04* (2018.01); *A61P 35/00* (2018.01); *A61K 2039/545* (2013.01); *A61K 2039/55561* (2013.01); *A61K 2039/55566* (2013.01); *A61K 2039/572* (2013.01); *A61K 2039/70* (2013.01)

(58) Field of Classification Search
CPC ...... A61K 31/713; A61K 39/39; A61K 47/18; A61K 2039/55561; A61P 37/04; C12N 15/111; C12N 15/113; C12N 15/117; C12N 2310/14; C12N 2310/17; C12N 2310/315; C12N 2310/3515; C12N 2320/32
USPC ............ 435/6.1, 91.1, 91.31, 455; 514/44 A; 536/23.1, 24.5; 424/9.1
See application file for complete search history.

(56) References Cited

U.S. PATENT DOCUMENTS

| | | | | |
|---|---|---|---|---|
| 10,117,941 B2 * | 11/2018 | Manoharan | ............ | A61K 47/44 |
| 2020/0022913 A1 * | 1/2020 | Mirkin | ................... | A61K 9/127 |

FOREIGN PATENT DOCUMENTS

| | | | | |
|---|---|---|---|---|
| WO | WO 01/12804 A2 | 2/2001 | | |
| WO | WO 03/066649 A1 | 8/2003 | | |
| WO | WO 2006/063252 A2 | 6/2006 | | |
| WO | WO 2010/023216 A1 | 3/2010 | | |
| WO | WO 2010/057150 A1 | 5/2010 | | |
| WO | WO-2012119780 A2 * | 9/2012 | ............. | A61P 17/02 |
| WO | WO 2013/151771 A1 | 10/2013 | | |
| WO | WO 2014/134698 A1 | 9/2014 | | |
| WO | WO 2015/105083 A1 | 7/2015 | | |

OTHER PUBLICATIONS

Liu et al, Nature, vol. 507, pp. 519-522. (Year: 2014).*
Huang et al, Chem. Comm., vol. 50, No. 23, pp. 3103-3105. (Year: 2014).*
Fedotenko et al, Langmuir, vol. 29, No. 30, pp. 9428-9435. (Year: 2013).*
Meng et al, BMC Biotechnology, vol. 11, No. 88, pp. 1-9. (Year: 2011).*
Extended European Search Report dated Apr. 29, 2019, for European Application No. 16851711.8.
Andrews et al., "Conjugation of Lipid and CpG-Containing Oligonucleotide Yields an Efficient Method for Liposome Incorporation," Bioconjug. Chem. (2011), vol. 22, No. 7, pp. 1279-1286.
International Prelimiary Report on Patentability and Written Opinion dated May 3, 2018, in PCT International Application No. PCT/JP2016/078765.
International Search Report dated Nov. 8, 2016, in PCT International Application No. PCT/JP2016/078765.
Liu et al., "Structure-based programming of lymph-node targeting in molecular vaccines," Nature (2014), vol. 507, No. 7493, pp. 519-522.
Park et al., "The production and immunostimulatory activity of double-stranded CpG-DNA," BMB Reports (2010), vol. 43, No. 3, pp. 164-169.

(Continued)

*Primary Examiner* — Jane J Zara
(74) *Attorney, Agent, or Firm* — Birch, Stewart, Kolasch & Birch, LLP

(57) ABSTRACT

The purpose of the present invention is to provide double-stranded oligonucleotides comprising the CpG oligonucleotide mentioned below, as a nucleic acid derivative having an immunostimulatory activity.
An adjuvant comprising a double-stranded oligonucleotide, wherein
a first strand is a CpG oligonucleotide consisting of 8 to 50 nucleotides,
a second strand is an oligonucleotide consisting of 8 to 60 nucleotides and comprising
a sequence capable of hybridizing with the first strand, and a lipid binds to the second strand through a linker.

19 Claims, 8 Drawing Sheets

Specification includes a Sequence Listing.

(56) References Cited

OTHER PUBLICATIONS

Rattanakiat et al., "Self-assembling CpG DNA nanoparticles for efficient antigen delivery and immunostimulation," Eur. J. Pharmaceutical Sciences (2012), vol. 47, No. 2, pp. 352-358.
Reed et al., "New horizons in adjuvants for vaccine development," Trends in Immunology (2009), vol. 30, No. 1, pp. 23-32.
Shivahare et al., "Combination of liposomal CpG oligodeoxynucleotide 2006 and miltefosine induces strong cell-mediated immunity during experimental visceral leishmaniasis," PLoS One (2014), vol. 9, No. 4, e94596, pp. 1-12.
Wilson et al., "Lipid-based delivery of CpG oligonucleotides enhances immunotherapeutic efficacy," Advanced Drug Delivery Reviews (2009), vol. 61, pp. 223-242.
Zelenay et al., "Immunostimulatory effects of plasmid DNA and synthetic oligodeoxynucleotides," Eur. J. Immunol. (2003), vol. 33, pp. 1382-1392.
Meng et al., "Nuclease-resistant immunostimulatory phosphodiester CpG oligodeoxynucleotides as human Toll-like receptor 9 agonists," BMC Biotechnology (2011), vol. 11, No. 88, pp. 1-9.

\* cited by examiner

[Fig. 1]
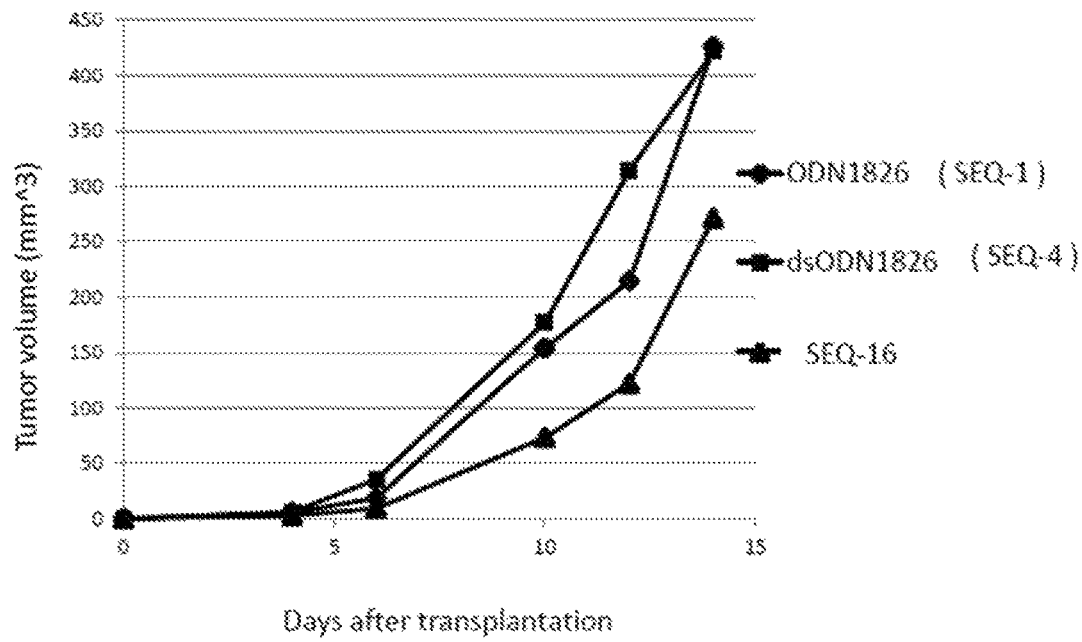
[Fig. 2]
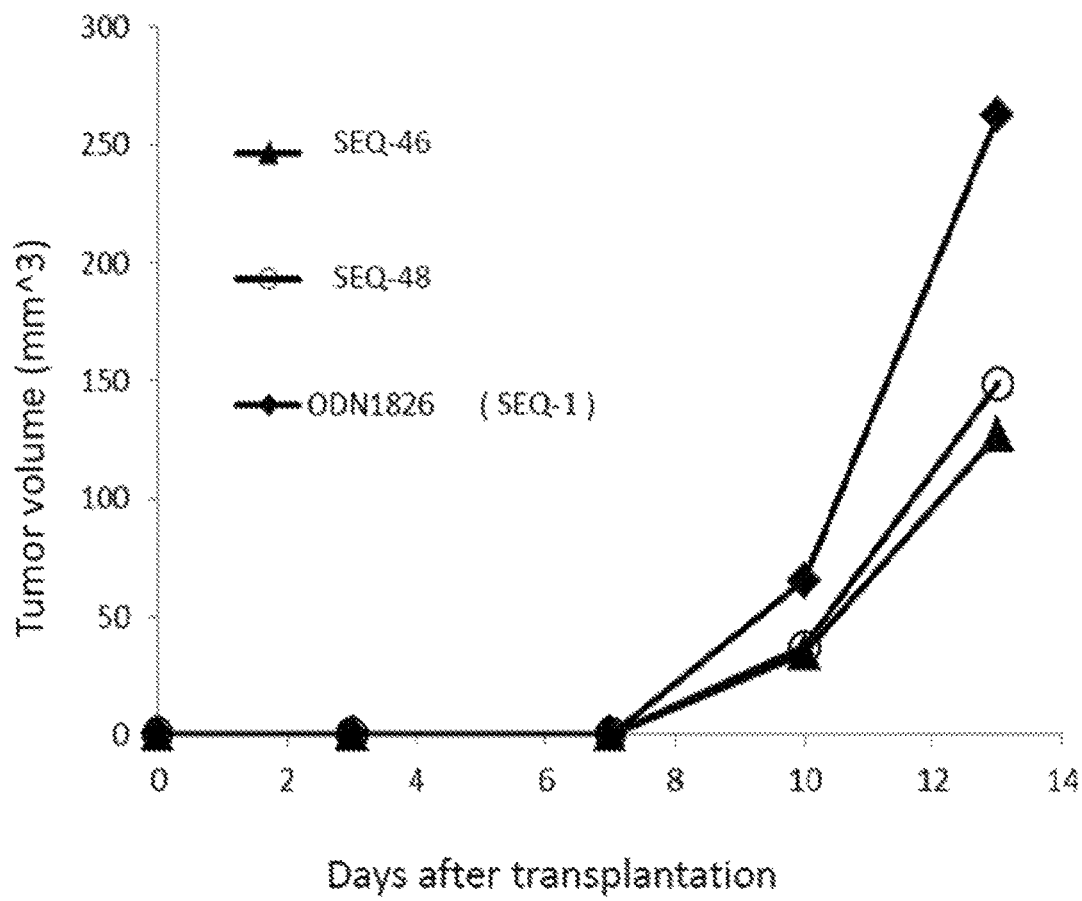

[Fig. 3]
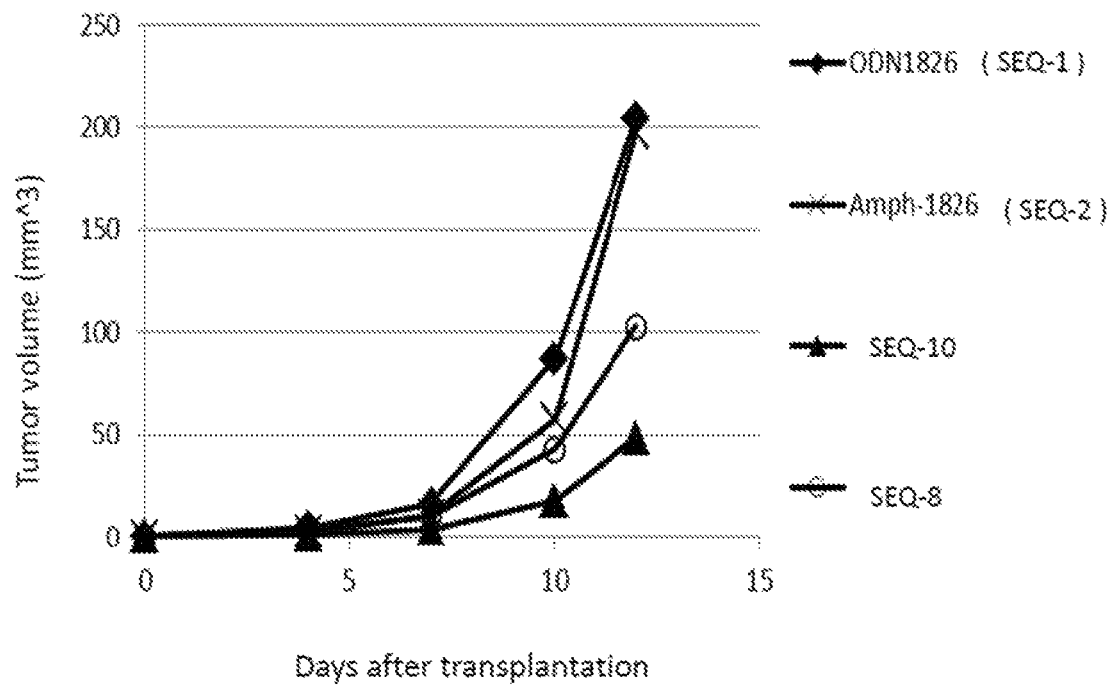
[Fig. 4]
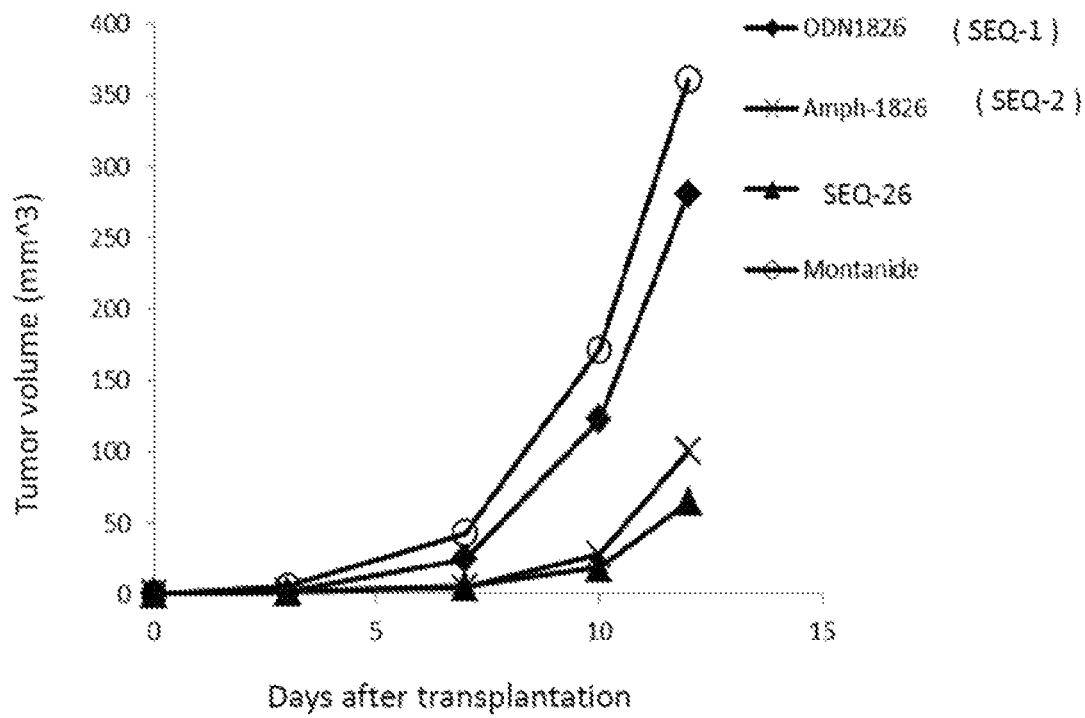

[Fig. 5]
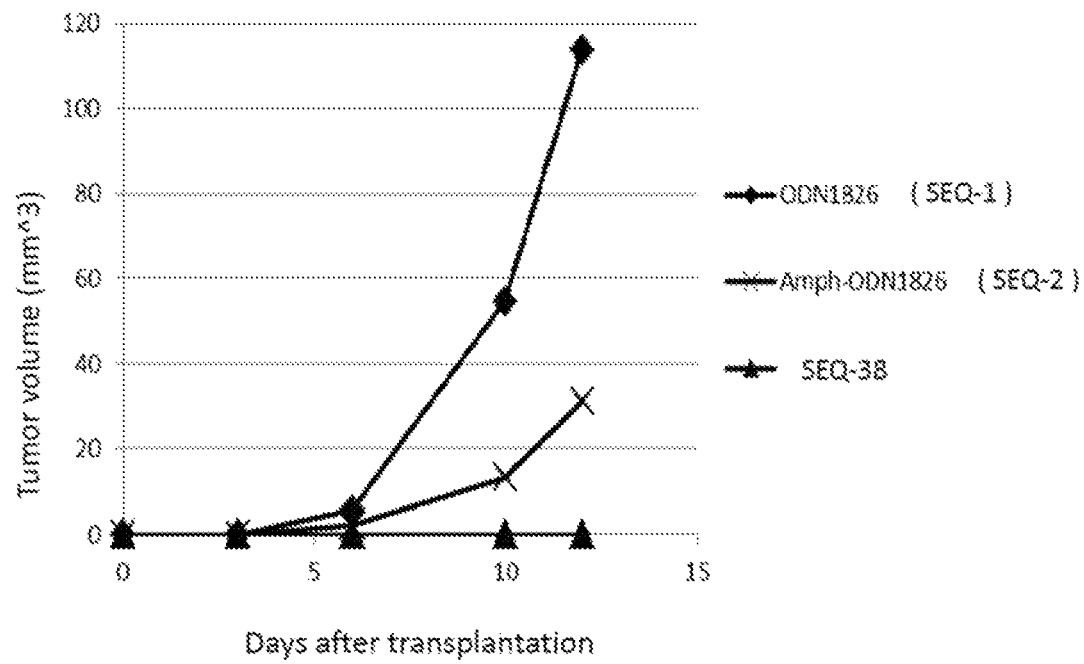
[Fig. 6]
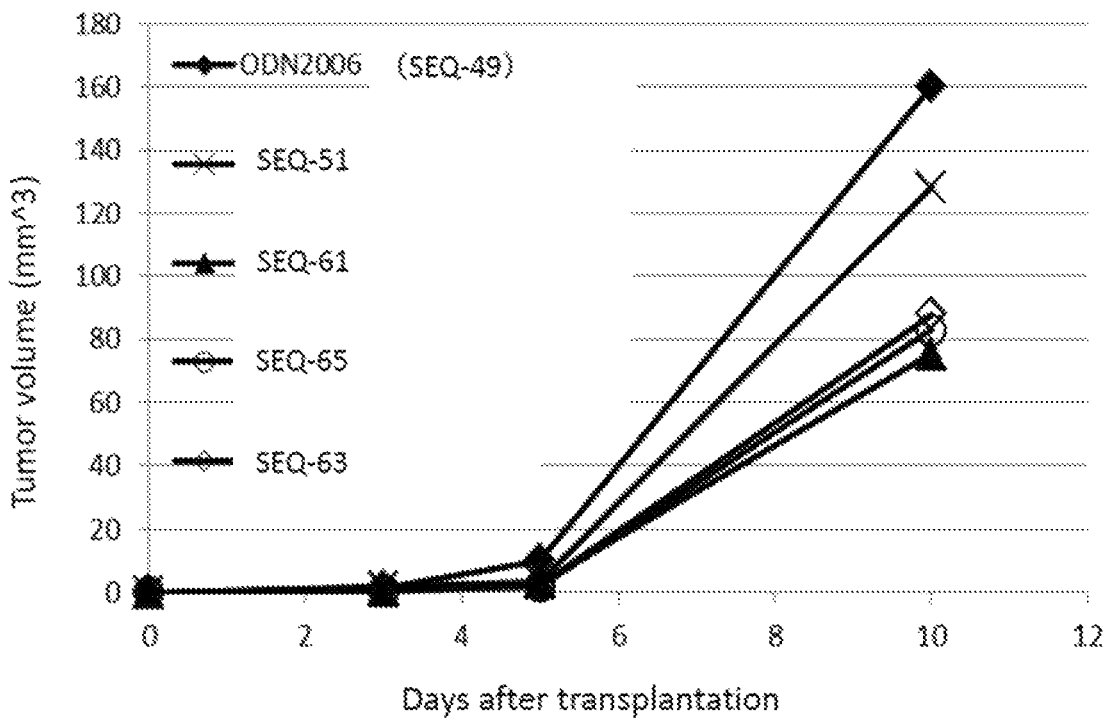

[Fig. 7]
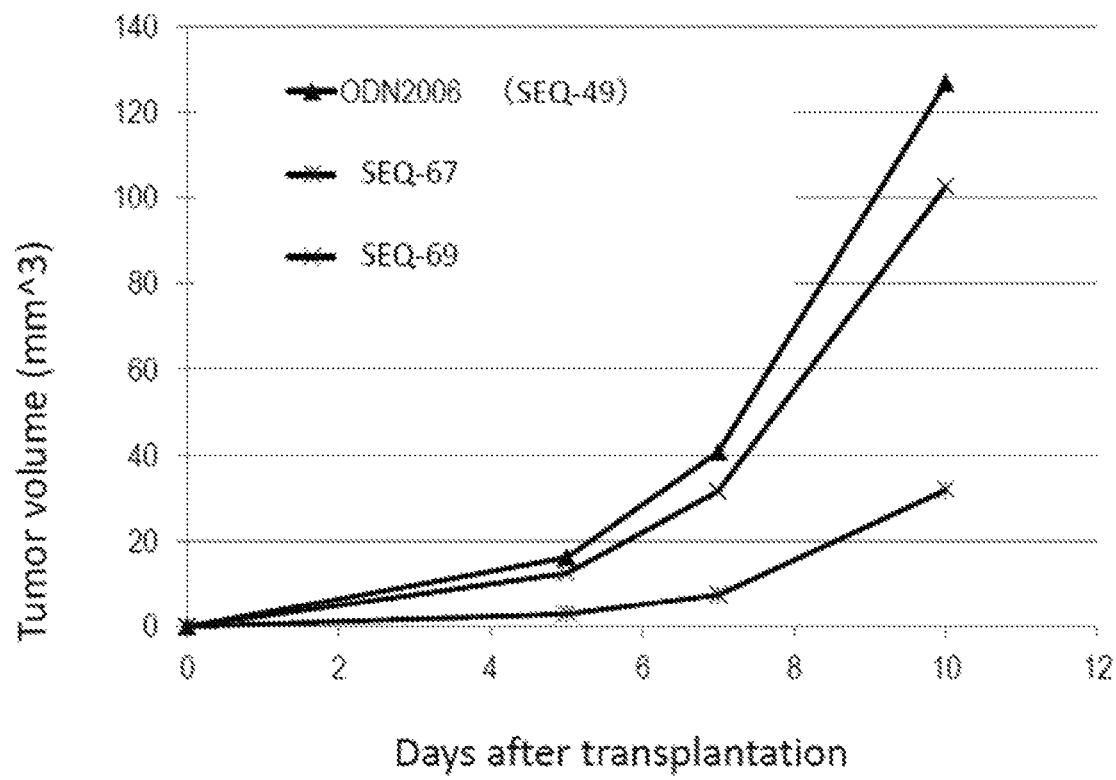
[Fig. 8]
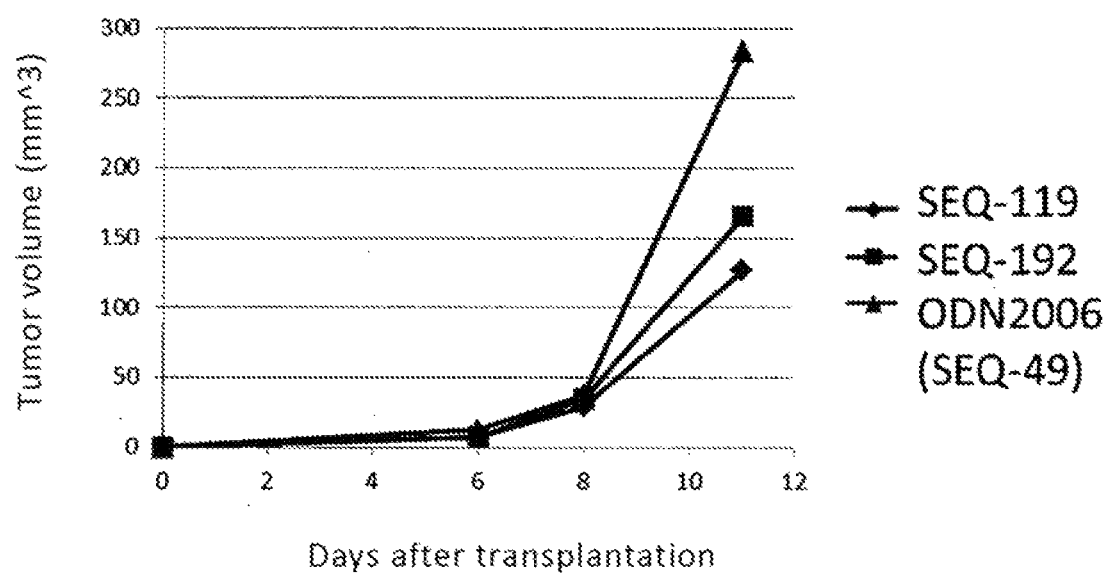

[Fig. 9]
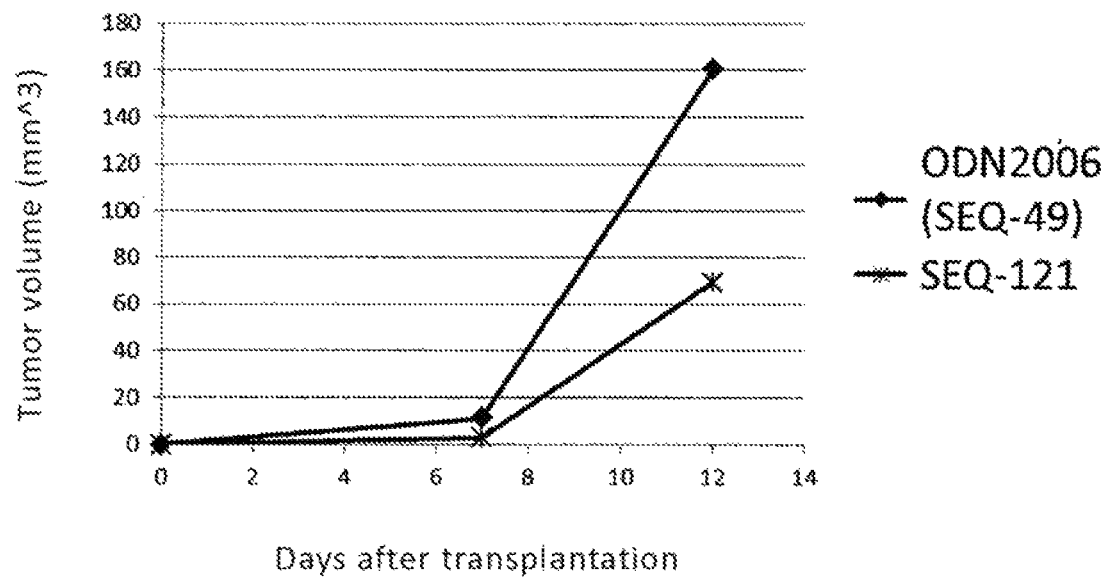
[Fig. 10]
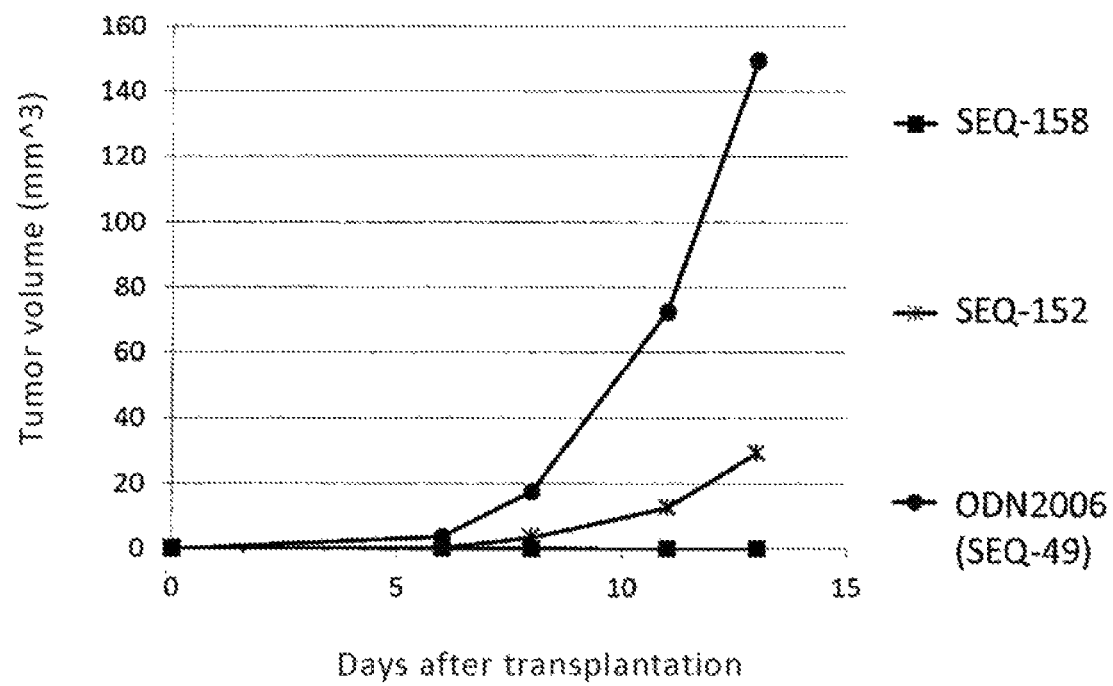

[Fig. 11]
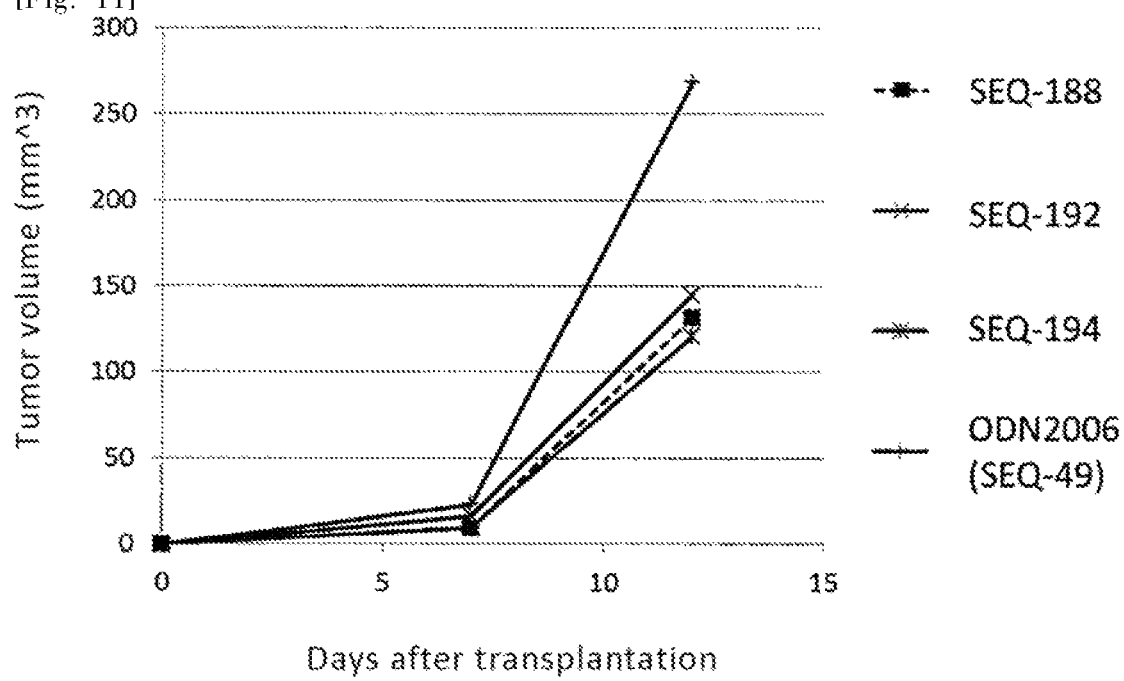
[Fig. 12]
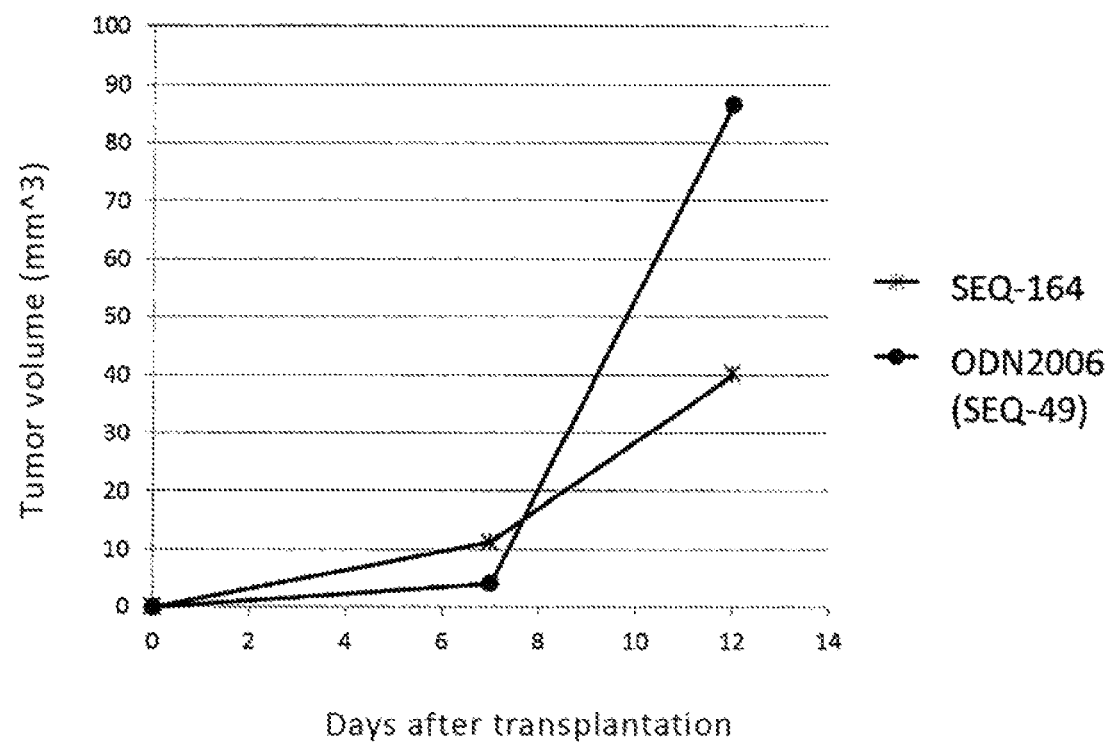

[Fig. 13]
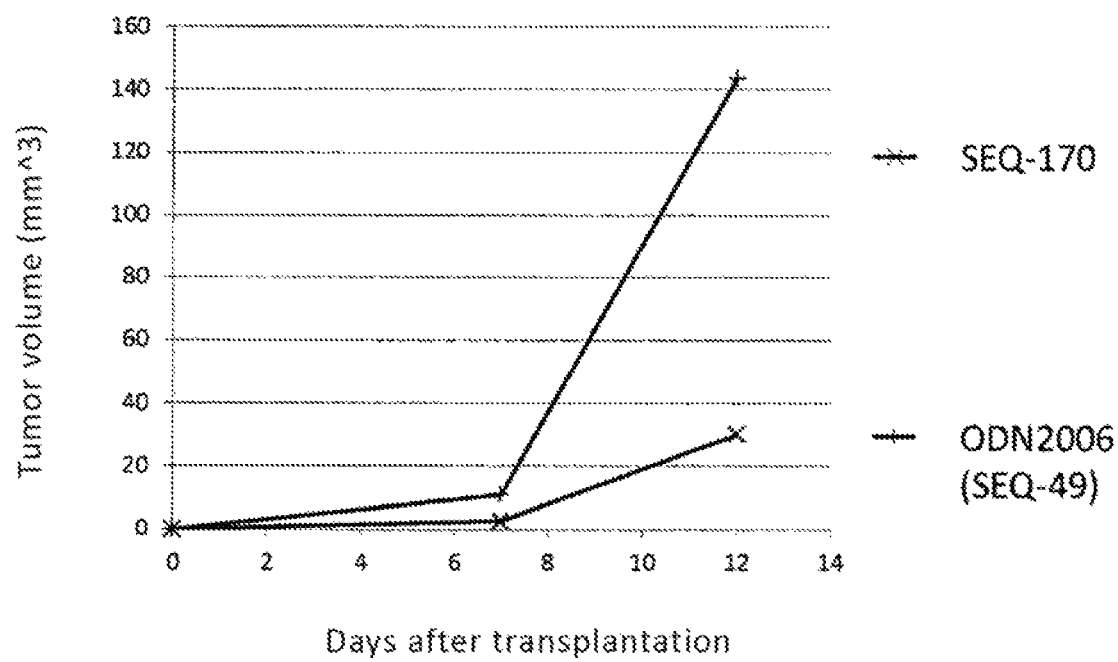
[Fig. 14]
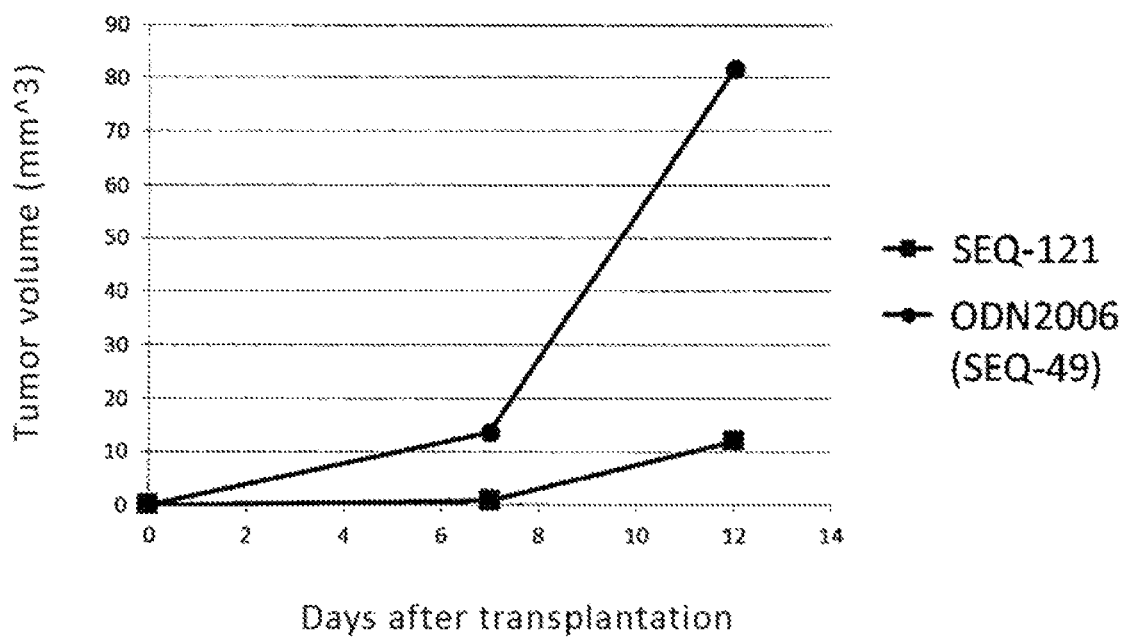

[Fig. 15]
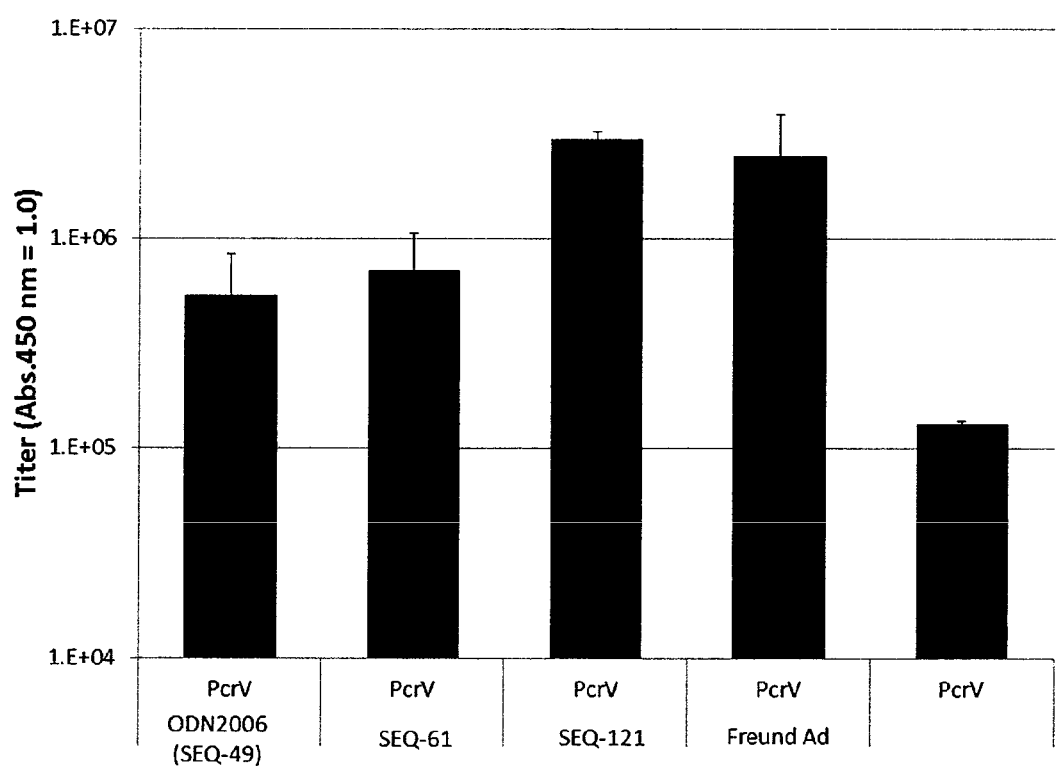

NUCLEIC ACID DERIVATIVE HAVING IMMUNOSTIMULATORY ACTIVITY

CROSS REFERENCE TO RELATED APPLICATIONS

The present application is a continuation application of International Application PCT/JP2016/078765, filed on Sep. 29, 2016, which claims priority to Japanese Patent Application No. 2015-192565, filed on Sep. 30, 2015, and of International Application PCT/JP2017/013025, filed on Mar. 29, 2017. The contents of these applications are incorporated herein by reference in their entirety.

REFERENCE TO SEQUENCE LISTING SUBMITTED VIA EFS-WEB

This application includes an electronically submitted sequence listing in .txt format. The .txt file contains a sequence listing entitled "20180604_1P00047US_1_SequenceListing TS.txt" created on May 30, 2018 and is 14,419 bytes in size. The sequence listing contained in this .txt file is part of the specification and is hereby incorporated by reference herein in its entirety.

REFERENCE TO SEQUENCE LISTING SUBMITTED VIA EFS-WEB

This application includes an electronically submitted sequence listing in .txt format. The .txt file contains a sequence listing entitled "2020-04-17_0032-0331PUS1_ST25" created on Apr. 17, 2020 and is 14,410 bytes in size. The sequence listing contained in this .txt file is part of the specification and is hereby incorporated by reference herein in its entirety.

FIELD OF THE INVENTION

The present invention relates to a nucleic acid derivative having immunostimulatory activity. In more detail, it relates to a double-stranded oligonucleotide wherein the first strand is a CpG oligonucleotide, and the second strand binds to a lipid.

BACKGROUND ART

A vaccine which is a medicine for infectious disease or cancer utilizes an antigen-specific immune response. An adjuvant is a compound having an immunostimulatory activity which is used to enhance efficacy or durability of a vaccine, and various kinds of adjuvants such as aluminum salt, emulsion and liposome have been researched or developed (Non-patent Document 1 or the like).

A single-strand oligodeoxynucleotide comprising a dinucleotide motif of unmethylated cytosine guanine (5'-CpG-3') (ssCpG ODN) is known as a one of the adjuvants. ssCpG ODNs are ligands of TLR9 (Toll-like receptor 9), and extremely efficient inducers of Th1 immunity or cytotoxic T-lymphocyte (CTL) responses thorough TLR9 to stimulate the immune system (Non-patent Document 1). However, there are problems related to in vivo stability, toxicity, pharmacokinetics or the like of ssCpG ODNs to use alone. A method that ssCpG ODN is encapsulated in a nanoparticle made of lipid bilayer (Non-patent Document 2), a method that lipid binds to 5' end of ssCpG ODN (Non-patent Document 3 or Patent Document 1) or the like is known as means for solving these problems.

Furthermore, it is known that the charactericity as an adjuvant was vanished when ssCpG ODN was administered as a double-stranded DNA (dsCpG ODN) by annealing the first strand and the second strand (Non-patent Document 4). Non-patent Document 5 discloses that only dsCpG ODN did not show the immunostimulatory activity, but when dsCpG ODN was encapsulated in a lipofectin particle, the dsCpG ODN comprising either CpG motif or GpC motif showed the immunostimulatory activity.

PRIOR ART DOCUMENT

Patent Document

Patent Document 1: WO2013/151771

Non-Patent Document

Non-patent Document 1: Trends in immunology, 2009, 30(1), 23-32
Non-patent Document 2: Advanced Drug Delivery Review, 2009, 61(3), 233-242
Non-patent Document 3: Nature, 2014, 507, 519-522
Non-patent Document 4: Eur. J. Immunol., 2003, 33, 1382-1392
Non-patent Document 5: BMB reports, 2010, 43(3), 164-169

SUMMARY OF THE INVENTION

Problems to be Solved by the Invention

The purpose of the present invention is to provide new nucleic acid derivatives having immunostimulatory activity which are useful as an adjuvant of a vaccine and/or a vaccine itself.

Means for Solving the Problem

Non-patent Documents 4 and 5 disclose that administering dsCpG ODN did not show the immunostimulatory activity. Furthermore, Non-patent Document 5 discloses that when dsCpG ODN was encapsulated in a lipofectin particle, the dsCpG ODN comprising either CpG motif (ODN4531) or GpC motif (ODN4531GC) induced IL-8 and HLR-DRA expression, that is, by a method which is independent of a CG sequence. It suggested based on the fact that dsCpG ODN was rapidly degraded in cells compared to ssCpG ODN that the reason why dsCpG ODN encapsulated in a lipofectin particle showed immunostimulatory activity is that encapsulation of dsCpG ODN may protect against rapid degradation (page 167, the right column, lines 10 to 16).

The present inventors have intensively studied to synthesize a double-stranded oligonucleotide (a lipid binding double-stranded oligonucleotide of the present invention) wherein a first strand is a CpG oligonucleotide, and a second strand is an oligonucleotide comprising a sequence capable of hybridizing with the first strand and binds to a lipid. They found that the inducibility of antigen-specific CTL by a vaccine was enhanced and showed the anti-tumor effect by administering a lipid binding double-stranded oligonucleotide of the present invention as an adjuvant with a tumor antigen peptide (when a lipid binding double-stranded oligonucleotide of the present invention is used as an adjuvant, it is also referred as "an adjuvant of the present invention").

In addition, they found that there is a lipid binding double-stranded oligonucleotide in the present invention which shows strong anti-tumor effect by itself, that is, which is useful as a cancer vaccine (when a lipid binding double-stranded oligonucleotide of the present invention is used as a vaccine, it is also referred as "a vaccine of the present invention"). That is, a lipid binding double-stranded oligonucleotide of the present invention has the immunostimulatory activity. Furthermore, lipid binding double-stranded oligonucleotides of the present invention have high metabolic stability, water solubility and less toxicity to be safe enough as a medicine.

For example, when an adjuvant of the present invention wherein the second strand is a DNA oligonucleotide, an oligonucleotide consisting of nucleoside derivatives having OMe at the 2' position of the sugar or an oligonucleotide consisting of nucleoside derivatives having F at the 2' position of the sugar was administered with a tumor antigen peptide, they showed the enhanced CTL inducibility or the strong anti-tumor effect compared to ssCpG ODN (e.g., Result 1-A, B, Result 7-A, B and Result 9-A, B in Example 3). On the other hand, the lipid binding double-stranded oligonucleotide wherein the second strand is a RNA oligonucleotide (SEQ-40) did not show the anti-tumor effect (Result 7-B).

When an adjuvant of the present invention wherein a lipid comprising two of the acyl chains having 14 to 24 carbon atoms binds at 3' or 5' end of the second strand was administered with a tumor antigen peptide, it showed the strong anti-tumor effect compared to ssCpG ODN (e.g., Result 2-A, B in Example 3). On the other hand, when a double-stranded oligonucleotide wherein a lipid comprising two acyl chains having 10 carbon atoms binds at 5' end of the second strand (SEQ-12) was administered with a tumor antigen peptide, it did not show the enhanced anti-tumor effect compared to ssCpG ODN. In addition, when an adjuvant of the present invention wherein a lipid comprising two of the acyl chains having 12 to 20 carbon atoms binds at 3' or 5' end of the second strand, and furthermore a lipid binds at the other end was administered with a tumor antigen peptide, it showed the enhanced CTL inducibility or the strong anti-tumor effect compared to ssCpG ODN (e.g., Result 3-A, B in Example 3).

When an adjuvant of the present invention wherein the length of the second strand is 50% to 100% of that of the first strand (the CpG oligonucleotide) was administered with a tumor antigen peptide, it showed the enhanced CTL inducibility or the strong anti-tumor effect compared to ssCpG ODN (e.g., Result 4-A, B, Result 5-A, Result 8-A, B, and Result 9-A, B in Example 3).

When an adjuvant of the present invention wherein a lipid binds to a second strand through an oligonucleotide linker (e.g., dGdG, dTdT and dAdA) was administered with a tumor antigen peptide, it showed the further enhanced CTL inducibility or the stronger anti-tumor effect compared to an adjuvant of the present invention without a linker (e.g., Result 8-A, B in Example 3).

In addition, lipid binding double-stranded oligonucleotides of the present invention have no systemic toxicity, and it suggested the high safety (Example 5).

Furthermore, the result of immunization with an adjuvant of the present invention and PCRV protein derived from *Pseudomonas aeruginosa* which is a cause of an infectious disease also suggested the immunostimulatory activity as an adjuvant of a vaccine for an infectious disease (Example 6).

When the adjuvant of the present invention wherein lipid binds to a second strand through an oligonucleotide linker (dGdGdGdGdG) (SEQ-121) was administered alone, it showed the strong antitumor effect compared to ssCpG ODN (Example 4).

That is, the present invention is related to the followings.

(A1) A double-stranded oligonucleotide, wherein
a first strand is a CpG oligonucleotide consisting of 8 to 50 nucleotides,
a second strand is an oligonucleotide consisting of 8 to 60 nucleotides and comprising a sequence capable of hybridizing with the first strand, but excluding a RNA oligonucleotide,
the length of the second strand is 50% or more of that of the first strand, and
a lipid comprising C12 to C30 hydrocarbon chain(s) binds to the second strand through a linker.

(A2) The double-stranded oligonucleotide of (A1), wherein the oligonucleotide of the second strand is an oligonucleotide consisting of DNA nucleosides and/or nucleoside derivatives.

(A3) The double-stranded oligonucleotide of (A2), wherein the nucleoside derivative is a nucleoside having a substituent at the 2' position of the sugar and/or a nucleoside having a bridge structure between the 4' and 2' positions of the sugar.

(A4) The double-stranded oligonucleotide of (A3), wherein the bridge structure between the 4' and 2' positions of the sugar is 4'-(CH2)m-O-2', wherein m is an integer of 1 to 4.

(A5) The double-stranded oligonucleotide of any one of (A1) to (A4), wherein the lipid is a diacyl lipid.

(A6) The double-stranded oligonucleotide of (A1) to (A5), wherein the lipid binds at the 3' end and/or 5' end of the second strand.

(A7) The double-stranded oligonucleotide of any one of (A1) to (A6), wherein the linker is an oligonucleotide linker.

(A8) The double-stranded oligonucleotide of (A7), wherein the linker is -(dX$^1$)u-, wherein X$^1$ is each independently, A, G, C or T, and u is an integer of 1 to 8.

(A9) The double-stranded oligonucleotide of (A1) selected from the group of consisting of SEQ-61, SEQ-119, SEQ-121, SEQ-170 and SEQ-192.

(A10) The double-stranded oligonucleotide of (A1) selected from the group of consisting of SEQ-59, SEQ-166, SEQ-168, SEQ-216, SEQ-272, SEQ-280, SEQ-290, SEQ-294, SEQ-310, SEQ-373 and SEQ-384.

(A11) A pharmaceutical composition comprising the double-stranded oligonucleotide of any one of (A1) to (A10).

(A12) The pharmaceutical composition of (A11), further comprising an antigen.

(A13) A method for treating or preventing a cancer or an infectious disease, comprising administering the double-stranded oligonucleotide of any one of (A1) to (A10).

(A14) Use of the double-stranded oligonucleotide of any one of (A1) to (A10) for the manufacture of an agent for treating or preventing a cancer or an infectious disease.

(A15) The double-stranded oligonucleotide of any one of (A1) to (A10) for treating or preventing a cancer or an infectious disease.

(A16) The pharmaceutical composition of (A12), wherein the antigen is a microbial antigen, a self-antigen, a neoantigen or an addictive substance.

(A17) The pharmaceutical composition of (A16), wherein the microbial antigen is a bacterial antigen, a viral antigen or a parasitic antigen.

(A18) The pharmaceutical composition of (A16), wherein the self-antigen is a tumor-associated self-antigen, an antigen associated with Alzheimer's Disease, an antigen against a human antibody, or an antigen that is expressed from human endogenous retroviral elements.

(A19) The pharmaceutical composition of (A16), the addictive substance is nicotine or cocaine.
(A20) A method for increasing an immune response in a subject comprising administering to the subject an effective amount of the pharmaceutical composition of any one of (A12), (A16) to (A19).
(A21) The method of (A20), wherein the immune response is an increase in inducibility of specific cytotoxic T-lymphocyte compared to a control.
(A22) The method of (A20) or (A21), wherein the subject has a cancer or an infectious disease.

In addition, the present invention includes the followings.
(B1) An adjuvant consisting of a double-stranded oligonucleotide, wherein a first strand is a CpG oligonucleotide consisting of 8 to 50 nucleotides, a second strand is an oligonucleotide consisting of 8 to 60 nucleotides and comprising a sequence capable of hybridizing with the first strand, and a lipid binds to the second strand through a linker.
(B2) The adjuvant of (B1), wherein the oligonucleotide of the second strand is an oligonucleotide consisting of DNA nucleosides and/or nucleoside derivatives.
(B3) The adjuvant of (B2), wherein the nucleoside derivative is a nucleoside having a substituent at the 2' position of the sugar and/or a nucleoside having a bridge structure between the 4' and 2' positions of the sugar.
(B4) The adjuvant of (B3), wherein the substituent is $OCH_3$.
(B5) The adjuvant of any one of (B1) to (B4), wherein the lipid is a diacyl lipid.
(B6) The adjuvant of (B5), wherein the acyl chain of the diacyl lipid has 14 to 30 carbon atoms.
(B7) The adjuvant of (B5) or (B6), wherein the lipid binds at the 5' the end of the second strand.
(B8) The adjuvant of any one of (B1) to (B7), wherein the length of the second strand is 50% or more of that of the first strand.
(B9) The adjuvant of any one of (B1) to (B8), wherein the linker is an oligonucleotide linker.
(B10) The adjuvant of (B9), wherein the linker is $dX^1dX^2$, wherein $X^1$ or $X^2$ is A, G, C or T.
(B11) A vaccine composition comprising an antigen and the adjuvant of any one of (B1) to (B10).
(B12) The vaccine composition of (B11) wherein the antigen is a microbial antigen, a self-antigen, a neoantigen or an addictive substance.
(B13) The vaccine composition of (B12) wherein the microbial antigen is a bacterial antigen, a viral antigen or a parasitic antigen.
(B14) The vaccine composition of (B12) wherein the self-antigen is a tumor-associated self-antigen, an antigen associated with Alzheimer's Disease, an antigen against a human antibody, or an antigen that is expressed from human endogenous retroviral elements.
(B15) The vaccine composition of (B12) wherein the addictive substance is nicotine or cocaine.
(B16) A method of increasing an immune response in a subject comprising administering to the subject an effective amount of the vaccine composition of any one of (B11) to (B15).
(B17) The method of (B16), wherein the immune response is an increase in inducibility of specific cytotoxic T-lymphocyte compared to a control.
(B18) The method of (B16) or (B17), wherein the subject has a cancer or an infectious disease.
(B19) A method of treating a cancer or an infectious disease comprising administering to the subject an effective amount of the vaccine composition of any of (B11) to (B14) to reduce one or more symptoms of the cancer or infectious disease compared to a control.

Effect of the Invention

Lipid binding double-stranded oligonucleotides of the present invention show the superior immunostimulatory activity against a target antigen. No systemic toxicity was detected, and therefore they are expected to apply to a medicine as an adjuvant of a vaccine and/or a vaccine itself.

BRIEF DESCRIPTION OF THE DRAWINGS

FIG. 1 The anti-tumor effect when ssCpG ODN (ODN1826, SEQ-1), dsCpG ODN (SEQ-4) or the adjuvant of the present invention (SEQ-16) was administered with a tumor antigen peptide (TRP2 peptide).

FIG. 2 The anti-tumor effect when ssCpG ODN (ODN1826, SEQ-1) or the adjuvant of the present invention having lipids at the both ends (SEQ-46 or SEQ-48) was administered with a tumor antigen peptide (TRP2 peptide).

FIG. 3 The anti-tumor effect when ssCpG ODN (ODN1826, SEQ-1), ssCpG ODN introducing a lipid ligand (SEQ-2) or the adjuvant of the present invention which the length of the complementary strand is different (SEQ-8 or SEQ-10) was administered with a tumor antigen peptide (TRP2 peptide).

FIG. 4 The anti-tumor effect when ssCpG ODN (ODN1826, SEQ-1), ssCpG ODN introducing a lipid ligand (SEQ-2), the adjuvant of the present invention (SEQ-26) or Montanide was administered with a tumor antigen peptide (TRP2 peptide).

FIG. 5 The anti-tumor effect when ssCpG ODN (ODN1826, SEQ-1), ssCpG ODN introducing a lipid ligand (SEQ-2) or the adjuvant of the present invention (SEQ-38) was administered with a tumor antigen peptide (TRP2 peptide).

FIG. 6 The anti-tumor effect when ssCpG ODN (ODN2006, SEQ-49), the adjuvant of the present invention which the length of the complementary strand is different (SEQ-51 or SEQ-61) or the adjuvant of the present invention having a linker (SEQ-63 or SEQ-65) was administered with a tumor antigen peptide (TRP2 peptide).

FIG. 7 The anti-tumor effect when ssCpG ODN (ODN2006, SEQ-49) or the adjuvant of the present invention wherein the nucleic monomer of the complementary strand is 2'-OMe-RNA (SEQ-67 or SEQ-69) was administered with a tumor antigen peptide (TRP2 peptide).

FIG. 8 The anti-tumor effect when ssCpG ODN (ODN2006, SEQ-49) or the adjuvant of the present invention having an oligonucleotide linker (SEQ-119 or SEQ-192) was administered with a tumor antigen peptide (TRP2 peptide).

FIG. 9 The anti-tumor effect when ssCpG ODN (ODN2006, SEQ-49) or the adjuvant of the present invention having an oligonucleotide linker (SEQ-121) was administered with a tumor antigen peptide (TRP2 peptide).

FIG. 10 The anti-tumor effect when ssCpG ODN (ODN2006, SEQ-49) or the adjuvant of the present invention having an oligonucleotide linker (SEQ-152 or SEQ-158) was administered with a tumor antigen peptide (TRP2 peptide).

FIG. 11 The anti-tumor effect when ssCpG ODN (ODN2006, SEQ-49) or the adjuvant of the present invention wherein a lipid binds at the 3' end and/or 5' end (SEQ-188, SEQ-192 or SEQ-194) was administered with a tumor antigen peptide (TRP2 peptide).

FIG. 12 The anti-tumor effect when ssCpG ODN (ODN2006, SEQ-49) or the adjuvant of the present invention having an oligonucleotide linker (SEQ-164) was administered with a tumor antigen peptide (TRP2 peptide).

FIG. 13 The anti-tumor effect when ssCpG ODN (ODN2006, SEQ-49) or the adjuvant of the present invention wherein a lipid binds only at the 3' end (SEQ-170) was administered with a tumor antigen peptide (TRP2 peptide).

FIG. 14 The anti-tumor effect of ssCpG ODN (ODN2006, SEQ-49) or the vaccine of the present invention (SEQ-121) under the absence of a tumor antigen peptide.

FIG. 15 Antibody titer after subcutaneous administration of PCRV antigen vaccine with ssCpG ODN (ODN2006, SEQ-49), the adjuvant of the present invention (SEQ-61 or SEQ-121) or Freund's adjuvant.

EMBODIMENTS FOR CARRYING OUT THE INVENTION

Terms used herein, unless otherwise indicated, are used in a sense normally used in the art.

In the present invention, a genetic manipulation method which is well known in the art can be used. For example, it is a method described in Molecular Cloning, A Laboratory Manual, Forth Edition, Cold Spring Harbor Laboratory Press (2012), or Current Protocols Essential Laboratory Techniques, Current Protocols (2012).

Terms used in this description are explained below. Each term, unless otherwise indicated, has the same meaning when it is used alone or together with other terms.

In this description, "adjuvant" means a compound having the immunostimulatory activity which is utilized to enhance efficacy or durability of immune response of a vaccine antigen.

A "nucleoside" means a compound that a nucleic acid base and a sugar are bonded by an N-glycoside bond.

An "oligonucleotide" means nucleotides that some of same or different kinds of nucleotide are bonded by an internucleoside linkage such as a phosphodiester bond.

A linkage between a sugar and a sugar in an oligonucleotide (internucleoside linkage) may be a linkage having a natural nucleic acid, phosphodiester (D-oligo), an artificially modified linkage or a linkage without phosphorus atom. Any linkage which is well-known in this field can be used. Examples of an artificially modified linkage are phosphorothioate (S-oligo), methylphosphonate (M-oligo) and boranophosphate. Furthermore, a linkage described in WO2013/022966, WO2011/005761, WO2014/012081, WO2015/125845 or the like can be used. An example of a linkage without phosphorus atom is a bivalent substituent deriving from non-aromatic carbocyclyl or the like substituted with alkyl, non-aromatic carbocyclyl, haloalkyl or halogen. Example is a bivalent substituent deriving from siloxane, sulfide, sulfoxide, sulfone, acetyl, acetyl formate, acetyl thioformate, acetyl methylene formate, acetyl thioformate, alkenyl, sulfamate, methyleneimino, methylenehydrazino, sulfonate, sulfonamide, amide or the like. In an oligonucleotide, linkages may be same or different.

In this description, a "DNA nucleoside" or "RNA nucleoside" means natural DNA nucleoside or natural RNA nucleoside, and a part of nucleotide, which is 1 unit for a component of an oligonucleotide. A "natural DNA nucleoside" is as below.

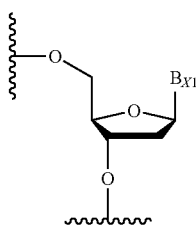

wherein $B_{X1}$ is adenine, guanine, cytosine or thymine.

A "natural RNA nucleoside" is as below.

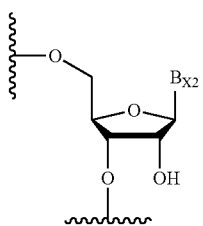

wherein $B_{X2}$ is adenine, guanine, cytosine or uracil.

A "DNA oligonucleotide" means an oligonucleotide which some DNA nucleosides are bounded, and an "RNA oligonucleotide" means an oligonucleotide which some RNA nucleosides are bounded.

In this description, a "nucleoside derivative" means a nucleoside whose nucleic base and/or sugar part of DNA nucleoside or RNA nucleoside was artificially modified. Any well-known modification for a nucleoside in this field can be used.

Examples of modification for a nucleic base are 5-methylcytosine, 5-hydroxy methylcytosine and 5-propynylcytosine.

An example of modification for a sugar part is a substituent at the 2' position of a sugar. Examples are 2'-F, 2'-OCH$_3$ (2'-OMe) and 2'-OCH$_2$CH$_2$OCH$_3$ (2'-MOE).

The other example is the following bridge structure between the 4' and 2' positions of a sugar.

4'-(CR$^1$R$^2$)m-O-2', 4'-(CR$^1$R$^2$)m-S-2', 4'-(CR$^1$R$^2$)m-O—C(=O)-2', 4'-(CR$^1$R$^2$)m-NR$^3$—O—(CR$^1$R$^2$)m$_1$-2', 4'-(CR$^1$R$^2$)m$_1$-C(=O)—NR$^3$-2', 4'-(CR$^1$R$^2$)m$_2$-C(=O)—NR$^3$—Y$^4$-2', 4'-(CR$^1$R$^2$)m$_1$-SO$_2$—NR$^3$-2', or

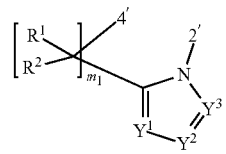

wherein
Y$^4$ is O, S, NH or CH$_2$,
R$^1$ is each independently, hydrogen atom, halogen, cyano, substituted or unsubstituted alkyl, substituted or unsubstituted alkenyl or substituted or unsubstituted alkynyl,
R$^2$ is each independently, hydrogen atom, halogen, cyano, substituted or unsubstituted alkyl, substituted or unsubstituted alkenyl or substituted or unsubstituted alkynyl,
R$^3$ is hydrogen atom, substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalky, substituted or unsubstituted non-aromatic carbocyclylalky, substituted or unsubstituted aromatic heterocyclylalkyl or substituted or unsubstituted non-aromatic heterocyclylalkyl, $Y^1$ is $CR^4$ or N,
$Y^2$ is $CR^5$ or N,
$Y^3$ is $CR^6$ or N, $R^4$, $R^5$ and $R^6$ are each independently, hydrogen atom, halogen, cyano, substituted or unsubstituted alkyl, substituted or unsubstituted alkenyl, substituted or unsubstituted alkynyl, substituted or unsubstituted amino, substituted or unsubstituted alkyloxy, substituted or unsubstituted alkylcarbonylamino, substituted or unsubstituted alkenylcarbonylamino, substituted or unsubstituted alkynylcarbonylamino, substituted or unsubstituted alkylcarbamoyl, substituted or unsubstituted alkenylcarbamoyl, or substituted or unsubstituted alkynylcarbamoyl, m is an integer of 1 to 4,
$m_1$ is an integer of 0 to 3, and
$m_2$ is 0 or 1.

$R^1$ and $R^2$ is preferably hydrogen atom.

$R^3$ is preferably hydrogen atom, alkyl, alkenyl, alkynyl, aromatic carbocyclyl, non-aromatic carbocyclyl, aromatic heterocyclyl, non-aromatic heterocyclyl, aromatic carbocyclylalky, non-aromatic carbocyclylalky, aromatic heterocyclylalkyl or non-aromatic heterocyclylalkyl, and may have one or more substituent(s) selected from Group α.

Group α: a hydroxyl group, alkyl, alkyloxy, mercapto, alkylthio, amino, alkylamino and halogen.

The bridge structure is preferably 4'-($CR^1R^2$)m-O-2' or 4'-($CR^1R^2$)$m_1$-C(=O)—$NR^3$-2' (AmNA, Bridged nucleic acid), wherein, $R^1$ is each independently, hydrogen atom, halogen, cyano, substituted or unsubstituted alkyl, substituted or unsubstituted alkenyl, or substituted or unsubstituted alkynyl, $R^2$ is each independently, hydrogen atom, halogen, cyano, substituted or unsubstituted alkyl, substituted or unsubstituted alkenyl, or substituted or unsubstituted alkynyl, $R^3$ is hydrogen atom, substituted or unsubstituted alkyl, substituted or unsubstituted alkenyl, or substituted or unsubstituted alkynyl, m is an integer of 1 to 4, and
$m_1$ is an integer of 0 to 2.

The bridge structure is more preferably 4'-($CH_2$)m-O-2', wherein m is an integer of 1 to 4, or 4'-C(=O)—$NR^3$-2', wherein $R^3$ is hydrogen atom or alkyl.

4'-($CH_2$)m-O-2', wherein m is an integer of 1 to 4, is more preferably 4'-$CH_2$-O-2' (LNA, Locked nucleic acid). Examples and the methods for preparation are described in WO98/39352, WO2003/068795, WO2005/021570 or the like.

4'-C(=O)—$NR^3$-2', wherein $R^3$ is hydrogen atom or alkyl, is more preferably 4'-C(=O)—$NCH_3$-2'. Examples and the methods for preparation are described in WO2011/052436.

Examples of the well-known modification of nucleotide and the method for modification in this field are described in the following patent documents. WO98/39352, WO99/014226, WO2000/056748, WO2005/021570, WO2003/068795, WO20111052436, WO2004/016749, WO2005/083124, WO2007/143315, WO2009/071680, WO2014/112463, WO2014/126229 and the like.

"Halogen" includes a fluorine atom, a chlorine atom, a bromine atom and an iodine atom. A fluorine atom and a chlorine atom are especially preferable.

"Alkyl" includes a C1 to C15, preferably a C1 to C10, more preferably a C1 to C6 and even more preferably a C1 to C4 linear or branched hydrocarbon group. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl and n-decyl.

A preferred embodiment of "alkyl" is methyl, ethyl, n-propyl, isopropyl, n-butyl, isobutyl, sec-butyl, tert-butyl or n-pentyl. A more preferred embodiment is methyl, ethyl, n-propyl, isopropyl or tert-butyl.

"Alkenyl" includes a C2 to C15, preferably a C2 to C10, more preferably a C2 to C6 and further preferably a C2 to C4 linear or branched hydrocarbon group having one or more double bond(s) at any position(s). Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl and pentadecenyl.

A preferred embodiment of "alkenyl" is vinyl, allyl, propenyl, isopropenyl or butenyl.

"Alkynyl" includes a C2 to C10, preferably a C2 to C8, more preferably a C2 to C6 and further preferably a C2 to C4 linear or branched hydrocarbon group having one or more triple bond(s) at any position(s). Examples include ethynyl, propynyl, butynyl, pentynyl, hexynyl, heptynyl, octynyl, nonynyl and decynyl. Furthermore, it may have double bond(s) at any position(s).

A preferred embodiment of "alkynyl" is ethynyl, propynyl, butynyl or pentynyl.

"Aromatic carbocyclyl" means a cyclic aromatic hydrocarbon group which is monocyclic or polycyclic having two or more rings. Examples include phenyl, naphthyl, anthryl and phenanthryl.

A preferred embodiment of "aromatic carbocyclyl" is phenyl.

"Non-aromatic carbocyclyl" means a cyclic saturated hydrocarbon group or cyclic unsaturated non-aromatic hydrocarbon group, which is monocyclic or polycyclic having two or more rings. Examples of the non-aromatic carbocyclyl, which is polycyclic having two or more rings, include a fused ring group wherein a non-aromatic carbocyclyl, which is monocyclic or polycyclic having two or more rings, is fused with a ring of the above "aromatic carbocyclyl".

In addition, examples of the "non-aromatic carbocyclyl" also include a group having a bridge and a group to form a spiro ring as follows:

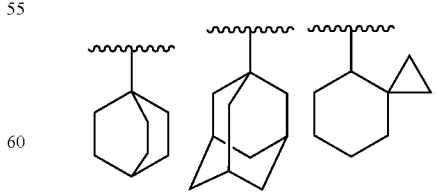

The non-aromatic carbocyclyl, which is monocyclic, is preferably C3 to C16, more preferably C3 to C12 and further preferably C4 to C8 carbocyclyl. Examples include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl and cyclohexadienyl.

Examples of non-aromatic carbocyclyl, which is polycyclic having two or more rings, include indanyl, indenyl, acenaphthyl, tetrahydronaphthyl and fluorenyl.

"Aromatic heterocyclyl" means an aromatic cyclyl, which is monocyclic or polycyclic having two or more rings, containing one or more of heteroatom(s) selected independently from O, S and N.

Examples of aromatic heterocyclyl, which is polycyclic having two or more rings, include a fused ring group wherein an aromatic heterocyclyl, which is monocyclic or polycyclic having two or more rings, is fused with a ring of the above "aromatic carbocyclyl" and/or "non-aromatic carbocyclyl".

The aromatic heterocyclyl, which is monocyclic, is preferably a 5- to 8-membered and more preferably 5- to 6-membered ring. Examples include pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl and thiadiazolyl.

Examples of aromatic heterocyclyl, which is bicyclic, include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl and thiazolopyridyl.

Examples of aromatic heterocyclyl, which is polycyclic having three or more rings, include carbazolyl, acridinyl, xanthenyl, phenothiazinyl, phenoxathiinyl, phenoxazinyl and dibenzofuryl.

"Non-aromatic heterocyclyl" means a non-aromatic cyclyl, which is monocyclic or polycyclic having two or more rings, containing one or more heteroatom(s) selected independently from O, S and N.

Examples of non-aromatic heterocyclyl, which is polycyclic having two or more rings, include a fused ring group wherein a non-aromatic heterocycle, which is monocyclic or polycyclic having two or more rings, is fused with a ring of "aromatic carbocyclyl", "non-aromatic carbocyclyl" and/or "aromatic heterocyclyl".

In addition, examples of the "non-aromatic heterocyclyl" also include a group having a bridge and a group to form a spiro ring as follows:

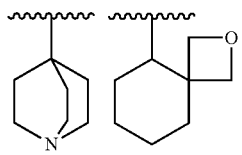

The non-aromatic heterocyclyl, which is monocyclic, is preferably a 3- to 8-membered and more preferably 5- to 6-membered ring. Examples include dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolinyl, oxepanyl, thiolanyl, thiinyl and thiazinyl.

Examples of non-aromatic heterocyclyl, which is polycyclic having two or more rings, include indolinyl, isoindolinyl, chromanyl and isochromanyl.

"Alkyloxy" means a group wherein "alkyl" binds to an oxygen atom. Examples include methyloxy, ethyloxy, n-propyloxy, isopropyloxy, n-butyloxy, tert-butyloxy, isobutyloxy, sec-butyloxy, pentyloxy, isopentyloxy and hexyloxy.

A preferred embodiment of "alkyloxy" is methyloxy, ethyloxy, n-propyloxy, isopropyloxy or tert-butyloxy.

"Haloalkyl" means a group wherein one or more "halogen" binds to "alkyl". Examples include monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, and 1,1,1-trifluoropropane-2-yl.

A preferred embodiment of "haloalkyl" is trifluoromethyl or trichloromethyl.

"Alkylthio" means a group wherein "alkyl" binds to sulfur atom.

"Alkylamino" includes monoalkylamino and dialkylamino.

"Monoalkylamino" means a group wherein a hydrogen atom attached to a nitrogen atom of an amino group is replaced with "alkyl". Examples include methylamino, ethylamino and isopropylamino. Preferably, it is methylamino or ethylamino.

"Dialkylamino" means a group wherein two hydrogen atoms attached to a nitrogen atom of an amino group are replaced with two "alkyl". These two alkyl groups may be the same or different. Examples include dimethylamino, diethylamino, N, N-diisopropylamino, N-methyl-N-ethylamino and N-isopropyl-N-ethylamino. Preferably, it is dimethylamino or diethylamino.

"Alkylcarbonylamino" means a group wherein one or two hydrogen atoms attached to a nitrogen atom of an amino group are replaced with one or two alkylcarbonyl. The two alkylcarbonyl groups may be the same or different. Examples include methylcarbonylamino, ethylcarbonylamino, propylcarbonylamino, isopropylcarbonylamino, tert-butylcarbonylamino, isobutylcarbonylamino, sec-butylcarbonylamino, dimethylcarbonylamino, diethylcarbonylamino and N, N-diisopropylcarbonylamino.

A preferred embodiment of "alkylcarbonylamino" is methylcarbonylamino and ethylcarbonylamino.

"Alkenylcarbonylamino" means a group wherein one or two hydrogen atoms attached to a nitrogen atom of an amino group are replaced with one or two alkenylcarbonyl. The two alkenylcarbonyl groups may be the same or different. Examples include vinylcarbonylamino and prop enylcarbonylamino.

"Alkynylcarbonylamino" means a group wherein one or two hydrogen atoms attached to a nitrogen atom of an amino group are replaced with one or two alkynylcarbonyl. The two alkynylcarbonyl groups may be the same or different. Examples include ethynylcarbonylamino and propynylcarbonylamino.

"Alkylcarbamoyl" means a group wherein one or two hydrogen atoms attached to a nitrogen atom of a carbamoyl group are replaced with one or two "alkyl". These two alkyl groups may be the same or different. Examples include methylcarbamoyl, ethylcarbamoyl, dimethylcarbamoyl and diethylcarbamoyl.

"Alkenylcarbamoyl" means a group wherein one or two hydrogen atoms attached to a nitrogen atom of a carbamoyl group are replaced with one or two "alkenyl". These two alkenyl groups may be the same or different. Examples include vinylcarbamoyl and propenylcarbamoyl.

"Alkynylcarbamoyl" means a group wherein one or two hydrogen atoms attached to a nitrogen atom of a carbamoyl group are replaced with one or two "alkynyl". These two alkynyl groups may be the same or different. Examples include ethynylcarbamoyl and propynylcarbamoyl.

Alkyl part of "aromatic carbocyclylalky", "non-aromatic carbocyclylalky", "aromatic heterocyclylalkyl" or "non-aromatic heterocyclylalkyl" is the same as "alkyl".

"Aromatic carbocyclylalkyl" means an alkyl substituted with one or more "aromatic carbocyclyl". Examples include benzyl, phenethyl, phenylpropyl, benzhydryl, trityl, naphthylmethyl and a group of the formula of

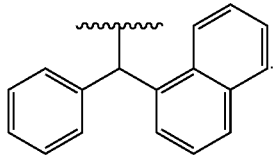 [SMILES: *C(c1ccccc1)c1cccc2ccccc12]

A preferred embodiment of "aromatic carbocyclylalkyl" is benzyl, phenethyl or benzhydryl.

"Non-aromatic carbocyclylalkyl" means an alkyl substituted with one or more "non-aromatic carbocyclyl". The "non-aromatic carbocyclylalkyl" also includes "non-aromatic carbocyclylalkyl" wherein the alkyl part is substituted with "aromatic carbocyclyl". Examples include cyclopropylmethyl, cyclobutylmethyl, cyclopenthylmethyl, cyclohexylmethyl and a group of the formula of

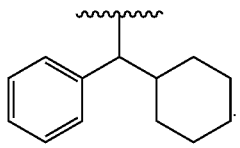

"Aromatic heterocyclylalkyl" means an alkyl substituted with one or more "aromatic heterocyclyl". The "aromatic heterocyclylalkyl" also includes "aromatic heterocyclylalkyl" wherein the alkyl part is substituted with the above "aromatic carbocyclyl" and/or "non-aromatic carbocyclyl". Examples include pyridylmethyl, furanylmethyl, imidazolylmethyl, indolylmethyl, benzothiophenylmethyl, oxazolylmethyl, isoxazolylmethyl, thiazolylmethyl, isothiazolylmethyl, pyrazolylmethyl, isopyrazolylmethyl, pyrroliclinylmethyl, benzoxazolylmethyl and groups of the formula of

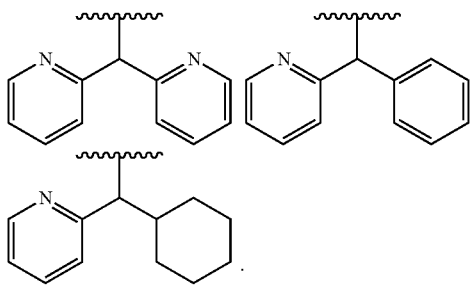

"Non-aromatic heterocyclylalkyl" means an alkyl substituted with one or more "non-aromatic heterocyclyl". The "non-aromatic heterocyclylalkyl" also includes "non-aromatic heterocyclylalkyl" wherein the alkyl part is substituted with "aromatic carbocyclyl", "non-aromatic carbocyclyl" and/or "aromatic heterocyclyl". Examples include tetrahydropyranylmethyl, morpholinylethyl, piperidinylmethyl, piperazinylmethyl and groups of the formula of

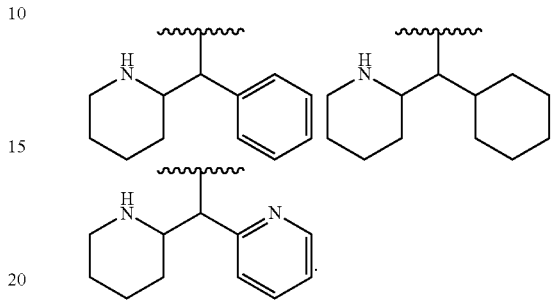

Examples of the substituents for "substituted or unsubstituted alkyl", "substituted or unsubstituted alkenyl", "substituted or unsubstituted alkynyl", "substituted or unsubstituted alkyloxy", "substituted or unsubstituted alkylcarbonylamino", "substituted or unsubstituted alkenylcarbonylamino", "substituted or unsubstituted alkynylcarbonylamino", "substituted or unsubstituted alkylcarbamoyl", "substituted or unsubstituted alkenylcarbamoyl" or "substituted or unsubstituted alkynylcarbamoyl" include the following substituents. A carbon atom at any position(s) may be bonded to one or more group(s) selected from the following substituents.

Substituent: halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, guanidino, trialkylsilyl, alkyloxy, alkenyloxy, alkynyloxy, haloalkyloxy, alkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyoxy, non-aromatic carbocyclylalkyoxy, aromatic heterocyclylalkyoxy, non-aromatic heterocyclylalkyloxy, aromatic carbocyclylalkyoxycarbonyl, non-aromatic carbocyclylalkyoxycarbonyl, aromatic heterocyclylalkyloxycarbonyl, non-aromatic heterocyclylalkyloxycarbonyl, aromatic carbocyclylalkyamino, non-aromatic carbocyclylalkyamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl, and non-aromatic heterocyclylsulfonyl. Furthermore, the substituent may have one or more substituent(s) selected from the above Group α.

Examples of the substituents on the ring of "aromatic carbocyclyl", "non-aromatic carbocyclyl", "aromatic heterocyclyl" or "non-aromatic heterocyclyl" of "substituted or unsubstituted aromatic carbocyclyl", "substituted or unsubstituted non-aromatic carbocyclyl", "substituted or unsubstituted aromatic heterocyclyl", and "substituted or unsubstituted non-aromatic heterocyclyl" include the following substituents. An atom at any position(s) on the ring may be bonded to one or more group(s) selected from the following substituents.

Substituent: halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, guanidino, trialkylsilyl, alkyl, alkenyl, alkynyl, haloalkyl, alkyloxy, alkenyloxy, alkynyloxy, haloalkyloxy, alkyloxyalkyl, alkyloxyalkyloxy, alkylcarbonyl, alkenylcarbonyl, alkynylcarbonyl, mono alkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalky, non-aromatic carbocyclylalky, aromatic heterocyclylalkyl, non-aromatic heterocyclylalkyl, aromatic carbocyclylalkyoxy, non-aromatic carbocyclylalkyoxy, aromatic heterocyclylalkyloxy, non-aromatic heterocyclylalkyloxy, aromatic carbocyclylalkyoxycarbonyl, non-aromatic carbocyclylalkyoxycarbonyl, aromatic heterocyclylalkyloxycarbonyl, non-aromatic heterocyclylalkyloxycarbonyl, aromatic carbocyclylalkyoxyalkyl, non-aromatic carbocyclylalkyoxyalkyl, aromatic heterocyclylalkyoxyalkyl, non-aromatic heterocyclylalkyloxyalkyl, aromatic carbocyclylalkyamino, non-aromatic carbocyclylalkyamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl, and non-aromatic heterocyclylsulfonyl. Furthermore, the substituent may have one or more substituent(s) selected from the above Group α.

Additionally, "substituted or unsubstituted non-aromatic carbocyclyl" and "substituted or unsubstituted non-aromatic heterocyclyl" may be substituted with "oxo". In this case, it means a group wherein two hydrogen atoms on a carbon atom are substituted as below.

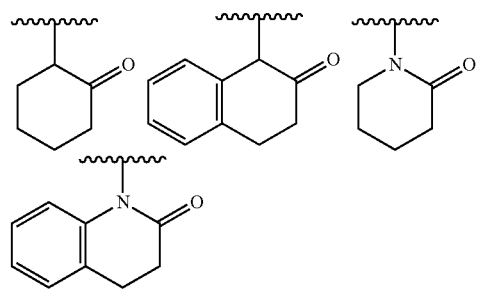

Here, the present invention is explained in detail.

A lipid binding double-stranded oligonucleotide of the present invention consists of a double-stranded oligonucleotide, wherein a first strand is a CpG oligonucleotide consisting of 8 to 50 nucleotides, a second strand is an oligonucleotide consisting of 8 to 60 nucleotides and comprising a sequence capable of hybridizing with the first strand, and a lipid binds to the second strand through a linker.

More preferably, it is a double-stranded oligonucleotide, wherein a first strand is a CpG oligonucleotide consisting of 8 to 50 nucleotides, a second strand is an oligonucleotide consisting of 8 to 60 nucleotides and comprising a sequence capable of hybridizing with the first strand, but excluding a RNA oligonucleotide, the length of the second strand is 50% or more of that of the first strand, and a lipid comprising C12 to C30 hydrocarbon chain(s) binds to the second strand through a linker.

A first strand of a lipid binding double-stranded oligonucleotide of the present invention is a CpG oligonucleotide consisting of 8 to 50 nucleotides.

The "CpG oligonucleotide (CpG ODN)" means a single-stranded oligonucleotide comprising dinucleotide of non-methylated cytosine guanine (5'-CpG-3') motif (CpG motif) and it is well known that it can be useful as a vaccine adjuvant because it induces acquired immune response through TLR9 (Nat Rev Drug Discov, 2006, 5, 471-484, Expert Rev Vaccines., 2011, 10(4), 499-511). The CpG oligonucleotide used for the present invention comprises at least one CpG motif and may comprise several CpG motifs.

The length of the CpG oligonucleotide used for the present invention is 8 to 50 nucleotides. For example, it is 8 to 50 nucleotides, 8 to 40 nucleotides, 8 to 30 nucleotides, 10 to 25 nucleotides, 15 to 25 nucleotides or 18 to 25 nucleotides.

As "the CpG oligonucleotide", it is not especially limited to the CpG oligonucleotide, which is well known for the immunostimulatory activity in this field can be used. For example, the CpG oligonucleotide or the method for preparing is described in WO2006/065751, WO2007/092315, WO2008/068638, WO2010/067262, WO2010/125480, WO2014/047588, WO2014/134698, WO2015/041318, US2011/0300163 or the like. These CpG oligonucleotides can be synthesized in reference to methods described in the above documents.

The CpG oligonucleotides are classified based on the sequence, secondary structure and effect on human peripheral blood mononuclear cells (PBMC), into class A, class B, class C, class P or class S (Advanced drug delivery reviews, 2009, 61(3), 195-204).

Class A: ODN1585, ODN2216, ODN2336 or the like;
Class B: ODNBW006, ODN D-SL01, ODN1668 (WO2005/063264), ODN1826 (WO2007/030580), ODN2006 (CpG7909, PF-3512676) (WO98/18810), ODN2007, ODN684 or the like; and
Class C: ODN D-SL03, ODN 2395, ODN M362 or the like.

These can be purchased from InvivoGen as a research reagent. In addition,

CpG-28 (WO2000/056342),
CpG-685 (GNKG-168) (Blood, 2010, 115(24), 5041),
CpG-ODN C274 (PLoS ONE, 2013, 8(4), e62373),
KSK-13 (KSK-CpG) (U57408050),
CpG ODN 10104 (CpG-10104) (Drug Data Rep, 2006, 28(3), 258),
CpG ODN-1585 (WO2001/022990),
ODN-5890 (WO2006/080946),
1018-ISS (WO2008/073661),
EMD-1201081 (HYB-2055, IMO-2055) (WO2005/009355),
D35-CpG, K3-CpG (GeneDesign, Inc.), or the like. For the present invention, the CpG oligonucleotides of any class can be used. The CpG oligonucleotides of class A (e.g., ODN2216, ODN2336 and D35-CpG), the CpG oligonucleotides of class B (e.g., ODN1826, ODN2006, CpG-28, 1018-ISS, IMO2055, K3-CpG, ODN684 and D-LS01) or the CpG oligonucleotides of class C (e.g., D-LS03, ODN2395 and ODN M362) is preferable. ODN1826 or ODN2006 is especially preferable.

A second strand of a lipid binding double-stranded oligonucleotide of the present invention is an oligonucleotide consisting of 8 to 60 nucleotides and comprising a sequence capable of hybridizing with the CpG oligonucleotide which is the first strand, but excluding a RNA oligonucleotide, Preferably, a second strand is an oligonucleotide consisting of 8 to 60 nucleotides and comprising a sequence capable of hybridizing with the CpG oligonucleotide which is a first strand under a stringent condition.

Any oligonucleotide can be used for a second strand as long as it can be hybridized with the CpG oligonucleotide under a stringent condition, and the one comprising 1 or several mismatch(es) in a part of hybridization can be exemplified.

For example, it is the oligonucleotide whose part for hybridization has at least 70% or more, preferably 80% or more, more preferably 90% or more, and most preferably 95% or more homology to a complementary sequence of the CpG oligonucleotide of a first strand.

The homology shows the similarity as a score, for example, by BLAST, a search program using algorithm discovered by Altschul et al. (The Journal of Molecular Biology, 215, 403-410 (1990).)

The "stringent conditions" mean conditions under which a base sequence forms hybrid (so-called specific hybrid) with a specific sequence but any base sequence without the equivalent function does not form hybrid (so-called non-specific hybrid) with the specific sequences. People skilled in the art can easily select the conditions by changing a temperature during hybridization reaction or washing, salt concentration in hybridization or washing buffer, or the like. In detail, an example of the stringent conditions of this invention is, but not limited to the condition, which the oligonucleotide is hybridized in 6×SSC (0.9 M NaCl, 0.09 M trisodium citrate) or 6×SSPE (3 M NaCl, 0.2 M NaH2PO4, 20 mM EDTA.2Na, pH 7.4) at 42° C. and washed with 0.5×SSC at 42° C. As a hybridization method, well-known methods in the art, for example, southern blot hybridization or the like can be used. In detail, it can be performed according to a method disclosed in Molecular Cloning: A Laboratory Manual, Second Edition (1989) (Cold Spring Harbor Laboratory Press), Current Protocols in Molecular Biology (1994) (Wiley-Interscience), DNA Cloning 1: Core Techniques, A Practical Approach, Second Edition (1995) (Oxford University Press) or the like.

"1 or several mismatch(es)" means 1 to 5, preferably 1 to 3, and more preferably 1 or 2 mismatches.

The length of a second strand of a lipid binding double-stranded oligonucleotide of the present invention is 8 to 60 nucleotides. For example, it is 8 to 60 nucleotides, 8 to 50 nucleotides, 8 to 40 nucleotides, 8 to 30 nucleotides, 10 to 25 nucleotides or 15 to 25 nucleotides. The length of the second strand can be same with that of the CpG oligonucleotide which is a first strand, and 1 or several nucleotide(s) shorter than that of the CpG oligonucleotide as long as it can be hybridized with the CpG oligonucleotide. Furthermore, the length of a second strand can be longer than that of the CpG oligonucleotide by adding 1 or several nucleotide(s) at one or both sides of a part hybridizing with the CpG oligonucleotide.

"1 or several nucleotide(s)" means 1 to 10, 1 to 5, 1 to 3, or 1 or 2 nucleotide(s).

A preferable length of a second strand depends on the length of the CpG oligonucleotide of a first strand. For example, it is a length of 50% or more, 60% or more, 70% or more, 50 to 100%, 60 to 100% or 70 to 100% of the length of a first strand. 50 to 100% of the length of a first strand is especially preferable.

The oligonucleotide of a second strand of a lipid binding double-stranded oligonucleotide of the present invention is an oligonucleotide which nucleosides selected from the group consisting of DNA nucleosides, RNA nucleosides and nucleoside derivatives are bounded. All nucleosides can be same, or two or more kinds of nucleoside. However, an RNA oligonucleotide which all nucleosides are a RNA nucleoside is excluded. As a nucleoside comprised in a second strand, an oligonucleotide which DNA nucleosides and/or nucleoside derivatives are bounded is preferable. All nucleosides can be a DNA nucleoside, nucleoside derivative, or both of them.

When an oligonucleotide comprises DNA nucleosides and nucleoside derivatives, an example is an oligonucleotide comprising a center region and end regions at the both sides of the center region, and comprising at least one nucleoside derivative in the end region at the both sides. In detail, 5' and/or 3' end region(s) comprises 1 or more, preferably 1 to 5, and more preferably 2 to 3 nucleoside derivatives. The kind, number and position of modification(s) in one end region may be same or different from those in the other end region. In the other embodiment, it is an oligonucleotide randomly comprising nucleoside derivatives.

As a nucleoside derivative in a second strand of a lipid binding double-stranded oligonucleotide of the present invention, any modification(s) for a nucleoside which is well-known in this field such as the above examples can be used.

A nucleoside having a substituent at the 2' position of sugar and/or a nucleoside having a bridge structure between at the 4' and 2' positions of sugar are preferable.

As a substituent at the 2' position of a sugar, F, $OCH_3$ or $OCH_2CH_2OCH_3$ is preferable. $OCH_3$ is especially preferable.

As a bridge structure between the 4' and 2' positions of a sugar, 4'-(CH$_2$)m-O-2', wherein m is an integer of 1 to 4, or 4'-C(=O)—NR$^3$-2', wherein R$^3$ is hydrogen atom or alkyl, is preferable.

As an internucleoside linkage in the oligonucleotide of a second strand of a lipid binding double-stranded oligonucleotide of the present invention, any well-known internucleoside linkage such as the above examples in this field can be used. All internucleoside linkages can be same, or two or more kinds of linkage. D-oligo and/or S-oligo is preferable.

When 2 or more kinds of internucleoside linkages are comprised such as D-oligo and S-oligo, an example is an oligonucleotide comprising a center region and end regions at the both sides of the center region, and comprising at least one unnatural internucleoside linkage (e.g., S-oligo) in the end region at the both sides and natural internucleoside linkage (e.g., D-oligo) in the center region. For example, 5' and/or 3' end region(s) comprises 1 or more, preferably 1 to 5, and more preferably 2 to 3 unnatural internucleoside linkages. The kind, number and position of modification(s) in one end region may be same or different from those in the other end region. In the other embodiment, it is an oligonucleotide randomly comprising unnatural internucleoside linkages.

The CpG oligonucleotide of a first strand and oligonucleotide of a second strand in a lipid binding double-stranded oligonucleotide of the present invention can be synthesized according to the usual methods in this field. For example, they can be easily synthesized by an automated nucleic acid synthesizer which is commercially available (e.g., the synthesizer by AppliedBiosystems, Dainippon Seiki and GE Healthcare). A method for synthesizing is solid-phase synthesis using phosphoramidite, solid-phase synthesis using hydrogen phosphonate or the like. Examples are disclosed in the following Example 1, Tetrahedron Letters 22, 1859-1862 (1981) and the like.

The synthesized first and second strands form a double-stranded oligonucleotide by hybridizing according to the well-known method. Examples are disclosed in the following Example 1, Example 1 in WO2013/089283 and the like.

In the lipid binding double-stranded oligonucleotide of the present invention, a lipid binds to the second strand through a linker.

"Lipid" means a hydrophobic compound. It is not limited as long as it is a well-known lipid, and may be a straight, branched or cyclic form. Examples are fatty acid with a C8 to C30 aliphatic chain(s) (e.g., farnesol), diacyl lipid, cholesterol, cholesterol derivatives, steroid acid (e.g., bile acid), lipid A, tocopherol and combination thereof. Examples of fatty acid with an aliphatic chain(s) are, but not limited to, unsaturated or saturated fatty acid in a straight or branched form, and fatty acid derivatives (e.g., fatty acid esters, fatty acid amides and fatty acid thioesters).

As a lipid used for the present invention, a lipid comprising a hydrocarbon chain(s) is preferable. Preferably, it is a lipid comprising 1 or 2 hydrocarbon chain(s) or the like. Especially preferably, a lipid binding double-stranded oligonucleotide of the present invention has a diacyl lipid. When lipids bind at two or more positions and one lipid is a diacyl lipid, the other lipid can be a lipid except for a diacyl lipid.

"Diacyl lipid" is phospholipid, glycolipid, sphingolipid or combination thereof, which comprising two hydrocarbon chains. Preferably, it is the group of the following (a) or (f).

Hydrocarbon chains in the lipid independently comprise about C8 to C30 carbon atoms. They can be saturated, unsaturated, or combination thereof, and branched. When the lipid has one chain, the length of the chain is preferably C8 to C30, and more preferably C8 to C20. When the lipid has two chains, the length of the chains is preferably C10 to C30, more preferably C12 to C30, and most preferably C14 to C24. When the lipid has two chains, the length of two chains may be same or different. Chains in a lipid bind a part comprising phosphoric acid, sugar or the like (a position binding with an oligonucleotide) through ester bond, amide bond, thioester bond, combination thereof or the like.

A lipid binding double-stranded oligonucleotide of the present invention has a lipid comprising a C12 to C30 hydrocarbon chain(s) in a second strand. When lipids bind at 2 or more positions and one lipid is a lipid comprising a C12 to C30 hydrocarbon chain(s), the number of carbon atoms of a hydrocarbon chain(s) in the other lipid can be less than 12.

Examples of "lipid" are the followings.

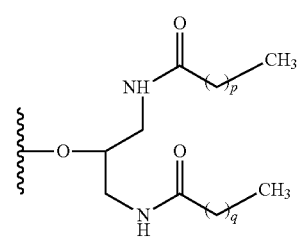

(a)

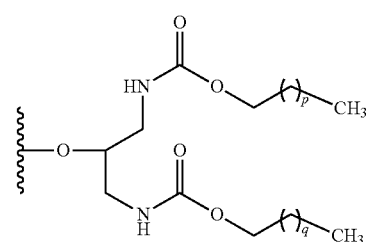

(b)

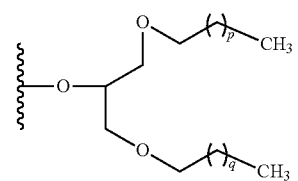

(c)

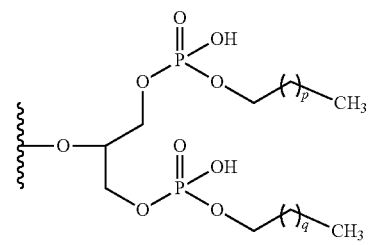

(d)

-continued (e)

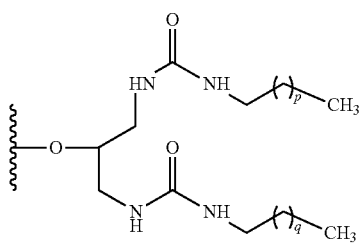

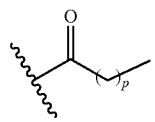

(f)

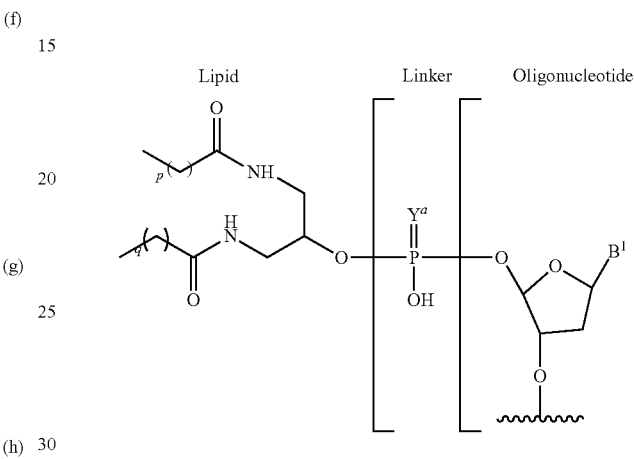

(g)

(h)

wherein p and q are each independently an integer of 6 to 28, preferably 8 to 28, more preferably 10 to 28, and most preferably 10 to 18.

In a lipid binding double-stranded oligonucleotide of the present invention, a lipid can bind at any position of the second strand. It can bind at the 3' end, the 5' end or in the second strand.

When the lipid binds at the 5' end, for example, it can bind as below.

wherein $B^1$ is a base at the 3' end of the second strand, $Y^a$ is O or S, and p or q is each independently an integer of 6 to 28, and preferably 10 to 18.

When the lipid binds at the 3' end, for example, it can bind as below.

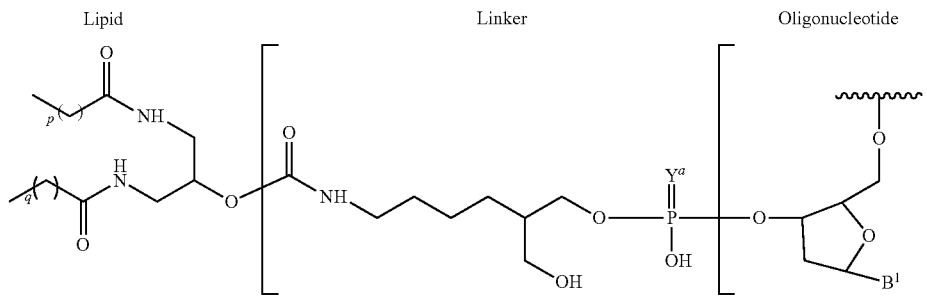

wherein $B^1$ is a base at the 5' end of the second strand, $Y^a$ is O or S, and p or q is each independently an integer of 6 to 28, and preferably 10 to 18.

When the lipid binds in a second strand, for example, it can bind as below.

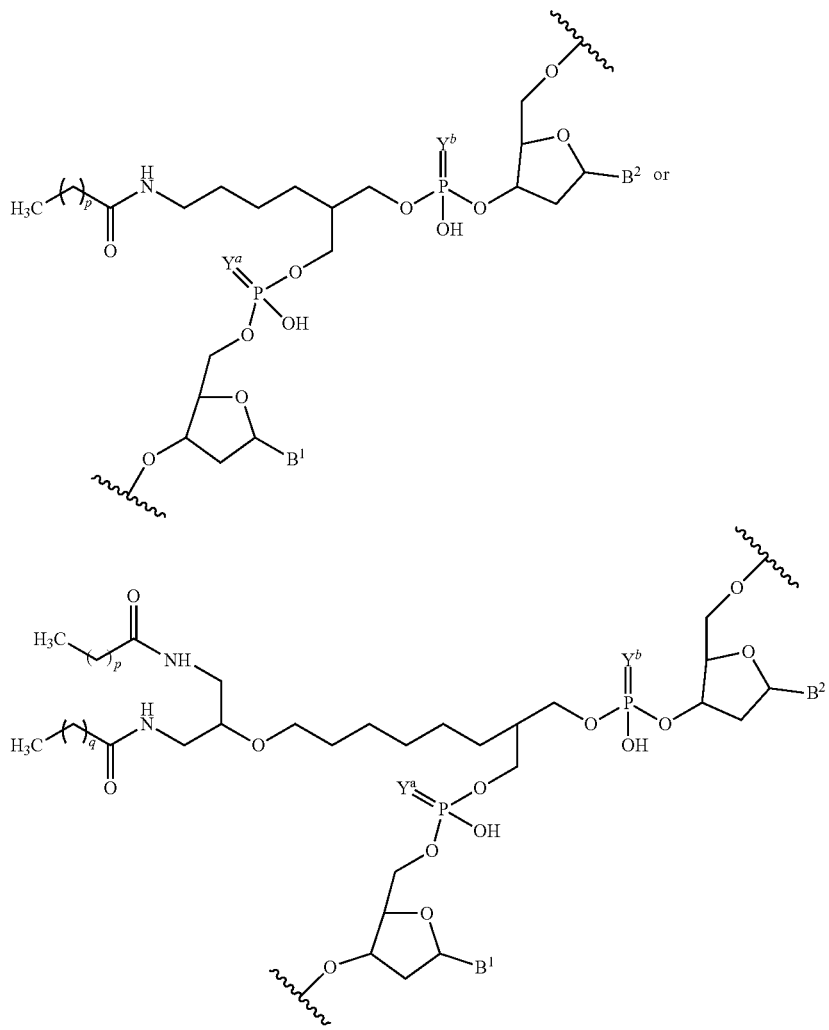

wherein $B^1$ and $B^2$ are the neighboring bases in the second strand, $Y^a$ or $Y^b$ is each independently O or S, and p and q is each independently an integer of 6 to 28, and preferably 10 to 18.

Furthermore, the lipid preferably binds at one or two position(s) in the second strand. It preferably binds at 3' and/or 5' end. It more preferably binds at 5' end.

The lipid can be synthesized in reference to well-known methods in this field. Examples of the lipid or the preparation methods are disclosed in the following Example 1, Patent Document 1 and the like.

In a lipid binding double-stranded oligonucleotide of the present invention, the lipid binds to a second strand through a linker. As a "linker", any linker used in this field can be used. Examples are polar linker, alkylene linker, ethylene glycol linker and ethylenediamine linker. When a lipid is a phospholipid, it is a linker which is 4 to 26 atoms between oxygen atom of a second strand and phosphorus atom of a lipid. Examples are an oligonucleotide linker or the following linkers.

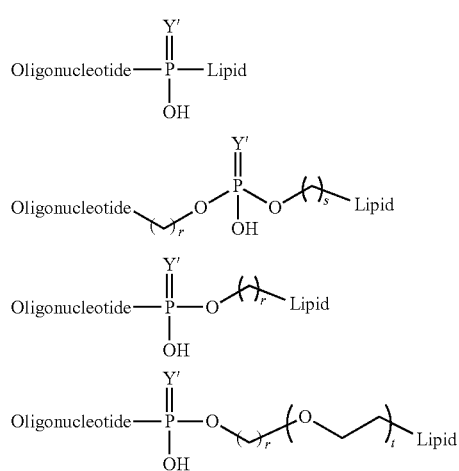

-continued

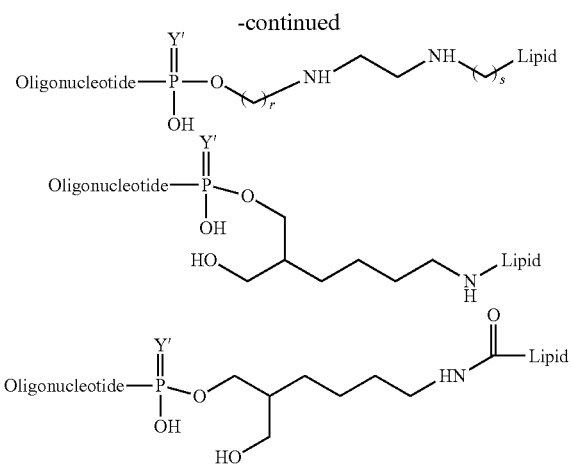

wherein Y' is O or S, and r or s is each independently an integer of 1 to 10, preferably 1 to 5, and more preferably 1 to 3. t is an integer of 1 to 4, preferably 1 to 3, and more preferably 2 or 3.

The linker can be synthesized in reference to the well-known method in this field. The oligonucleotide linker can be synthesized by the method similar to the method for synthesizing the oligonucleotides in the above example.

The linker is preferably an oligonucleotide linker. The length of an oligonucleotide linker is 2 to 10, 2 to 5, 2, 3, 4 or 5 nucleotides and may comprise nucleoside derivatives. An example is the following.

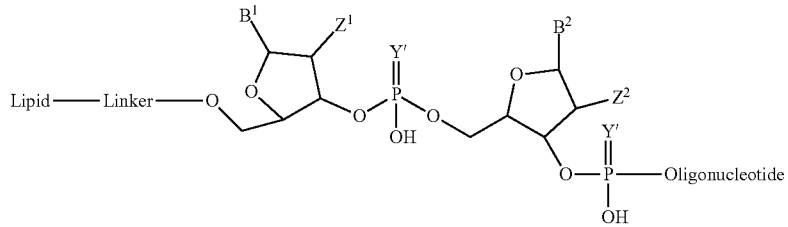

wherein $B^1$ or $B^2$ is H, adenine (A), guanine (G), cytosine (C), 5-methylcytosine (5-Me-C), thymine (T) or uracil (U). Y' is each independently O or S. $Z^1$ or $Z^2$ is each independently H or OH, and preferably H.

An example of an oligonucleotide linker is a DNA linker, that is, -(dX$^1$)u-, wherein $X^1$ is each independently A, G, C or T, and u is an integer of 1 to 8. In detail, it is dG, dGdG, dGdGdGdG, dGdGdGdGdG, dT, dTdT, dTdTdTdT, dTdTdTdTdT or the like. dGdG, dGdGdGdGdG or dTdT is especially preferable. The internucleoside linkage in the DNA linker is preferably phosphorothioate linkage.

3' end, 5' end or linker without binding lipid of a lipid binding double-stranded oligonucleotide of the present invention can be further modified. To be capable of tracking of the oligonucleotide, to improve pharmacokinetics or pharmacodynamics of the oligonucleotide, or to enhance the stability or binding affinity of the oligonucleotide, the well-known modified group in this field can be used. Examples are a protecting group of a hydroxyl group, reporter molecule, cholesterol, phospholipid, pigment, fluorescent molecule and the like.

Furthermore, 3' or 5' end without binding the lipid of a lipid binding double-stranded oligonucleotide of the present invention may comprise a phosphate ester moiety. The "phosphate ester moiety" means a phosphate group at the end comprising phosphate ester or modified phosphate ester. Although the phosphate ester moiety may be at the either end, it is preferably 5' end nucleoside. In detail, it is a group of the formula: —O—P(=O)(OH)OH or the modified group. That is, one or more of O or OH is optionally substituted with H, O, OR', S, N(R'), wherein R' is H, amino-protecting group, or substituted or unsubstituted alkyl, or alkyl. 5' or 3' end may each independently comprise substituted or unsubstituted 1 to 3 phosphate ester moiety.

The present invention encompasses a pharmaceutical composition (a pharmaceutical composition of the present invention) or a vaccine composition (a vaccine composition of the present invention) comprising a lipid binding double-stranded oligonucleotide of the present invention (a vaccine or adjuvant of the present invention of the present invention).

In addition, the present invention encompasses a pharmaceutical or vaccine composition comprising an antigen and a lipid binding double-stranded oligonucleotide of the present invention (an adjuvant of the present invention).

An "antigen" is a molecule that is capable of inducing an immune response. Examples include, but are not limited to, cells, cell extracts, proteins, recombinant proteins, purified proteins, polypeptides, peptides, polysaccharides, polysaccharide conjugates, peptide or non-peptide mimics of polysaccharides, other molecules encoded by plasmid DNA, haptens, small molecules, lipids, glycolipids, carbohydrates, whole killed pathogens, viruses, viral extracts, live attenuated virus, viral vector, live attenuated bacteria, bacterial vectors, multicellular organisms such as parasites and allergens.

The antigen may be provided as a single antigen or combination of antigens. The antigen may be provided as a complex mixture of polypeptide or oligonucleotide.

Antigens include, but are not limited to, microbial antigens, self-antigens, neoantigens and addictive substances.

A "microbial antigen" means an antigen of a microorganism, and the microorganism includes, but is not limited to, a bacterium, virus, parasite and fungus.

A "bacterium" is not especially limited as long as it is a bacterium which causes a disease in human, pet, livestock or the like. In detail, it is *Streptococcus* (*Streptococcus pyogens, Streptococcus pneumoniae* or the like), *Staphylococcus aureus* (MSSA, MRSA or the like), *Staphylococcus epidermidis, Enterococcus*, bacteria belonging to the genus *Listeria*, bacteria causing meningitis, Gonococcus, pathogenic *Escherichia coli, Friedlander bacilli, Proteus bacilli, Bordetella pertussis, Pseudomonas aeruginosa, Serratia marcescens, Citrobacter, Acinetobacter, Enterobacter, Mycoplasma, Clostridia, Tubercle bacilli, Cholera bacilli, Yersinia pestis, Corynebacterium diphtherias, Dysentery* bacillus, *Bacillus anthracis, Treponema pallidum, Tetanus bacillus, Mycobacterium leprae, Legionella pneumophila, Leptospira, Borrelia, Francisella, Coxiella, Rickettsia, Chlamydia, Burkholderia mallei, Helicobacter pylori* or the like.

A "virus" is not especially limited as long as it is a virus which causes a disease in human, pet, livestock or the like. Examples are influenza virus, respiratory syncytial virus (RSV), papilloma virus, hepatitis virus (type A, B, C, D, E, F, G, TT or the like), rhinovirus, variola virus, morbillivirus, rubella virus, poliovirus, varicella zoster virus, norovirus, Norwalk virus, sapovirus, Sapporo virus, mumps virus, adenovirus, enterovirus, rotavirus, human immunodeficiency virus such as HIV-1 and HIV-2, rabies virus, T-lymphotrophic virus, yellow fever virus, cytomegalovirus, SARS-CoV, coronavirus such as MERS-CoV, ebola virus, polyomavirus, JC virus, BK virus, herpes virus such as herpes simplex virus 1 (HSV1) and herpes simplex virus 2 (HSV2), lymphocryptovirus, roseolovirus, Japanese encephalitis virus, Coxsackie virus, dengue virus, West Nile virus, coronavirus, parvovirus, Epstein-Barr virus, Marburg virus, hantavirus, Lassa virus, Chikungunya virus, Hantaan virus, louping ill virus, lymphocytic choriomeningitis virus, bornavirus, Rift Valley fever, Thogoto virus, Dhori virus, foot-and-mouth disease virus, Newcastle disease virus, bovine papular stomatitis virus, rinderpest virus, swine vesicular disease virus, calicivirus, torovirus, African horse sickness virus, arterivirus, sheep pox virus, capripoxvirus, sheep-associated malignant catarrhal fever virus, viral hemorrhagic septicemia virus and vesicular stomatitis virus.

A "parasite" is not especially limited as long as it is a parasite which causes a disease in human, pet, livestock or the like. Examples are entamoeba histolytica, malaria, toxoplasma, leishmania, cryptosporidium, trypanosoma, echinococcus, schistosoma japonicum, filaria, roundworm and *diphyllobothrium*.

A "Fungus" is not especially limited as long as it is a fungus which causes a disease in human, pet, livestock or the like. In detail, it is aspergilloma, candida, cryptococcus, trichophyton, histoplasma, pneumocystis or the like.

A "self-antigen" means a tumor-associated self-antigen, an antigen associated with Alzheimer's disease, an antigen against a human antibody, an antigen expressed from human endogenous retroviral elements or the like.

A "neoantigen" means is an antigen to which the immune system has not previously been exposed, especially one that arises by host antigens by viral infection, neoplastic transformation, drug metabolism, etc (see Science. 2015; 348 (6236):803-8).

An example of a "tumor antigen" of this description is an antigen specifically expressed in cancer cells, i.e., a tumor-associated self-antigen or neoantigen. Examples include protein, peptide and fusion peptide comprising them. Examples are peptides described in WO2006/090810, WO2007/145318, WO2008/047473, WO2008/102557, WO2009/025117, WO2009/025196, WO2009/1539992, WO2010/013485, WO2010/021112, WO2010/073551, WO2010/095428, WO2010/131452, WO2010/137295, WO2011/067920, WO2011/074236, WO2011/089921, WO2011/111392, WO2012/053200, WO2012/053206, WO2012/169200, WO2013/024582, WO2013/061594, WO2014/041784, WO2014/087626 and the like.

Examples of an antigen associated with Alzheimer's disease are tau and β-amyloid.

An example of an antigen against a human antibody is IgE.

An "addictive substance" means nicotine, cocaine or the like. An example of a nicotine antigen is a nicotine hapten conjugated to a carrier (e.g., diphtheria toxin).

A pharmaceutical or vaccine composition of the present invention can further comprise a well-known adjuvant(s) as long as the effect of the lipid binding double-stranded oligonucleotide of the present invention is maintained. For example, it is *Cholera* toxin, *Salmonella* toxin, alum or an agonist for a Toll-like receptor (TLR) that is not TLR9. Examples of agonists for TLR are an agonist for TLR3 such as stabilized poly(I:C); an agonist for TLR4 such as a derivative of lipopolysaccharide (LPS) (e.g., MPL and GLA); an agonist for TLR5 such as flagellin; an agonist for TLR7; and an agonist for TLR8. Examples include aluminum salt such as aluminum hydroxide, an immune stimulatory complex (ISCOM), oil-in-water or water-in-oil emulsion, liposome and a delivery system such as nanoparticle and microparticle.

As the following examples, a pharmaceutical or vaccine composition of the present invention comprising a tumor antigen has any or all of the following excellent characteristics:

a) 1% or more CTL inducibility.
b) Inhibition on tumor progression.
c) Effect of tumor regression
d) Good pharmacokinetics such as a high bioavailability and moderate clearance. Especially, efficient delivery to lymphnodes.
e) High metabolic stability.
f) No cytokine release syndrome.
g) Weak local irritation.
h) No mutagenicity.
i) Low cardiovascular risk.
j) Low acute toxicity risk.

Any administration method and formulation for the pharmaceutical or vaccine composition of the present invention can be used if it is a well-known administration method and formulation in this field.

A pharmaceutical or vaccine composition of the present invention may be administered in a number of ways depending upon whether local or systemic treatment is desired and upon the area to be treated. Examples of an administration method include topical (including ophthalmic, intravaginal, intrarectal, intranasal and transdermal), oral and parenteral. Examples of parenteral administration include intravenous injection or drip, subdermal, intraperitoneal or intramuscular injection, lung administration by aspiration or inhalation, intrathecal administration and intraventricular administration. Intravenous injection or subcutaneous administration is preferable.

When the pharmaceutical or vaccine composition of the present invention is topically administered, a formulation such as a transdermal patch, ointment, lotion, cream, gel, drop, suppository, spray, liquid and powder can be used.

Examples of the composition for oral administration include powder, granule, suspension or solution dissolved in water or non-aqueous vehicle, capsule, powder and tablet.

Examples of the composition for parenteral, intrathecal or intraventricular administration include sterile aqueous solutions which contain buffers, diluents and other suitable additives.

A pharmaceutical or vaccine composition of the present invention can be obtained by mixing an effective amount with various pharmaceutical additives suitable for the administration form, such as excipients, binders, moistening agents, disintegrants, lubricants and diluents as needed.

When the composition is an injection, it together with a suitable carrier can be sterilized to obtain a composition.

Examples of the excipients include lactose, saccharose, glucose, starch, calcium carbonate and crystalline cellulose.

Examples of the binders include methylcellulose, carboxymethylcellulose, hydroxypropylcellulose, gelatin and polyvinylpyrrolidone.

Examples of the disintegrants include carboxymethylcellulose, sodium carboxymethylcellulose, starch, sodium alginate, agar and sodium lauryl sulfate.

Examples of the lubricants include talc, magnesium stearate and macrogol. Cacao oil, macrogol, methylcellulose or the like may be used as base materials of suppositories.

When the composition is prepared as solutions, emulsified injections or suspended injections, solubilizing agents, suspending agents, emulsifiers, stabilizers, preservatives, isotonic agents and the like which are usually used may be added as needed. For oral administration, sweetening agents, flavors or the like may be added.

Dosing is dependent on severity and responsiveness of the disease state to be treated, with the course of treatment lasting from several days to several months, or until a cure is effected or a diminution of the disease state is achieved. Optimal dosing schedules can be calculated from measurements of a pharmaceutical or vaccine composition accumulation in the body. Persons of ordinary skill in the art can determine optimal dosages, dosing methodologies and repetition rates.

The content rate of a lipid binding double-stranded oligonucleotide of the present invention of a pharmaceutical or vaccine composition of the present invention is, but not especially limited to, usually about 0.01 to 99.99 wt % against 100 wt % of a pharmaceutical or vaccine composition.

When an antigen was comprised, considering the content rate of the antigen and an adjuvant of the present invention, the adjuvant is usually about 10 to 1000 parts by weight against 1 part by weight of the antigen.

The dosage of a pharmaceutical or vaccine composition is diversified depending on the desired degree of immune stimulation, age of the subject of administration, sex or the like, so it can be appropriately set, e.g., 0.001 to 10 mg/kg weight/day, to which it is not especially limited.

In addition, according to the degree of effectiveness of the desired pharmaceutical or vaccine composition, age of the subject of administration, sex or the like, a pharmaceutical or vaccine composition of the present invention can be administered to the same subject at several times, e.g., up to about 2 to 4 times. When a pharmaceutical or vaccine composition of the present invention is administered to the same subject at several times, the interval can be appropriately set, e.g., about 14 to 30 days.

A pharmaceutical or vaccine composition of the present invention can be administered in combination of 1 or more kind(s) of medicines. The therapeutic agent known as a therapeutic agent for the target disease in this field can be used as the medicines. For example, when the disease is cancer, a pharmaceutical or vaccine composition of the present invention can be co-administered with a chemotherapeutic agent(s). When the disease is bacterial infections, a pharmaceutical or vaccine composition of the present invention can be co-administered with an antibiotic(s). A pharmaceutical or vaccine composition of the present invention may be simultaneously or separately administered with the agent(s). In addition, a pharmaceutical or vaccine composition of the present invention and the therapeutic agent(s) may be administered as the different formulations independently comprising each one or a single formulation comprising the pharmaceutical or vaccine composition and the therapeutic agent(s). Furthermore, when the disease is cancer, a pharmaceutical or vaccine composition of the present invention can be administered in combination of the surgical treatment which is known in this field.

Moreover, the present invention encompasses a method for increasing an immune response in a subject, comprising administering to the subject an effective amount of a pharmaceutical or vaccine composition of the present invention. An example of "immune response" is an increase in inducibility of specific cytotoxic T-lymphocyte (CTL) or antibody production compared to a control. A specific method for measuring CTL inducibility is disclosed in, e.g., the following Example 3 and WO2013/024582. A specific method for measuring inducibility of antibody production is disclosed in, e.g., the following Example 6.

Furthermore, the present invention encompassed a method for treating a cancer or infectious disease, comprising administering to a subject an effective amount of a pharmaceutical or vaccine composition of the present invention to reduce one or more symptoms of the cancer or infectious disease compared to a control.

"The subject" means any individual which is a target for a treatment with a pharmaceutical or vaccine composition of the present invention. Examples include mammals such as humans, laboratory animals (e.g., mice and rats), pets (e.g., dogs, cats, ferrets and birds) and livestock (e.g., cattle, pigs, chickens, goats, ostriches, sheep and horses).

"An effective amount" means enough dosage to induce or enhance the immune response, provide the desired pharmacological and/or physiological effect, or provide a treatment for the disorder, disease or status. The exact dosage may be changeable depending on various factors such as the subject-dependent variable (e.g., age and health condition of immune system), disease, stage of disease and the provided treatment.

"Cancer" is not especially limited as long as it is a cancer which a human, pet, livestock or the like may contract. Examples are chronic myeloid leukemia (CML), acute myeloid leukemia (AML), lymphoma, Hodgkin's disease, Non-Hodgkin lymphoma, multiple myeloma, brain tumor, breast cancer, endometrial carcinoma, cervical cancer, ovarian cancer, esophageal cancer, stomach cancer such as diffuse gastric cancer, appendiceal cancer, colorectal cancer, liver cancer, hepatocellular carcinoma, gallbladder cancer, cholangiocarcinoma, pancreatic cancer, adrenal cancer, gastrointestinal stromal tumor, mesothelioma, head and neck carcinoma, laryngeal cancer, oral cancer, gingival cancer, tongue cancer, buccal mucosa cancer, salivary gland cancer, paranasal cancer, carcinoma of maxillary sinus, carcinoma of the frontal sinus, ethmoid sinus cancer, sphenoid sinus cancer, thyroid cancer, renal cancer, lung cancer such as Non-Small Cell Lung Cancer (NSCLC) and small cell lung cancer (SCLC), osteosarcoma, prostate cancer, testicular cancer, bladder cancer, rhabdomyosarcoma, skin cancer, anal carcinoma, chondrosarcoma, synovial sarcoma, endometriosis, soft tissue tumor and osteoblastoma.

An "infectious disease" means acute or chronic infectious disease, especially viral infectious disease. Examples include, but not limited to, local or systemic viral infections such as immunodeficiency by HIV or the like, papilloma by HPV or the like, herpes by HSV or the like, encephalitis, influenza by human influenza virus A or the like and cold by human rhinovirus.

In this description, meaning of each abbreviation is as follows:

Ac: acetyl
CPG: Controlled Pore Glass
DIEA: N,N-diisopropylethylamine
DMAP: 4-dimethylaminopyridine
DMTr dimethoxytrityl
DMT-MM: 4-(4,6-dimethoxy1,3,5-triazine2-yl)-4-methyl-morpholinium chloride
DMF: N,N'-dimethylformamide
Et: ethyl
Fmoc: 9-fluorenylmethyloxycarbonyl
HBTU: O-benzotriazole-N,N,N',N'-tetramethyluronium-hexafluoro-phosphate
Me: methyl
MMTr: 4-methoxyphenyldiphenylmethyl
MMTrCl: 4-methoxytrityl chloride
PBS: phosphate buffered saline
TBS: tert-butyldimethylsilyl
TBAF: tetrabutylammonium fluoride
TFA: trifluoroacetic acid
THF: tetrahydrofuran

EXAMPLES

The present invention will be described in more detail with reference to, but not limited to, the following Examples, Reference Examples and Test Examples.

NMR analysis of each compound obtained in Examples was performed by 300 MHz or 400 MHz using $CD_3OD$, $CDCl_3$ or DMSO-d6.

UPLC analysis was performed under the following conditions.
Mobile phases: [A] is 0.1% aqueous formic solution, [B] is acetonitrile solution containing 0.1% aqueous formic acid
Gradient: linear gradient of 5% to 100% solvent [B] for 3.5 minutes was performed, and 100% solvent [B] was maintained for 0.5 minute.
Column: ACQUITY UPLC (Registered trademark) BEH C18 (1.7 μm, i.d. 2.1×50 mm) (Waters)
Flow rate: 0.8 mL/min
PDA detection wavelength: 254 nm (Detection range 210-500 nm)

Example 1 Synthesis of a Lipid Binding Double-Stranded Oligonucleotide of the Present Invention A) Synthesis of Lipids
1-1) Synthesis of 4-n

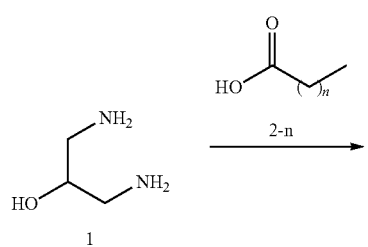

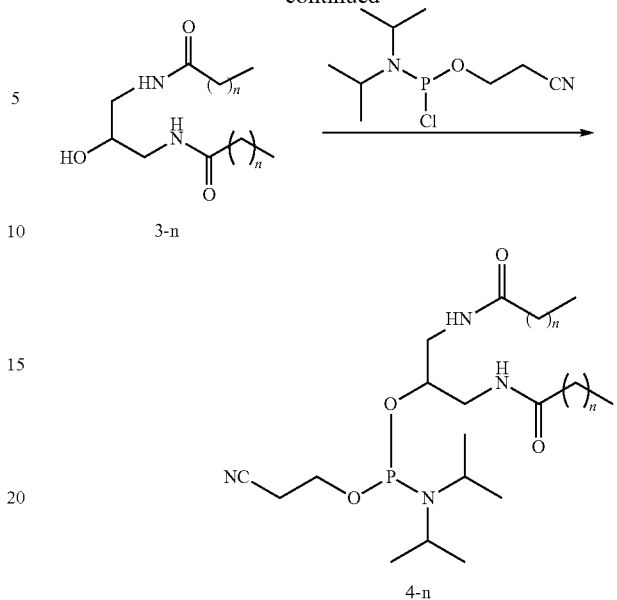

wherein n is an integer of 6 to 28.

1-1-1) Synthesis of Compound 3-6

Step 1

Compound 2-6 (3.20 g, 22.2 mmol, Tokyo Chemical Industry Co., Ltd.) was dissolved in THF-DMF (5:1, 60 mL), and DIEA (4.84 mL, 27.7 mmol) and HBTU (8.84 g, 23.3 mmol) were added thereto. The mixture was stirred at room temperature for 30 minutes. Compound 1 (2.2 g, 24.41 mmol) in DMF solution (5 mL) was added dropwise over 10 minutes and stirred for 3 hours. The amount of the reaction mixture was concentrated to the half under reduced pressure, and it was added dropwise to water (100 mL). The mixture was stirred for 10 minutes, and the resulting solid was collected by filtration. The solid was washed with water (50 mL) and acetonitrile (150 mL) to obtain Compound 3-6 (3.2 g, 9.34 mmol) as a white solid.

$^1$H-NMR ($CDCl_3$) δ: 6.45 (2H, t, J=6.0 Hz), 4.39 (1H, s), 3.78-3.73 (1H, m), 3.33 (4H, t, J=5.6 Hz), 2.22 (4H, t, J=7.7 Hz), 1.67 (4H, dt, J=31.0, 14.1 Hz), 1.30-1.27 (16H, m), 0.88 (6H, t, J=6.8 Hz).

1-1-2) Synthesis of Compound 4-8

Step 1

Compound 2-8 (7.65 g, 44.40 mmol, Wako Pure Chemical Industries, Ltd.) was dissolved in DMF (50.0 mL) and dichloromethane (100.0 mL). DIEA (8.72 mL, 66.6 mmol) and HBTU (18.52 g, 48.8 mmol) were added thereto, and the mixture was vigorously stirred at room temperature for 30 minutes. To the resulting suspended solution, Compound 1 (2.0 g, 22.2 mmol) was added at room temperature, and the mixture was vigorously stirred for 3 hours. To the reaction mixture, was added aqueous saturated sodium bicarbonate solution (20 mL), the resulting white solid was collected by filtration. The resulting solid was washed with water (100 mL) and acetonitrile (100 mL) and dried to obtain Compound 3-8 (6.6 g, 16.6 mmol) as a white solid.

$^1$H-NMR ($CDCl_3$) δ:6.29 (brs, 2H), 4.12 (s, 1H), 3.76 (dd, 1H, J=4.5, 4.5 Hz), 3.42-3.35 (m, 2H), 3.31-3.25 (m, 2H), 2.22 (t, 4H, J=7.5 Hz), 1.65-1.60 (m, 4H), 1.29-1.26 (m, 24H), 0.88 (t, 6H, J=6.5 Hz).

ESI-MS(m/z) 340 (M+1).
Step 2
Compound 3-8 (2.88 g, 7.22 mmol) was suspended in dichloromethane (60 mL), and DIEA (5.30 mL, 30.3 mmol) was added thereto. Then, 2-cyanoethyl N,N-diisopropylchlorophosphoramidite (3.23 mL, 14.5 mmol) was added at room temperature, and the mixture was heated under reflux for 2 hours. After cooling to room temperature, the reaction mixture was partitioned by the reparatory funnel, and the organic layer diluted with dichloromethane (80 mL) was washed twice with aqueous saturated sodium bicarbonate solution (20 mL), twice with water (20 mL), and once with brine (20 mL). After the resulting organic layer was dried over magnesium sulfate, the solvent was concentrated under reduced pressure. The resulting brown oil, Compound 4-8 (2.88 g, 4.81 mmol) was obtained as a crude product. Formation of the compound was determined based on introduction of trivalent phosphorus by $^{31}$P-NMR.
$^{31}$P-NMR (CDCl$_3$) δ:148.2 (s)

1-1-3) Synthesis of Compound 4-10
Step 1
Compound 2-10 (9.78 g, 48.8 mmol, Tokyo Chemical Industry Co., Ltd.) was dissolved in DMF (150 mL) and dichloromethane (75 mL). DIEA (12.79 mL, 73.2 mmol) and HBTU (20.37 g, 53.7 mmol) were added thereto, and the mixture was vigorously stirred at room temperature for 45 minutes. To the resulting suspended solution, Compound 1 (2.2 g, 24.41 mmol) was added at room temperature, and the mixture was vigorously stirred. Then, the mixture was heated to 80° C., and then stirred for 4 hours. To the reaction mixture, was added aqueous saturated sodium bicarbonate solution (200 mL) and water (50 mL), the resulting white solid was collected by filtration. The resulting solid was washed with water (200 mL) and acetonitrile (400 mL) to obtain Compound 3-10 (9.95 g, 21.88 mmol) as a white solid.
$^1$H-NMR (CDCl$_3$) δ: 6.25 (2H, t, J=5.8 Hz), 4.07 (1H, s), 3.75 (1H, s), 3.44-3.38 (2H, m), 3.29-3.23 (2H, m), 2.22 (4H, t, J=7.6 Hz), 1.67-1.59 (4H, m), 1.30-1.25 (64H, m), 0.88 (6H, t, J=6.8 Hz).
Step 2
Compound 3-10 (230 mg, 0.506 mmol) was suspended in dichloromethane (11 mL), and DIEA (0.353 mL, 2.023 mmol) was added thereto. Then, 2-cyanoethyl N,N-diisopropylchlorophosphoramidite (0.226 mL, 1.012 mmol) was added at room temperature, and the mixture was heated under reflux for 2 hours. After cooling to room temperature, the reaction mixture was partitioned by the reparatory funnel, and the organic layer was washed twice with aqueous saturated sodium bicarbonate solution (10 mL), five times with water (10 mL) and once with brine (10 mL). After the resulting organic layer was dried over magnesium sulfate, the solvent was concentrated under reduced pressure. The resulting brown oil, Compound 4-10 (365 mg) was obtained as a crude product. Formation of the compound was determined based on introduction of trivalent phosphorus by $^{31}$P-NMR.
$^{31}$P-NMR (CDCl$_3$) δ:148.2 (s)

1-1-4) Synthesis of Compound 4-12
Step 1
Compound 2-12 (5.07 g, 22.19 mmol, Tokyo Chemical Industry Co., Ltd.) was dissolved in DMF (51.8 mL) and dichloromethane (28.6 mL). DIEA (5.81 mL, 33.3 mmol) and HBTU (9.26 g, 24.4 mmol) were added thereto, and the mixture was vigorously stirred at room temperature for 30 minutes. To the resulting suspended solution, Compound 1 (1.0 g, 11.1 mmol) was added at room temperature, and the mixture was vigorously stirred. Then, the mixture was heated to 40° C., and then stirred for 2 hours. To the reaction mixture, was added aqueous saturated sodium bicarbonate solution (10 mL), the resulting white solid was collected by filtration. The resulting solid was washed with water (50 mL), acetonitrile (50 mL) and dichloromethane (50 mL) to obtain Compound 3-12 (4.8 g, 9.4 mmol) as a white solid.
$^1$H-NMR (CDCl$_3$) δ:6.20 (brs, 2H), 3.96 (d, 1H, J=4.0 Hz, 1H), 3.75 (m, 1H), 3.40 (dd, 2H, J=4.0, 12.0 Hz), 3.25 (dd, 2H, J=4.0, 12.0 Hz), 2.22 (t, 4H, J=12.0 Hz, 2H), 1.62 (d, 4H, J=8.0 Hz), 1.29-1.25 (m, 40H), 0.90-0.86 (m, 6H) ESI-MS(m/z) 512 (M+1).
Step 2
Compound 3-12 (5.10 g, 9.98 mmol) was suspended in dichloromethane (257 mL), and DIEA (6.97 mL, 39.9 mmol) was added thereto. Then, 2-cyanoethyl N,N-diisopropylchlorophosphoramidite (4.46 mL, 20.0 mmol) was added at room temperature, and the mixture was heated under reflux for 2 hours. After cooling to room temperature, the reaction mixture was partitioned by the separatory funnel, and the organic layer was washed twice with aqueous saturated sodium bicarbonate solution (100 mL), twice with water (100 mL) and once with brine (100 mL). After the resulting organic layer was dried over magnesium sulfate, the solvent was concentrated under reduced pressure. The resulting brown oil, Compound 4-12 (4.80 g, 6.75 mmol) was obtained as a crude product. Formation of the compound was determined based on introduction of trivalent phosphorus by $^{31}$P-NMR.
$^{31}$P-NMR (CDCl$_3$) δ:148.2 (s)

1-1-5) Synthesis of Compound 4-14
Compound 2-14 (12.52 g, 48.8 mmol, Tokyo Chemical Industry Co., Ltd.) was dissolved in DMF (150 mL) and dichloromethane (75 mL). DIEA (12.79 mL, 73.2 mmol) and HBTU (20.37 g, 53.7 mmol) were added thereto, and the mixture was vigorously stirred at room temperature for 2.5 hours. To the resulting suspended solution, Compound 1 (2.2 g, 24.41 mmol) was added at room temperature, and the mixture was vigorously stirred. Then, the mixture was heated to 80° C., and then stirred for 5 hours. To the reaction mixture was added aqueous saturated sodium bicarbonate solution (800 mL) and water (50 mL), the resulting white solid was collected by filtration. The resulting solid was washed with water (500 mL), acetonitrile (300 mL) and dichloromethane (100 mL) to obtain Compound 3-14 (10.9 g, 19.23 mmol) as a white solid.
$^1$H-NMR (CDCl$_3$) δ: 6.21 (2H, s), 3.97 (1H, d, J=4.0 Hz), 3.77-3.74 (1H, m), 3.45-3.38 (2H, m), 3.28-3.22 (2H, m), 2.22 (4H, t, J=7.6 Hz), 1.65-1.61 (4H, m), 1.29-1.25 (48H, m), 0.88 (6H, t, J=6.8 Hz).
Step 2
Compound 3-14 (1.00 g, 1.76 mmol) was suspended in dichloromethane (50 mL), and DIEA (0.924 mL, 5.29 mmol) was added thereto. Then, 2-cyanoethyl N,N-diisopropylchlorophosphoramidite (0.870 mL, 3.53 mmol) was added at room temperature, and the mixture was heated under reflux for 2 hours. After cooling to room temperature, the reaction mixture was diluted with dichloromethane (50 mL). The solution was partitioned by the reparatory funnel, and then the organic layer was washed twice with aqueous saturated sodium bicarbonate solution (100 mL), twice with water (100 mL) and once with brine (100 mL). After the resulting organic layer was dried over magnesium sulfate, the solvent was concentrated under reduced pressure. The resulting white amorphous, Compound 4-14 (1.00 g, 1.30 mmol) was obtained as a crude product. Formation of the compound was determined based on introduction of trivalent phosphorus by $^{31}$P-NMR.

$^{31}$P-NMR (CDCl$_3$) δ:148.2 (s)

1-1-6) Synthesis of Compound 4-16

According to methods described in Non-patent Document 3, Compound 3-16 was synthesized from Compound 2-16, and then Compound 4-16 was synthesized. Compound 3-16: $^1$H-NMR (CDCl$_3$) δ:6.20 (brs, 2H), 3.95 (m, 1H), 3.76 (m, 1H), 3.40 (m, 2H), 3.25 (m, 2H), 2.24 (m, 4H), 1.68-1.20 (m, 60H), 0.88 (t, 6H, J=8.0 Hz) Compound 4-16: $^{31}$P-NMR (CDCl$_3$) δ:148.2 (s)

1-1-7) Synthesis of Compound 4-18

Step 1

Compound 2-18 (13.9 g, 44.4 mmol, Tokyo Chemical Industry Co., Ltd.) was dissolved in DMF (207 mL) and dichloromethane (214 mL). DIEA (16.3 mL, 93 mmol) and HBTU (18.5 g, 48.8 mmol) were added thereto, and the mixture was vigorously stirred at room temperature for 30 minutes. To the resulting suspended solution, Compound 1 (2.0 g, 22.2 mmol) was added at room temperature, and the mixture was vigorously stirred. Then, the mixture was heated to 40° C., and then stirred for 2 hours. To the reaction mixture, was added aqueous saturated sodium bicarbonate solution (10 mL), the resulting white solid was collected by filtration. The resulting solid was washed with water (100 mL), acetonitrile (100 mL) and dichloromethane (100 mL) to obtain Compound 3-18 (10.0 g, 14.7 mmol) as a white solid.

$^1$H-NMR (CDCl$_3$) δ:6.20 (brs, 2H), 3.96 (m, 1H), 3.75 (m, 1H), 3.42 (m, 2H), 3.23 (m, 2H), 2.22 (m, 4H), 1.68-1.20 (m, 68H), 0.88 (m, 6H)

Step 2

Compound 3-18 (3.8 g, 5.60 mmol) was suspended in dichloromethane (230 mL), DIEA (5.86 mL, 33.6 mmol) was added thereto. Then, 2-cyanoethyl N,N-diisopropylchlorophosphoramidite (3.74 mL, 16.79 mmol) was added at room temperature, and the mixture was heated under reflux for 2 hours. After cooling to room temperature, the reaction mixture was partitioned by the separatory funnel, and the organic layer was washed twice with aqueous saturated sodium bicarbonate solution (100 mL), once with water (50 mL) and once with brine (50 mL). After the resulting organic layer was dried over magnesium sulfate, the solvent was concentrated under reduced pressure. After adding acetonitrile to the residue, white solid was collected by filtration. The resulting solid was washed with aqueous saturated sodium bicarbonate solution, water and acetonitrile to obtain Compound 4-18 (4.13 g, 4.70 mmol) as a white solid. Formation of the compound was determined based on introduction of trivalent phosphorus by $^{31}$P-NMR.

$^{31}$P-NMR (CDCl$_3$) δ:148.2 (s)

1-1-8) Synthesis of Compound 4-20

Step 1

Compound 2-20 (10.2 g, 30.0 mmol, Tokyo Chemical Industry Co., Ltd.) was dissolved in DMF (250 mL) and dichloromethane (250 mL). DIEA (7.86 mL, 45 mmol) and HBTU (12.52 g, 33.0 mmol) were added thereto, and the mixture was vigorously stirred at room temperature for 30 minutes. To the resulting suspended solution, Compound 1 (1.35 g, 15.0 mmol) was added at room temperature, and the mixture was vigorously stirred. Then, the mixture was heated to 40° C., and then stirred for 2 hours. To the reaction mixture, was added aqueous saturated sodium bicarbonate solution (50 mL), the resulting white solid was collected by filtration. The resulting solid was washed with water (50 mL), acetonitrile (50 mL) and dichloromethane (50 mL) to obtain Compound 3-20 (7.20 g, 9.79 mmol) as a white solid.

$^1$H-NMR (CDCl$_3$) δ:6.18 (brs, 2H), 3.75 (m, 1H), 3.41 (m, 2H), 3.27 (m, 2H), 2.22 (m, 4H), 1.58-1.25 (m, 76H), 0.89-0.86 (m, 6H)

Step 2

Compound 3-20 (1.0 g, 1.36 mmol) was suspended in chloroform (50 mL), and DIEA (0.713 mL, 4.08 mmol) was added thereto. Then, 2-cyanoethyl N,N-diisopropylchlorophosphoramidite (0.607 mL, 2.72 mmol) was added at room temperature, and the mixture was heated under reflux for 2 hours. After cooling to room temperature, the reaction mixture was added dropwise to acetonitrile (300 mL) under vigorously stirring. The precipitated solid was collected by filtration, and the solid was washed twice with aqueous saturated sodium bicarbonate solution (20 mL), twice with water (20 mL) and twice with acetonitrile (20 mL). The resulting solid was dried under reduced pressure to obtain Compound 4-20 (843 mg, 0.901 mmol) as a white solid. Formation of the compound was determined based on introduction of trivalent phosphorus by $^{31}$P-NMR.

$^{31}$P-NMR (CDCl$_3$) δ:148.2 (s)

1-1-9) Synthesis of Compound 4-22

Step 1

Compound 2-22 (8.79 g, 23.8 mmol, Wako Pure Chemical Industries, Ltd.) was dissolved in DMF (250 mL) and dichloromethane (250 mL). DIEA (6.25 mL, 35.8 mmol) and HBTU (9.95 g, 26.2 mmol) were added thereto, and the mixture was vigorously stirred at room temperature for 30 minutes. To the resulting suspended solution, Compound 1 (1.07 g, 11.9 mmol) was added at room temperature, and the mixture was vigorously stirred. Then, the mixture was heated to 40° C., and then stirred for 2 hours. To the reaction mixture was added aqueous saturated sodium bicarbonate solution (50 mL), the resulting white solid was collected by filtration. The resulting solid was washed with water (50 mL), acetonitrile (50 mL) and dichloromethane (50 mL) to obtain Compound 3-22 (8.10 g, 8.17 mmol) as a white solid.

$^1$H-NMR (CDCl$_3$) δ:6.06 (brs, 2H), 3.73 (m, 1H), 3.36 (dd, 2H, J=6.0, 14.4 Hz), 3.22 (dd, 2H, J=5.2, 14.4 Hz), 2.17 (m, 4H), 1.61 (m, 4H), 1.59-1.24 (m, 80H), 0.87-0.84 (m, 6H)

Step 2

Compound 3-22 (1.0 g, 1.36 mmol) was suspended in chloroform (50 mL), and DIEA (0.713 mL, 4.08 mmol) was added thereto. Then, 2-cyanoethyl N,N-diisopropylchlorophosphoramidite (0.607 mL, 2.72 mmol) was added at room temperature, and the mixture was heated under reflux for 2 hours. After cooling to room temperature, the reaction mixture was added dropwise to acetonitrile (300 mL) under vigorously stirring. The precipitated solid was collected by filtration, and the solid was washed twice with aqueous saturated sodium bicarbonate solution (20 mL), twice with water (20 mL) and twice with acetonitrile (20 mL). The resulting solid was dried under reduced pressure to obtain Compound 4-22 (814 mg, 0.821 mmol) as a white solid. Formation of the compound was determined based on introduction of trivalent phosphorus by $^{31}$P-NMR.

$^{31}$P-NMR (CDCl$_3$) δ:148.2 (s)

1-2) Synthesis of Compound 4-n,o

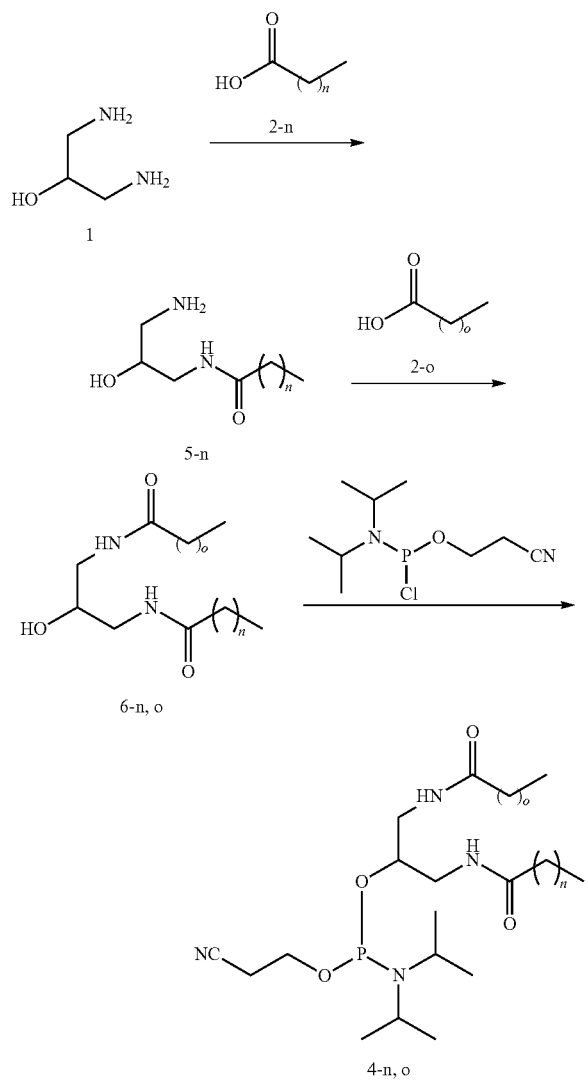

wherein n or o is an integer of 6 to 28.

1-2-1) Synthesis of Compound 4-8, 18
Step 1

Compound 2-8 is dissolved in DMF and dichloromethane. DIEA and HBTU are added thereto, and the mixture is stirred at room temperature. To the resulting suspended solution, Compound 1 is added at room temperature, and the mixture was stirred. The activated solution of Compound 2-18 which is separately prepared [Compound 2-18 is dissolved in DMF and dichloromethane. DIEA and HBTU are added thereto, and the mixture is stirred at room temperature] was added to the reaction vessel, and the mixture is stirred at room temperature. The mixture is heated to 40° C. and then stirred. To the reaction mixture, is added aqueous saturated sodium bicarbonate solution, the resulting solid is collected by filtration. The resulting solid is washed with water, acetonitrile and dichloromethane to obtain Compound 6-8, 18.

Step 2

Compound 6-8, 18 is suspended in chloroform, and DIEA is added thereto. Then, 2-cyanoethyl N,N-diisopropylchlorophosphoramidite is added at room temperature, and the mixture is heated under reflux. After cooling to room temperature, the reaction mixture is added dropwise to acetonitrile under stirring. The precipitated solid is collected by filtration, and the solid is washed twice with aqueous saturated sodium bicarbonate solution, twice with water and twice with acetonitrile. The resulting solid is dried under reduced pressure to obtain Compound 4-8, 18. Formation of the compound is determined based on introduction of trivalent phosphorus by $^{31}$P-NMR.

2) Synthesis of Compound 8-n

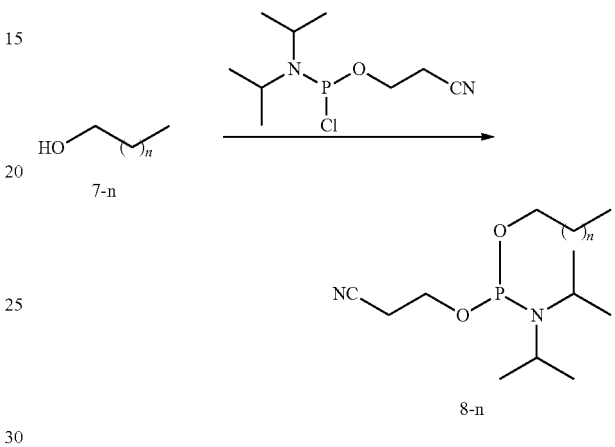

wherein n is an integer of 6 to 28.

2-1) Synthesis of Compound 8-6

Compound 7-6 (1.00 g, 7.68 mmol, Tokyo Chemical Industry Co., Ltd.) was dissolved in dichloromethane (15 mL), and triethylamine (2.13 mL, 15.4 mmol) was added thereto. Then, 2-cyanoethyl N,N-diisopropylchlorophosphoramidite (1.71 mL, 7.68 mmol) was added at room temperature, and the mixture was stirred at room temperature for 3 hours. The reaction was stopped by aqueous saturated sodium bicarbonate solution, and the mixture was extracted twice with ethyl acetate (50 mL). The organic layer was washed once with aqueous saturated sodium bicarbonate solution (10 mL), three times with water (10 mL) and once with brine (10 mL), and then dried over magnesium sulfate. The organic layer was concentrated under reduced pressure to obtain brown oil, Compound 8-6 (2.60 g) as a crude product. Formation of the compound was determined based on introduction of trivalent phosphorus by $^{31}$P-NMR.

$^{31}$P-NMR (CDCl$_3$) δ:147.2 (s)

2-2) Synthesis of Compound 8-10

Compound 7-10 (1.00 g, 5.37 mmol, Tokyo Chemical Industry Co., Ltd.) was dissolved in dichloromethane (15 mL), and triethylamine (1.49 mL, 10.7 mmol) was added thereto. Then, 2-cyanoethyl N,N-diisopropylchlorophosphoramidite (1.20 mL, 5.37 mmol) was added at room temperature, and the mixture was stirred at room temperature for 3 hours. The reaction was stopped by aqueous saturated sodium bicarbonate solution, and the mixture was extracted twice with ethyl acetate (50 mL). The organic layer was washed once with aqueous saturated sodium bicarbonate solution (10 mL), three times with water (10 mL) and once with brine (10 mL), and then dried over magnesium sulfate. The organic layer was concentrated under reduced pressure to obtain brown oil, Compound 8-10 (2.09 g) as a crude product. Formation of the compound was determined based on introduction of trivalent phosphorus by $^{31}$P-NMR.

$^{31}$P-NMR (CDCl$_3$) δ:147.2 (s)

2-3) Synthesis of Compound 8-12

Compound 7-12 (4.29 g, 20.0 mmol, Tokyo Chemical Industry Co., Ltd.) was dissolved in dichloromethane (52 mL), and DIEA (10.5 mL, 60.0 mmol) was added thereto. Then, 2-cyanoethyl N,N-diisopropylchlorophosphoramidite (5.36 mL, 24.00 mmol) was added at room temperature, and the mixture was stirred at room temperature for 12 hours. The reaction was stopped by aqueous saturated sodium bicarbonate solution (20 mL), and then the mixture was partitioned by the separatory funnel. After the organic layer was washed once with water (100 mL), the organic layer was washed once with aqueous saturated sodium bicarbonate solution (100 mL) and twice with water (100 mL), and then dried over magnesium sulfate. The organic layer was concentrated under reduced pressure to obtain brown oil, Compound 8-12 (4.80 g, 11.6 mmol) as a crude product. Formation of the compound was determined based on introduction of trivalent phosphorus by $^{31}$P-NMR.

$^{31}$P-NMR (CDCl$_3$) δ:147.3 (s)

2-4) Synthesis of Compound 8-14

Compound 7-14 (1.00 g, 4.12 mmol, NACALAI TESQUE, INC.) was dissolved in dichloromethane (15 mL), and triethylamine (1.14 mL, 8.25 mmol) was added thereto. Then, 2-cyanoethyl N,N-diisopropylchlorophosphoramidite (0.92 mL, 4.12 mmol) was added at room temperature, and the mixture was stirred at room temperature for 3 hours. The reaction was stopped by aqueous saturated sodium bicarbonate solution, and the mixture was extracted twice with ethyl acetate (50 mL). The organic layer was washed once with aqueous saturated sodium bicarbonate solution (10 mL), three times with water (10 mL) and once with brine (10 mL), and then dried over magnesium sulfate. The organic layer was concentrated under reduced pressure to obtain brown oil, Compound 8-14 (1.87 g). Formation of the compound was determined based on introduction of trivalent phosphorus by $^{31}$P-NMR.

$^{31}$P-NMR (CDCl$_3$) δ:147.2 (s)

2-5) Synthesis of Compound 8-16

Compound 7-16 (5.41 g, 20.0 mmol, Tokyo Chemical Industry Co., Ltd.) was dissolved in dichloromethane (52 mL), and DIEA (10.5 mL, 60.0 mmol) was added thereto. Then, 2-cyanoethyl N,N-diisopropylchlorophosphoramidite (4.91 mL, 22.00 mmol) was added at room temperature, and the mixture was stirred at room temperature for 12 hours. The reaction was stopped with aqueous saturated sodium bicarbonate solution (20 mL), and then the mixture was partitioned by the separatory funnel. After the organic layer was washed with water (100 mL), the organic layer was washed once with aqueous saturated sodium bicarbonate solution (100 mL) and twice with water (100 mL), and then dried over magnesium sulfate. The organic layer was concentrated under reduced pressure to obtain brown oil, Compound 8-16 (4.60 g, 9.77 mmol) as a crude product. Formation of the compound was determined based on introduction of trivalent phosphorus by $^{31}$P-NMR.

$^{31}$P-NMR (CDCl$_3$) δ:147.3 (s)

2-6) Synthesis of Compound 8-18

Compound 7-18 (2.99 g, 10.0 mmol, Tokyo Chemical Industry Co., Ltd.) was dissolved in chloroform (81 mL), and DIEA (3.67 mL, 21.0 mmol) was added thereto. Then, 2-cyanoethyl N,N-diisopropylchlorophosphoramidite (2.34 mL, 10.5 mmol) was added at room temperature, and the mixture was stirred at room temperature for 12 hours. The reaction mixture was concentrated, and the residue was washed with acetonitrile (50 mL). The precipitated solid was collected by filtration, and washed with acetonitrile (50 mL). Then, yellow solid was dried under reduced pressure to obtain Compound 8-18 (1.22 g, 2.45 mmol). Formation of the compound was determined based on introduction of trivalent phosphorus by $^{31}$P-NMR.

$^{31}$P-NMR (CDCl$_3$) δ:147.2 (s)

2-7) Synthesis of Compound 8-20

Compound 7-20 (3.27 g, 10.0 mmol, Tokyo Chemical Industry Co., Ltd.) was dissolved in chloroform (81 mL), and DIEA (3.67 mL, 21.0 mmol) was added thereto. Then, 2-cyanoethyl N,N-diisopropylchlorophosphoramidite (2.34 mL, 10.5 mmol) was added at room temperature, and the mixture was stirred at room temperature for 12 hours. The reaction mixture was concentrated, and the residue was washed with acetonitrile (50 mL). The precipitated solid was collected by filtration, and washed with acetonitrile (50 mL). Then, yellow solid was dried under reduced pressure to obtain Compound 8-20 (3.19 g, 6.06 mmol). Formation of the compound was determined based on introduction of trivalent phosphorus by $^{31}$P-NMR.

$^{31}$P-NMR (CDCl$_3$) δ:147.2 (s)

2-8) Synthesis of Compound 8-22

Compound 7-22 (3.55 g, 10.0 mmol, Tokyo Chemical Industry Co., Ltd.) was dissolved in chloroform (81 mL), and DIEA (3.67 mL, 21.0 mmol) was added thereto. Then, 2-cyanoethyl N,N-diisopropylchlorophosphoramidite (2.34 mL, 10.5 mmol) was added at room temperature, and the mixture was stirred at room temperature for 12 hours. The reaction mixture was concentrated, and the residue was washed with acetonitrile (50 mL). The precipitated solid was collected by filtration, and washed with acetonitrile (50 mL). Then, yellow solid was dried under reduced pressure to obtain Compound 8-22 (4.97 g, 8.96 mmol). Formation of the compound was determined based on introduction of trivalent phosphorus by $^{31}$P-NMR.

$^{31}$P-NMR (CDCl$_3$) δ:147.2 (s)

3) Synthesis of Compound 10-n

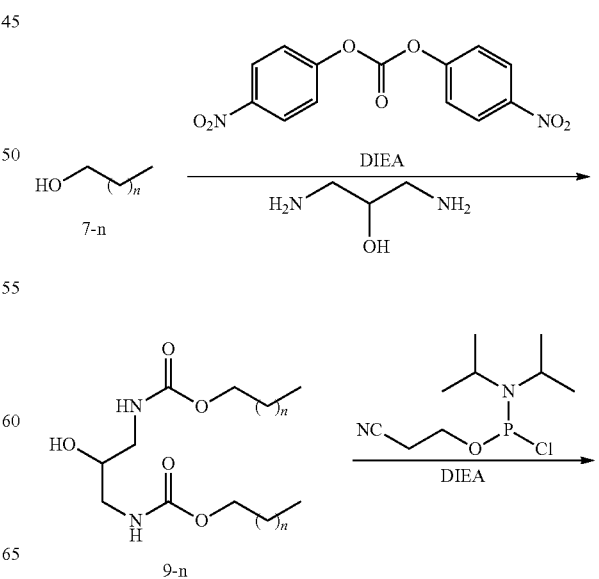

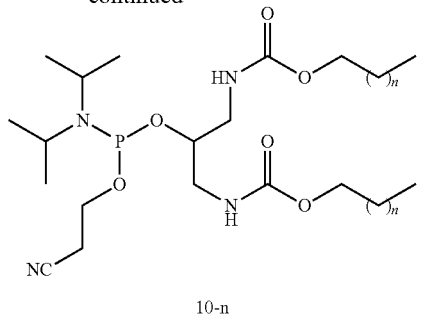

10-n wherein n is an integer of 6 to 28.
3-1) Synthesis of Compound 10-16
Step 1

Under nitrogen atmosphere, to Compound 7-16 (12.1 g, 44.4 mmol) in DMF (104 mL)-dichloromethane (57.1 mL) solution, bis-(p-nitrophenyl) carbonate (13.5 g, 44.4 mmol) and DIEA (11.6 mL, 66.6 mmol) were added, and then the mixture was stirred at room temperature for 8 hours. Next, Compound 1 (2.0 g, 22.2 mmol) was added thereto, and the mixture was heated under reflux at 60° C. for 2 hours. The resulting solid was collected by filtration and washed with dichloromethane (100 mL), water (100 mL) and acetonitrile (100 mL), and then dried under reduced pressure to obtain Compound 9-16 (15.44 g, 22.6 mmol) as a white solid.

$^1$H-NMR (CDCl$_3$) δ:5.20 (brs, 2H), 4.05 (m, 4H), 3.79 (m, 1H), 3.24 (m, 4H), 1.55-1.21 (m, 68H), 0.88 (m, 6H)

Step 2

Under nitrogen atmosphere, to Compound 9-16 suspended in dichloromethane (582 mL), DIEA (15.8 mL, 90.0 mmol) and 2-cyanoethyl N,N-diisopropylchlorophosphoramidite (10.1 mL, 45.2 mmol) were added, and then the mixture was heated under reflux at 50° C. for 2 hours. After cooling the reaction mixture to room temperature, the organic layer was washed twice with aqueous saturated sodium bicarbonate solution (300 mL), once with water (300 mL) and once with brine (300 mL). The organic layer was dried over magnesium sulfate, and then concentrated under reduced pressure. The residue was dissolved in dichloromethane (50 mL), and added dropwise to acetonitrile (150 mL) to powderize. The resulting solid was dried under reduced pressure to obtain Compound 10-16 (14.2 g, 16.1 mmol).

$^{31}$P-NMR (CDCl$_3$) δ:149.1 (s)

3-2) Synthesis of Compound 10-18
Step 1

Under nitrogen atmosphere, to Compound 7-18 (4 g, 13.4 mmol) in DMF (60 mL)-dichloromethane (40 mL) solution, bis-(p-nitrophenyl) carbonate (4.1 g, 13.4 mmol) and DIEA (3.5 mL, 20.1 mmol) were added, and then the mixture was stirred at room temperature for 5 hours. Next, Compound 1 (0.6 g, 6.7 mmol) in DMF solution (5 mL) was added thereto, and the mixture was stirred overnight. The resulting solid was collected by filtration and washed with dichloromethane, water and acetonitrile, and then dried under reduced pressure to obtain Compound 9-18 (4.1 g, 5.55 mmol) as a white solid.

$^1$H-NMR (CDCl$_3$) δ:5.20 (brs, 2H), 4.05 (t, 4H, J=8 Hz), 3.79 (s, 1H), 3.32 (m, 2H), 3.23 (m, 2H), 1.25 (s, 72H), 0.88 (t, 6H, J=8 Hz)

Step 2

Under nitrogen atmosphere, to Compound 9-18 (1.0 g, 1.35 mmol) suspended in dichloromethane (60 mL), DIEA (1.2 mL, 6.8 mmol) and 2-cyanoethyl N,N-diisopropylchlorophosphoramidite (0.75 mL, 3.4 mmol) were added, and the mixture was stirred at 50° C. for 1.5 hours. The reaction mixture was cooled to room temperature, diluted with dichloromethane (40 mL), and washed with aqueous saturated sodium bicarbonate solution (40 mL×2), water (40 mL) and brine (40 mL). The organic layer was dried over magnesium sulfate, and then concentrated under reduced pressure. The residue was dissolved in dichloromethane (15 mL), and added dropwise to acetonitrile (150 mL) to powderize. The resulting solid was dried under reduced pressure to obtain Compound 10-18 (0.98 g, 1.04 mmol) as a white solid.

$^{31}$P-NMR (CDCl$_3$) δ:149.1 (s)

4) Synthesis of Compound 15-n

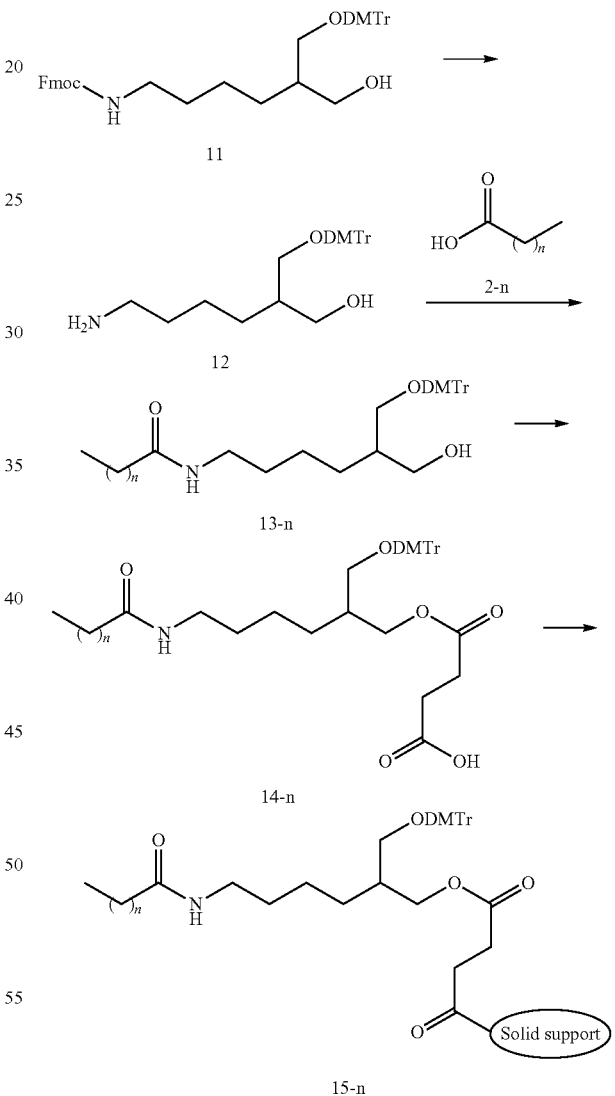

wherein n is an integer of 6 to 28.
4-1) Synthesis of Compound 15-6
Steps 1 and 2

To Compound 11 (US2014/0142253) (722 mg, 1.075 mmol) in dichloromethane (5.6 mL), diethylamine (1.4 mL, 13.40 mmol) was added, and the mixture was stirred at room temperature for 17 hours. After ethanol was added to the reaction mixture, and the mixture was stirred, the solvent was concentrated under reduced pressure. The resulting residue was coevaporated twice with ethanol to obtain the crude product of Compound 12.

To Compound 2-6 (239 mg, 1.505 mmol) in ethanol solution (5.0 mL), DMT-MM (476 mg, 1.720 mmol) was added, the mixture was stirred at room temperature for 15 minutes. The resulting reaction mixture was added to the crude product of Compound 12 in ethanol solution (2.5 mL), and the mixture was stirred at room temperature for 4.5 hours. After the solvent was concentrated under reduced pressure, aqueous saturated sodium bicarbonate solution and water were added to the resulting residue, and extracted with ethyl acetate. The organic layer was washed with water and brine, and then dried over sodium sulfate. The solvent was concentrated under reduced pressure, and the resulting crude product was purified by silica gel column chromatography (n-hexane:ethyl acetate=70:30→20:80) to obtain Compound 13-6 (320 mg, Yield 52%) as colorless oil.

$^1$H-NMR (CDCl$_3$) δ: 7.42-7.40 (2H, m), 7.32-7.26 (6H, m), 7.21 (1H, t, J=7.2 Hz), 6.83 (4H, d, J=8.8 Hz), 5.37 (1H, s), 3.79 (6H, s), 3.71-3.65 (1H, m), 3.63-3.57 (1H, m), 3.27 (1H, dd, J=9.2, 4.0 Hz), 3.25-3.15 (2H, m), 3.07 (1H, dd, J=9.2, 7.2 Hz), 2.45 (1H, t, J=5.6 Hz), 2.12 (2H, t, J=7.6 Hz), 1.78 (1H, s), 1.62-1.58 (2H, m), 1.47-1.40 (2H, m), 1.36-1.20 (12H, m), 0.87 (3H, t, J=6.8 Hz).

Step 3

To Compound 13-6 (310 mg, 0.538 mmol) in dichloromethane (3.0 mL), DMAP (6.6 mg, 0.054 mmol), DIEA (0.282 mL, 1.614 mmol) and succinic anhydride (81 mg, 0.807 mmol) were added, and the mixture was stirred at room temperature for 2 days. The solvent was concentrated under reduced pressure, and then the resulting crude product was purified by silica gel column chromatography (chloroform:methanol=100:0→90:10) to obtain Compound 14-6 (360 mg, Yield 99%) as colorless oil.

$^1$H-NMR (CDCl$_3$) δ: 7.42-7.40 (2H, m), 7.31-7.25 (6H, m), 7.19 (1H, t, J=7.2 Hz), 6.82 (4H, d, J=8.8 Hz), 5.74 (1H, t, J=5.6 Hz), 4.24 (1H, dd, J=10.8, 5.2 Hz), 4.12 (1H, dd, J=10.8, 6.0 Hz), 3.79 (6H, s), 3.52-3.45 (1H, m), 3.24-2.98 (4H, m), 2.90 (1H, q, J=7.2 Hz), 2.59-2.50 (3H, m), 2.14 (2H, t, J=7.6 Hz), 1.90-1.85 (1H, m), 1.61-1.58 (2H, m), 1.48-1.18 (14H, m), 0.87 (3H, t, J=6.8 Hz).

Step 4

To Compound 14-6 (216 mg, 0.320 mmol) in acetonitrile solution (42 mL), DIEA (0.186 mL, 1.065 mmol) and HBTU (89 mg, 0.234 mmol) were added, and the mixture was shaken at room temperature for 15 minutes. To the reaction mixture, Native Amino lcaa CPG 1000 Å (ChemGenes Corporation) (4.2 g) was added, and the mixture was shaken for 24 hours. After the reaction mixture was filtered, CPG resin was washed three times with acetonitrile and three times with diethyl ether, and dried under reduced pressure. To the dried CPG, a mixture of CapA (PROLIGO, L840045-06) and CapB (PROLIGO, L850045-06) (1:1, 42 mL) was added, and the mixture was shaken for 1.5 hours. After filtrating the reaction mixture, CPG resin was washed twice with pyridine, twice with isopropanol and twice with diethyl ether, and dried under reduced pressure. The supported amount of Compound 14-6 was calculated by colorimetric assay of the DMTr cation, and Compound 15-6 whose supported amount is 53 μmol/g was obtained.

4-2) Synthesis of Compound 15-10

Steps 1 and 2

In a similar method to Step 1 of 4-1), the crude product of Compound 12 (392 mg) was obtained.

To Compound 2-10 (155 mg, 0.772 mmol) in ethanol solution (2.6 mL), DMT-MM (214 mg, 0.772 mmol) was added, the mixture was stirred at room temperature for 30 minutes. The resulting reaction mixture was added to the crude product of Compound 12 (392 mg) in ethanol solution (1.3 mL), and the mixture was stirred at room temperature for 4 hours. To Compound 2-10 (71 mg, 0.356 mmol) in ethanol solution (1.3 mL), DMT-MM (99 mg, 0.356 mmol) was added, and the mixture was stirred at room temperature for 15 minutes. The mixture was combined with the other reaction mixture and stirred at room temperature for 1.5 hours. After the solvent was concentrated under reduced pressure, aqueous saturated sodium bicarbonate solution and water were added to the resulting residue, and extracted with ethyl acetate. The organic layer was washed with water and brine, and dried over sodium sulfate. The solvent was concentrated under reduced pressure, and the resulting crude product was purified by silica gel column chromatography (n-hexane:ethyl acetate=80:20→30:70) to obtain Compound 13-10 (165 mg, 44%) as colorless oil.

$^1$H-NMR (CDCl$_3$) δ: 7.41 (2H, d, J=8.0 Hz), 7.31-7.26 (6H, m), 7.21 (1H, t, J=6.6 Hz), 6.83 (4H, d, J=8.4 Hz), 5.35 (1H, s), 3.79 (6H, s), 3.70-3.57 (2H, m), 3.28-3.16 (3H, m), 3.07 (1H, t, J=8.0 Hz), 2.43 (1H, s), 2.12 (2H, t, J=7.2 Hz), 1.78 (1H, s), 1.61-1.58 (2H, m), 1.46-1.39 (2H, m), 1.25 (20H, s), 0.87 (3H, t, J=6.0 Hz).

Step 3

To Compound 13-10 (222 mg, 0.352 mmol) in dichloromethane (2.2 mL), DMAP (4.3 mg, 0.035 mmol), DIEA (0.184 mL, 1.055 mmol) and succinic anhydride (53 mg, 0.528 mmol) were added, and the mixture was stirred at room temperature for 2 days. The solvent was concentrated under reduced pressure, and then the resulting crude product was purified by silica gel column chromatography (chloroform:methanol=100:0→90:10) to obtain Compound 14-10 (243 mg, 94%) as colorless oil.

$^1$H-NMR (CDCl$_3$) δ: 7.41 (2H, d, J=6.0 Hz), 7.31-7.26 (6H, m), 7.20 (1H, d, J=7.2 Hz), 6.82 (4H, d, J=7.6 Hz), 5.59 (1H, s), 4.29 (1H, d, J=10.4 Hz), 4.17-4.13 (1H, m), 3.79 (6H, s), 3.23-2.98 (4H, m), 2.58 (4H, s), 2.16 (2H, t, J=8.0 Hz), 1.90 (1H, s), 1.60 (2H, s), 1.42-1.19 (22H, m), 0.88 (3H, t, J=6.8 Hz).

Step 4

To Compound 14-10 (209 mg, 0.285 mmol) in acetonitrile solution (38 mL), DIEA (0.166 mL, 0.950 mmol) and HBTU (79 mg, 0.209 mmol) were added, and the mixture was shaken at room temperature for 15 minutes. To the reaction mixture, Native Amino lcaa CPG 1000 Å (ChemGenes Corporation) (3.8 g) was added, and the mixture was shaken for 23 hours. After the reaction mixture was filtered, CPG resin was washed three times with acetonitrile and three times diethyl ether, and dried under reduced pressure. To the dried CPG, a mixture of CapA (PROLIGO, L840045-06) and CapB (PROLIGO, L850045-06) (1:1, 38 mL) was added, and the mixture was shaken for 1.5 hours. After filtrating the reaction mixture, CPG resin was washed twice with pyridine, twice with isopropanol and twice with diethyl ether, and dried under reduced pressure. The supported amount of Compound 14-10 was calculated by colorimetric assay of the DMTr cation, and Compound 15-10 whose supported amount is 40 μmol/g was obtained.

4-3) Synthesis of Compound 15-14

Steps 1 and 2

In a similar method to Step 1 of 4-1), the crude product of Compound 12 (392 mg) was obtained.

To Compound 2-14 (345 mg, 1.346 mmol) in ethanol solution (4.0 mL), DMT-MM (372 mg, 1.346 mmol) was added, and the mixture was stirred at room temperature for 15 minutes. The resulting reaction mixture was added to crude product of Compound 12 in ethanol solution (2.0 mL), and the mixture was stirred at room temperature for 28 hours. After the solvent was concentrated under reduced pressure, aqueous saturated sodium bicarbonate solution and water were added to the resulting residue, and extracted with ethyl acetate. The organic layer was washed with water and brine, and dried over sodium sulfate. The solvent was concentrated under reduced pressure, and the resulting crude product was purified by silica gel column chromatography (n-hexane:ethyl acetate=70:30→20:80) to obtain Compound 13-14 (228 mg, Yield 37%) as colorless oil.

$^1$H-NMR (CDCl$_3$) δ: 7.40 (2H, d, J=6.8 Hz), 7.31-7.21 (7H, m), 6.83 (4H, d, J=6.4 Hz), 5.35 (1H, s), 3.79 (6H, s), 3.67 (1H, s), 3.61 (1H, s), 3.28-3.19 (3H, m), 3.07 (1H, t, J=7.2 Hz), 2.43 (1H, s), 2.12 (2H, t, J=6.0 Hz), 1.77 (1H, s), 1.59 (2H, s), 1.43 (2H, s), 1.25 (28H, s), 0.88 (3H, s).

Step 3

To Compound 13-14 (224 mg, 0.326 mmol) in dichloromethane (2.2 mL), DMAP (4.0 mg, 0.033 mmol), DIEA (0.171 mL, 0.977 mmol) and succinic anhydride (49 mg, 0.488 mmol) were added, and the mixture was stirred at room temperature for 2 days. The solvent was concentrated under reduced pressure, and the resulting crude product was purified by silica gel column chromatography (chloroform:methanol=100:0→90:10) to obtain Compound 14-14 (163 mg, Yield 64%) as colorless oil.

$^1$H-NMR (CDCl$_3$) δ: 7.40 (2H, d, J=6.4 Hz), 7.30-7.26 (6H, m), 7.19 (1H, t, J=7.2 Hz), 6.81 (4H, d, J=7.2 Hz), 5.57 (1H, s), 4.29 (1H, d, J=10.8 Hz), 4.17-4.13 (1H, m), 3.79 (6H, s), 3.23-2.98 (4H, m), 2.58 (4H, s), 2.15 (2H, t, J=7.2 Hz), 1.90 (1H, s), 1.59 (4H, s), 1.46-1.25 (28H, m), 0.87 (3H, t, J=5.6 Hz).

Step 4

To Compound 14-14 (162 mg, 0.206 mmol) in acetonitrile solution (28 mL), DIEA (0.122 mL, 0.700 mmol) and HBTU (58 mg, 0.154 mmol) were added, and the mixture was shaken at room temperature for 15 minutes. To the reaction mixture, Native Amino lcaa CPG 1000 Å (ChemGenes Corporation) (2.8 g) was added, and the mixture was shaken for 24 hours. After the reaction mixture was filtered, CPG resin was washed three times with acetonitrile and three times with diethyl ether, and dried under reduced pressure. To the dried CPG, a mixture of CapA (PROLIGO, L840045-06) and CapB (PROLIGO, L850045-06) (1:1, 28 mL) was added, and the mixture was shaken for 1.5 hours. After filtrating the reaction mixture, CPG resin was washed twice with pyridine, twice with isopropanol and twice with diethyl ether, and dried under reduced pressure. The supported amount of Compound 14-14 was calculated by colorimetric assay of the DMTr cation, and Compound 15-14 whose supported amount is 42 μmol/g was obtained.

4-4) Synthesis of Compound 15-18

Steps 1 and 2

In a similar method to Step 1 of 4-1), the crude product of Compound 12 (392 mg) was obtained.

To Compound 2-18 (466 mg, 1.490 mmol) in ethanol solution (5.0 mL), DMT-MM (471 mg, 1.702 mmol) was added, the mixture was stirred at room temperature for 15 minutes. The resulting reaction mixture was added to the crude product of Compound 12 in ethanol solution (2.5 mL), the mixture was stirred at room temperature for 4.5 hours. After the solvent was concentrated under reduced pressure, aqueous saturated sodium bicarbonate solution and water were added to the resulting residue, and extracted with ethyl acetate. The organic layer was washed with water and brine, and dried over sodium sulfate. The solvent was concentrated under reduced pressure, and the resulting crude product was purified by silica gel column chromatography (n-hexane:ethyl acetate=70:30→20:80) to obtain Compound 13-18 (494 mg, Yield 62%) as colorless oil.

$^1$H-NMR (CDCl$_3$) δ: 7.41 (2H, d, J=7.2 Hz), 7.32-7.26 (6H, m), 7.21 (1H, t, J=7.2 Hz), 6.83 (4H, d, J=8.8 Hz), 5.36 (1H, s), 3.79 (6H, s), 3.70-3.65 (1H, m), 3.63-3.57 (1H, m), 3.27 (1H, dd, J=9.2, 4.0 Hz), 3.24-3.13 (2H, m), 3.07 (1H, dd, J=9.2, 7.2 Hz), 2.45 (1H, t, J=5.6 Hz), 2.12 (2H, t, J=7.6 Hz), 1.78 (1H, s), 1.63-1.25 (40H, m), 0.88 (3H, t, J=6.8 Hz).

Step 3

To Compound 13-18 (352 mg, 0.473 mmol) in dichloromethane (3.5 mL), DMAP (5.8 mg, 0.047 mmol), DIEA (0.248 mL, 1.419 mmol) and succinic anhydride (71 mg, 0.709 mmol) were added, and the mixture was stirred at room temperature for 2 days. The solvent was concentrated under reduced pressure, and then the resulting crude product was purified by silica gel column chromatography (chloroform:methanol=100:0→90:10) to obtain Compound 14-18 (225 mg, 56%) as colorless oil.

$^1$H-NMR (CDCl$_3$) δ:7.41 (2H, d, J=7.2 Hz), 7.31-7.26 (6H, m), 7.20 (1H, t, J=6.4 Hz), 6.82 (4H, d, J=7.6 Hz), 5.57 (1H, s), 4.30 (1H, dd, J=10.4, 2.4 Hz), 4.15 (1H, dd, J=10.4, 6.4 Hz), 3.79 (6H, s), 3.24-2.98 (4H, m), 2.59 (4H, s), 2.16 (2H, t, J=7.6 Hz), 1.90 (1H, s), 1.59 (4H, s), 1.44-1.21 (36H, m), 0.88 (3H, t, J=5.6 Hz).

Step 4

To Compound 14-18 (223 mg, 0.264 mmol) in acetonitrile solution (35 mL), DIEA (0.154 mL, 0.880 mmol) and HBTU (73 mg, 0.194 mmol) were added, and the mixture was shaken at room temperature for 15 minutes. To the reaction mixture, Native Amino lcaa CPG 1000 Å (ChemGenes Corporation) (3.5 g) was added, and the mixture was shaken for 24 hours. After the reaction mixture was filtered, CPG resin was washed three times with acetonitrile and three times diethyl ether, and dried under reduced pressure. To the dried CPG, a mixture of CapA (PROLIGO, L840045-06) and CapB (PROLIGO, L850045-06) (1:1, 35 mL) was added, and the mixture was shaken for 1.5 hours. After filtrating the reaction mixture, CPG resin was washed twice with pyridine, twice with isopropanol and twice with diethyl ether, and dried under reduced pressure. The supported amount of Compound 14-18 was calculated by colorimetric assay of the DMTr cation, and Compound 15-18 whose supported amount is 56 μmol/g was obtained.

5) Synthesis of Compound 17

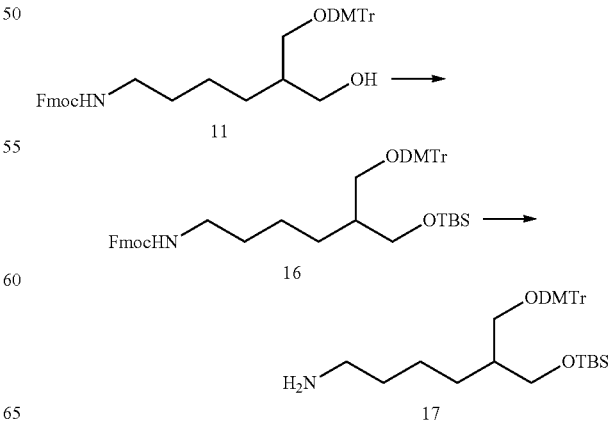

Steps 1 and 2

To Compound 11 (US2014/0142253, 292 mg, 0.435 mmol) in DMF solution (2.0 mL), imidazole (71 mg, 1.044 mmol) and t-butylchlorodimethylsilane (79 mg, 0.522 mmol) were added, and the mixture was stirred at room temperature for 16 hours. The reaction mixture was diluted with water and extracted with cyclopentyl methyl ether. The organic layer was washed with water and brine, and dried over sodium sulfate. The solvent was concentrated under reduced pressure to obtain the crude product of Compound 16 (352 mg).

To the crude product of Compound 16 (352 mg) in dichloromethane (2.4 mL), diethylamine (0.6 mL, 5.74 mmol) was added, and the mixture was stirred at room temperature for 16 hours. After ethanol was added to the reaction mixture, the solvent was concentrated under reduced pressure. The residue was coevaporated twice with ethanol, and the resulting crude product was purified by amino silica gel column chromatography (chloroform) to obtain Compound 17 (190 mg, 78%) as colorless oil.

$^1$H-NMR (CDCl$_3$) δ: 7.45-7.43 (2H, m), 7.32 (4H, d, J=8.8 Hz), 7.29-7.25 (2H, m), 7.22-7.18 (1H, m), 6.81 (4H, d, J=8.8 Hz), 3.79 (6H, s), 3.68-3.61 (2H, m), 3.08-3.02 (2H, m), 2.63 (2H, t, J=7.2 Hz), 1.75-1.69 (1H, m), 1.41-1.30 (6H, m), 1.27-1.15 (2H, m), 0.84 (9H, s), 0.01 (6H, s).

6) Synthesis of Compound 22-n

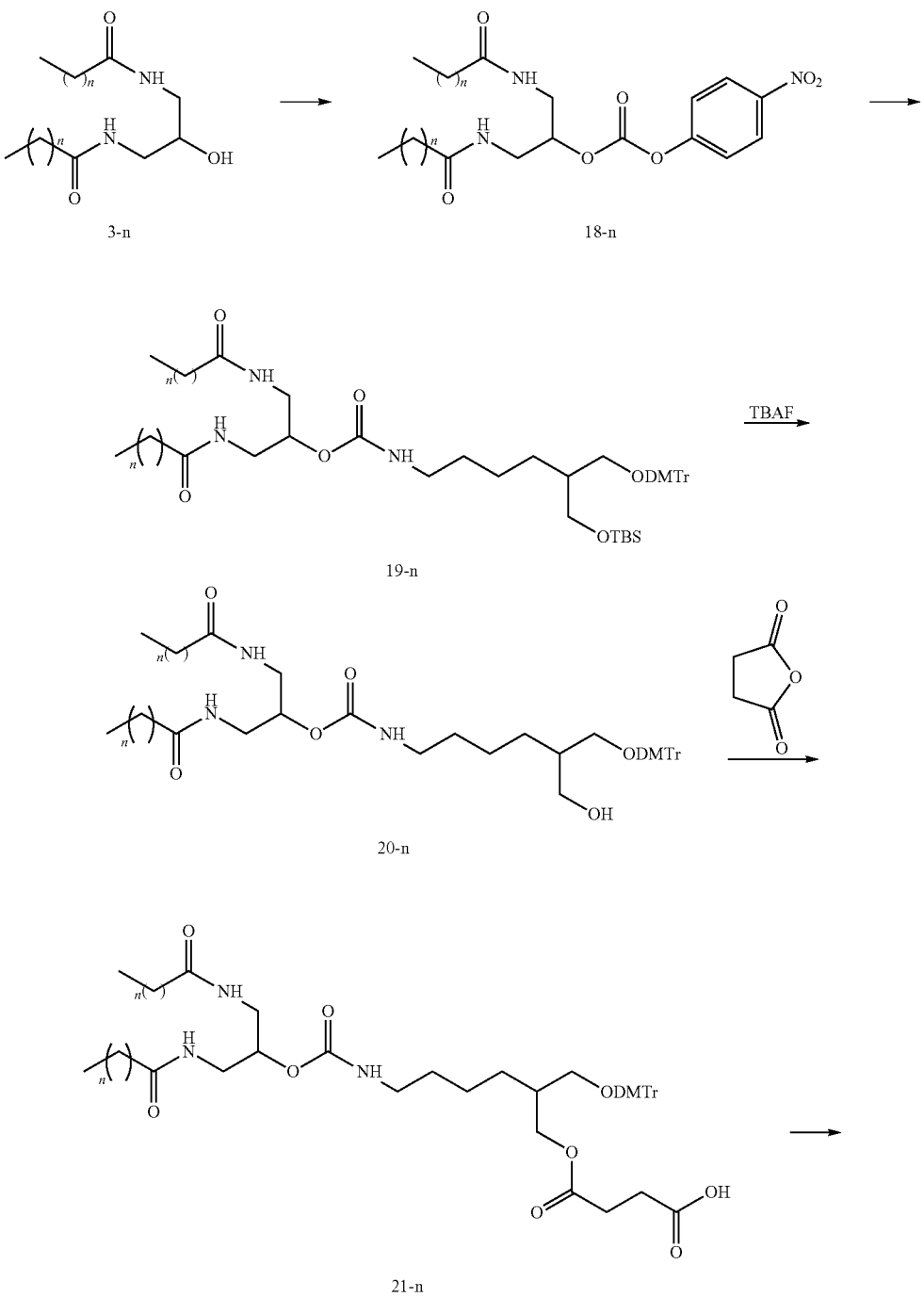

-continued

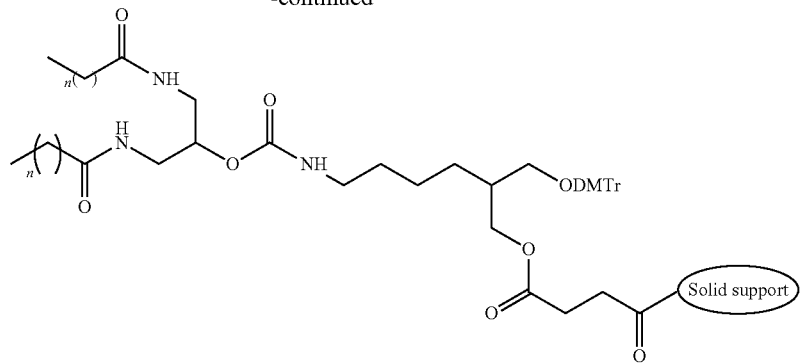

22-n wherein n is an integer of 6 to 28.

6-1) Synthesis of Compound 22-6

Step 1

To Compound 3-6 (1.0 g, 2.92 mmol) in THF (20 mL)-chloroform (20 mL) solution, DIEA (1.53 mL, 8.76 mmol), bis(nitrophenyl) carbonate (1.33 g, 4.38 mmol) and DMAP (178 mg, 1.46 mmol) were added, and the mixture was stirred at 60° C. for 1 hour. The reaction mixture was filtered. After the mother liquid was concentrated under reduced pressure, the resulting crude product was purified by silica gel column chromatography (hexane:ethyl acetate=60:40→20:80) to obtain Compound 18-6 (982 mg, 66%) as a white solid.

$^1$H-NMR (CDCl$_3$) δ: 8.32-8.26 (2H, m), 7.42 (2H, dt, J=9.9, 2.5 Hz), 6.36 (2H, t, J=6.4 Hz), 4.80 (1H, ddd, J=10.7, 5.6, 3.3 Hz), 3.65-3.50 (4H, m), 2.26 (4H, t, J=7.6 Hz), 1.69-1.62 (4H, m), 1.28 (16H, dt, J=19.1, 4.7 Hz), 0.87 (6H, t, J=6.8 Hz).

Step 2

To Compound 17 (500 mg, 0.89 mmol) in dichloromethane (10.0 mL), Compound 18-6 (450 mg, 0.89 mmol) was added, and the mixture was stirred at room temperature for 2 hours. The reaction mixture was concentrated under reduced pressure, and purified by amino silica gel column chromatography (hexane:ethyl acetate=65:35→40:90) to obtain Compound 19-6 (625 mg, 76%) as colorless oil.

$^1$H-NMR (CDCl$_3$) δ: 7.42 (2H, d, J=7.4 Hz), 7.31 (4H, t, J=6.2 Hz), 7.26 (3H, t, J=3.9 Hz), 7.19 (1H, t, J=7.2 Hz), 6.82 (4H, t, J=6.0 Hz), 6.25 (2H, t, J=5.8 Hz), 4.70 (2H, dd, J=10.3, 5.3 Hz), 3.79 (6H, d, J=4.4 Hz), 3.62 (2H, dd, J=10.1, 5.1 Hz), 3.51 (2H, dd, J=13.3, 6.4 Hz), 3.32-3.26 (2H, m), 3.08 (4H, dt, J=20.2, 6.6 Hz), 2.19 (4H, t, J=7.7 Hz), 1.70 (1H, t, J=5.7 Hz), 1.61 (8H, t, J=9.3 Hz), 1.42 (2H, t, J=7.3 Hz), 1.26 (20H, tt, J=26.0, 10.5 Hz), 0.88 (6H, dd, J=12.0, 5.3 Hz), 0.83 (9H, s).

Step 3

To Compound 19-6 (625 mg, 0.67 mmol) in THF (10 mL), TBAF (1M THF, 1.34 mL, 1.34 mmol) was added, and the mixture was stirred at room temperature for 24 hours. The reaction mixture was concentrated under reduced pressure, and the resulting crude product was purified by diol silica gel column chromatography (hexane:ethyl acetate=50:50→10:90) to obtain Compound 20-6 (541 mg, 99%) as colorless liquid.

$^1$H-NMR (CDCl$_3$) δ: 7.41 (2H, t, J=4.3 Hz), 7.26 (9H, ddt, J=31.6, 12.0, 4.9 Hz), 6.83 (4H, d, J=8.8 Hz), 6.38 (2H, q, J=6.1 Hz), 4.88 (1H, t, J=5.6 Hz), 4.67 (1H, t, J=5.0 Hz), 3.79 (6H, t, J=7.5 Hz), 3.69-3.61 (2H, m), 3.50-3.44 (2H, m), 3.30 (3H, tt, J=20.6, 6.5 Hz), 3.15-3.06 (3H, m), 2.63 (1H, s), 2.21-2.17 (4H, m), 1.78 (1H, s), 1.62 (4H, t, J=6.9 Hz), 1.43 (2H, t, J=5.4 Hz), 1.30 (20H, dt, J=29.2, 11.0 Hz), 0.87 (6H, t, J=6.9 Hz).

Step 4

To Compound 20-6 (541 mg, 0.66 mmol) in dichloromethane (2 mL), DIEA (0.35 mL, 1.98 mmol), DMAP (8.0 mg, 0.066 mmol) and succinic anhydride (132 mg, 1.32 mmol) were added, and the mixture was stirred at room temperature for 4 hours. The reaction mixture was concentrated under reduced pressure, and the resulting crude product was purified by silica gel column chromatography (chloroform:methanol=40:1→40:1) to obtain Compound 21-6 (591 mg, 97%) as colorless liquid.

$^1$H-NMR (CDCl$_3$) δ: 7.41 (2H, d, J=7.5 Hz), 7.31-7.25 (8H, m), 7.20 (1H, t, J=7.2 Hz), 6.82 (4H, d, J=8.5 Hz), 6.62 (1H, t, J=6.3 Hz), 6.48 (1H, t, J=6.5 Hz), 5.91 (1H, t, J=5.5 Hz), 4.71 (1H, t, J=5.3 Hz), 4.42 (1H, dd, J=11.0, 3.2 Hz), 4.14 (1H, dd, J=10.9, 5.9 Hz), 3.79 (6H, s), 3.40 (4H, tt, J=20.4, 7.0 Hz), 3.08 (4H, dq, J=33.3, 8.0 Hz), 2.69-2.49 (4H, m), 2.20 (4H, dd, J=15.6, 8.2 Hz), 1.95 (1H, s), 1.61 (4H, d, J=7.0 Hz), 1.27 (22H, d, J=5.0 Hz), 0.87 (6H, dd, J=6.8, 5.1 Hz).

Step 5

To Compound 21-6 (312 mg, 0.34 mmol) in a mixture of acetonitrile/dichloromethane (4:1, 25 mL), DIEA (0.30 mL, 1.70 mmol) and HBTU (142 mg, 0.37 mmol) were added, and the mixture was shaken at room temperature for 15 minutes. To the reaction mixture, HybridCPG amino form 2000 Å (Prime Synthesis, Inc.) (2.8 g) was added, and the mixture was shaken for 24 hours. After the reaction mixture was filtered, HybridCPG resin was washed three times with acetonitrile and three times with diethyl ether, and dried under reduced pressure. To the dried HybridCPG, a mixture of THF/acetic anhydride/pyridine (8:1:1, 30 mL) was added, and the mixture was shaken for 3 hours. After the reaction mixture was filtered, HybridCPG resin was washed twice with pyridine, twice with isopropanol and twice with diethyl ether, and dried under reduced pressure. The supported amount of Compound 21-6 was calculated by colorimetric assay of the DMTr cation, and Compound 22-6 whose supported amount is 114 μmol/g was obtained.

6-2) Synthesis of Compound 22-8

Step 1

To Compound 3-8 (1 g, 2.5 mmol) in THF (20 mL) and chloroform (20 mL), bis(nitrophenyl) carbonate (1.14 g, 3.76 mmol), DIEA (1.3 mL, 7.5 mmol) and DMAP (0.15 g, 1.25 mmol) were added, ant the mixture was stirred at 60°

C. for 1 hour. The reaction mixture was filtered. After the mother liquid was concentrated under reduced pressure, the resulting crude product was purified by silica gel column chromatography (hexane:ethyl acetate=60:40→20:80) to obtain Compound 18-8 (1.17 g, 83%) as a white solid.

$^1$H-NMR (CDCl$_3$) δ: 8.27 (2H, dt, J=9.9, 2.5 Hz), 7.41 (2H, dt, J=9.9, 2.5 Hz), 6.42 (2H, t, J=6.5 Hz), 4.81-4.78 (1H, m), 3.65-3.50 (4H, m), 2.26 (4H, t, J=7.6 Hz), 1.68-1.62 (4H, m), 1.28 (24H, t, J=9.5 Hz), 0.87 (6H, t, J=6.8 Hz).

Step 2

To Compound 17 (500 mg, 0.89 mmol) in dichloromethane (10.0 mL), Compound 18-8 (500 mg, 0.89 mmol) and DIEA (0.23 mL, 1.33 mmol) were added, and the mixture was stirred at room temperature for 2 hours. The reaction mixture was concentrated under reduced pressure, and then purified by amino silica gel column chromatography (hexane:ethyl acetate=50:50→10:90) to obtain Compound 19-8 (661 mg, 75%) as a pale yellow solid.

$^1$H-NMR (CDCl$_3$) δ: 7.42 (2H, d, J=7.4 Hz), 7.31 (4H, t, J=6.3 Hz), 7.26 (3H, t, J=3.9 Hz), 7.19 (1H, t, J=7.2 Hz), 6.81 (4H, d, J=8.8 Hz), 6.25 (2H, t, J=6.0 Hz), 4.70 (2H, q, J=5.4 Hz), 3.79 (6H, s), 3.63 (2H, t, J=5.3 Hz), 3.51 (2H, dd, J=13.1, 6.5 Hz), 3.29 (2H, dd, J=12.9, 7.0 Hz), 3.08 (4H, dt, J=20.0, 6.5 Hz), 2.18 (4H, t, J=7.7 Hz), 1.70 (1H, t, J=5.8 Hz), 1.62 (6H, d, J=11.2 Hz), 1.42 (2H, t, J=7.2 Hz), 1.27 (28H, dt, J=37.9, 14.6 Hz), 0.87 (6H, t, J=6.8 Hz), 0.83 (9H, s).

Step 3

To Compound 19-8 (661 mg, 0.669 mmol) in THF (10 mL), TBAF (1 M THF, 1.34 mL, 1.34 mmol) was added, and the mixture was stirred at room temperature for 25 hours. The reaction mixture was concentrated under reduced pressure, and then purified by diol silica gel column chromatography (hexane:ethyl acetate=50:50→10:90) to obtain Compound 20-8 (549 mg, 94%) as colorless oil.

$^1$H-NMR (CDCl$_3$) δ: 7.41 (2H, t, J=4.4 Hz), 7.32-7.19 (9H, m), 6.84 (4H, d, J=8.8 Hz), 6.35 (2H, q, J=6.1 Hz), 4.85 (1H, t, J=5.8 Hz), 4.67 (1H, t, J=5.1 Hz), 3.79 (6H, s), 3.64 (2H, dd, J=14.3, 7.4 Hz), 3.47 (2H, dt, J=14.1, 5.8 Hz), 3.30 (3H, tt, J=19.5, 6.2 Hz), 3.15-3.06 (3H, m), 2.60 (1H, s), 2.21-2.17 (4H, m), 1.78 (1H, s), 1.62 (4H, s), 1.44 (2H, d, J=5.1 Hz), 1.27 (28H, dd, J=11.0, 3.7 Hz), 0.87 (6H, t, J=6.8 Hz).

Step 4

To Compound 20-8 (549 mg, 0.63 mmol) in dichloromethane (10 mL), DMAP (7.7 mg, 0.063 mmol), succinic anhydride (126 mg, 1.25 mmol) and DIEA (0.32 mL, 1.88 mmol) were added, and the mixture was stirred at room temperature for 4 hours. After the reaction mixture was concentrated under reduced pressure, the resulting crude product was purified by silica gel column chromatography (chloroform:methanol=20:1→40:1) to obtain Compound 21-8 (582 mg, 95%) as colorless liquid.

$^1$H-NMR (CDCl$_3$) δ: 7.41 (2H, d, J=7.5 Hz), 7.31-7.25 (8H, m), 7.20 (1H, t, J=7.2 Hz), 6.82 (4H, d, J=8.7 Hz), 6.61 (1H, t, J=6.2 Hz), 6.47 (1H, t, J=6.4 Hz), 5.91 (1H, t, J=5.6 Hz), 4.71 (1H, t, J=5.1 Hz), 4.42 (1H, dd, J=11.0, 3.2 Hz), 4.14 (1H, dd, J=10.9, 5.8 Hz), 3.80 (6H, d, J=6.1 Hz), 3.47-3.33 (4H, m), 3.08 (4H, ddd, J=33.6, 15.6, 8.5 Hz), 2.69-2.49 (4H, m), 2.20 (4H, dd, J=15.6, 8.2 Hz), 1.95 (1H, s), 1.55 (4H, dt, J=34.3, 6.5 Hz), 1.27 (30H, t, J=7.2 Hz), 0.87 (6H, t, J=6.8 Hz).

Step 5

To Compound 21-8 (300 mg, 0.31 mmol) in a mixture of acetonitrile/dichloromethane (4:1, 25 mL), DIEA (0.27 mL, 1.54 mmol) and HBTU (128 mg, 0.34 mmol) were added, and the mixture was shaken at room temperature for 15 minutes. HybridCPG amino form 2000 Å (Prime Synthesis, Inc.)(2.5 g) was added to the reaction mixture, and the mixture was shaken for 24 hours. After the reaction mixture was filtered, HybridCPG resin was washed three times with acetonitrile and three times with diethyl ether, and dried under reduced pressure. To the dried HybridCPG, a mixture of THF/acetic anhydride/pyridine (8:1:1, 30 mL) was added, and the mixture was shaken for 3 hours. After the reaction mixture was filtered, HybridCPG resin was washed twice with pyridine, twice with isopropanol, and twice with diethyl ether, and dried under reduced pressure. The supported amount of Compound 21-8 was calculated by colorimetric assay of the DMTr cation, and Compound 22-8 whose supported amount is 107 μmol/g was obtained.

6-3) Synthesis of Compound 22-10

Step 1

To Compound 3-10 (2.0 g, 3.92 mmol) in THF (50 mL), pyridine (0.379 mL, 4.70 mmol) and 4-nitrophenyl chloroformate (947 mg, 4.70 mmol) were added, and the mixture was stirred at 60° C. for 1 hour. The reaction mixture was filtered. After the mother liquid was concentrated under reduced pressure, the resulting crude product was purified by silica gel column chromatography (chloroform:methanol=100:0→90:10) to obtain Compound 18-10 (1.1 g, 42%) as a white solid.

$^1$H-NMR (CDCl$_3$) δ: 8.28 (2H, d, J=8.8 Hz), 7.42 (2H, d, J=8.8 Hz), 6.91 (2H, d, J=9.1 Hz), 4.80 (1H, s), 3.57 (4H, m), 2.26 (4H, t, J=7.6 Hz), 1.66 (4H, t, J=6.9 Hz), 1.27 (40H, d, J=20.2 Hz), 0.88 (6H, t, J=6.7 Hz).

Step 2

To Compound 17 (41 mg, 0.074 mmol) in dichloromethane (5.0 mL), Compound 18-10 (50 mg, 0.074 mmol) was added, and the mixture was stirred at room temperature for 1 hour. The reaction mixture was purified by silica gel column chromatography (chloroform:methanol=100:0→90:10) to obtain Compound 19-10 (80 mg, 98%) as yellow liquid.

$^1$H-NMR (CDCl$_3$) δ: 7.42 (2H, d, J=7.5 Hz), 7.31 (7H, t, J=6.4 Hz), 6.81 (4H, d, J=8.8 Hz), 6.23 (2H, d, J=5.5 Hz), 4.68 (1H, s), 3.79 (6H, s), 3.63 (2H, t, J=5.4 Hz), 3.52 (2H, t, J=6.8 Hz), 3.28 (2H, t, J=7.3 Hz), 3.11-3.04 (4H, m), 2.18 (4H, t, J=7.5 Hz), 1.62 (6H, t, J=7.2 Hz), 1.25 (40H, s), 0.88 (6H, t, J=6.8 Hz), 0.84 (9H, s), 0.01 (6H, s)

Step 3

To Compound 19-10 (559.2 mg, 0.535 mmol) in THF (5 mL), triethylamine (4.4 mL, 7.21 mmol) and TBAF (1 M THF, 0.4 mL, 0.40 mmol) were added, and the mixture was stirred at room temperature for 12 hours. The reaction mixture was diluted with chloroform (10 mL), and then washed with aqueous saturated sodium bicarbonate solution (10 mL). After the resulting organic layer was concentrated under reduced pressure, the resulting crude product was purified by silica gel column chromatography (chloroform:methanol=100:0→90:10) to obtain Compound 20-10 (384 mg, 77%) as colorless liquid.

$^1$H-NMR (CDCl$_3$) δ: 7.41 (2H, t, J=4.3 Hz), 7.31 (7H, d, J=8.5 Hz), 6.84 (4H, d, J=8.8 Hz), 6.32 (2H, t, J=6.3 Hz), 4.83 (1H, t, J=6.0 Hz), 4.67 (1H, s, J=5.2 Hz), 3.79 (6H, s), 3.68-3.63 (2H, m), 3.47 (2H, dd, J=12.9, 6.1 Hz), 3.34-3.24 (3H, m), 3.10 (3H, dt, J=17.5, 5.6 Hz), 2.59 (1H, s), 2.21-2.17 (4H, m), 1.71 (1H, m), 1.62 (4H, t, J=7.2 Hz), 1.25 (36H, s), 0.88 (6H, t, J=6.8 Hz).

Step 4

To Compound 20-10 (384 mg, 0.431 mmol) in dichloromethane (10.1 mL), DMAP (5.04 mg, 0.041 mmol) and succinic anhydride (62.0 mg, 0.619 mmol) were added, and the mixture was stirred at room temperature for 1 day. After the reaction mixture was concentrated under reduced pressure, the resulting crude product was purified by diol silica gel column chromatography (chloroform methanol=100:0→90:10) to obtain Compound 21-10 (308 mg, 71%) as colorless liquid.

$^1$H-NMR (CDCl$_3$) δ: 7.41 (2H, t, J=4.3 Hz), 7.31 (6H, d, J=8.5 Hz), 6.84 (4H, d, J=8.8 Hz), 6.81 (1H, br s), 6.61 (1H, br s), 5.83 (1H, br s), 4.70 (1H, s), 4.38 (1H, m), 4.13 (1H, d, J=10.4 Hz), 3.79 (6H, s), 3.78-3.41 (6H, m), 3.05 (6H, m), 2.89 (6H, m), 2.62-2.55 (6H, m), 2.20 (4H, d, J=7.2 Hz), 1.94 (1H, s), 1.62 (4H, t, J=7.2 Hz), 1.25 (36H, s), 0.88 (6H, t, J=7.2 Hz).

Step 5

To Compound 21-10 (247 mg, 0.240 mmol) in a mixture of acetonitrile/dichloromethane (1:1, 20 mL), DIEA (0.168 mL, 0.982 mmol) and HBTU (100 mg, 0.264 mmol) were added, and the mixture was shaken at room temperature for 20 minutes. To the reaction mixture, Native Amino lcaa CPG 1000 Å (ChemGenes Corporation)(2.0 g) was added, and the mixture was shaken for 12 hours. After the reaction mixture was filtered, CPG resin was washed three times with dichloromethane and three times with diethyl ether, and dried under reduced pressure. To the dried HybridCPG, a mixture of CapA (PROLIGO, L840045-06) and CapB (PROLIGO, L850045-06) (1:1, 20 mL) was added, and the mixture was shaken for 30 minutes. After the reaction mixture was filtered, CPG resin was washed twice with dichloromethane and twice with diethyl ether, and dried under reduced pressure. The supported amount of Compound 21-10 was calculated by colorimetric assay of the DMTr cation, and Compound 22-10 whose supported amount is 69 μmol/g was obtained.

6-4) Synthesis of Compound 22-12

Step 1

To Compound 3-12 (2.0 g, 3.92 mmol) in THF (50 mL), pyridine (0.379 mL, 4.70 mmol) and 4-nitrophenyl chloroformate (947 mg, 4.70 mmol) were added, and the mixture was stirred at 60° C. for 1 hour. The reaction mixture was filtered. After the mother liquid was concentrated under reduced pressure, the resulting crude product was purified by silica gel column chromatography (chloroform:methanol=100:0→90:10) to obtain Compound 18-12 (1.1 g, 42%) as a white solid.

$^1$H-NMR (CDCl$_3$) δ: 8.28 (2H, d, J=8.8 Hz), 7.42 (2H, d, J=8.8 Hz), 6.91 (2H, d, J=9.1 Hz), 4.80 (1H, s), 3.57 (4H, m), 2.26 (4H, t, J=7.6 Hz), 1.66 (4H, t, J=6.9 Hz), 1.27 (40H, d, J=20.2 Hz), 0.88 (6H, t, J=6.7 Hz).

Step 2

To Compound 17 (41 mg, 0.074 mmol) in dichloromethane (5.0 mL), Compound 18-12 (50 mg, 0.074 mmol) was added, and the mixture was stirred at room temperature for 1 hour. The reaction mixture was purified by silica gel column chromatography (chloroform:methanol=100:0→90:10) to obtain Compound 19-12 (80 mg, 98%) as yellow liquid.

$^1$H-NMR (CDCl$_3$) δ: 7.42 (2H, d, J=7.5 Hz), 7.31 (6H, t, J=6.4 Hz), 6.81 (4H, d, J=8.8 Hz), 6.23 (2H, d, J=5.5 Hz), 4.68 (1H, s), 3.79 (6H, s), 3.63 (2H, t, J=5.4 Hz), 3.52 (2H, t, J=6.8 Hz), 3.28 (2H, t, J=7.3 Hz), 3.11-3.04 (4H, m), 2.18 (4H, t, J=7.5 Hz), 1.62 (6H, t, J=7.2 Hz), 1.25 (40H, s), 0.88 (6H, t, J=6.8 Hz), 0.84 (6H, s), 0.01 (6H, s)

Step 3

To Compound 19-12 (90 mg, 0.082 mmol) in THF (5 mL), triethylamine (1.0 mL, 7.21 mmol) and TBAF (1 M THF, 0.4 mL, 0.40 mmol) were added, and the mixture was stirred at room temperature for 12 hours. The reaction mixture was diluted with chloroform (10 mL), and then washed with aqueous saturated sodium bicarbonate solution (10 mL). After the resulting organic layer was concentrated under reduced pressure, the resulting crude product was purified by silica gel column chromatography (chloroform:methanol=100:0→95:5) to obtain Compound 20-12 (84 mg, 100%) as colorless liquid.

$^1$H-NMR (CDCl$_3$) δ: 7.41 (2H, t, J=4.3 Hz), 7.31 (6H, d, J=8.5 Hz), 6.84 (4H, d, J=8.8 Hz), 6.34 (2H, t, J=6.3 Hz), 4.83 (1H, s), 4.67 (1H, s), 3.79 (6H, s), 3.68-3.63 (2H, m), 3.47 (2H, dd, J=12.9, 6.1 Hz), 3.34-3.24 (3H, m), 3.10 (3H, dt, J=17.5, 5.6 Hz), 2.60 (1H, s), 2.21-2.17 (4H, m), 1.62 (4H, t, J=6.9 Hz), 1.25 (40H, s), 0.88 (6H, t, J=6.8 Hz).

Step 4

To Compound 20-12 (60 mg, 0.061 mmol) in pyridine solution (2 mL), DMAP (0.7 mg, 0.006 mmol) and succinic anhydride (7.3 mg, 0.073 mmol) were added, and the mixture was stirred at room temperature for 4 days. After the reaction mixture was concentrated under reduced pressure, the resulting crude product was purified by silica gel column chromatography (chloroform:methanol=100:0→95:5) to obtain Compound 21-12 (56 mg, 85%) as colorless liquid.

ESI-MS (m/z): 1085 (M–H).

Step 5

To Compound 21-12 (52 mg, 0.048 mmol) in a mixture of acetonitrile/chloroform (1:1, 10 mL), DIEA (0.043 mL, 0.248 mmol) and HBTU (31 mg, 0.083 mmol) were added, and the mixture was shaken at room temperature for 15 minutes. To the reaction mixture, Native Amino lcaa CPG 1000 Å (Chem Genes Corporation) (0.5 g) was added, and the mixture was shaken for 23 hours. After the reaction mixture was filtered, CPG resin was washed three times with acetonitrile and three times with diethyl ether, and dried under reduced pressure. To the dried CPG, a mixture of CapA (PROLIGO, L840045-06) and CapB (PROLIGO, L850045-06) (1:1, 5 mL) was added, and the mixture was shaken for 1.5 hours. After the reaction mixture was filtered, CPG resin was washed twice with pyridine, twice with isopropanol and twice with diethyl ether, and then dried under reduced pressure. The supported amount of Compound 21-12 was calculated by colorimetric assay of the DMTr cation, and Compound 22-12 whose supported amount is 31 μmol/g was obtained.

6-5) Synthesis of Compound 22-14

Step 1

To Compound 3-14 (1.5 g, 3.92 mmol) in THF (60 mL), pyridine (0.320 mL, 3.97 mmol) and 4-nitrophenyl chloroformate (800 mg, 3.97 mmol) were added, and the mixture was heated under reflux for 3 hours. The reaction mixture was filtered. After the mother liquid was concentrated under reduced pressure, the resulting crude product was purified by silica gel column chromatography (hexane:ethyl acetate=66:34→45:55) to obtain Compound 18-14 (1.56 g, 81%) as a white solid.

$^1$H-NMR (CDCl$_3$) δ: 8.29 (2H, d, J=10.0 Hz), 7.43 (2H, d, J=10.0 Hz), 6.31 (2H, t, J=6.4 Hz), 4.81-4.76 (1H, m), 3.65-3.58 (2H, m), 3.55-3.48 (2H, m), 2.25 (4H, t, J=7.6 Hz), 1.67-1.61 (4H, m), 1.25 (48H, s), 0.88 (6H, t, J=6.8 Hz).

Step 2

To Compound 17 (1.06 g, 1.88 mmol) in dichloromethane (30 mL), Compound 18-14 (1.38 g, 1.88 mmol) was added, and the mixture was stirred at room temperature for 1 hour. After the solvent was concentrated under reduced pressure, the resulting crude product was purified by silica gel column chromatography (hexane:ethyl acetate=66:34→45:55) to obtain Compound 19-14 (1.47 g, 68%) as a white solid.

ESI-MS (m/z): 1155 (M−H).
Step 3

To Compound 19-14 (1.47 g, 1.27 mmol) in THF (30 mL), TBAF (1 M THF, 3.81 mL, 3.81 mmol) was added, and the mixture was stirred at room temperature for 18 hours. After the reaction mixture was diluted with ethyl acetate, the solvent was concentrated under reduced pressure. The resulting crude product was purified by silica gel column chromatography (hexane:ethyl acetate=50:50→5:95) to obtain Compound 20-14 (1.04 g, 79%) as a white solid.

$^1$H-NMR (CDCl$_3$) δ: 7.41 (2H, d, J=7.6 Hz), 7.32-7.27 (6H, m), 7.21 (1H, t, J=7.2 Hz), 6.83 (4H, d, J=8.8 Hz), 6.37-6.35 (2H, m), 4.86 (1H, t, J=5.6 Hz), 4.69-4.64 (1H, m), 3.79 (6H, s), 3.69-3.61 (2H, m), 3.50-3.24 (6H, m), 3.15-3.06 (3H, m), 2.61 (1H, s), 2.21-2.17 (4H, m), 1.25 (58H, s), 0.88 (6H, t, J=6.8 Hz).

Step 4

To Compound 20-14 (1.04 g, 0.998 mmol) in dichloromethane (20 mL), DMAP (12 mg, 0.10 mmol), DIEA (0.523 mL, 2.99 mmol) and succinic anhydride (170 mg, 1.70 mmol) were added, and the mixture was stirred at room temperature for 16 hours. After the reaction mixture was concentrated under reduced pressure, the resulting crude product was purified by diol silica gel column chromatography (chloroform) to obtain Compound 21-14 (1.17 g) as a white solid.

ESI-MS (m/z) 1141 (M−H).

Step 5

To Compound 21-14 (585 mg, 0.512 mmol) in a mixture of acetonitrile/dichloromethane (1:1, 40 mL), DIEA (0.447 mL, 2.56 mmol) and HBTU (214 mg, 0.563 mmol) were added, and the mixture was shaken at room temperature for 15 minutes. To the reaction mixture, Native Amino lcaa CPG 1000 Å (ChemGenes Corporation) (4.0 g) was added, and the mixture was shaken for 21 hours. After the reaction mixture was filtered, CPG resin was washed with a mixture of acetonitrile/dichloromethane (1:1, 120 mL) and diethyl ether (60 mL), and then dried under reduced pressure. To the dried CPG, a mixture of CapA (PROLIGO, L840045-06) and CapB (PROLIGO, L850045-06) (1:1, 40 mL) was added, and the mixture was shaken for 1.5 hours. After the reaction mixture was filtered, CPG resin was washed with pyridine (40 mL), isopropanol (60 mL) and diethyl ether (60 mL), and then dried under reduced pressure. The supported amount of Compound 21-14 was calculated by colorimetric assay of the DMTr cation, and Compound 22-14 whose supported amount is 40 μmol/g was obtained.

6-6) Synthesis of Compound 22-18

Step 1

To Compound 3-18 (1.0 g, 1.47 mmol) in THF (40 mL), pyridine (0.143 mL, 1.76 mmol) and 4-nitrophenyl chloroformate (356 mg, 1.77 mmol) were added, and the mixture was stirred at 60° C. for 1 hour. After the reaction mixture was filtered, the mother liquid was concentrated under reduced pressure. The crude product of resulting solid was washed with ethyl acetate to obtain Compound 18-18 (508 mg, 41%) as a white solid.

$^1$H-NMR (CDCl$_3$) δ: 8.29 (2H, d, J=8.8 Hz), 7.43 (2H, d, J=9.1 Hz), 6.29 (2H, s), 3.60-3.50 (4H, m), 2.25 (4H, t, J=7.6 Hz), 1.64 (4H, d, J=6.6 Hz), 1.25 (64H, s), 0.88 (6H, t, J=6.4 Hz).

Step 2

To Compound 17 (62 mg, 0.110 mmol) in dichloromethane (4.0 mL), Compound 18-18 (93 mg, 0.110 mmol) was added, and the mixture was stirred at room temperature for 1 hour. The reaction mixture was purified by silica gel column chromatography (chloroform:methanol=100:0→90:10) to obtain Compound 19-18 (113 mg, 81%) as yellow liquid.

$^1$H-NMR (CDCl$_3$) δ: 7.42 (2H, d, J=13.4 Hz), 7.31 (7H, d, J=9.3 Hz), 6.81 (4H, d, J=8.8 Hz), 6.22 (2H, s), 4.69 (1H, s), 3.78 (6H, s), 3.62 (2H, t, J=5.6 Hz), 3.51 (2H, dd, J=10.9, 6.1 Hz), 3.32-3.27 (2H, m), 3.11-3.04 (4H, m), 2.17 (4H, t, J=3.7 Hz), 1.62 (6H, dd, J=10.5, 4.7 Hz), 1.25 (64H, s), 0.88 (6H, t, J=6.8 Hz), 0.83 (9H, s), 0.01 (6H, s).

Step 3

To Compound 19-18 (100 mg, 0.079 mmol) in THF (4 mL), triethylamine (0.1 mL, 0.79 mmol) and TBAF (1 M THF, 0.32 mL, 0.32 mmol) were added, and the mixture was stirred at room temperature for 24 hours. The reaction mixture was diluted with chloroform (10 mL), and then washed with aqueous saturated sodium bicarbonate solution (10 mL). After the resulting organic layer was dried over magnesium sulfate and concentrated under reduced pressure, the resulting crude product was purified by silica gel column chromatography (chloroform:methanol=100:0→95:5) to obtain Compound 20-18 (90 mg, 99%) as colorless liquid.

$^1$H-NMR (CDCl$_3$) δ: 7.41 (2H, d, J=8.6 Hz), 7.31 (7H, d, J=8.8 Hz), 6.84 (4H, d, J=8.6 Hz), 6.31 (2H, s), 4.81 (1H, s), 4.67 (1H, s), 3.79 (6H, s), 3.71-3.63 (2H, m), 3.49 (2H, dd, J=14.7, 11.1 Hz), 3.30 (3H, tt, J=18.8, 7.4 Hz), 3.13-3.07 (3H, m), 2.58 (1H, s), 2.18 (4H, d, J=7.6 Hz), 1.60 (6H, dd, J=9.2, 4.4 Hz) 1.25 (64H, s), 0.88 (6H, t, J=6.3 Hz).

Step 4

To Compound 20-18 (87 mg, 0.075 mmol) in pyridine solution (2 mL), DMAP (0.9 mg, 0.007 mmol) and succinic anhydride (15.8 mg, 0.151 mmol) were added, and the mixture was stirred at room temperature for 7 days. After the reaction mixture was concentrated under reduced pressure, the resulting crude product was purified by silica gel column chromatography (chloroform:methanol=100:0→95:5) to obtain Compound 21-18 (85 mg, 90%) as colorless liquid.

ESI-MS (m/z): 1253 (M−H).

Step 5

To Compound 21-18 (85 mg, 0.068 mmol) in a mixture of acetonitrile/chloroform (1:1, 10 mL), DIEA (0.043 mL, 0.248 mmol) and HBTU (38 mg, 0.10 mmol) were added, and the mixture was stirred at room temperature for 15 minutes. To the reaction mixture, Native Amino lcaa CPG 1000 Å (Chem Genes Corporation) (0.5 g) was added, and the mixture was shaken at room temperature for 23 hours. After the reaction mixture was filtered, CPG resin was washed three times with acetonitrile and three times with diethyl ether, and dried under reduced pressure. To the dried CPG, a mixture of CapA (PROLIGO, L840045-06) and CapB (PROLIGO, L850045-06) (1:1, 5 mL) was added, and the mixture was shaken for 1.5 hours. After the reaction mixture was filtered, CPG resin was washed twice with pyridine, twice with isopropanol and twice with diethyl ether, and dried under reduced pressure. The supported amount of Compound 21-18 was calculated by colorimetric assay of the DMTr cation, and Compound 22-18 whose supported amount is 15 μmol/g was obtained.

6-7) Synthesis of Compound 22-20

Step 1

To Compound 3-20 (1.0 g, 1.36 mmol) in THF (35 mL), bis(4-nitrophenyl)carbonate (1.241 mL, 4.08 mmol) and DMAP (498 mg, 4.08 mmol) were added, and the mixture was stirred at 55° C. for 1 hour. The reaction mixture was concentrated under reduced pressure. To the residue, acetonitrile (50 mL) was added and the mixture was stirred until the solid was precipitated. To the suspended solution, water (20 mL) was added and the mixture was vigorously stirred. The resulting solid was collected by filtration and washed with water (50 mL) and acetonitrile (50 mL) in order to obtain Compound 18-20 (1.1 g, 92%) as a white solid.

$^1$H-NMR (CDCl$_3$) δ: 8.28 (2H, dd, J=2.0, 6.8 Hz), 7.42 (2H, dd, J=2.4, 7.2 Hz), 6.30 (2H, s), 4.79 (1H, s), 3.61 (2H, m), 3.52 (2H, m), 2.20 (4H, m), 1.66 (4H, m), 1.25 (72H, m), 0.88 (6H, t, J=6.8 Hz).

Step 2

To Compound 17 (219 mg, 0.388 mmol) in THF (6.5 mL), Compound 18-20 (350 mg, 0.388 mmol) and DMAP (47.5 mg, 0.388 mmol) were added, and the mixture was stirred at 65° C. for 2 hours. To the reaction mixture, 10% hydrous acetonitrile solution (70 ml) was added, and the mixture was stirred for a while. The precipitated solid was collected by filtration to obtain Compound 19-20 (420 mg, 82%) as a white solid.

$^1$H-NMR (CDCl$_3$) δ: 7.43 (2H, d, J=7.6 Hz), 7.31 (7H, m), 6.81 (4H, d, J=8.4 Hz), 6.26 (2H, br s), 4.73 (1H, br s), 4.69 (1H, br s), 3.79 (6H, s), 3.79 (6H, s), 3.63 (2H, m), 3.49 (2H, m), 3.29 (2H, d, J=14.0 Hz), 3.10-3.06 (4H, m), 2.18 (4H, t, J=7.6 Hz), 1.68 (4H, m), 1.42-1.25 (m, 72H), 0.88 (6H, t, J=6.4 Hz), 0.83 (s, 9H), 0.00 (s, 6H).

Step 3

To Compound 19-20 (559 mg, 0.422 mmol) in THF (5 mL), TBAF (1 M THF, 0.506 mL, 0.506 mmol) was added, and the mixture was stirred at 50° C. for 5 hours. The reaction mixture was added dropwise to 10% hydrous acetonitrile solution (100 mL), and then the precipitated solid was collected by filtration to obtain Compound 20-20 (344 mg, 67%) as a white solid.

$^1$H-NMR (CDCl$_3$) δ: 7.41 (2H, t, J=4.3 Hz), 7.31 (7H, d, J=8.5 Hz), 6.84 (4H, d, J=8.8 Hz), 6.35 (2H, br s), 4.85 (1H, s), 4.67 (1H, s), 3.79 (6H, s), 3.68 (2H, m), 3.47 (2H, dd, J=12.9, 6.1 Hz), 3.34-3.24 (3H, m), 3.10 (3H, dt, J=17.5, 5.6 Hz), 2.60 (1H, s), 2.21-2.17 (4H, m), 1.62 (4H, m), 1.60-1.45 (m, 4H), 1.25-1.01 (72H, m), 0.88 (6H, t, J=6.8 Hz).

Step 4

To Compound 20-20 (344 mg, 0.284 mmol) in dichloromethane (10 mL), DMAP (3.5 mg, 0.0284 mmol) and succinic anhydride (42.6 mg, 0.426 mmol) were added, and the mixture was stirred at room temperature overnight. The reaction mixture was added dropwise to 10% hydrous acetonitrile solution (100 mL), and the precipitated solid was collected by filtration to obtain Compound 21-20 (361 mg, 97%) as a white solid.

$^1$H-NMR (CDCl$_3$) δ: 7.42 (2H, d, J=7.6 Hz), 7.31-7.26 (7H, m), 6.83 (4H, t, J=8.4 Hz), 6.56 (1H, br s), 6.40 (1H, br s), 5.89 (1H, br s), 4.71 (1H, s), 4.41 (1H, d, J=8.0 Hz), 4.14 (1H, dd, J=6.0, 11.2 Hz), 3.79 (6H, s), 3.65 (1H, m), 3.43-3.37 (4H, m), 3.05-3.02 (4H, m), 2.19-2.17 (4H, m), 1.61-1.25 (76H, m), 0.88 (6H, t, J=6.8 Hz).

Step 5

To Compound 21-20 (190 mg, 0.145 mmol) in a mixture of acetonitrile/chloroform (1:3, 10 mL), DIEA (0.127 mL, 0.725 mmol) and HBTU (60.5 mg, 0.159 mmol) were added, and the mixture was shaken at 40° C. for 15 minutes. To the reaction mixture, Native Amino lcaa CPG 1000 Å (ChemGenes Corporation) (3.0 g) was added, and the mixture was shaken for 2 hours. After the reaction mixture was filtered, CPG resin was washed three times with chloroform, once with ethanol and three times with acetonitrile, and dried under reduced pressure. To the dried CPG, a mixture of CapA (PROLIGO, L840045-06) and CapB (PROLIGO, L850045-06) (1:1, 20 mL) was added, and the mixture was shaken for 1.5 hours.

After the reaction mixture was filtered, CPG resin was washed three times with chloroform and three times with acetonitrile, and then dried under reduced pressure. The supported amount of Compound 21-20 was calculated by colorimetric assay of the DMTr cation, and Compound 22-20 whose supported amount is 48 μmol/g was obtained.

6-8) Synthesis of Compound 22-22

Step 1

To Compound 3-22 (2.0 g, 2.53 mmol) in THF (35 mL), bis-(p-nitrophenyl) carbonate (1.54 g, 5.05 mmol) and DMAP (618 mg, 5.05 mmol) were added, and the mixture was stirred at 65° C. for 2 hours. The reaction mixture was concentrated under reduced pressure. To the residue, acetonitrile (100 mL) was added, and the mixture was stirred until the solid was precipitated. To the suspended solution, water (20 mL) was added, and the mixture was vigorously stirred. The resulting solid was collected by filtration and washed in order with water (100 mL) and acetonitrile (100 mL) to obtain Compound 18-22 (2.27 g, 89%) as a white solid.

$^1$H-NMR (CDCl$_3$) δ: 8.28 (2H, d, J=8.8 Hz), 7.43 (2H, d, J=8.82 Hz), 6.29 (2H, br t, J=6.4 Hz), 4.79 (1H, br s), 3.61 (2H, m), 3.52 (2H, m), 2.25 (4H, t, J=7.6 Hz), 1.64 (4H, m), 1.26 (84H, m), 0.88 (6H, t, J=6.0 Hz)

Step 2

To Compound 17 (666 mg, 1.81 mmol) in THF (10.0 mL), DMAP (144 mg, 1.81 mmol) and Compound 18-22 (1.13 g, 1.18 mmol) were added, and the mixture was stirred at 65° C. for 2 hours. To the reaction mixture, acetonitrile (150 mL) was added slowly. The resulting precipitate was collected by filtration and washed three times with acetonitrile to obtain Compound 19-22 (1.5 g, 92%) as a white solid.

$^1$H-NMR (CDCl$_3$) δ: 7.42 (2H, d, J=6.8 Hz), 7.32-7.20 (7H, m), 6.81 (4H, d, J=6.8 Hz), 6.26 (2H, br m), 4.70 (2H, s), 3.63 (2H, m), 3.49 (2H, m), 3.31 (2H, m), 3.09-3.04 (4H, m), 2.18 (4H, m), 1.60 4H, m), 1.25 (84H, m), 0.86 (6H, t, J=6.8 Hz), 0.84 (9H, s), 0.01 (6H, s)

Step 3

To Compound 19-22 (1.5 g, 1.07 mmol) in THF (8.9 mL), TBAF (1 M THF, 1.64 mL, 1.69 mmol) was added, and the mixture was stirred at 65° C. for 2 hours. To the reaction mixture, acetonitrile (150 mL) was added slowly. The resulting precipitate was collected by filtration and washed three times with acetonitrile to obtain Compound 20-22 (1.2 g, 87%) as a white solid.

$^1$H-NMR (CDCl$_3$) δ: 7.41 (2H, t, J=7.2 Hz), 7.31-7.21 (7H, m), 6.84 (4H, d, J=8.0 Hz), 6.34 (2H, m), 4.83 (1H, s), 4.67 (1H, s), 3.79 (6H, s), 3.67 (2H, m), 3.46 (2H, m), 3.33-3.24 (3H, m), 3.10 (3H, m), 2.17 (4H, t, J=7.6 Hz), 1.78 (4H, m), 1.44-1.25 (84H, m), 0.88 (6H, t, J=6.0 Hz).

Step 4

To Compound 20-22 (100 mg, 0.079 mmol) in dichloromethane (3 mL), DMAP (1 mg, 0.008 mmol) and succinic anhydride (11.9 mg, 0.118 mmol) were added, and the mixture was stirred at 45° C. for 4 hours. To the reaction mixture, acetonitrile (10 mL) was added dropwise, and the precipitated solid was collected by filtration. The resulting solid was washed three times with acetonitrile to obtain Compound 21-22 (361 mg, 97%) as a white solid.

$^1$H-NMR (CDCl$_3$) δ: 7.42 (2H, d, J=7.6 Hz), 7.31-7.26 (7H, m), 6.81 (4H, t, J=8.8 Hz), 6.58 (1H, br m), 6.43 (1H, br m), 5.88 (1H, br m), 4.71 (1H, m), 4.40 (1H, d, J=8.0 Hz), 4.14 (1H, dd, J=6.0, 10.8 Hz), 3.79 (6H, s), 3.65 (1H, m), 3.43-3.37 (4H, m), 3.13-3.02 (4H, m), 2.63-2.53 (4H, m), 2.23-2.18 (4H, dd, J=7.2, 14.8 Hz), 2.00-1.25 (4H, m) 1.25-1.11 (84H, m), 0.88 (6H, t, J=6.8 Hz).

Step 5

To Compound 21-22 (92 mg, 0.067 mmol) in a mixture of acetonitrile/dichloromethane/chloroform (1:2:2, 10 mL), DIEA (0.059 mL, 0.336 mmol) and HBTU (28 mg, 0.074 mmol) were added, and the mixture was shaken at 40° C. for 15 minutes. To the reaction mixture, Native Amino lcaa CPG 1000 Å (ChemGenes Corporation) (0.9 g) was added, and the mixture was shaken at 40° C. for 3 hours. After the reaction mixture was filtered, CPG resin was washed three times with chloroform, three times with acetonitrile and three times with ethanol, and dried under reduced pressure. To the dried CPG, a mixture of CapA (PROLIGO, L840045-06) and CapB (PROLIGO, L850045-06) (1:1, 60 mL) was added, and the mixture was shaken for 1.5 hours. After the reaction mixture was filtered, CPG resin was washed three times with acetonitrile, and dried under reduced pressure. The supported amount of Compound 21-22 was calculated by colorimetric assay of the DMTr cation, and Compound 22-22 whose supported amount is 47 μmol/g was obtained.

8-1) Synthesis of Compound 26

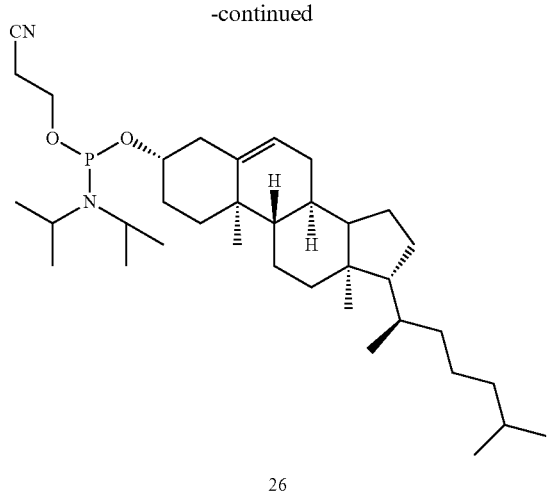

26

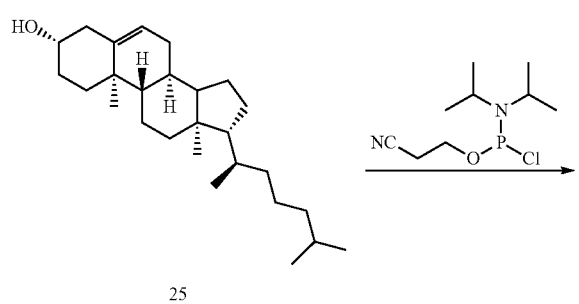

25

Under nitrogen atmosphere, to cholesterol (Compound 25, 1.00 g, 2.59 mmol, Wako Pure Chemical Industries, Ltd.) in dichloromethane (10 mL), DIEA (0.9 mL, 5.17 mmol) was added, and the mixture was cooled with ice-cold water. 2-cyanoethyl N,N-diisopropylchlorophosphoramidite (0.86 mL, 3.85 mmol) was added thereto and the mixture was stirred under ice cooling for 40 minutes. The reaction mixture was diluted with dichloromethane and ethyl acetate (100 mL), and then washed with aqueous saturated sodium bicarbonate solution (100 mL) and brine (100 mL). The organic layer was dried over magnesium sulfate, filtered, and then concentrated under reduced pressure. The resulting residue was purified by silica gel column chromatography (SiO$_2$:20 g, n-hexane:ethyl acetate=50:50→0:100) to obtain Compound 26 (1.45 g, Yield 95%) as colorless foam. Formation of the compound was determined based on introduction of trivalent phosphorus by $^{31}$P-NMR.

$^{31}$P-NMR (CDCl$_3$) δ:145.46 (d)

8-2) Synthesis of Compound 5

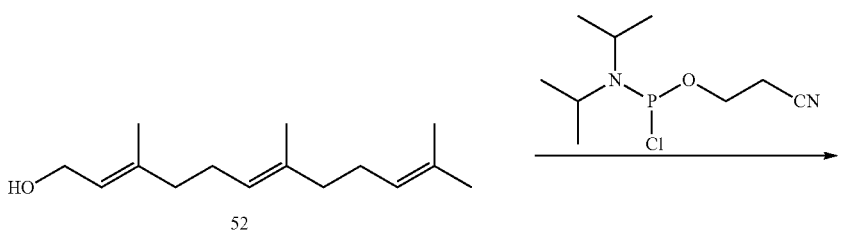

52

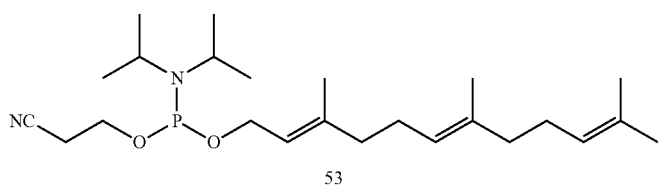

53

Farnesol (Compound 52, 1.0 mL, 3.99 mmol, Junsei Chemical Co., Ltd.) was dissolved in dichloromethane (8.9 mL), and DIEA (1.53 mL, 8.78 mmol) was added thereto. Then, 2-cyanoethyl N, N-diisopropylchlorophosphoramidite (0.98 mL, 4.39 mmol) was added thereto at room temperature, and the mixture was stirred at room temperature for 40 minutes. Dichloromethane (90 mL) and aqueous saturated sodium bicarbonate solution (100 mL) were added to the reaction solvent to stop the reaction, and then the mixture was partitioned by the separatory funnel. The organic layer was washed with brine (100 mL), and then dried over magnesium sulfate. The organic layer was concentrated under reduced pressure to obtain Compound 53 (1.20 g, 2.84 mmol) as pale yellow oil as a crude product. Formation of the compound was determined based on introduction of trivalent phosphorus by $^{31}$P-NMR $^1$H-NMR (CDCl$_3$) δ: 5.37 (1H, t, J=6.6 Hz), 5.10-5.08 (2H, m), 4.19-4.13 (2H, m), 3.90-3.77 (2H, m), 3.66-3.54 (2H, m), 2.64 (2H, t, J=6.6 Hz), 2.08-1.99 (8H, m), 1.68-1.67 (6H, m), 1.61-1.60 (6H, m), 1.20-1.17 (12H, m).

$^{31}$P-NMR (CDCl$_3$) δ: 147.92 (1H, s).

9) Synthesis of Compound 36-n

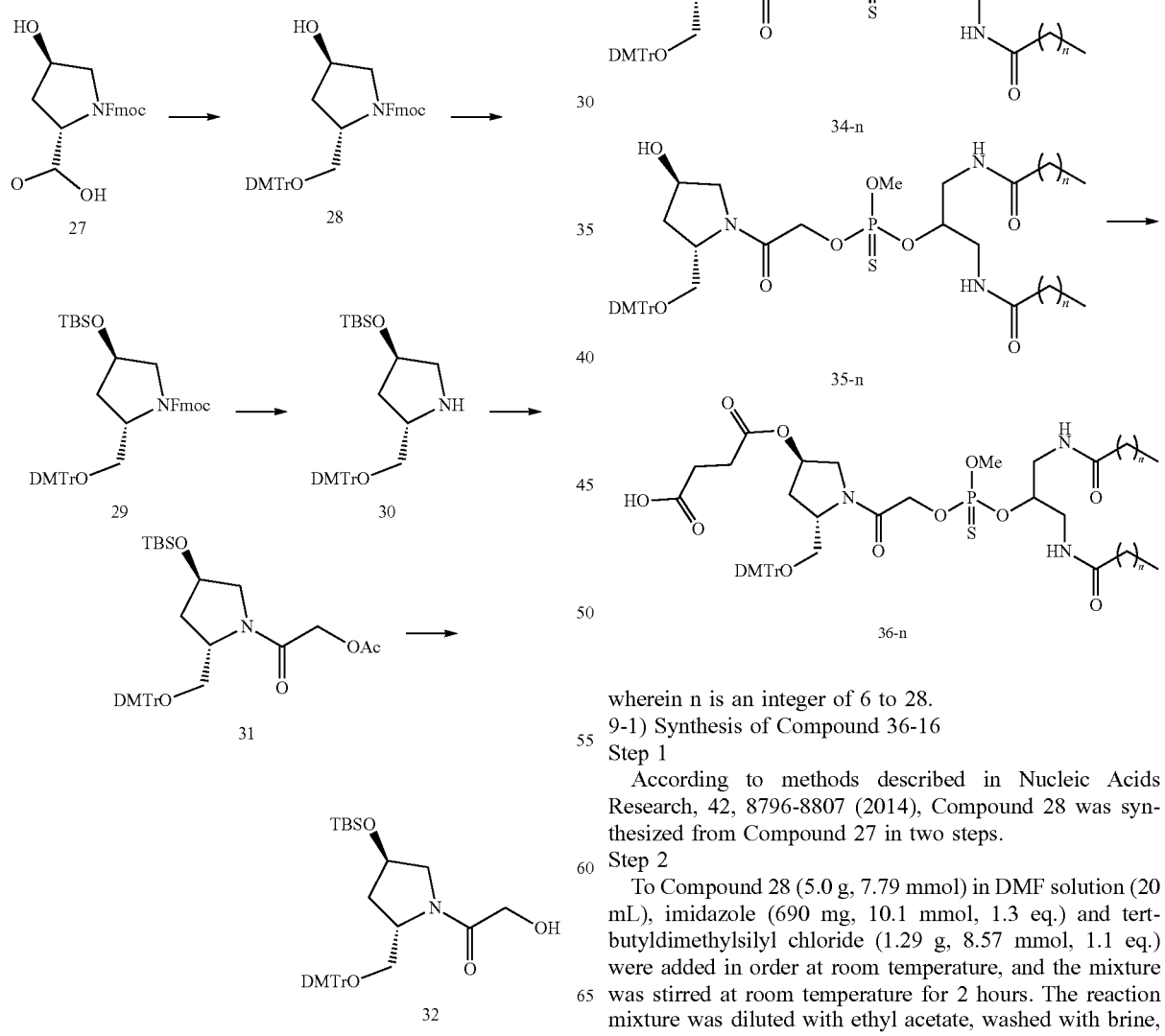

wherein n is an integer of 6 to 28.

9-1) Synthesis of Compound 36-16

Step 1

According to methods described in Nucleic Acids Research, 42, 8796-8807 (2014), Compound 28 was synthesized from Compound 27 in two steps.

Step 2

To Compound 28 (5.0 g, 7.79 mmol) in DMF solution (20 mL), imidazole (690 mg, 10.1 mmol, 1.3 eq.) and tert-butyldimethylsilyl chloride (1.29 g, 8.57 mmol, 1.1 eq.) were added in order at room temperature, and the mixture was stirred at room temperature for 2 hours. The reaction mixture was diluted with ethyl acetate, washed with brine, and then dried over magnesium sulfate. The solvent was concentrated under reduced pressure. The resulting residue was purified by silica gel column chromatography (SiO$_2$:120 g, n-hexane:ethyl acetate:triethylamine=90:10:1→65:35:1) to obtain Compound 29 (5.50 g, Yield 93%) as colorless foam. By $^1$H-NMR, it was observed a mixture of rotamers, which is 1:1.

ESI-MS (m/z): 778 (M+H).

$^1$H-NMR (CDCl$_3$) δ: 7.68 (d, J=7.5 Hz, 1H), 7.62 (d, J=7.5 Hz, 1H), 7.58-7.51 (m, 1H), 7.40-7.05 (m, 14H), 6.74-6.63 (m, 5H), 4.61-4.49 (m, 1H), 4.33-4.15 (2m, 1H), 4.12-4.03 (m, 1H), 3.93-3.85 (m, 1H), 3.62 (s, 6H), 3.56 (dd, J=10.7, 5.4 Hz, 0.5H), 3.41-3.31 (m, 1H), 3.16 (dd, J=9.0, 4.3 Hz, 0.5H), 3.00 (m, 0.5H), 2.90 (m, 0.5H), 2.13-2.02 (m, 1H), 1.97-1.82 (m, 1H), 0.82 (s, 1.5H), 0.81 (s, 3H), 0.779 (s, 3H), 0.787 (s, 1.5H), 0.007 (s, 1.5H), 0.000 (s, 1.5H), −0.015 (s, 1.5H), −0.026 (s, 1.5H).

Step 3

To Compound 29 (2.63 g, 3.48 mmol) in DMF solution (10 piperidine (0.379 ml, 3.83 mmol, 1.1 eq.) was added. The mixture was stirred at room temperature for 2 hours, and then concentrated under reduced pressure. The residue was diluted with ethyl acetate, washed with brine, and then dried over magnesium sulfate. The solvent was concentrated under reduced pressure. Methanol (10 ml) was added thereto, and the resulting precipitate was filtered. The filtrate was concentrated to obtain the crude product of Compound 30 (2.20 g).

ESI-MS (m/z): 524 (M+H). HPLC Peak RT=3.29 min.

Step 4

To Compound 30 (2.20 g, crude) in dichloromethane (15 triethylamine (3.65 ml, 36.9 mmol) and acetoxyacetyl chloride (3.65 ml, 36.9 mmol) were added in order at room temperature, and the mixture was stirred at room temperature for 2 hours. The reaction mixture was diluted with ethyl acetate, washed with brine, and then dried over magnesium sulfate. The solvent was concentrated under reduced pressure to obtain the crude product of Compound 31.

ESI-MS (m/z): 634 (M+H). HPLC Peak RT=3.40 min.

Step 5

After Compound 31 obtained in Step 4 was dissolved in methanol (10 ml), 28% sodium methoxide-methanol solution (0.60 ml) was added thereto, and the mixture was stirred at room temperature for 1 hour. The reaction mixture was diluted with ethyl acetate, washed with brine, and then dried over magnesium sulfate. The solvent was concentrated under reduced pressure. The resulting residue was purified by silica gel column chromatography (SiO$_2$:80 g, n-hexane:ethyl acetate:triethylamine=80:20:1→65:35:1) to obtain Compound 32 (1.45 g, Yield from Compound 30: 71%) as colorless foam. By $^1$H-NMR, it was observed a mixture of rotamers, which is 78:22.

ESI-MS (m/z) 592 (M+H). HPLC Peak RT=3.36 min.

$^1$H-NMR (CDCl$_3$) δ: (Major) 7.39-7.32 (m, 2H), 7.32-7.18 (m, 7H), 6.86-6.79 (m, 4H), 4.73 (m, 1H), 4.35 (m, 1H), 4.06 (dd, J=15.1, 4.4 Hz, 1H), 3.98 (dd, J=15.1, 4.4 Hz, 1H), 3.79 (s, 6H), 3.57 (dd, J=10.0, 4.0 Hz, 1H), 3.52 (dd, J=10.0, 6.0 Hz, 1H), 3.47 (dd, J=4.4, 4.4 Hz, 1H), 3.13 (dd, J=10.0, 2.5 Hz, 1H), 3.08 (dd, J=10.0, 5.0 Hz, 1H), 2.19 (m, 1H), 1.93 (ddd, J=13.0, 8.8, 6.0 Hz, 1H), 0.87 (s, 9H), 0.08 (s, 3H), 0.07 (s, 3H). (Minor) 7.39-7.32 (m, 2H), 7.32-7.18 (m, 7H), 6.86-6.79 (m, 4H), 4.54 (m, 1H), 4.06-3.98 (m, 1H), 3.92 (dd, J=14.6, 4.3 Hz, 1H), 3.79 (s, 6H), 3.68 (dd, J=12.0, 4.0 Hz, 1H), 3.62-3.42 (m, 2H), 3.16-3.02 (m, 2H), 2.11 (ddd, J=13.0, 5.8, 4.0 Hz, 1H), 2.02 (m, 1H), 0.86 (s, 9H), 0.051 (s, 3H), 0.049 (s, 3H).

Step 6

To Compound 3-16 (2.00 g, 3.21 mmol), which was synthesized in a similar method to 1-1-6), suspended in dichloromethane (60 ml), DIEA (3.36 mL, 19.3 mmol, 4.0 eq.) was added, and the solution was added to methyl N,N-diisopropylchlorophosphoramidite (2.54 g, 12.8 mmol, 2.0 eq.) in dichloromethane (10 ml). The mixture was stirred at 45° C. for 10 minutes.

After cooling to room temperature, the mixture was poured to aqueous saturated sodium bicarbonate solution, extracted with chloroform, and then washed with brine. After drying over magnesium sulfate, the solvent was concentrated under reduced pressure. Over stirring, acetonitrile (20 ml) was added to the resulting residue. The precipitated object was collected by filtration to obtain Compound 33-16 (2.36 g, Yield 94%) as a white solid.

$^1$H-NMR (CDCl$_3$) δ:6.39 (t, J=5.5 Hz, 1H, —NH), 6.18 (t, J=5.5 Hz, 1H, —NH), 3.95 (m, 0.5H), 3.67-3.51 (m, 4.5H), 3.42 (s, 1.5H), 3.39 (s, 1.5H), 3.19-3.11 (m, 1H), 3.05-2.97 (m, 1H), 2.30-2.15 (m, 4H), 1.70-1.57 (m, 4H), 1.36-1.23 (m, 56H), 1.23-1.14 (m, 12H), 0.88 (t, J=6.5 Hz, 6H). $^{31}$P-NMR (CDCl$_3$) δ: 149.06

Step 7

To Compound 32 (700 mg, 1.18 mmol) and Compound 33-16 (1.87 g, 2.37 mmol, 2.0 eq.) dissolved in dichloromethane (14 ml), 1H-tetrazole (124 mg, 1.77 mmol, 1.5 eq.) was added, and the mixture was stirred at room temperature for 2 hours. 0.5 M DDTT solution ([(dimethyl-amino-methylidene)amino]-3H-1,2,4-dithiazolin-3-thion, 4.73 ml, dissolved in 3-picoline:acetonitrile=1:1) was added thereto, and the mixture was stirred at same temperature for 1 hour. The reaction mixture was diluted with ethyl acetate, washed with 10% citric acid solution, aqueous saturated sodium bicarbonate solution and brine in order, and then dried over magnesium sulfate. The solvent was concentrated under reduced pressure, and the resulting residue was purified by silica gel column chromatography (SiO$_2$:45 g, n-hexane:ethyl acetate:triethylamine=75:25:1→50:50:1) to obtain Compound 34-16 (1.19 g, Yield 79%) as colorless foam.

$^1$H-NMR (CDCl$_3$) δ:7.40-7.11 (m, 9H), 6.87-6.78 (m, 4H), 4.94-4.84 (m, 1H), 4.82-4.72 (m, 1H), 4.58-4.43 (m, 2H), 4.38-4.31 (m, 1H), 3.86-3.53 (m, 4H), 3.80 (s, 3H), 3.79 (s, 6H), 3.33-2.99 (m, 4H), 2.30-1.88 (m, 6H), 1.65-1.55 (m, 4H), 1.35-1.20 (m, 56H), 0.91-0.84 (m, 15H), 0.08 (s, 3H), 0.01 (s, 3H).

Step 8

To Compound 34-16 (1.02 g, 0.780 mmol) in THF (10 ml), 1 mol/l TBAF-THF (0.937 ml, 1.2 eq.) was added at room temperature, and the mixture was stirred at room temperature for 1 hour. The reaction mixture was concentrated under reduced pressure. The resulting residue was purified by silica gel column chromatography (SiO$_2$:30 g, chloroform:methanol:triethylamine=97.5:2.5:1→90:10:1) to obtain Compound 35-16 (608 mg, Yield 65%).

$^1$H-NMR (CDCl$_3$) δ:7.40-7.17 (m, 9H), 6.91 (m, 1H, —NH), 6.88-6.78 (m, 5H), 5.00-4.35 (m, 5H), 3.85-3.44 (m, 4H), 3.79 (s, 3H), 3.78 (s, 6H), 3.35-3.06 (m, 4H), 2.31-2.09 (m, 5H), 2.06-1.94 (m, 1H), 1.68-1.52 (m, 4H), 1.36-1.18 (m, 56H), 0.88 (t, J=7.0 Hz, 6H).

Step 9

To Compound 35-16 (210 mg, 0.176 mmol) in dichloromethane (3 ml), triethylamine (0.073 ml, 0.528 mmol, 3.0 eq.), succinic anhydride (35 mg, 0.352 mmol, 2.0 eq.) and DMAP (4 mg, 0.033 mmol) was added in order at room temperature, and the mixture was stirred at room temperature for 12 hours. The reaction mixture was concentrated under reduced pressure. The resulting residue was purified by silica gel column chromatography (SiO$_2$:24 g, chloroform:methanol:triethylamine=100:0:1→95:5:1) to obtain Compound 36-16 (172 mg, Yield 76%) as a colorless solid.

$^1$H-NMR (CDCl$_3$) δ:7.38-7.32 (m, 2H), 7.38-7.32 (m, 7H), 6.90-6.76 (m, 4H), 5.42 (br.s, 1H), 5.04-4.39 (m, 4H), 3.87-3.55 (m, 4H), 3.79 (s, 3H), 3.78 (s, 6H), 3.31-3.07 (m, 4H), 2.65-2.43 (m, 4H), 2.38-2.28 (m, 1H), 2.28-2.08 (m, 5H), 1.67-1.53 (m, 4H), 1.35-1.19 (m, 56H), 0.88 (t, J=6.5 Hz, 6H).

10) Synthesis of Compound 46-n

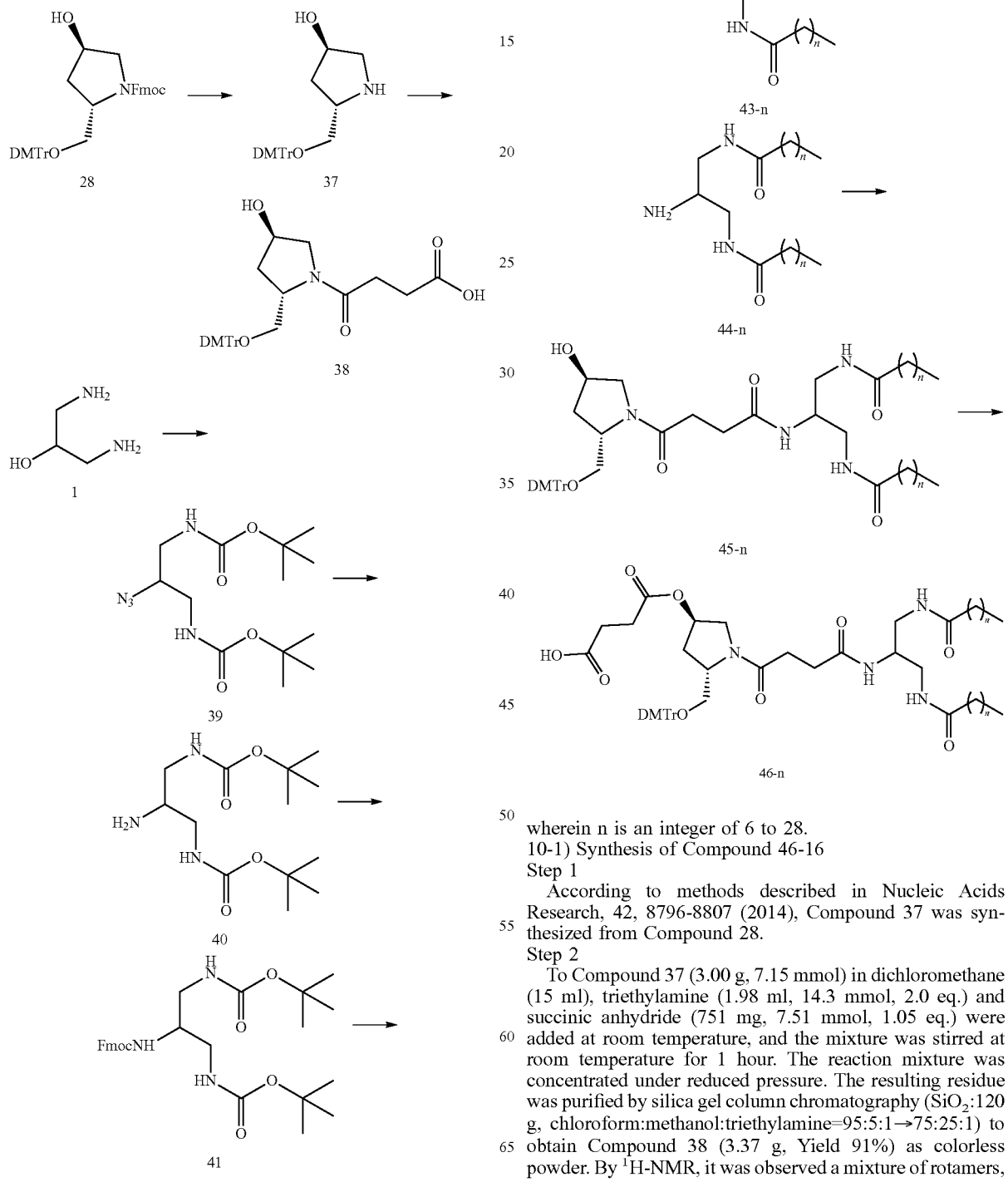

wherein n is an integer of 6 to 28.

10-1) Synthesis of Compound 46-16

Step 1

According to methods described in Nucleic Acids Research, 42, 8796-8807 (2014), Compound 37 was synthesized from Compound 28.

Step 2

To Compound 37 (3.00 g, 7.15 mmol) in dichloromethane (15 ml), triethylamine (1.98 ml, 14.3 mmol, 2.0 eq.) and succinic anhydride (751 mg, 7.51 mmol, 1.05 eq.) were added at room temperature, and the mixture was stirred at room temperature for 1 hour. The reaction mixture was concentrated under reduced pressure. The resulting residue was purified by silica gel column chromatography (SiO$_2$:120 g, chloroform:methanol:triethylamine=95:5:1→75:25:1) to obtain Compound 38 (3.37 g, Yield 91%) as colorless powder. By $^1$H-NMR, it was observed a mixture of rotamers, which is 63:37.

ESI-MS (m/z): 530 (M+H). HPLC Peak RT=1.86 min.

¹H-NMR (CDCl₃) δ:(Major) 7.39-7.33 (m, 2H), 7.30-7.22 (m, 6H), 7.22-7.16 (m, 1H), 6.85-6.77 (m, 4H), 4.50 (br.s, 1H), 4.41 (m, 1H), 3.88 (d, J=11.0 Hz, 1H), 3.775 (s, 6H), 3.65 (dd, J=11.0, 4.0 Hz, 1H), 3.43 (dd, J=9.2, 4.5 Hz, 1H), 3.14 (dd, J=9.2, 2.7 Hz, 1H), 2.85-1.97 (m, 6H). (Minor) 7.39-7.33 (m, 2H), 7.30-7.22 (m, 6H), 7.22-7.16 (m, 1H), 6.85-6.77 (m, 4H), 4.41 (m, 1H), 4.31 (br.s, 1H), 4.11 (d, J=12.3 Hz, 1H), 3.783 (s, 6H), 3.25 (dd, J=12.3, 3.5 Hz, 1H), 3.18 (dd, J=9.5, 4.8 Hz, 1H), 3.10 (dd, J=9.5, 4.8 Hz, 1H), 2.85-1.97 (m, 6H).

Step 3

According to methods described in Journal of Medicinal Chemistry, 48, 7781 (2005), Compound 39 was synthesized from Compound 1.

Step 4

To Compound 39 (3.00 g, 7.15 mmol) in a mixture of THF-water (9:1) (30 ml), triphenylphosphine (1.98 ml, 14.3 mmol, 2.0 eq.) was added at room temperature, and the mixture was stirred at room temperature for 1 hour. The temperature was raised up to 70° C., and the mixture was stirred for 4 hours. After cooling to room temperature, the reaction mixture was concentrated under reduced pressure to the crude product of obtain Compound 40 as colorless oil.

Step 5

To Compound 40 (7.15 mmol) in dichloromethane (30 ml), triethylamine (2.10 ml, 15.1 mmol, 1.2 eq.) and Fmoc-Cl (3.59 g, 13.9 mmol, 1.1 eq.) were added at room temperature, and the mixture was stirred at room temperature for 1 hour. The reaction mixture was diluted with chloroform, washed with brine, and then dried over magnesium sulfate. The solvent was concentrated under reduced pressure. The resulting solid was washed with n-hexane and a little of chloroform, and then purified by silica gel column chromatography (SiO₂:120 g, n-hexane:ethyl acetate=75:25→0:100) to obtain Compound 41 (4.18 g, Yield from Compound 39: 65%) as colorless foam.

ESI-MS (m/z): 512 (M+H). HPLC Peak RT=2.71 min.

¹H-NMR (CDCl₃) δ:7.80 (d, J=7.5 Hz, 2H), 7.60 (d, J=7.5 Hz, 2H), 7.40 (dd, J=7.5, 7.5 Hz, 2H), 7.30 (dd, J=7.5, 7.5 Hz, 2H), 6.02 (br.s, 1H), 5.21 (br.s, 2H), 4.46-4.27 (m, 2H), 4.21 (m, 1H), 3.59 (m, 1H), 3.45-3.29 (m, 2H), 3.27-3.13 (m, 2H), 1.46 (s, 18H).

Step 6

To Compound 41 (3.00 g, 7.15 mmol), TFA (30 ml) was added, and the mixture was stirred at room temperature for 1 hour. The mixture was concentrated under reduced pressure to obtain the crude product of Compound 42.

ESI-MS (m/z): 312 (M+H). HPLC Peak RT=1.00 min.

Step 7

To Compound 42 in dichloromethane (10 ml), triethylamine (1.17 ml, 8.44 mmol, 6.0 eq.) and stearoyl chloride (938 mg, 3.10 mmol, 2.2 eq.) was added at room temperature, and the mixture was stirred at room temperature for 1 hour. The resulting white precipitate was collected by filtration, washed with a little of chloroform, water and n-hexane, and then dried under reduced pressure to obtain Compound 43-16 (888 mg, Yield from Compound 40: 75%) as a colorless solid.

¹H-NMR (CDCl₃) δ:7.76 (d, J=7.5 Hz, 2H), 7.60 (d, J=7.5 Hz, 2H), 7.34 (d, J=7.5, 7.5 Hz, 2H), 7.31 (d, J=7.5, 7.5 Hz, 2H), 6.51 (br.s, 2H), 6.39 (br.s, 1H), 4.39-4.26 (m, 2H), 4.21 (m, 1H), 3.68-3.54 (m, 2H), 3.26-3.07 (m, 2H), 2.29-2.18 (m, 4H), 1.70-1.58 (m, 4H), 1.37-1.17 (m, 56H), 0.88 (t, J=7.0 Hz, 6H).

Step 8

To Compound 43-16 (860 mg, 1.02 mmol) in DMF solution (5 ml), piperidine (0.111 ml, 1.12 mmol, 1.1 eq.) was added, and the mixture was stirred at 80° C. for 1.5 hours. After standing still at room temperature for 2 hours, the resulting precipitate was collected by filtration, washed with n-hexane, and dried under reduced pressure. The resulting solid was purified by silica gel column chromatography (SiO₂:24 g, chloroform:methanol=98:2→75:25) to obtain Compound 44-16 (198 mg, Yield 31%) as a colorless solid.

¹H-NMR (CDCl₃) δ:6.34 (br.s, 2H), 3.48-3.36 (m, 2H), 3.06-2.98 (m, 2H), 2.99 (s, 1H), 2.25-2.18 (m, 4H), 1.70-1.58 (m, 4H), 1.37-1.18 (m, 56H), 0.88 (t, J=7.0 Hz, 6H).

Step 9

To Compound 38 (134 mg, 0.257 mmol) derived from Step 2 in DMF solution (2 mL), DIEA (225 µl, 1.29 mmol) and HBTU (127 mg, 0.334 mmol) were added at room temperature, and the mixture was stirred at room temperature for 10 minutes. The mixture was added to Compound 44-16 (218 mg, 17.1 mmol) in dichloromethane (3 mL) at 45° C., and then the mixture was stirred for 30 minutes at 45° C. The reaction mixture was washed with brine. After drying over magnesium sulfate, the solvent was concentrated under reduced pressure. The resulting residue was dissolved in ethyl acetate, and n-hexane was added thereto at 80° C. The precipitated solid was collected by filtration to obtain Compound 45-16 (244 mg, Yield 85%) as a colorless solid. By ¹H-NMR, it was observed a mixture of rotamers, which is 63:37.

¹H-NMR (CDCl₃) δ:(Major) 7.35-7.32 (m, 2H), 7.31-7.16 (m, 7H), 6.85-6.77 (m, 4H), 6.46 (br.s, 1H, —NH), 4.38 (br.s, 1H), 3.781 (s, 6H), 3.72-3.58 (m, 2H), 3.51-3.36 (m, 2H), 3.28-3.08 (m, 3H), 2.78-2.60 (m, 2H), 2.48-1.98 (m, 7H), 1.64-1.56 (m, 4H), 1.35-1.19 (m, 56H), 0.88 (t, J=7.0 Hz, 6H). (Minor) 7.35-7.32 (m, 2H), 7.31-7.16 (m, 7H), 6.85-6.77 (m, 4H), 6.46 (br.s, 1H, —NH), 4.53 (br.s, 1H), 3.783 (s, 6H), 3.72-3.58 (m, 2H), 3.51-3.36 (m, 2H), 3.28-3.08 (m, 3H), 2.48-1.98 (m, 7H), 1.64-1.56 (m, 4H), 1.35-1.19 (m, 56H), 0.88 (t, J=7.0 Hz, 6H).

Step 10

To Compound 45-16 (340 mg, 0.303 mmol) in dichloromethane (3 ml), triethylamine (0.237 ml, 1.71 mmol, 5.6 eq.), succinic anhydride (85 mg, 0.844 mmol, 2.8 eq.) and DMAP (4 mg) were added in order at room temperature. After the mixture was stirred at 45° C. for 2 hours, the reaction mixture was concentrated under reduced pressure. The resulting residue was purified by silica gel column chromatography (SiO₂:12 g, chloroform:methanol:triethylamine=100:0:1→80:20:1), and then washed with n-hexane to obtain Compound 46-16 (246 mg, Yield 66%) as a colorless solid. By ¹H-NMR, it was observed a mixture of rotamers, which is 77:23.

¹H-NMR (CDCl₃) δ:(Major) 7.38-7.31 (m, 2H), 7.31-7.12 (m, 6H), 7.17-7.11 (m, 1H), 7.00 (br.s, 1H), 6.85-6.77 (m, 4H), 6.74 (br.s, 1H, —NH), 5.33 (br.s, 1H), 4.34 (br.s, 1H), 3.90-3.74 (m, 2H), 3.788 (s, 6H), 3.64-3.37 (m, 2H), 3.35-3.11 (m, 2H), 3.11-2.92 (m, 2H), 2.68-2.07 (m, 11H), 1.68-1.51 (m, 4H), 1.37-1.16 (m, 56H), 0.88 (t, J=6.6 Hz, 6H). (Minor) 7.38-7.31 (m, 2H), 7.31-7.12 (m, 6H), 7.17-7.11 (m, 1H), 7.00 (br.s, 1H), 6.85-6.77 (m, 4H), 6.74 (br.s, 1H, —NH), 5.20 (br.s, 1H), 4.17 (br.s, 1H), 3.90-3.74 (m, 2H), 3.678 (a, 6H), 3.64-3.37 (m, 2H), 3.35-3.11 (m, 2H), 3.11-2.92 (m, 2H), 2.68-2.07 (m, 11H), 1.68-1.51 (m, 4H), 1.37-1.16 (m, 56H), 0.88 (t, J=6.6 Hz, 6H).

11) Synthesis of Compound 49-n

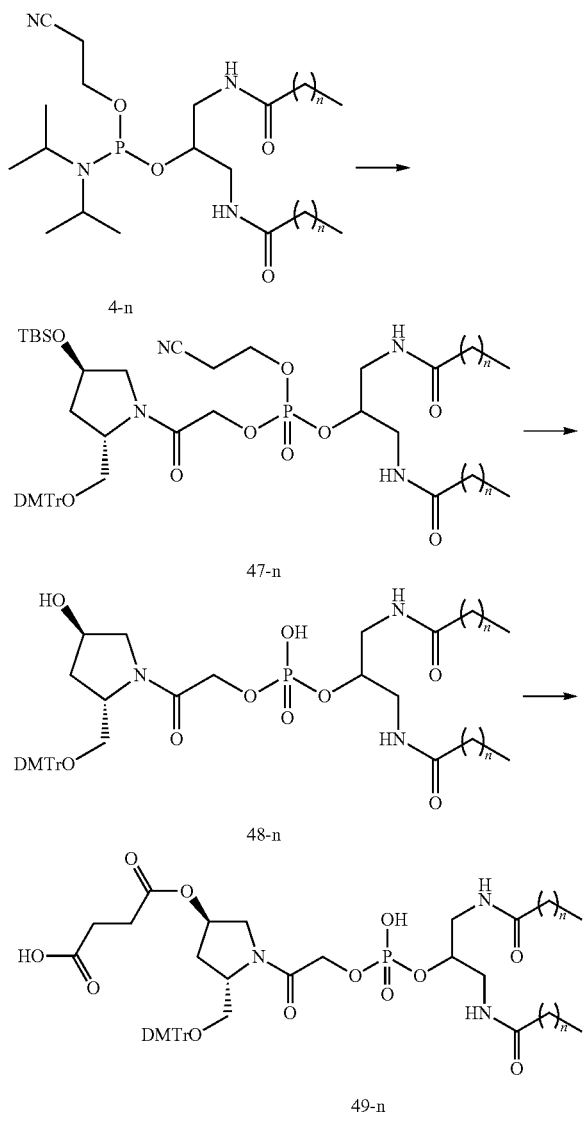

wherein n is an integer of 6 to 28.

11-1) Synthesis of Compound 49-16
Step 1
In a similar method to synthesis of Compound 34-16 described in 9-1), Compound 47-16 was obtained as colorless foam (Yield 78%).

$^1$H-NMR (CDCl$_3$) δ:7.34 (d, J=8.0 Hz, 2H), 7.31-7.21 (m, 6H), 7.18 (m, 1H), 6.87-6.79 (m, 4H), 3.78 (s, 6H), 2.25-2.02 (m, 5H), 1.94-1.84 (m, 1H), 1.64-1.49 (m, 4H), 1.33-1.16 (m, 56H), 0.88 (t, J=7.0 Hz, 6H), 0.87 (s, 9H), 0.06 (s, 6H).

Step 2
In a similar method to synthesis of Compound 35-16 described in 9-1), Compound 48-16 was obtained as colorless foam (Yield 61%).

ESI-MS (m/z) 1177 (M+). HPLC Peak RT=3.64 min.

$^1$H-NMR (CDCl$_3$) δ:7.35 (d, J=7.8 Hz, 2H), 7.31-7.16 (m, 7H), 6.87-6.78 (m, 4H), 4.98-4.49 (m, 3H), 4.48-4.31 (m, 2H), 3.91-3.44 (m, 5H), 3.78 (s, 6H), 3.37-3.08 (m, 4H), 2.27-2.11 (m, 5H), 2.08-1.94 (m, 1H), 1.66-1.52 (m, 4H), 1.34-1.21 (m, 56H), 0.88 (t, J=6.7 Hz, 6H).

Step 3
To Compound 48-16 (624 mg, 0.529 mmol) in dichloromethane (5 ml), triethylamine (0.330 ml, 2.39 mmol, 4.5 eq.), succinic anhydride (106 mg, 0.159 mmol, 3.0 eq.) and DMAP (13 mg, 10.6 μmol, 0.2 eq.) were added in order at room temperature, and the mixture was stirred at room temperature for 12 hours. The reaction mixture was concentrated under reduced pressure. The resulting residue was purified by silica gel column chromatography (SiO$_2$:24 g, chloroform:methanol:triethylamine=97.5:2.5:1→80:20:1) to obtain Compound 49-16 (482 mg, Yield 71%) as a colorless solid.

Although Compound 49-16 was a mixture of 2 kinds of isomers, a part of the mixture was separated by silica gel column chromatography and the various equipment data were measured.

Isomer 1 of Compound 49-16 (isomer which has higher Rf value based on TLC deploying with the solvent of chloroform:methanol=5:1): By $^1$H-NMR, it was observed a mixture of rotamers, which is 65:35.

ESI-MS (m/z): 1277 (M+). HPLC Peak RT=3.72 min.

$^1$H-NMR (CDCl$_3$) δ:(Major) 7.34 (d, J=7.5 Hz, 2H), 7.31-7.14 (m, 7H), 6.83 (d, J=8.3 Hz, 4H), 5.45 (br.s, 1H), 4.75 (dd, J=14.1, 8.3 Hz, 1H), 4.55-4.38 (m, 2H), 4.33 (m, 1H), 3.79 (s, 6H), 3.72-3.48 (m, 4H), 3.44-3.08 (m, 4H), 2.70-2.44 (m, 4H), 2.38-2.14 (m, 6H), 1.68-1.51 (m, 4H), 1.34-1.21 (m, 56H), 0.88 (t, J=6.7 Hz, 6H). (Minor) 7.34 (d, J=7.5 Hz, 2H), 7.31-7.14 (m, 7H), 6.83 (d, J=8.3 Hz, 4H), 5.20 (br.s, 1H), 4.84 (m, 1H), 4.55-4.38 (m, 2H), 4.33 (m, 1H), 3.79 (s, 6H), 3.72-3.48 (m, 4H), 3.44-3.08 (m, 4H), 2.70-2.44 (m, 4H), 2.38-2.14 (m, 6H), 1.68-1.51 (m, 4H), 1.34-1.21 (m, 56H), 0.88 (t, J=6.7 Hz, 6H). $^{31}$P-NMR (CDCl$_3$) δ: 58.1

Isomer 2 of Compound 49-16 (isomer which has lower Rf value based on TLC deploying with the solvent of chloroform methanol=5:1)

ESI-MS (m/z): 1277 (M+). HPLC Peak RT=3.72 min.

$^1$H-NMR (CDCl$_3$) δ:7.83 (br.s, 1H), 7.37-7.10 (m, 9H), 6.74 (d, J=8.6 Hz, 4H), 5.30 (br.s, 1H), 4.62 (dd, J=14.0, 9.2 Hz, 1H), 4.42-4.33 (m, 2H), 4.30 (dd, J=14.0, 9.2 Hz, 1H), 3.71 (s, 6H), 2.63-2.34 (m, 4H), 2.31-2.21 (m, 1H), 2.16-2.03 (m, 5H), 1.59-1.42 (m, 4H), 1.24-1.09 (m, 56H), 0.81 (t, J=6.7 Hz, 6H). $^{31}$P-NMR (CDCl$_3$) δ: 57.3

12) Synthesis of Compound 50-n

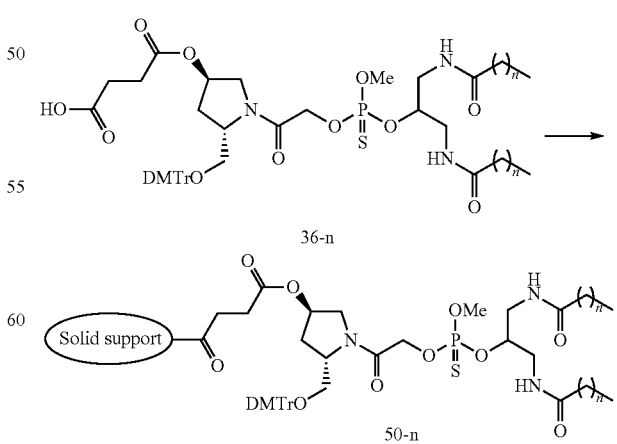

wherein n is an integer of 6 to 28.

12-1) Synthesis of Compound 50-16

Compound 50-16 was obtained by subjecting Compound 36-16 obtained from 9-1) to the similar condition of a reaction to support on solid resin in 4). The supported amount of Compound 36-16 was calculated by colorimetric assay of the DMTr cation, and Compound 50-16 whose supported amount is 32 umol/g was obtained.

In a similar method, Compound 49-n can be supported on solid resin.

13) Synthesis of Compound 51-n

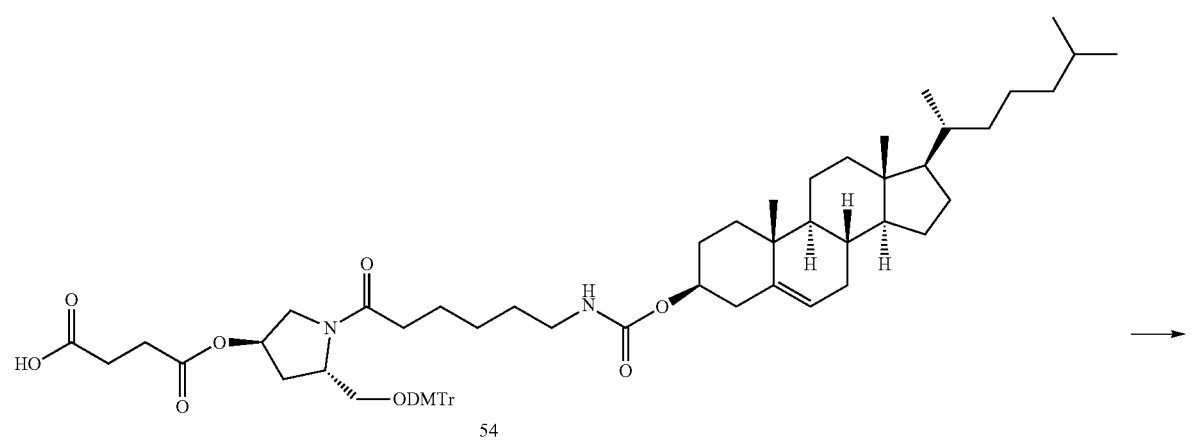

46-n

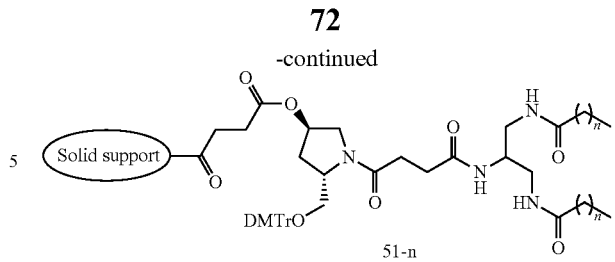

51-n wherein n is an integer of 6 to 28.

13-1) Synthesis of compound 51-16

Compound 51-16 was obtained by subjecting Compound 46-16 obtained from 10-1) to the similar condition of a reaction to support on solid resin in 4). The supported amount of Compound 46-16 was calculated by colorimetric assay of the DMTr cation, and Compound 51-16 whose supported amount is 33 umol/g was obtained.

14) Synthesis of compound 55

54

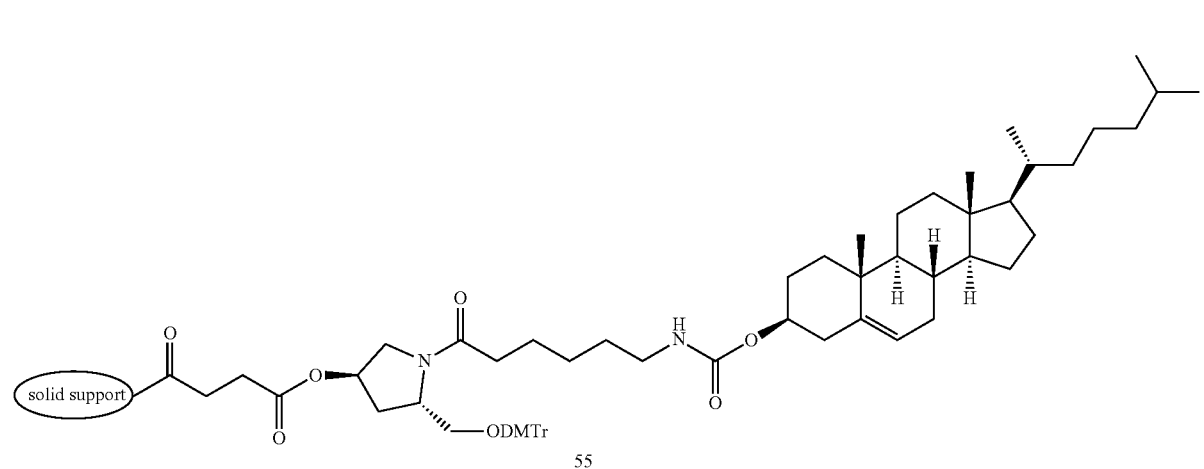

55

Compound 55 was obtained by subjecting Compound 54 described in US2008/0085869 to the similar condition of a reaction to support on solid resin in 4). The supported amount of Compound 54 was calculated by colorimetric assay of the DMTr cation, and Compound 55 whose supported amount is 90 umol/g was obtained.
15) Synthesis of compound 63-n
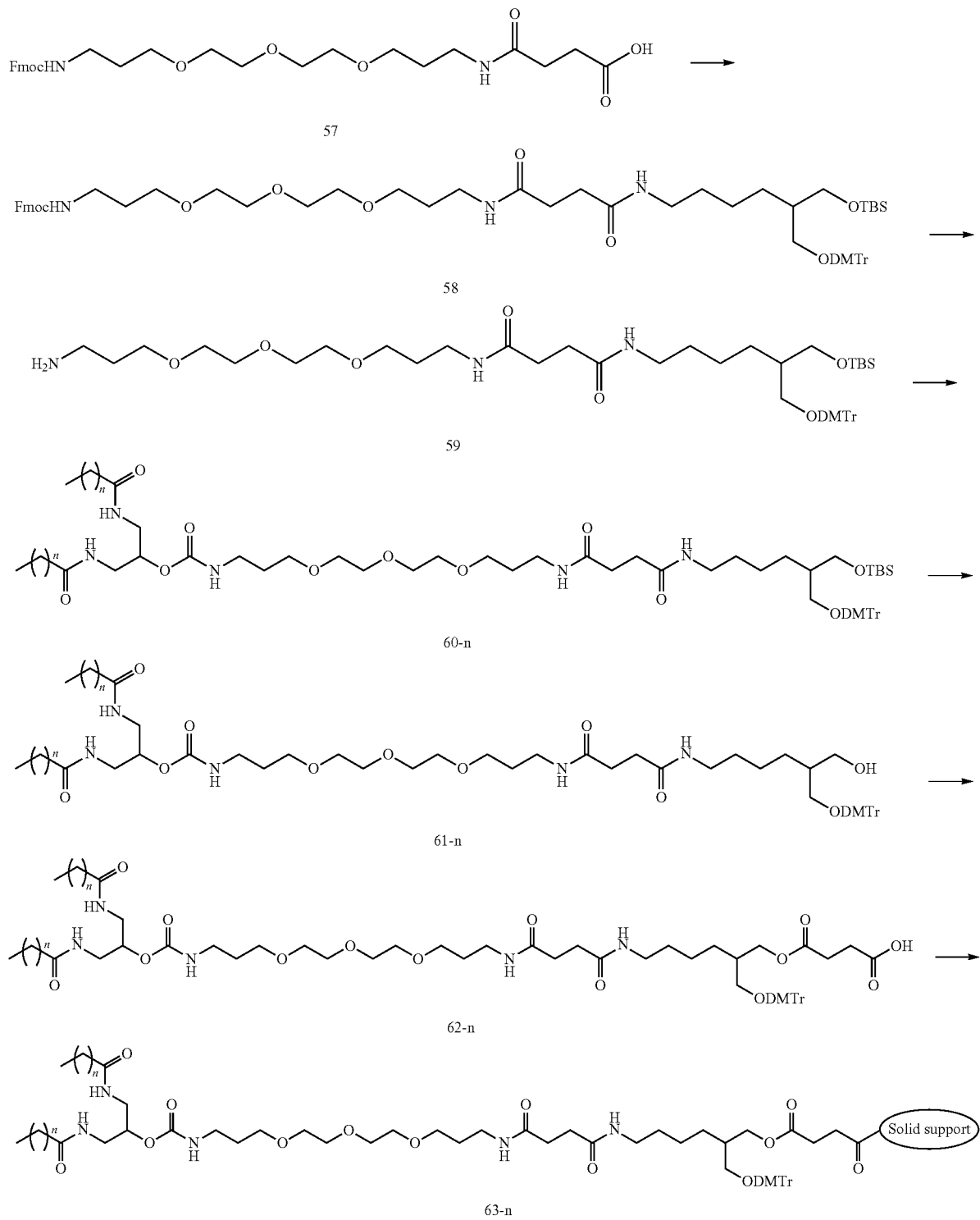
wherein n is an integer of 6 to 28.

15-1) Synthesis of Compound 63-18
Step 1
To Compound 57 (Sigma-Aldrich, 0.517 g, 0.952 mmol) in DMF solution (4.9 mL), DIEA (0.447 mL, 3.46 mmol) and HBTU (349 mg, 1.04 mmol) were added, and the mixture was stirred at room temperature for 30 minutes. Then, Compound 17 (0.488 g, 0.865 mmol) in DMF solution was added thereto, and the mixture was stirred overnight. After separating and extracting with hexane/ethyl acetate=1:1 (2×50 mL) and aqueous saturated sodium bicarbonate solution (50 mL), the organic layers were combined, washed with brine (50 mL), and dried over magnesium sulfate. After filtrating, it was concentrated by rotary evaporator under reduced pressure, and purified by silica gel column chromatography (chloroform:methanol=100:0→70:30) to give Compound 58 (0.837 g, 85%) as a colorless solid.

1H-NMR (CDCl$_3$) δ: 7.75 (2H, d, J=7.5 Hz), 7.60 (2H, d, J=7.4 Hz), 7.42-7.38 (4H, m), 7.32-7.28 (7H, m), 7.24 (1H, s), 7.18 (1H, t, J=7.3 Hz), 6.81 (4H, d, J=8.9 Hz), 6.49 (1H, s), 6.08 (1H, s), 5.56 (1H, s), 4.39 (2H, d, J=6.9 Hz), 4.21 (1H, t, J=6.7 Hz), 3.79 (6H, s), 3.63-3.52 (15H, m), 3.34-3.28 (4H, m), 3.14 (2H, dd, J=13.9, 6.4 Hz), 3.03 (2H, d, J=5.6 Hz), 1.80-1.65 (5H, m), 1.63 (4H, s), 1.43-1.36 (2H, m), 1.31-1.26 (2H, m), 1.18-1.12 (2H, m), 0.84 (9H, s), 0.01 (6H, s).

Step 2
To Compound 58 (800 mg, 0.735 mmol) in DMF solution (8 mL), piperidine (80 uL) was added, and the mixture was stirred at room temperature for 2 hours. After separating and extracting with hexane/ethyl acetate=1:4 and water, it was dried over anhydrous sodium sulfate overnight. After filtrating, it was concentrated by rotary evaporator under reduced pressure, and purified by amino silica gel column chromatography (chloroform:methanol=100:0→97:3) to give Compound 59 (0.178 g, 0.205 mmol) as colorless oil.

$^1$H-NMR (CDCl$_3$) δ: 7.37 (8H, dt, J=50.4, 5.2 Hz), 7.26-7.18 (2H, m), 6.89 (1H, s), 6.82 (4H, t, J=5.9 Hz), 6.25 (1H, t, J=5.1 Hz), 3.81 (6H, s), 3.66-3.53 (15H, m), 3.35 (2H, q, J=6.0 Hz), 3.16 (2H, dd, J=13.9, 6.5 Hz), 3.04 (2H, d, J=5.5 Hz), 2.80 (2H, t, J=6.7 Hz), 1.80-1.17 (17H, m), 0.85 (9H, s), 0.03-0.01 (6H, m).

Step 3
After Compound 3-18 (140 mg, 0.205 mmol) and DMAP (63 mg, 0.514 mmol) were broken into small pieces in a flask, it dissolved in THF (1.8 mL). bis(4-nitrophenyl) carbonate (156 mg, 0.514 mmol) was added thereto, the mixture was stirred at 55° C. for 30 minutes. After cooling to room temperature, THF was concentrated under reduced pressure, and the residue was suspended in acetonitrile (10 mL) again. After heating to be almost solution, it cooled to room temperature, and the solid was precipitated. Then, the precipitation is promoted by ultrasonic breaking. The precipitated solid was collected by filtration, washed with acetonitrile (10 mL), water (10 mL) and acetonitrile (10 mL) in order, and then dried under vacuum to give Compound 18-18 (196 mg, 0.232 mmol) as a pale yellow solid. Compound 18-18 (196 mg) was dissolved in THF (1.8 mL). Compound 59 (178 mg, 0.205 mmol) and DMAP (25 mg, 0.205 mmol) were added thereto, and the mixture was stirred at 55° C. for 2 hours. After cooling to room temperature, the solid was precipitated, and acetonitrile (18 mL) was added thereto. After heating and ultrasonic breaking, water (1.8 mL) was added thereto, and then the object, Compound 60-18 (251 mg, 0.160 mmol) as a pale yellow solid, was obtained by filtration with a Kyriyama funnel.

Step 4
After Compound 60-18 (246 mg, 0.157 mmol) in THF (4.9 mL) was cooled by ice-water bath, TBAF solution (1 M THF, 495 uL, 0.495 mmol) was added thereto, and the mixture was stirred and warmed to room temperature for 30 minutes. After the solvent was concentrated under reduced pressure, the resulting crude product was purified by amino silica gel column chromatography (only chloroform) to give Compound 61-18 (192 mg, 0.132 mmol) as a colorless solid.

1H-NMR (CDCl$_3$) δ: 7.41 (2H, d, J=7.3 Hz), 7.30 (5H, dd, J=8.9, 2.1 Hz), 7.21 (1H, t, J=7.2 Hz), 6.83 (5H, d, J=8.7 Hz), 6.76 (1H, t, J=6.2 Hz), 6.44 (1H, t, J=6.6 Hz), 5.63 (1H, t, J=5.7 Hz), 4.72-4.66 (1H, m), 3.79 (6H, s), 3.76-3.74 (1H, m), 3.64-3.48 (17H, m), 3.39-3.14 (6H, m), 3.06 (2H, dd, J=9.0, 7.6 Hz), 2.76 (1H, t, J=5.8 Hz), 2.50-2.46 (6H, m), 2.19 (6H, t, J=7.6 Hz), 1.79-1.73 (7H, m), 1.49-1.42 (6H, m), 1.24 (68H, d, J=11.8 Hz), 0.89-0.87 (6H, t, J=6.3 Hz).

Step 5
To Compound 61-18 (191 mg, 0.131 mmol) in dichloromethane (1.9 mL), DIEA (0.069 mL, 0.393 mmol), DMAP (1.6 mg, 0.013 mmol) and succinic anhydride (20 mg, 0.197 mmol) were added, and the mixture was stirred under reflux for 3 hours. The solvent was concentrated under reduced pressure, and the residue was purified by diol silica gel column chromatography (only chloroform) to give Compound 62-18 (201 mg, 0.129 mmol) as a colorless solid.

1H-NMR (CDCl$_3$) δ: 7.42 (2H, d, J=7.4 Hz), 7.30 (5H, d, J=8.7 Hz), 7.19 (1H, t, J=7.2 Hz), 6.81 (5H, d, J=8.7 Hz), 6.74 (1H, t, J=5.8 Hz), 6.26 (1H, t, J=5.9 Hz), 5.55 (1H, t, J=5.9 Hz), 4.72-4.67 (1H, m), 3.79 (6H, s), 3.58-3.49 (17H, m), 3.32-3.27 (6H, m), 3.14 (2H, q, J=6.5 Hz), 3.04 (2H, d, J=5.4 Hz), 2.49-2.46 (4H, m), 2.20 (5H, t, J=7.5 Hz), 1.76-1.72 (4H, m), 1.65-1.62 (10H, m), 1.42-1.41 (3H, m), 1.25 (68H, s), 0.88 (6H, t, J=6.6 Hz).

Step 6
After Compound 62-18 (153 mg, 0.098 mmol) was dissolved in a mixture of acetonitrile/dichloromethane (1:1, 10 mL), DIEA (0.067 mL, 0.392 mmol) and HBTU (41 mg, 0.108 mmol) were added, and the mixture was shaken at room temperature for 20 minutes. To the reaction mixture, Native Amino lcaa CPG 1000 Å (ChemGenes Corporation) (1.0 g) was added, and the mixture was shaken for 24 hours. After the reaction mixture was filtered, CPG resin was washed twice with acetonitrile, twice with dichloromethane and twice with diethyl ether, and dried under reduced pressure. To the dried CPG, a mixture of CapA (PROLIGO, L840045-06) and CapB (PROLIGO, L850045-06) (1:1, 20 mL) was added, and the mixture was shaken for 30 minutes. After the reaction mixture was filtered, CPG resin was washed twice with acetonitrile, twice with dichloromethane and twice with diethyl ether, and dried under reduced pressure. The supported amount of Compound 62-18 was calculated by colorimetric assay of the DMTr cation, and Compound 63-18 whose supported amount is 56 umol/g was obtained.

B) Synthesis of Oligonucleotides
Oligonucleotides used in examples of this description were synthesized using phosphoramidite method by AKTA Oligopilot10 (GE Healthcare), NS-8-I (Dainippon Seiki co., ltd.) or NS-8-II (Dainippon Seiki co., ltd.). A monomer was prepared in 0.1 M acetonitrile solution using the amidite derived from the above amidite synthesis. The coupling time was 32 seconds to 10 minutes, and 8 to 10 equivalents of the amidite unit were used to condense with one monomer. 0.02 M Oxidizer (Sigma-Aldrich) and iodine/pyridine/water/= 12.7/9/1 (w/v/v) were used for PO oxidation. 50 mM DDTT ((dimethylamino-methylidyne) amino-3H-1,2,4-dithiazoline-3-thion) in acetonitrile/3-picoline 1/1 (v/v) or 1/4 (v/v) and acetonitrile/pyridine 1/4 (v/v) solution were used for PS oxidation. ETT activator (5-ethylthio)-1H-tetrazole) (Sigma-Aldrich) was used as an activator, CapA and CapB (Sigma-Aldrich) was used as a capping reagent. Deb (3 w/v % TCA $CH_2Cl_2$ solution) (Wako Pure Chemical Industries, Ltd.) or Deb (3 w/v % Dichloroacetic acid, Toluene Solution) was used as a detritylation reagent.

SEQ-321, SEQ-323, SEQ-340, SEQ-343, SEQ-346, SEQ-349, SEQ-352, SEQ-355 and SEQ-358 were derived by providing Compound 22-18 to GeneDesign Inc. to consign nucleic synthesis and purification of oligonucleotides. DMT-butanediol phosphoramidite used for synthesis of SEQ-316 were purchased from ChemGenes Corporation.

C) Synthesis of Lipid-Binding Oligonucleotides

1) Preparation of Lipid-Binding Oligonucleotides from the Synthesized Amidite Unit Described Above A stirrer, Molecular Sieves 4A 1/16 and the amidite synthesized in the above A) (e.g., Compound 4-n, Compound 4-n,o, Compound 8-n and Compound 10-n. 10 to 100 equivalents of an oligonucleotide) were put in a microwave tube (2-5 ml, 10-20 ml) made by Biotage, and the solution was adjusted to 0.2 M with chloroform (added 2-methyl-2-butane as a stabilizer). After drying for 5 hours, a oligonucleotides supported to solid phase (CPG resin or polystyrene resin) and 0.25 M ETT activator, which is ((5-ethylthio)-1H-tetrazole) dichloromethane (the same amount of chloroform) were added, sealed and heated at 40° C. for 10 minutes to 1 hour. After cooling to room temperature, the reaction mixture was diluted twice with chloroform, and the resin was collected by filtration. The resulting resin was used in PS oxidation in NS-8-I (Dainippon Seiki co., ltd.) or NS-8-II (Dainippon Seiki co., ltd.). Then the dried resin was subject to the following deprotection condition I or II to synthesize the target lipid-binding oligonucleotide.

2) Synthesis from Lipid-Supported Resin

Using a resin supported lipid synthesized in the above A) (e.g., Compound 15-n, Compound 22-n, Compound 50-n, Compound 51-n, Compound 55 and Compound 63-n), the target lipid-binding oligonucleotides were synthesized in a similar method to the above B).

D) Deprotection

1) Cleavage from the Resin, and Phosphate Deprotection and Base Deprotection

For cutting out DNA oligonucleotide, 28% ammonia water (SEQ-1, 3 or 49) or 28% ammonia water/EtOH4/1 (v/v)(Single strand oligonucleotides described in Examples except for SEQ-1, 3 and 49) was used and the solution was shaken at room temperature for 1 hour and at 55° C. for 5 hours. 1 ml, 5 ml or 10 ml of ammonia solution was used for 1 µmol, 5 µmol or 10 µmol synthesis, respectively, for cutting-out reaction. After the resin was washed with 50% ethanol water, the filtrate was concentrated under reduced pressure to about 1 to 5 mL.

When the sequence contains RNA, the resulting solution was lyophilized to obtain white powder, and then the following deprotection reaction of the 2'-TBS group was performed.

2) Deprotection of 2'-TBS Group

To the resulting white powder, N-methylpyrrolidone/triethylamine/triethylamine trihydrofluoride=6/1/2 (v/v) was added and the solution was stirred at 65° C. for 1.5 hours. To the reaction mixture was added the same amount of ethoxytrimethylsilane, and the solution was vigorously stirred at room temperature for 10 minutes to obtain the precipitate. After centrifugation at 2500×g (2 minutes), the organic solvent layer was carefully removed. To the resulting precipitate, diethyl ether was added, and the solution was vigorously stirred. Then, in a similar way, the centrifugation was carried out and removed the organic solvent to obtain crude RNA unit (white solid).

E) Purification

Oligonucleotides without a lipid ligand such as SEQ-1, 3 and 49 were purified by reversed phase HPLC in Condition 1.

Condition for Reversed Phase HPLC

Condition 1

Mobile Phases

Buffer A: 100 mM TEAA (triethylammoniumacetate, pH 7.0) aqueous solution or 100 mM AcONa aqueous solution (pH5.4)

Buffer B: acetonitrile

B concentration gradient: 10-30%

(Condition 1-1)

Column: Hydrosphere C18 (YMC co., ltd.) 100×20 mm I.D., S-5 µm, 12 nm

Flow rate: 10 mL/min

Column temperature: room temperature

Detection UV: 260 nm (Condition 1-2)

Column: Hydrosphere C18 (YMC co., ltd.) 150×10 mm I.D., S-5 µm, 12 nm

Flow rate: 4 mL/min

Column temperature: room temperature

Detection UV: 260 nm

Single strand oligonucleotides with a lipid ligand(s) (Single strand oligonucleotides described in Examples except for SEQ-1, 3 and 49) was purified by reversed phase HPLC in Condition 2.

Condition 2

Condition for reversed phase HPLC

According to lipid solubility of the compound, B concentration at the beginning was adjusted from 20% to 50%.

Mobile Phases

Buffer A: 100 mM TEAA (Triethylammonium acetate pH7.0) aqueous solution or 100 mM AcONa aqueous solution (pH5.4)

Buffer B: acetonitrile

B concentration gradient: 20-80% (compounds having $L_{4\text{-}8}$ or $L_{4\text{-}10}$), 30-60% (compounds having $L_{Toc}$ or $L_{chol}$), 30-80% (compounds having $L_{4\text{-}12}$, $L_{4\text{-}14}$, $L_{4\text{-}16}$, $L_{4\text{-}18}$, $M_{22\text{-}12}$ or $M_{51\text{-}16}$), 40-80% (compounds having $L_{4\text{-}20}$ or $L_{4\text{-}22}$), 50-80% (compounds having $M_{22\text{-}18}$)

(Condition 2-1)

Column: YMC-Pack C4 (YMC co., ltd.) 100×20 mm I.D., S-5 µm, 12 nm

Flow rate: 10 mL/min

Column temperature: room temperature

Detection UV: 260 nm (Condition 2-2)

Column: YMC-Pack C4 (YMC co., ltd.) 150×10 mm I.D., S-5 µm, 12 nm

Flow rate: 4 mL/min

Column temperature: room temperature

Detection UV: 260 nm

F) Desalting and Freeze-Drying of the Purified Oligonucleotide

Using VivaSpin20 (MWCO 3000) (Sartorius) and Amicon Ultra-4 Centrifugal Filter Units-3K, ultrafiltration was repeated for the resulting oligonucleotide to remove salt component from the fraction. Then, it was lyophilized to obtain the target oligonucleotide as powder. For the oligonucleotides purified using TEAA solvent, the desalting procedure was carried out after transforming the salt form with 100 mM sodium acetate solution (20 mL).

G) Purity Analysis of Oligonucleotides

The resulting oligonucleotide was confirmed as the target sequence by matching the found molecular weights determined by UPLC/MS measurement and the calculated molecular weights.

Condition 1 (SEQ-1, 3 or 49)
Xevo G2 Tof System (Waters)
Column: Aquity OST C18 (2.1×50 mm) (Waters)
Mobile Phases
  Buffer A: 200 mM 1,1,1,3,3,3-hexafluoro-2-propanol/8 mM triethylamine aqueous solution
  Buffer B: methanol
  B concentration gradient: 10-30% (10 min)
  Temperature: 50° C.
  Flow rate: 0.2 mL/min Condition 2 (Single Strand Oligonucleotides Described in Examples Except for SEQ-1, 3 and 49)
Xevo G2 T of System (Waters)
Column: ACQUITY UPLC Protein BEH C4 Column, 300 Å, 1.7 μm, 2.1 mm×100 mm, 1/pkg (Waters)
Mobile Phases
  Buffer A: 200 mM 1,1,1,3,3,3-hexafluoro-2-propanol/8 mM triethylamine aqueous solution
  Buffer B: methanol
  B concentration gradient: 10-95% (10 min)
  Temperature: 50° C.
  Flow rate: 0.2 mL/min The results were shown in Tables 1 to 3.

TABLE 1

| No. | Theoretical Mw [M − H]− | Found Mw [M] |
|---|---|---|
| SEQ-1 | 6363 | 6365 |
| SEQ-2 | 7064 | 7065 |
| SEQ-3 | 6254 | 6256 |
| SEQ-5 | 6955 | 6955 |
| SEQ-7 | 3842 | 3842 |
| SEQ-9 | 5367 | 5367 |
| SEQ-11 | 6731 | 6731 |
| SEQ-13 | 6843 | 6843 |
| SEQ-15 | 7012 | 7011 |
| SEQ-17 | 6698 | 6699 |
| SEQ-19 | 6369 | 6370 |
| SEQ-21 | 6040 | 6040 |
| SEQ-23 | 5736 | 5736 |
| SEQ-25 | 5423 | 5423 |
| SEQ-27 | 5133 | 5134 |
| SEQ-29 | 4829 | 4829 |
| SEQ-31 | 4500 | 4500 |
| SEQ-33 | 4211 | 4211 |
| SEQ-35 | 3898 | 3898 |
| SEQ-37 | 7570 | 7570 |
| SEQ-39 | 7291 | 7291 |
| SEQ-41 | 7330 | 7331 |
| SEQ-43 | 5844 | 5845 |
| SEQ-45 | 7363 | 7363 |
| SEQ-47 | 7419 | 7419 |
| SEQ-49 | 7697 | 7698 |
| SEQ-50 | 8211 | 8212 |
| SEQ-52 | 7569 | 7568 |
| SEQ-54 | 6967 | 6966 |
| SEQ-56 | 6348 | 6348 |
| SEQ-58 | 5722 | 5722 |
| SEQ-60 | 5409 | 5409 |
| SEQ-62 | 6049 | 6050 |
| SEQ-64 | 6099 | 6099 |
| SEQ-66 | 8932 | 8933 |
| SEQ-68 | 5859 | 5860 |
| SEQ-70 | 6816 | 5817 |

TABLE 1-continued

| No. | Theoretical Mw [M − H]− | Found Mw [M] |
|---|---|---|
| SEQ-72 | 6451 | 8452 |
| SEQ-74 | 5161 | 5160 |
| SEQ-76 | 5117 | 5116 |
| SEQ-78 | 5554 | 5554 |
| SEQ-80 | 5610 | 5610 |
| SEQ-82 | 5666 | 5666 |
| SEQ-84 | 6798 | 6799 |
| SEQ-86 | 6854 | 6855 |
| SEQ-88 | 6910 | 6911 |
| SEQ-90 | 8451 | 8452 |
| SEQ-92 | 8451 | 8452 |
| SEQ-94 | 8451 | 8452 |
| SEQ-96 | 8563 | 8564 |
| SEQ-98 | 8731 | 8733 |
| SEQ-100 | 8675 | 8677 |
| SEQ-102 | 8731 | 8733 |
| SEQ-104 | 8395 | 8396 |
| SEQ-106 | 8507 | 8508 |
| SEQ-108 | 8563 | 8564 |
| SEQ-110 | 6042 | 6042 |
| SEQ-112 | 6362 | 6363 |
| SEQ-114 | 7323 | 7323 |
| SEQ-116 | 6067 | 6067 |
| SEQ-118 | 6412 | 6413 |
| SEQ-120 | 7448 | 7447 |
| SEQ-122 | 7287 | 7287 |
| SEQ-124 | 7607 | 7607 |
| SEQ-126 | 8568 | 8569 |
| SEQ-128 | 7312 | 7812 |
| SEQ-130 | 7657 | 7658 |
| SEQ-132 | 8693 | 8693 |
| SEQ-134 | 8385 | 8386 |
| SEQ-136 | 5598 | 5599 |
| SEQ-138 | 8216 | 8218 |
| SEQ-140 | 5430 | 5431 |
| SEQ-142 | 8399 | 8398 |
| SEQ-143 | 9089 | 9090 |
| SEQ-144 | 8652 | 8651 |
| SEQ-145 | 5426 | 5427 |
| SEQ-147 | 5410 | 5410 |
| SEQ-149 | 5470 | 5470 |

TABLE 2

| No. | Theoretical Mw [M − H]− | Found Mw [M] |
|---|---|---|
| SEQ-151 | 6758 | 6758 |
| SEQ-153 | 7102 | 7102 |
| SEQ-155 | 7793 | 7793 |
| SEQ-157 | 8139 | 8139 |
| SEQ-159 | 8484 | 8484 |
| SEQ-161 | 7761 | 7761 |
| SEQ-163 | 8074 | 8075 |
| SEQ-165 | 5912 | 5912 |
| SEQ-167 | 6602 | 6603 |
| SEQ-169 | 7638 | 7638 |
| SEQ-171 | 6380 | 6380 |
| SEQ-173 | 7368 | 7368 |
| SEQ-175 | 5782 | 5785 |
| SEQ-177 | 6408 | 6408 |
| SEQ-179 | 7509 | 7508 |
| SEQ-181 | 8481 | 8482 |
| SEQ-183 | 5694 | 5695 |
| SEQ-185 | 6073 | 6075 |
| SEQ-187 | 6764 | 6765 |
| SEQ-189 | 7800 | 7801 |
| SEQ-191 | 6129 | 6130 |
| SEQ-193 | 6820 | 6819 |
| SEQ-195 | 7856 | 7856 |
| SEQ-197 | 6017 | 6018 |
| SEQ-199 | 6707 | 6709 |

TABLE 2-continued

| No. | Theoretical Mw [M − H]− | Found Mw [M] |
|---|---|---|
| SEQ-201 | 6073 | 6074 |
| SEQ-203 | 6764 | 6766 |
| SEQ-205 | 6007 | 6008 |
| SEQ-207 | 6063 | 6063 |
| SEQ-209 | 6119 | 6120 |
| SEQ-211 | 6698 | 6698 |
| SEQ-213 | 6754 | 6754 |
| SEQ-215 | 6810 | 6812 |
| SEQ-217 | 6119 | 6119 |
| SEQ-219 | 6175 | 6177 |
| SEQ-221 | 6810 | 6811 |
| SEQ-223 | 6867 | 6869 |
| SEQ-225 | 6192 | 6192 |
| SEQ-227 | 6028 | 6027 |
| SEQ-229 | 5992 | 5992 |
| SEQ-231 | 6048 | 6049 |
| SEQ-233 | 5987 | 5987 |
| SEQ-235 | 8370 | 8370 |
| SEQ-237 | 6700 | 6701 |
| SEQ-239 | 7390 | 7392 |
| SEQ-241 | 6756 | 6757 |
| SEQ-243 | 7446 | 7448 |
| SEQ-245 | 6644 | 6645 |
| SEQ-247 | 7334 | 7336 |
| SEQ-249 | 6700 | 6701 |
| SEQ-251 | 7390 | 7391 |
| SEQ-253 | 6348 | 6349 |
| SEQ-254 | 5793 | 5792 |
| SEQ-256 | 6326 | 6328 |
| SEQ-257 | 5615 | 5615 |
| SEQ-259 | 5687 | 5687 |
| SEQ-261 | 5743 | 5743 |
| SEQ-263 | 5967 | 5968 |
| SEQ-265 | 6023 | 6024 |
| SEQ-267 | 5951 | 5952 |
| SEQ-269 | 6007 | 6010 |
| SEQ-271 | 6063 | 6064 |
| SEQ-273 | 6642 | 6642 |
| SEQ-275 | 6698 | 6699 |
| SEQ-277 | 6754 | 6754 |
| SEQ-279 | 6468 | 6469 |
| SEQ-281 | 6524 | 6525 |
| SEQ-283 | 6552 | 6553 |
| SEQ-285 | 7609 | 7608 |
| SEQ-287 | 7196 | 7196 |
| SEQ-289 | 8441 | 8442 |
| SEQ-291 | 7252 | 7252 |
| SEQ-293 | 8498 | 8499 |
| SEQ-295 | 7180 | 7184 |
| SEQ-297 | 7236 | 7240 |
| SEQ-299 | 7292 | 7296 |
| SEQ-301 | 7870 | 7873 |
| SEQ-303 | 7926 | 7929 |

TABLE 3

| No. | Theoretical Mw [M − H]− | Found Mw [M] |
|---|---|---|
| SEQ-305 | 7983 | 7986 |
| SEQ-307 | 8425 | 8426 |

TABLE 3-continued

| No. | Theoretical Mw [M − H]− | Found Mw [M] |
|---|---|---|
| SEQ-309 | 8537 | 8541 |
| SEQ-311 | 9115 | 9118 |
| SEQ-313 | 9171 | 9175 |
| SEQ-315 | 9227 | 9230 |
| SEQ-317 | 6247 | 6248 |
| SEQ-319 | 6213 | 6214 |
| SEQ-321 | 6109 | 6107 |
| SEQ-323 | 4248 | 4249 |
| SEQ-325 | 7236 | 7238 |
| SEQ-327 | 7392 | 7293 |
| SEQ-329 | 7348 | 7350 |
| SEQ-331 | 7926 | 7929 |
| SEQ-333 | 7983 | 7985 |
| SEQ-335 | 8039 | 8041 |
| SEQ-337 | 5619 | 5619 |
| SEQ-339 | 6433 | 6434 |
| SEQ-340 | 5775 | 5773 |
| SEQ-342 | 7342 | 7341 |
| SEQ-343 | 5936 | 5934 |
| SEQ-345 | 8341 | 8339 |
| SEQ-346 | 5944 | 5942 |
| SEQ-348 | 9346 | 9345 |
| SEQ-349 | 5919 | 5916 |
| SEQ-351 | 7048 | 7046 |
| SEQ-352 | 5921 | 5920 |
| SEQ-354 | 8050 | 8049 |
| SEQ-355 | 5927 | 5926 |
| SEQ-357 | 6778 | 6777 |
| SEQ-358 | 5775 | 5771 |
| SEQ-360 | 5574 | 5575 |
| SEQ-362 | 5839 | 5840 |
| SEQ-364 | 5895 | 5897 |
| SEQ-366 | 5631 | 5631 |
| SEQ-368 | 5895 | 5896 |
| SEQ-370 | 5951 | 5953 |
| SEQ-372 | 8481 | 8483 |
| SEQ-374 | 8537 | 8539 |
| SEQ-376 | 8593 | 8595 |
| SEQ-378 | 9171 | 9173 |
| SEQ-380 | 7151 | 7154 |
| SEQ-381 | 5860 | 5861 |
| SEQ-383 | 8833 | 8835 |

I) Preparation of the Double-Stranded Oligonucleotide

Lipid binding double-stranded oligonucleotides of the present invention were prepared as below, After mixing the equimolecular amount of 100 μM solution of each oligonucleotide, the solution was heated at 75° C. for 5 minutes, and naturally cooled to room temperature to obtain the double-stranded nucleic acids. Conformation of the double-stranded formation was carried out with size exclusion chromatography.

Column: YMC-PAC Diol-120 (4.6×300 mm) (YMC co., ltd.)

Mobile phases: 40% acetonitrile in 1×PBS solution

Flow rate: 0.6 mL/min

Temperature: room temperature

The synthesized oligonucleotides are shown in Tables 4 to 27.

TABLE 4

| No. | SEQ ID NO | ID | Sequence: CpG(5'⇒ 3') Complementary strand (3'⇒ 5') |
|---|---|---|---|
| SEQ-1 | 1 | ODN1826 | 5'-t^c-^c^a^t^g^a^c^g^t^t^c^c^t^g^a^c^g^t^t-3' |
| SEQ-2 | 1 | Amph1826 | 5'-L$_{4-16}$^t^c-^c^a^t^g^a^c^g^t^t^c^c^t^g^a^c^g^t^t-3' |

TABLE 4-continued

| No. | SEQ ID NO | ID | Sequence: CpG(5'⇒ 3') Complementary strand (3'⇒ 5') |
|---|---|---|---|
| SEQ-3 | 2 | S-1 | 3'-a^g^gtactgcaaggactg^c^a^a-5' |
| SEQ-4 | 1 | ODN1826 | 5'-t^c-^c^a^t^g^a^a^c^g^t^t^c^c^t^g^a^c^g^t^t-3' |
|  | 2 | S-1 | 3'-a^g^gtactgcaaggactg^c^a^a-5' |
| SEQ-5 | 2 | S-2 | 3'-a^g^gtactgcaaggactg^c^a^a$L_{4-16}$-5' |
| SEQ-6 | 1 | ODN1826 | 5'-t^c-^c^a^t^g^a^a^c^g^t^t^c^c^t^g^a^c^g^t^t-3' |
|  | 2 | S-2 | 3'-a^g^gtactgcaaggactg^c^a^a$L_{4-16}$-5' |
| SEQ-7 | 3 | S-3 | 3'-a^g^gactg^c^a^a$L_{4-16}$-5' |
| SEQ-8 | 1 | ODN1826 | 5'-t^c-^c^a^t^g^a^a^c^g^t^t^c^c^t^g^a^c^g^t^t-3' |
|  | 3 | S-3 | 3'-a^g^gactg^c^a^a$L_{4-16}$-5' |
| SEQ-9 | 4 | S-4 | 3'-c^t^gcaaggactg^c^a^a$L_{4-16}$-5' |
| SEQ-10 | 1 | ODN1826 | 5'-t^c-^c^a^t^g^a^a^c^g^t^t^c^c^t^g^a^c^g^t^t-3' |
|  | 4 | S-4 | 3'-c^t^gcaaggactg^c^a^a$L_{4-16}$-5' |
| SEQ-11 | 2 | S-5 | 3'-a^g^gtactgcaaggactg^c^a^a$L_{4-8}$-5' |
| SEQ-12 | 1 | ODN1826 | 5'-t^c-^c^a^t^g^a^a^c^g^t^t^c^c^t^g^a^c^g^t^t-3' |
|  | 2 | S-5 | 3'-a^g^gtactgcaaggactg^c^a^a$L_{4-8}$-5' |
| SEQ-13 | 2 | S-6 | 3'-a^g^gtactgcaaggactg^c^a^a$L_{4-12}$-5' |
| SEQ-14 | 1 | ODN1826 | 5'-t^c-^c^a^t^g^a^a^c^g^t^t^c^c^t^g^a^c^g^t^t-3' |
|  | 2 | S-6 | 3'-a^g^gtactgcaaggactg^c^a^a$L_{4-12}$-5' |
| SEQ-15 | 2 | S-7 | 3'-a^g^gtactgcaaggactg^c^a^a$L_{4-18}$-5' |
| SEQ-16 | 1 | ODN1826 | 5'-t^c-^c^a^t^g^a^a^c^g^t^t^c^c^t^g^a^c^g^t^t-3' |
|  | 7 | S-7 | 3'-a^g^gtactgcaaggactg^c^a^a$L_{4-18}$-5' |
| SEQ-17 | 5 | S-8 | 3'-g^g^tactgcaaggactg^c^a^a$L_{4-18}$-5' |
| SEQ-18 | 1 | ODN1826 | 5'-t^c-^c^a^t^g^a^a^c^g^t^t^c^c^t^g^a^c^g^t^t-3' |
|  | 5 | S-8 | 3'-g^g^tactgcaaggactg^c^a^a$L_{4-18}$-5' |
| SEQ-19 | 6 | S-9 | 3'-g^t^actgcaaggactg^c^a^a$L_{4-18}$-5' |
| SEQ-20 | 1 | ODN1826 | 5'-t^c-^c^a^t^g^a^a^c^g^t^t^c^c^t^g^a^c^g^t^t-3' |
|  | 6 | S-9 | 3'-g^t^actgcaaggactg^c^a^a$L_{4-18}$-5' |
| SEQ-21 | 7 | S-10 | 3'-t^a^ctgcaaggactg^c^a^a$L_{4-18}$-5' |
| SEQ-22 | 1 | ODN1826 | 5'-t^c-^c^a^t^g^a^a^c^g^t^t^c^c^t^g^a^c^g^t^t-3' |
|  | 7 | S-10 | 3'-t^a^ctgcaaggactg^c^a^a$L_{4-18}$-5' |
| SEQ-23 | 8 | S-11 | 3'-a^c^tgcaaggactg^c^a^a$L_{4-18}$-5' |
| SEQ-24 | 8 | ODN1826 | 5'-t^c-^c^a^t^g^a^a^c^g^t^t^c^c^t^g^a^c^g^t^t-3' |
|  |  | S-11 | 3'-a^c^tgcaaggactg^c^a^a$L_{4-18}$-5' |
| SEQ-25 | 4 | S-12 | 3'-c^t^gcaaggactg^c^a^a$L_{4-18}$-5' |
| SEQ-26 | 4 | ODN1826 | 5'-t^c-^c^a^t^g^a^a^c^g^t^t^c^c^t^g^a^c^g^t^t-3' |
|  |  | S-12 | 3'-c^t^gcaaggactg^c^a^a$L_{4-18}$-5' |
| SEQ-27 | 9 | S-13 | 3'-t^g^caaggactg^c^a^a$L_{4-18}$-5' |
| SEQ-28 | 1 | ODN1826 | 5'-t^c-^c^a^t^g^a^a^c^g^t^t^c^c^t^g^a^c^g^t^t-3' |
|  | 9 | S-13 | 3'-t^g^caaggactg^c^a^a$L_{4-18}$-5' |

TABLE 5

| No. | SEQ ID NO | ID | Sequence: CpG(5'⇒ 3') Complementary strand (3' ⇒ 5') |
|---|---|---|---|
| SEQ-29 | 10 | S-14 | 3'-g^c^aaggactg^c^a^a^L$_{4-18}$-5' |
| SEQ-30 | 1 | ODN1826 | 5'-t^c^c^a^t^g^a^c^g^t^t^c^c^t^g^a^c^g^t^t-3' |
|  | 10 | S-14 | 3'-g^c^aaggactg^c^a^a^L$_{4-18}$-5' |
| SEQ-31 | 11 | S-15 | 3'-c^a^aggactg^c^a^a^L$_{4-18}$-5' |
| SEQ-32 | 1 | ODN1826 | 5'-t^c^c^a^t^g^a^c^g^t^t^c^c^t^g^a^c^g^t^t-3' |
|  | 11 | S-15 | 3'-c^a^aggactg^c^a^a^L$_{4-18}$-5' |
| SEQ-33 | 12 | S-16 | 3'-a^a^ggactg^c^a^a^L$_{4-18}$-5' |
| SEQ-34 | 1 | ODN1826 | 5'-t^c^c^a^t^g^a^c^g^t^t^c^c^t^g^a^c^g^t^t-3' |
|  | 12 | S-16 | 3'-a^a^ggactg^c^a^a^L$_{4-18}$-5' |
| SEQ-35 | 3 | S-17 | 3'-a^g^gactg^c^a^a^L$_{4-18}$-5' |
| SEQ-36 | 1 | ODN1826 | 5'-t^c^c^a^t^g^a^c^g^t^t^c^c^t^g^a^c^g^t^t-3' |
|  | 3 | S-17 | 3'-a^g^gactg^c^a^a^L$_{4-18}$-5' |
| SEQ-37 | 2 | S-18 | 3'-a$_{oMe}$^g$_{OMe}$^g$_{OMe}$u$_{OMe}$u$_{OMe}$a$_{OMe}$c$_{OMe}$u$_{OMe}$u$_{OMe}$g$_{OMe}$c$_{OMe}$a$_{OMe}$a$_{OMe}$g$_{OMe}$g$_{OMe}$a$_{OMe}$c$_{OMe}$u$_{OMe}$u$_{OMe}$g$_{OMe}$^c$_{OMe}$^a$_{OMe}$^a$_{OMe}$^L$_{4-18}$-5' |
| SEQ-38 | 1 | ODN1826 | 5'-t^c^c^a^t^g^a^c^g^t^t^c^c^t^g^a^c^g^t^t-3' |
|  | 2 | S-18 | 3'-a$_{oMe}$^g$_{OMe}$^g$_{OMe}$u$_{OMe}$u$_{OMe}$a$_{OMe}$c$_{OMe}$u$_{OMe}$u$_{OMe}$g$_{OMe}$c$_{OMe}$a$_{OMe}$a$_{OMe}$g$_{OMe}$g$_{OMe}$a$_{OMe}$c$_{OMe}$u$_{OMe}$u$_{OMe}$g$_{OMe}$^c$_{OMe}$^a$_{OMe}$^a$_{OMe}$^L$_{4-18}$-5' |
| SEQ-39 | 2 | S-19 | 3'-A^G^GTACTGCAAGGACTG^C^A^A^L$_{4-18}$-5' |
| SEQ-40 | 1 | ODN1826 | 5'-t^c^c^a^t^g^a^c^g^t^t^c^c^t^g^a^c^g^t^t-3' |
|  | 2 | S-19 | 3'-A^G^GTACTGCAAGGACTG^C^A^A^L$_{4-18}$-5' |
| SEQ-41 | 2 | S-20 | 3'-A$_F$^G$_F$^G$_F$U$_F$A$_F$C$_F$U$_F$G$_F$C$_F$A$_F$A$_F$G$_F$G$_F$A$_F$C$_F$U$_F$G$_F$^C$_F$^A$_F$^A$_P$^L$_{4-18}$-5' |
| SEQ-42 | 1 | ODN1826 | 5'-t^c^c^a^t^g^a^c^g^t^t^c^c^t^g^a^c^g^t^t-3' |
|  | 2 | S-20 | 3'-A$_F$^G$_F$^G$_F$U$_F$A$_F$C$_F$U$_F$G$_F$C$_F$A$_F$A$_F$G$_F$G$_F$A$_F$C$_F$U$_F$G$_F$^C$_F$^A$_F$^A$_P$^L$_{4-18}$-5' |
| SEQ-43 | 4 | S-21 | 3'-c$_{oMe}$^u$_{OMe}$u$_{OMe}$^g$_{OMe}$c$_{OMe}$a$_{OMe}$a$_{OMe}$g$_{OMe}$g$_{OMe}$a$_{OMe}$c$_{OMe}$u$_{OMe}$u$_{OMe}$g$_{OMe}$^c$_{OMe}$^a$_{OMe}$^a$_{OMe}$^L$_{4-18}$-5' |
| SEQ-44 | 1 | ODN1826 | 5'-t^c^c^a^t^g^a^c^g^t^t^c^c^t^g^a^c^g^t-3' |
|  | 4 | S-21 | 3'-c$_{oMe}$^u$_{OMe}$u$_{OMe}$^g$_{OMe}$c$_{OMe}$a$_{OMe}$a$_{OMe}$g$_{OMe}$g$_{OMe}$a$_{OMe}$c$_{OMe}$u$_{OMe}$u$_{OMe}$g$_{OMe}$^c$_{OMe}$^a$_{OMe}$^a$_{OMe}$^L$_{4-18}$-5' |
| SEQ-45 | 5 | S-22 | 3'-M$_{15-6}$^a^g^gtactgcaaggactg^c^a^a^L$_{4-18}$-5' |
| SEQ-46 | 1 | ODN1826 | 5'-t^c^c^a^t^g^a^c^g^t^t^c^c^t^g^a^c^g^t^t-3' |
|  | 2 | S-22 | 3'-M$_{15-6}$^a^g^gtactgcaaggactg^c^a^a^L$_{4-18}$-5' |
| SEQ-47 | 2 | S-23 | 3'-M$_{15-10}$^a^g^gtactgcaaggactg^c^a^a^L$_{4-18}$-5' |
| SEQ-48 | 1 | ODN1826 | 5'-t^c^c^a^t^g^a^c^g^t^t^c^c^t^g^a^c^g^t^t-3' |
|  | 2 | S-23 | 3'-M$_{15-10}$^a^g^gtactgcaaggactg^c^a^a^L$_{4-18}$-5' |
| SEQ-49 | 13 | ODN2006 | 5'-t^c^g^t^c^g^t^t^t^t^g^t^c^g^t^t^t^t^g^t^c^g^t^t-3' |

TABLE 6

| No. | SEQ ID NO | ID | Sequence: CpG(5'⇒ 3') Complementary strand (3' ⇒ 5') |
|---|---|---|---|
| SEQ-50 | 14 | S-24 | 3'-a^g^cagcaaaacagcaaaacag^c^a^a^L$_{4-18}$-5' |
| SEQ-51 | 13 | ODN2006 | 5'-t^c^g^t^c^g^t^t^t^t^g^t^c^g^t^t^t^t^g^t^c^g^t^t-3' |
|  | 14 | S-24 | 3'-a^g^cagcaaaacagcaaaacag^c^a^a^L$_{4-18}$-5' |
| SEQ-52 | 15 | S-25 | 3'-c^a^gcaaaacagcaaaacag^c^a^a^L$_{4-18}$-5' |
| SEQ-53 | 13 | ODN2006 | 5'-t^c^g^t^c^g^t^t^t^t^g^t^c^g^t^t^t^t^g^t^c^g^t^t-3' |
|  | 15 | S-25 | 3'-c^a^gcaaaacagcaaaacag^c^a^a^L$_{4-18}$-5' |

TABLE 6-continued

| No. | SEQ ID NO | ID | Sequence: CpG(5'⇒ 3') Complementary strand (3'⇒ 5') |
|---|---|---|---|
| SEQ-54 | 16 | S-26 | 3'-g^c^aaaacagcaaaacag^c^a^a^L$_{4-18}$-5' |
| SEQ-55 | 13 | ODN2006 | 5'-t^c^g^t^c^g^t^t^t^t^g^t^c^g^t^t^t^t^g^t^c^g^t^t-3' |
|  | 16 | S-26 | 3'-g^c^aaaacagcaaaacag^c^a^a^L$_{4-18}$-5' |
| SEQ-56 | 17 | S-27 | 3'-a^a^aacagcaaaacag^c^a^a^L$_{4-18}$-5' |
| SEQ-57 | 13 | ODN2006 | 5'-t^c^g^t^c^g^t^t^t^t^g^t^c^g^t^t^t^t^g^t^c^g^t^t-3' |
|  | 17 | S-27 | 3'-a^a^aacagcaaaacag^c^a^a^L$_{4-18}$-5' |
| SEQ-58 | 18 | S-28 | 3'-a^a^cagcaaaacag^c^a^a^L$_{4-18}$-5' |
| SEQ-59 | 13 | ODN2006 | 5'-t^c^g^t^c^g^t^t^t^t^g^t^c^g^t^t^t^t^g^t^c^g^t^t-3' |
|  | 18 | S-28 | 3'-a^a^cagcaaaacag^c^a^a^L$_{4-18}$-5' |
| SEQ-60 | 19 | S-29 | 3'-a^c^agcaaaacag^c^a^a^L$_{4-18}$-5' |
| SEQ-61 | 13 | ODN2006 | 5'-t^c^g^t^c^g^t^t^t^t^g^t^c^g^t^t^t^t^g^t^c^g^t^t-3' |
|  | 19 | S-29 | 3'-a^c^agcaaaacag^c^a^a^L$_{4-18}$-5' |
| SEQ-62 | 19 | S-30 | 3'-a^c^agcaaaacag^c^a^a^t^t^L$_{4-18}$-5' |
| SEQ-63 | 13 | ODN2006 | 5'-t^c^g^t^c^g^t^t^t^t^g^t^c^g^t^t^t^t^g^t^c^g^t^t-3' |
|  | 19 | S-30 | 3'-a^c^agcaaaacag^c^a^a^t^t^L$_{4-18}$-5' |
| SEQ-64 | 19 | S-31 | 3'-a^c^agcaaaacag^c^a^a^g^g^L$_{4-18}$-5' |
| SEQ-65 | 13 | ODN2006 | 5'-t^c^g^t^c^g^t^t^t^t^g^t^c^g^t^t^t^t^g^t^c^g^t^t-3' |
|  | 19 | S-31 | 3'-a^c^agcaaaacag^c^a^a^g^g^L$_{4-18}$-5' |
| SEQ-66 | 14 | S-32 | 3'-a$_{oMe}$^g$_{OMe}$^c$_{OMe}$a$_{OMe}$g$_{OMe}$c$_{OMe}$a$_{OMe}$a$_{OMe}$a$_{OMe}$a$_{OMe}$c$_{OMe}$a$_{OMe}$ g$_{OMe}$c$_{OMe}$a$_{OMe}$a$_{OMe}$a$_{OMe}$a$_{OMe}$c$_{OMe}$a$_{OMe}$g$_{OMe}$^c$_{OMe}$^a$_{OMe}$^a$_{OMe}$^L$_{4-18}$-5' |
| SEQ-67 | 13 | ODN2006 | 5'-t^c^g^t^c^g^t^t^t^t^g^t^c^g^t^t^t^t^g^t^c^g^t^t-3' |
|  | 14 | S-32 | 3'-a$_{oMe}$^g$_{OMe}$^c$_{OMe}$a$_{OMe}$g$_{OMe}$c$_{OMe}$a$_{OMe}$a$_{OMe}$a$_{OMe}$a$_{OMe}$c$_{OMe}$a$_{OMe}$ g$_{OMe}$c$_{OMe}$a$_{OMe}$a$_{OMe}$a$_{OMe}$a$_{OMe}$c$_{OMe}$a$_{OMe}$g$_{OMe}$^c$_{OMe}$^a$_{OMe}$^a$_{OMe}$^L$_{4-18}$-5' |

TABLE 7

| No. | SEQ ID NO | ID | Sequence: CpG(5'⇒ 3') Complementary strand (3'⇒ 5') |
|---|---|---|---|
| SEQ-68 | 13 | S-33 | 3'-a$_{OMe}$^c$_{OMe}$^a$_{OMe}$g$_{OMe}$c$_{OMe}$a$_{OMe}$a$_{OMe}$a$_{OMe}$a$_{OMe}$c$_{OMe}$a$_{OMe}$g$_{OMe}$^c$_{OMe}$^a$_{OMe}$^a$_{OMe}$^L$_{4-18}$-5' |
| SEQ-69 | 13 | ODN2006 | 5'-t^c^g^t^c^g^t^t^t^t^g^t^c^g^t^t^t^t^g^t^c^g^t^t-3' |
|  | 19 | S-33 | 3'-a$_{oMe}$^c$_{OMe}$^a$_{OMe}$g$_{OMe}$c$_{OMe}$a$_{OMe}$a$_{OMe}$a$_{OMe}$a$_{OMe}$c$_{OMe}$a$_{OMe}$g$_{OMe}$^c$_{OMe}$^a$_{OMe}$^a$_{OMe}$^L$_{4-18}$-5' |
| SEQ-70 | 19 | S-34 | 3'-M$_{15-10}$a^c^agcaaaacag^c^a^a^L$_{4-18}$-5' |
| SEQ-71 | 13 | ODN2006 | 5'-t^c^g^t^c^g^t^t^t^t^g^t^c^g^t^t^t^t^g^t^c^g^t^t-3' |
|  | 19 | S-34 | 3'-M$_{15-10}$^a^c^agcaaaacag^c^a^a^L$_{4-18}$-5' |
| SEQ-72 | 14 | S-35 | 3'-M$_{15-10}$^a^g^cagcaaaacagcaaaacag^c^a^a^L$_{4-12}$-5' |
| SEQ-73 | 13 | ODN2006 | 5'-t^c^g^t^c^g^t^t^t^t^g^t^c^g^t^t^t^t^g^t^c^g^t^t-3' |
|  | 14 | S-35 | 3'-M$_{15-10}$^a^g^cagcaaaacagcaaaacag^c^a^a^L$_{4-12}$-5' |
| SEQ-74 | 19 | S-36 | 3'-a^c^agcaaaacag^c^a^a^L$_{Toc}$-5' |
| SEQ-75 | 13 | ODN2006 | 5'-t^c^g^t^c^g^t^t^t^t^g^t^c^g^t^t^t^t^g^t^c^g^t^t-3' |
|  | 19 | S-36 | 3'-a^c^agcaaaacag^c^a^a^L$_{Toc}$-5' |

TABLE 7-continued

| No. | SEQ ID NO | ID | Sequence: CpG(5'⇒ 3') Complementary strand (3'⇒ 5') |
|---|---|---|---|
| SEQ-76 | 19 | S-37 | 3'-a^c^agcaaaacag^c^a^a^$L_{Chol}$-5' |
| SEQ-77 | 13 | ODN2006 | 5'-t^c^g^t^c^g^t^t^t^t^g^t^c^g^t^t^t^t^g^t^c^g^t^t-3' |
|  | 19 | S-37 | 3'-a^c^agcaaaacag^c^a^a^$L_{Chol}$-5' |
| SEQ-78 | 18 | S-38 | 3'-a^a^cagcaaaacag^c^a^a^$L_{4-12}$-5' |
| SEQ-79 | 13 | ODN2006 | 5'-t^c^g^t^c^g^t^t^t^t^g^t^c^g^t^t^t^t^g^t^c^g^t^t-3' |
|  | 18 | S-38 | 3'-a^a^cagcaaaacag^c^a^a^$L_{4-12}$-5' |
| SEQ-80 | 18 | S-39 | 3'-a^a^cagcaaaacag^c^a^a^$L_{4-14}$-5' |
| SEQ-81 | 13 | ODN2006 | 5'-t^c^g^t^c^g^t^t^t^t^g^t^c^g^t^t^t^t^g^t^c^g^t^t-3' |
|  | 18 | S-39 | 3'-a^a^cagcaaaacag^c^a^a^$L_{4-14}$-5' |
| SEQ-82 | 18 | S-40 | 3'-a^a^cagcaaaacag^c^a^a^$L_{4-16}$-5' |
| SEQ-83 | 13 | ODN2006 | 5'-t^c^g^t^c^g^t^t^t^t^g^t^c^g^t^t^t^t^g^t^c^g^t^t-3' |
|  | 18 | S-40 | 3'-a^a^cagcaaaacag^c^a^a^$L_{4-16}$-5' |

TABLE 8

| No. | SEQ ID NO | ID | Sequence: CpG(5'⇒ 3') Complementary strand (3'⇒ 5') |
|---|---|---|---|
| SEQ-84 | 16 | S-41 | 3'-g^c^aaaacagcaaaacag^c^a^a^$L_{4-12}$-5' |
| SEQ-85 | 13 | ODN2006 | 5'-t^c^g^t^c^g^t^t^t^t^g^t^c^g^t^t^t^t^g^t^c^g^t^t-3' |
|  | 16 | S-41 | 3'-g^c^aaaacagcaaaacag^c^a^a^$L_{4-12}$-5' |
| SEQ-86 | 16 | S-42 | 3'-g^c^aaaacagcaaaacag^c^a^a^$L_{4-14}$-5' |
| SEQ-87 | 13 | ODN2006 | 5'-t^c^g^t^c^g^t^t^t^t^g^t^c^g^t^t^t^t^g^t^c^g^t^t-3' |
|  | 16 | S-42 | 3'-g^c^aaaacagcaaaacag^c^a^a^$L_{4-14}$-5' |
| SEQ-88 | 16 | S-43 | 3'-g^c^aaaacagcaaaacag^c^a^a^$L_{4-16}$-5' |
| SEQ-89 | 13 | ODN2006 | 5'-t^c^g^t^c^g^t^t^t^t^g^t^c^g^t^t^t^t^g^t^c^g^t^t-3' |
|  | 16 | S-43 | 3'-g^c^aaaacagcaaaacag^c^a^a^$L_{4-16}$-5' |
| SEQ-90 | 14 | S-44 | 3'-$M_{15-6}$^a^g^cagcaaaacagcaaaacag^c^a^a^$L_{4-14}$-5' |
| SEQ-91 | 13 | ODN2006 | 5'-t^c^g^t^c^g^t^t^t^t^g^t^c^g^t^t^t^t^g^t^c^g^t^t-3' |
|  | 14 | S-44 | 3'-$M_{15-6}$^a^g^cagcaaaacagcaaaacag^c^a^a^$L_{4-14}$-5' |
| SEQ-92 | 14 | S-45 | 3'-$M_{15-14}$^a^g^cagcaaaacagcaaaacag^c^a^a^$L_{4-10}$-5' |
| SEQ-93 | 13 | ODN2006 | 5'-t^c^g^t^c^g^t^t^t^t^g^t^c^g^t^t^t^t^g^t^c^g^t^t-3' |
|  | 14 | S-45 | 3'-$M_{15-14}$^a^g^cagcaaaacagcaaaacag^c^a^a^$L_{4-10}$-5' |
| SEQ-94 | 14 | S-46 | 3'-$M_{15-18}$^a^g^cagcaaaacagcaaaacag^c^a^a^$L_{4-8}$-5' |
| SEQ-95 | 13 | ODN2006 | 5'-t^c^g^t^c^g^t^t^t^t^g^t^c^g^t^t^t^t^g^t^c^g^t^t-3' |
|  | 14 | S-46 | 3'-$M_{15-18}$^a^g^cagcaaaacagcaaaacag^c^a^a^$L_{4-8}$-5' |
| SEQ-96 | 14 | S-47 | 3'-$M_{15-6}$^a^g^cagcaaaacagcaaaacag^c^a^a^$L_{4-18}$-5' |
| SEQ-97 | 13 | ODN2006 | 5'-t^c^g^t^c^g^t^t^t^t^g^t^c^g^t^t^t^t^g^t^c^g^t^t-3' |
|  | 14 | S-47 | 3'-$M_{15-6}$^a^g^cagcaaaacagcaaaacag^c^a^a^$L_{4-18}$-5' |

TABLE 9

| No. | SEQ ID NO | ID | Sequence: CpG(5'⇒ 3') Complementary strand (3'⇒ 5') |
|---|---|---|---|
| SEQ-98 | 14 | S-48 | 3'-M$_{15-10}$^a^g^cagcaaaacagcaaaacag^c^a^a^L$_{4-18}$-5' |
| SEQ-99 | 13 | ODN2006 | 5'-t^c^g^t^c^g^t^t^t^t^g^t^c^g^t^t^t^t^g^t^c^g^t^t-3' |
|  | 14 | S-48 | 3'-M$_{15-10}$^a^g^cagcaaaacagcaaaacag^c^a^a^L$_{4-18}$-5' |
| SEQ-100 | 14 | S-49 | 3'-M$_{15-14}$^a^g^cagcaaaacagcaaaacag^c^a^a^L$_{4-18}$-5' |
| SEQ-101 | 13 | ODN2006 | 5'-t^c^g^t^c^g^t^t^t^t^g^t^c^g^t^t^t^t^g^t^c^g^t^t-3' |
|  | 14 | S-49 | 3'-M$_{15-14}$^a^g^cagcaaaacagcaaaacag^c^a^a^L$_{4-18}$-5' |
| SEQ-102 | 14 | S-50 | 3'-M$_{15-18}$^a^g^cagcaaaacagcaaaacag^c^a^a^L$_{4-18}$-5' |
| SEQ-103 | 13 | ODN2006 | 5'-t^c^g^t^c^g^t^t^t^t^g^t^c^g^t^t^t^t^g^t^c^g^t^t-3' |
|  | 14 | S-50 | 3'-M$_{15-18}$^a^g^cagcaaaacagcaaaacag^c^a^a^L$_{4-18}$-5' |
| SEQ-104 | 14 | S-51 | 3'-M$_{15-6}$^a^g^cagcaaaacagcaaaacag^c^a^a^L$_{4-12}$-5' |
| SEQ-105 | 13 | ODN2006 | 5'-t^c^g^t^c^g^t^t^t^t^g^t^c^g^t^t^t^t^g^t^c^g^t^t-3' |
|  | 14 | S-51 | 3'-M$_{15-6}$^a^g^cagcaaaacagcaaaacag^c^a^a^L$_{4-12}$-5' |
| SEQ-106 | 14 | S-52 | 3'-M$_{15-14}$^a^g^cagcaaaacagcaaaacag^c^a^a^L$_{4-12}$-5' |
| SEQ-107 | 13 | ODN2006 | 5'-t^c^g^t^c^g^t^t^t^t^g^t^c^g^t^t^t^t^g^t^c^g^t^t-3' |
|  | 14 | S-52 | 3'-M$_{15-14}$^a^g^cagcaaaacagcaaaacag^c^a^a^L$_{4-12}$-5' |
| SEQ-108 | 14 | S-53 | 3'-M$_{15-18}$^a^g^cagcaaaacagcaaaacag^c^a^a^L$_{4-12}$-5' |
| SEQ-109 | 13 | ODN2006 | 5'-t^c^g^t^c^g^t^t^t^t^g^t^c^g^t^t^t^t^g^t^c^g^t^t-3' |
|  | 14 | S-53 | 3'-M$_{15-18}$^a^g^cagcaaaacagcaaaacag^c^a^a^L$_{4-12}$-5' |
| SEQ-110 | 18 | S-54 | 3'-a^a^cagcaaaacag^c^a^a^t^L$_{4-18}$-5' |
| SEQ-111 | 13 | ODN2006 | 5'-t^c^g^t^c^g^t^t^t^t^g^t^c^g^t^t^t^t^g^t^c^g^t^t-3' |
|  | 18 | S-54 | 3'-a^a^cagcaaaacag^c^a^a^t^L$_{4-18}$-5' |

TABLE 10

| No. | SEQ ID NO | ID | Sequence: CpG(5'⇒ 3') Complementary strand (3'⇒ 5') |
|---|---|---|---|
| SEQ-112 | 18 | S-55 | 3'-a^a^cagcaaaacag^c^a^a^t^t^L$_{4-18}$-5' |
| SEQ-113 | 13 18 | ODN2006 | 5'-t^c^g^t^c^g^t^t^t^t^g^t^c^g^t^t^t^t^g^t^c^g^t^t-3' |
|  |  | S-55 | 3'-a^a^cagcaaaacag^c^a^a^t^t^L$_{4-18}$-5' |
| SEQ-114 | 18 | S-56 | 3'-a^a^cagcaaaacag^c^a^a^t^t^t^t^L$_{4-19}$-5' |
| SEQ-115 | 13 18 | ODN2006 | 5'-t^c^g^t^c^g^t^t^t^t^g^t^c^g^t^t^t^t^g^t^c^g^t^t-3' |
|  |  | S-56 | 3'-a^a^cagcaaaacag^c^a^a^t^t^t^t^L$_{4-18}$-5' |
| SEQ-116 | 18 | S-57 | 3'-a^a^cagcaaaacag^c^a^a^g^L$_{4-18}$-5' |
| SEQ-117 | 13 18 | ODN2006 | 5'-t^c^g^t^c^g^t^t^t^t^g^t^c^g^t^t^t^t^g^t^c^g^t^t-3' |
|  |  | S-57 | 3'-a^a^cagcaaaacag^c^a^a^g^L$_{4-18}$-5' |
| SEQ-118 | 18 | S-58 | 3'-a^a^cagcaaaacag^c^a^a^g^g^L$_{4-18}$-5' |
| SEQ-119 | 13 18 | ODN2006 | 5'-t^c^g^t^c^g^t^t^t^t^g^t^c^g^t^t^t^t^g^t^c^g^t^t-3' |
|  |  | S-58 | 3'-a^a^cagcaaaacag^c^a^a^g^g^L$_{4-18}$-5' |
| SEQ-120 | 18 | S-59 | 3'-a^a^cagcaaaacag^c^a^a^g^g^g^g^L$_{4-18}$-5' |
| SEQ-121 | 13 | ODN2006 | 5'-t^c^g^t^c^g^t^t^t^t^g^t^c^g^t^t^t^t^g^t^c^g^t^t-3' |
|  |  | S-59 | 3'-a^a^cagcaaaacag^c^a^a^g^g^g^g^L$_{4-18}$-5' |

TABLE 10-continued

| No. | SEQ ID NO | ID | Sequence: CpG(5'⇒ 3') Complementary strand (3'⇒ 5') |
|---|---|---|---|
| SEQ-122 | 16 | S-60 | 3'-g^c^aaaacagcaaaacag^c^a^a^t^L$_{4-18}$-5' |
| SEQ-123 | 16 16 | ODN2006 S-60 | 5'-t^c^g^t^c^g^t^t^t^t^g^t^c^g^t^t^t^t^g^t^c^g^t^t-3'<br>3'-g^c^aaaacagcaaaacag^c^a^a^t^L$_{4-18}$-5' |
| SEQ-124 | 16 | S-61 | 3'-g^c^aaaacagcaaaacag^c^a^a^t^t^L$_{4-18}$-5' |
| SEQ-125 | 13 16 | ODN2006 S-61 | 5'-t^c^g^t^c^g^t^t^t^t^g^t^c^g^t^t^t^t^g^t^c^g^t^t-3'<br>3'-g^c^aaaacagcaaaacag^c^a^a^t^t^L$_{4-18}$-5' |
| SEQ-126 | 16 | S-62 | 3'-g^c^aaaacagcaaaacag^c^a^a^t^t^t^L$_{4-18}$-5' |
| SEQ-127 | 13 16 | ODN2006 S-62 | 5'-t^c^g^t^c^g^t^t^t^t^g^t^c^g^t^t^t^t^g^t^c^g^t^t-3'<br>3'-g^c^aaaacagcaaaacag^c^a^a^t^t^t^L$_{4-18}$-5' |
| SEQ-128 | 16 | S-63 | 3'-g^c^aaaacagcaaaacag^c^a^a^g^L$_{4-18}$-5' |
| SEQ-129 | 13 16 | ODN2006 S-63 | 5'-t^c^g^t^c^g^t^t^t^t^g^t^c^g^t^t^t^t^g^t^c^g^t^t-3'<br>3'-g^c^aaaacagcaaaacag^c^a^a^g^L$_{4-18}$-5' |

TABLE 11

| No. | SEQ ID NO | ID | Sequence: CpG(5'⇒ 3') Complementary strand (3'⇒ 5') |
|---|---|---|---|
| SEQ-130 | 16 | S-64 | 3'-g^c^aaaacagcaaaacag^c^a^a^g^g^L$_{4-18}$-5' |
| SEQ-131 | 13 16 | ODN2006 S-64 | 5'-t^c^g^t^c^g^t^t^t^t^g^t^c^g^t^t^t^t^g^t^c^g^t^t-3'<br>3'-g^c^aaaacagcaaaacag^c^a^a^g^g^L$_{4-18}$-5' |
| SEQ-132 | 16 | S-65 | 3'-g^c^aaaacagcaaaacag^c^a^a^g^g^g^g^L$_{4-18}$-5' |
| SEQ-133 | 13 16 | ODN2006 S-65 | 5'-t^c^g^t^c^g^t^t^t^t^g^t^c^g^t^t^t^t^g^t^c^g^t^t-3'<br>3'-g^c^aaaacagcaaaacag^c^a^a^g^g^g^g^L$_{4-18}$-5' |
| SEQ-134 | 14 | S-66 | 3'-M$_{22-18}$^a^g^cagcaaaacagcaaaacag^c^a^a-5' |
| SEQ-135 | 13 14 | ODN2006 S-66 | 5'-t^c^g^t^c^g^t^t^t^t^g^t^c^g^t^t^t^t^g^t^c^g^t^t-3'<br>3'-M$_{22-18}$^a^g^cagcaaaacagcaaaacag^c^a^a-5' |
| SEQ-136 | 20 | S-67 | 3'-M$_{22-18}$^a^g^cagcaaaaca^g^c^a-5' |
| SEQ-137 | 13 20 | ODN2006 S-67 | 5'-t^c^g^t^c^g^t^t^t^t^g^t^c^g^t^t^t^t^g^t^c^g^t^t-3'<br>3'-M$_{22-18}$^a^g^cagcaaaaca^g^c^a-5' |
| SEQ-138 | 14 | S-68 | 3'-M$_{22-12}$^a^g^cagcaaaacagcaaaacag^c^a^a-5' |
| SEQ-139 | 13 14 | ODN2006 S-68 | 5'-t^c^g^t^c^g^t^t^t^t^g^t^c^g^t^t^t^t^g^t^c^g^t^t-3'<br>3'-M$_{22-12}$^a^g^cagcaaaacagcaaaacag^c^a^a-5' |
| SEQ-140 | 20 | S-68 | 3'-M$_{22-12}$^a^g^cagcaaaaca^g^c^a-5' |
| SEQ-141 | 13 20 | ODN2006 S-69 | 5'-t^c^g^t^c^g^t^t^t^t^g^t^c^g^t^t^t^t^g^t^c^g^t^t-3'<br>3'-M$_{22-12}$^a^g^cagcaaaaca^g^c^a-5' |
| SEQ-142 | 13 | Amph2006 | 5'-L$_{4-16}$^t^c^g^t^c^g^t^t^t^t^g^t^c^g^t^t^t^t^g^t^c^g^t^t-3' |

TABLE 11-continued

| No. | SEQ ID NO | ID | Sequence: CpG(5'⇒ 3') Complementary strand (3'⇒ 5') |
|---|---|---|---|
| SEQ-143 | 13 | Amph2006GG | 5'-$L_{4-16}$^g^g^t^c^g^t^c^g^t^t^t^t^g^t^c^g^t^t^t^t^g^t^c^g^t^t-3' |
| SEQ-144 | 13 | 3'-Amph2006 | 5'-t^c^g^t^c^g^t^t^t^t^g^t^c^g^t^t^t^t^g^t^c^g^t^t^$M_{51-16}$-3' |

TABLE 12

| No. | SEQ ID NO | ID | Sequence: CpG(5'⇒ 3') Complementary strand (3'⇒ 5') |
|---|---|---|---|
| SEQ-145 | 20 | S-70 | 3'-a^g^cagcaaaaca^g^c^a^$L_{4-18}$-5' |
| SEQ-146 | 13<br>20 | ODN2006<br>S-70 | 5'-t^c^g^t^c^g^t^t^t^t^g^t^c^g^t^t^t^t^g^t^c^g^t^t-3'<br>3'-a^g^cagcaaaaca^g^c^a^$L_{4-18}$-5' |
| SEQ-147 | 21 | S-71 | 3'-g^c^aaaacagcaaa^a^c^$L_{4-18}$-5' |
| SEQ-148 | 13<br>21 | ODN2006<br>S-71 | 5'-t^c^g^t^c^g^t^t^t^t^g^t^c^g^t^t^t^t^g^t^c^g^t^t-3'<br>3'-g^c^aaaacagcaaa^a^c^$L_{4-18}$-5' |
| SEQ-149 | 19 | S-72 | 3'-a^c^agcaaaacag^c^a^a^$L_{10-18}$-5' |
| SEQ-150 | 13<br>19 | ODN2006<br>S-72 | 5'-t^c^g^t^c^g^t^t^t^t^g^t^c^g^t^t^t^t^g^t^c^g^t^t-3'<br>3'-a^c^agcaaaacag^c^a^a^$L_{10-18}$-5' |

TABLE 13

| No. | SEQ ID NO | ID | Sequence: CpG(5'⇒ 3') Complementary strand (3'⇒ 5') |
|---|---|---|---|
| SEQ-151 | 18 | S-73 | 3'-a^a^cagcaaaacag^c^a^a^g^g^g^$L_{4-18}$-5' |
| SEQ-152 | 13<br>18 | ODN2006<br>S-73 | 5'-t^c^g^t^c^g^t^t^t^t^g^t^c^g^t^t^t^t^g^t^c^g^t^t-3'<br>3'-a^a^cagcaaaacag^c^a^a^g^g^g^$L_{4-18}$-5' |
| SEQ-153 | 18 | S-74 | 3'-a^a^cagcaaaacag^c^a^a^g^g^g^$L_{4-18}$-5' |
| SEQ-154 | 13<br>18 | ODN2006<br>S-74 | 5'-t^c^g^t^c^g^t^t^t^t^g^t^c^g^t^t^t^t^g^t^c^g^t^t-3'<br>3'-a^a^cagcaaaacag^c^a^a^g^g^g^$L_{4-18}$-5' |
| SEQ-155 | 18 | S-75 | 3'-a^a^cagcaaaacag^c^a^a^g^g^g^g^g^$L_{4-18}$-5' |
| SEQ-156 | 13<br>18 | ODN2006<br>S-75 | 5'-t^c^g^t^c^g^t^t^t^t^g^t^c^g^t^t^t^t^g^t^c^g^t^t-3'<br>3'-a^a^cagcaaaacag^c^a^a^g^g^g^g^g^$L_{4-18}$-5' |
| SEQ-157 | 18 | S-76 | 3'-a^a^cagcaaaacag^c^a^a^g^g^g^g^g^g^g^$L_{4-18}$-5' |
| SEQ-158 | 13<br>18 | ODN2006<br>S-76 | 5'-t^c^g^t^c^g^t^t^t^t^g^t^c^g^t^t^t^t^g^t^c^g^t^t-3'<br>3'-a^a^cagcaaaacag^c^a^a^g^g^g^g^g^g^g^$L_{4-18}$-5' |

TABLE 14

| No. | SEQ ID NO | ID | Sequence: CpG(5'⇒ 3') Complementary strand (3'⇒ 5') |
|---|---|---|---|
| SEQ-159 | 18 | S-77 | 3'-a^a^cagcaaaacag^c^a^a^g^g^g^g^g^g^g^g^$L_{4-18}$-5' |
| SEQ-160 | 13<br>18 | ODN2006<br>S-77 | 5'-t^c^g^t^c^g^t^t^t^t^g^t^c^g^t^t^t^t^g^t^c^g^t^t-3'<br>3'-a^a^cagcaaaacag^c^a^a^g^g^g^g^g^g^g^g^$L_{4-18}$-5' |

TABLE 14-continued

| No. | SEQ ID NO | ID | Sequence: CpG(5'⇒ 3') Complementary strand (3'⇒ 5') |
|---|---|---|---|
| SEQ-161 | 24 | S-78 | 3'-a^a^acagcaaaacag^c^a^a^g^g^g^g^$L_{4-18}$-5' |
| SEQ-162 | 13 | ODN2006 | 5'-t^c^g^t^c^g^t^t^t^t^g^t^c^g^t^t^t^t^g^t^c^g^t^t-3' |
|  | 24 | S-78 | 3'-a^a^acagcaaaacag^c^a^a^g^g^g^g^$L_{4-18}$-5' |
| SEQ-163 | 17 | S-79 | 3'-a^a^aacagcaaaacag^c^a^a^g^g^g^g^g^$L_{4-18}$-5' |
| SEQ-164 | 13 | ODN2006 | 5'-t^c^g^t^c^g^t^t^t^t^g^t^c^g^t^t^t^t^g^t^c^g^t^t-3' |
|  | 17 | S-79 | 3'-a^a^aacagcaaaacag^c^a^a^g^g^g^g^g^$L_{4-18}$-5' |
| SEQ-165 | 25 | S-80 | 3'-$M_{22-18}$^a^g^cagcaaaacag^c^a^a-5' |
| SEQ-166 | 13 | ODN2006 | 5'-t^c^g^t^c^g^t^t^t^t^g^t^c^g^t^t^t^t^g^t^c^g^t^t-3' |
|  | 25 | S-80 | 3'-$M_{22-18}$^a^g^cagcaaaacag^c^a^a-5' |
| SEQ-167 | 25 | S-81 | 3'-$M_{22-18}$^g^g^a^g^cagcaaaacag^c^a^a-5' |
| SEQ-168 | 13 | ODN2006 | 5'-t^c^g^t^c^g^t^t^t^t^g^t^c^g^t^t^t^t^g^t^c^g^t^t-3' |
|  | 25 | S-81 | 3'-$M_{22-18}$^g^g^-a^g^cagcaaaacag^c^a^a-5' |
| SEQ-169 | 25 | S-82 | 3'-$M_{22-18}$^g^g^g^g^a^g^cagcaaaacag^c^a^a-5' |
| SEQ-170 | 13 | ODN2006 | 5'-t^c^g^t^c^g^t^t^t^t^g^t^c^g^t^t^t^t^g^t^c^g^t^t-3' |
|  | 25 | S-82 | 3'-$M_{22-18}$^g^g^g^g^a^g^cagcaaaacag^c^a^a-5' |
| SEQ-171 | 18 | S-83 | 3'-a^a^cagcaaaacag^c^a^a^a^a^$L_{4-18}$-5' |
| SEQ-172 | 13 | ODN2006 | 5'-t^c^g^t^c^g^t^t^t^t^g^t^c^g^t^t^t^t^g^t^c^g^t^t-3' |
|  | 18 | S-83 | 3'-a^a^cagcaaaacag^c^a^a^a^a^$L_{4-18}$-5' |
| SEQ-173 | 18 | S-84 | 3'-a^a^cagcaaaacag^c^a^a-^a^a^a^a^$L_{4-18}$-5' |
| SEQ-174 | 13 | ODN2006 | 5'-t^c^g^t^c^g^t^t^t^t^g^t^c^g^t^t^t^t^g^t^c^g^t^t-3' |
|  | 18 | S-84 | 3'-a^a^cagcaaaacag^c^a^a^a^a^a^a^$L_{4-18}$-5' |

TABLE 15

| No. | SEQ ID NO | ID | Sequence: CpG(5'⇒ 3') Complementary strand (3'⇒ 5') |
|---|---|---|---|
| SEQ-175 | 25 | S-85 | 3'-a^g^cagcaaaacag^c^a^a^$L_{10-18}$-5' |
| SEQ-176 | 13 | ODN2006 | 5'-t^c^g^t^c^g^t^t^t^t^g^t^c^g^t^t^t^t^g^t^c^g^t^t-3' |
|  | 25 |  |  |
|  |  | S-85 | 3'-a^g^cagcaaaacag^c^a^a^$L_{10-18}$-5' |
| SEQ-177 | 17 | S-86 | 3'-a^a^aacagcaaaacag^c^a^a^$L_{10-18}$-5' |
| SEQ-178 | 13 | ODN2006 | 5'-t^c^g^t^c^g^t^t^t^t^g^t^c^g^t^t^t^t^g^t^c^g^t^t-3' |
|  | 17 |  |  |
|  |  | S-86 | 3'-a^a^aacagcaaaacag^c^a^a^$L_{10-18}$-5' |
| SEQ-179 | 25 | S-87 | 3'-a^g^cagcaaaacag^c^a^a^g^g^g^g^g^$L_{10-18}$-5' |
| SEQ-180 | 13 | ODN2006 | 5'-t^c^g^t^c^g^t^t^t^t^g^t^c^g^t^t^t^t^g^t^c^g^t^t-3' |
|  | 25 |  |  |
|  |  | S-87 | 3'-a^g^cagcaaaacag^c^a^a^g^g^g^g^g^$L_{10-18}$-5' |
| SEQ-181 | 14 | S-88 | 3'-$M_{22-12}$^a^g^cagcaaaacagcaaaacag^c^a^a^$L_{8-10}$-5' |
| SEQ-182 | 13 | ODN2006 | 5'-t^c^g^t^c^g^t^t^t^t^g^t^c^g^t^t^t^t^g^t^c^g^t^t-3' |
|  | 14 |  |  |
|  |  | S-88 | 3'-$M_{22-12}$^a^g^cagcaaaacagcaaaacag^c^a^a^$L_{8-10}$-5' |
| SEQ-183 | 19 | S-89 | 3'-$M_{22-12}$^a^c^agcaaaacag^c^a^a^$L_{8-10}$-5' |
| SEQ-184 | 13 | ODN2006 | 5't^c^g^t^c^g^t^t^t^t^g^t^c^g^t^t^t^t^g^t^c^g^t^t-3' |
|  | 19 |  |  |
|  |  | S-89 | 3'-$M_{22-12}$^a^c^agcaaaacag^c^a^a^$L_{8-10}$-5' |
| SEQ-185 | 18 | S-90 | 3'-$M_{15-6}$^a^a^cagcaaaacag^c^a^a^$L_{4-18}$-5' |

TABLE 15-continued

| No. | SEQ ID NO | ID | Sequence: CpG(5'⇒ 3') Complementary strand (3'⇒ 5') |
|---|---|---|---|
| SEQ-186 | 13 | ODN2006 | 5'-t^c^g^t^c^g^t^t^t^t^g^t^c^g^t^t^t^t^g^t^c^g^t^t-3' |
|  | 18 | S-90 | 3'-M$_{15-6}$^a^a^cagcaaaacag^c^a^a^L$_{4-18}$-5' |
| SEQ-187 | 18 | S-91 | 3'-M$_{15-6}$^a^a^cagcaaaacag^c^a^a^g^g^L$_{4-18}$-5' |
| SEQ-188 | 13 | ODN2006 | 5'-t^c^g^t^c^g^t^t^t^t^g^t^c^g^t^t^t^t^g^t^c^g^t^t-3' |
|  | 18 | S-91 | 3'-M$_{15-6}$^a^a^cagcaaaacag^c^a^a^g^g^L$_{4-18}$-5' |
| SEQ-189 | 18 | S-92 | 3'-M$_{15-6}$^a^a^cagcaaaacag^c^a^a^g^g^g^g^L$_{4-18}$-5' |
| SEQ-190 | 13 | ODN2006 | 5'-t^c^g^t^c^g^t^t^t^t^g^t^c^g^t^t^t^t^g^t^c^g^t^t-3' |
|  | 18 | S-92 | 3'-M$_{15-6}$^a^a^cagcaaaacag^c^a^a^g^g^g^g^L$_{4-18}$-5' |

TABLE 16

| No. | SEQ ID NO | ID (SEQ ID) | Sequence: CpG(5'⇒ 3') Complementary strand (3'⇒ 5') |
|---|---|---|---|
| SEQ-191 | 18 | S-93 | 3'-M$_{15-10}$^a^a^cagcaaaacag^c^a^a^L$_{4-18}$-5' |
| SEQ-192 | 13 | ODN2006 | 5'-t^c^g^t^c^g^t^t^t^t^g^t^c^g^t^t^t^t^g^t^c^g^t^t-3' |
|  | 18 | S-93 | 3'-M$_{15-10}$^a^a^cagcaaaacag^c^a^a^L$_{4-18}$-5' |
| SEQ-193 | 18 | S-94 | 3'-M$_{15-10}$^a^a^cagcaaaacag^c^a^a^g^g^L$_{4-18}$-5' |
| SEQ-194 | 13 | ODN2006 | 5'-t^c^g^t^c^g^t^t^t^t^g^t^c^g^t^t^t^t^g^t^c^g^t^t-3' |
|  | 18 | S-94 | 3'-M$_{15-10}$^a^a^cagcaaaacag^c^a^a^g^g^L$_{4-18}$-5' |
| SEQ-195 | 18 | S-95 | 3'-M$_{15-10}$^a^a^cagcaaaacag^c^a^a^g^g^g^g^L$_{4-18}$-5' |
| SEQ-196 | 13 | ODN2006 | 5'-t^c^g^t^c^g^t^t^t^t^g^t^c^g^t^t^t^t^g^t^c^g^t^t-3' |
|  | 18 | S-95 | 3'-M$_{15-10}$^a^a^cagcaaaacag^c^a^a^g^g^g^g^L$_{4-18}$-5' |
| SEQ-197 | 18 | S-96 | 3'-M$_{15-6}$^a^a^cagcaaaacag^c^a^a^L$_{4-16}$-5' |
| SEQ-198 | 13 | ODN2006 | 5'-t^c^g^t^c^g^t^t^t^t^g^t^c^g^t^t^t^t^g^t^c^g^t^t-3' |
|  | 18 | S-96 | 3'-M$_{15-6}$^a^a^cagcaaaacag^c^a^a^L$_{4-16}$-5' |
| SEQ-199 | 18 | S-97 | 3'-M$_{15-6}$^a^a^cagcaaaacag^c^a^a^g^g^L$_{4-16}$-5' |
| SEQ-200 | 13 | ODN2006 | 5'-t^c^g^t^c^g^t^t^t^t^g^t^c^g^t^t^t^t^g^t^c^g^t^t-3' |
|  | 18 | S-97 | 3'-M$_{15-6}$^a^a^cagcaaaacag^c^a^a^g^g^L$_{4-16}$-5' |
| SEQ-201 | 18 | S-98 | 3'-M$_{15-10}$^a^a^cagcaaaacag^c^a^a^L$_{4-16}$-5' |
| SEQ-202 | 13 | ODN2006 | 5'-t^c^g^t^c^g^t^t^t^t^g^t^c^g^t^t^t^t^g^t^c^g^t^t-3' |
|  | 18 | S-98 | 3'-M$_{15-10}$^a^a^cagcaaaacag^c^a^a^L$_{4-16}$-5' |
| SEQ-203 | 18 | S-99 | 3'M$_{15-10}$^a^a^cagcaaaacag^c^a^a^g^g^L$_{4-16}$-5' |
| SEQ-204 | 13 | ODN2006 | 5'-t^c^g^t^c^g^t^t^t^t^g^t^c^g^t^t^t^t^g^t^c^g^t^t-3' |
|  | 18 | S-99 | 3'-M$_{15-10}$^a^a^cagcaaaacag^c^a^a^g^g^L$_{4-16}$-5' |
| SEQ-205 | 25 | S-100 | 3'-M$_{22-14}$^a^g^cagcaaaacag^c^a^a^L$_{8-6}$-5' |
| SEQ-206 | 13 | ODN2006 | 5'-t^c^g^t^c^g^t^t^t^t^g^t^c^g^t^t^t^t^g^t^c^g^t^t-3' |
|  | 25 | S-100 | 3'-M$_{22-14}$^a^g^cagcaaaacag^c^a^a^L$_{8-6}$-5' |
| SEQ-207 | 25 | S-101 | 3'-M$_{22-14}$^a^g^cagcaaaacag^c^a^a^L$_{8-10}$-5' |
| SEQ-208 | 13 | ODN2006 | 5'-t^c^g^t^c^g^t^t^t^t^g^t^c^g^t^t^t^t^g^t^c^g^t^t-3' |
|  | 28 | S-101 | 3'-M$_{22-14}$^a^g^cagcaaaacag^c^a^a^L$_{8-10}$-5' |

TABLE 17

| No. | SEQ ID NO | ID | Sequence: CpG(5'⇒ 3') Complementary strand (3'⇒ 5') |
|---|---|---|---|
| SEQ-209 | 25 | S-102 | 3'-M$_{22-14}$^a^g^cagcaaaacag^c^a^a^L$_{8-14}$-5' |
| SEQ-210 | 13 | ODN2006 | 5'-t^c^g^t^c^g^t^t^t^t^g^t^c^g^t^t^t^t^g^t^c^g^t^t-3' |
|  | 25 | S-102 | 3'-M$_{22-14}$^a^g^cagcaaaacag^c^a^a^L$_{8-14}$-5' |
| SEQ-211 | 25 | S-103 | 3'-M$_{22-14}$^g^g^a^g^cagcaaaacag^c^a^a^L$_{8-6}$-5' |
| SEQ-212 | 13 | ODN2006 | 5'-t^c^g^t^c^g^t^t^t^t^g^t^c^g^t^t^t^t^g^t^c^g^t^t-3' |
|  | 25 | S-103 | 3'-M$_{22-14}$^g^g^a^g^cagcaaaacag^c^a^a^L$_{8-6}$-5' |
| SEQ-213 | 25 | S-104 | 3'-M$_{22-14}$^g^g^a^g^cagcaaaacag^c^a^a^L$_{8-10}$-5' |
| SEQ-214 | 13 | ODN2006 | 5'-t^c^g^t^c^g^t^t^t^t^g^t^c^g^t^t^t^t^g^t^c^g^t^t-3' |
|  | 25 | S-104 | 3'-M$_{22-14}$^g^g^a^g^cagcaaaacag^c^a^a^L$_{8-10}$-5' |
| SEQ-215 | 25 | S-105 | 3'-M$_{22-14}$^g^g^a^g^cagcaaaacag^c^a^a^L$_{8-14}$-5' |
| SEQ-216 | 13 | ODN2006 | 5'-t^c^g^t^c^g^t^t^t^t^g^t^c^g^t^t^t^t^g^t^c^g^t^t-3' |
|  | 25 | S-105 | 3'-M$_{22-14}$^g^g^a^g^cagcaaaacag^c^a^a^L$_{8-14}$-5' |
| SEQ-217 | 25 | S-106 | 3'-M$_{22-18}$^a^g^cagcaaaacag^c^a^a^L$_{8-6}$-5' |
| SEQ-218 | 13 | ODN2006 | 5'-t^c^g^t^c^g^t^t^t^t^g^t^c^g^t^t^t^t^g^t^c^g^t^t-3' |
|  | 25 | S-106 | 3'-M$_{22-18}$^a^g^cagcaaaacag^c^a^a^L$_{8-6}$-5' |
| SEQ-219 | 25 | S-107 | 3'-M$_{22-18}$^a^g^cagcaaaacag^c^a^a^L$_{8-10}$-5' |
| SEQ-220 | 13 | ODN2006 | 5'-t^c^g^t^c^g^t^t^t^t^g^t^c^g^t^t^t^t^g^t^c^g^t^t-3' |
|  | 25 | S-107 | 3'-M$_{22-18}$^a^g^cagcaaaacag^c^a^a^L$_{8-10}$-5' |
| SEQ-221 | 25 | S-108 | 3'-M$_{22-18}$^g^g^a^g^cagcaaaacag^c^a^a^L$_{8-6}$-5' |
| SEQ-222 | 13 | ODN2006 | 5'-t^c^g^t^c^g^t^t^t^t^g^t^c^g^t^t^t^t^g^t^c^g^t^t-3' |
|  | 25 | S-108 | 3'-M$_{22-18}$^g^g^a^g^cagcaaaacag^c^a^a^L$_{8-6}$-5' |
| SEQ-223 | 25 | S-109 | 3'-M$_{22-18}$^g^g^a^g^cagcaaaacag^c^a^a^L$_{8-10}$-5' |
| SEQ-224 | 13 | ODN2006 | 5'-t^c^g^t^c^g^t^t^t^t^g^t^c^g^t^t^t^t^g^t^c^g^t^t-3' |
|  | 25 | S-109 | 3'-M$_{22-18}$^g^g^a^g^cagcaaaacag^c^a^a^L$_{8-10}$-5' |
| SEQ-225 | 18 | S-110 | 3'-M$_{22-12}$^a^a^cagcaaaacag^c^a^a^L$_{chol}$-5' |
| SEQ-226 | 13 | ODN2006 | 5'-t^c^g^t^c^g^t^t^t^t^g^t^c^g^t^t^t^t^g^t^c^g^t^t-3' |
|  | 28 | S-110 | 3'-M$_{22-12}$^a^a^cagcaaaacag^c^a^a^L$_{chol}$-5' |
| SEQ-227 | 18 | S-111 | 3'-M$_{22-12}$^a^a^cagcaaaacag^c^a^a^L$_{far1}$-5' |
| SEQ-228 | 13 | ODN2006 | 5'-t^c^g^t^c^g^t^t^t^t^g^t^c^g^t^t^t^t^g^t^c^g^t^t-3' |
|  | 18 | S-111 | 3'-M$_{22-12}$^a^a^cagcaaaacag^c^a^a^L$_{far1}$-5' |

TABLE 18

| No. | SEQ ID NO | ID | Sequence: CpG(5'⇒ 3') Complementary strand (3'⇒ 5') |
|---|---|---|---|
| SEQ-229 | 18 | S-112 | 3'-M$_{22-12}$^a^a^cagcaaaacag^c^a^a^L$_{8-10}$-5' |
| SEQ-230 | 13 | ODN2006 | 5'-t^c^g^t^c^g^t^t^t^t^g^t^c^g^t^t^t^t^g^t^c^g^t^t-3' |
|  | 18 | S-112 | 3'-M$_{22-12}$^a^a^cagcaaaacag^c^a^a^L$_{8-10}$-5' |
| SEQ-231 | 18 | S-113 | 3'-M$_{22-12}$^a^a^cagcaaaacag^c^a^a^L$_{8-14}$-5' |
| SEQ-232 | 13 | ODN2006 | 5'-t^c^g^t^c^g^t^t^t^t^g^t^c^g^t^t^t^t^g^t^c^g^t^t-3' |
|  | 18 | S-113 | 3'-M$_{22-12}$^a^a^cagcaaaacag^c^a^a^L$_{8-14}$-5' |
| SEQ-233 | 18 | S-114 | 3'-M$_{chol}$^a^a^cagcaaaacag^c^a^a^L$_{far1}$-5' |
| SEQ-234 | 13 | ODN2006 | 5'-t^c^g^t^c^g^t^t^t^t^g^t^c^g^t^t^t^t^g^t^c^g^t^t-3' |
|  | 18 | S-114 | 3'-M$_{chol}$^a^a^cagcaaaacag^c^a^a^L$_{far1}$-5' |
| SEQ-235 | 14 | S-115 | 3'-a^g^cagcaaaacaK$_{22-18}$gcaaaacag^c^a^a-5' |
| SEQ-236 | 13 | ODN2006 | 5'-t^c^g^t^c^g^t^t^t^t^g^t^c^g^t^t^t^t^g^t^c^g^t^t-3' |
|  | 14 | S-115 | 3'-a^g^cagcaaaacaK$_{22-18}$gcaaaacag^c^a^a-5' |

TABLE 18-continued

| No. | SEQ ID NO | ID | Sequence: CpG(5'⇒ 3') Complementary strand (3'⇒ 5') |
|---|---|---|---|
| SEQ-237 | 17 | S-116 | 3'-$M_{15-6}$^a^a^aacagcaaaacag^c^a^a^$L_{4-18}$-5' |
| SEQ-238 | 13 | ODN2006 | 5'-t^c^g^t^c^g^t^t^t^t^g^t^c^g^t^t^t^t^g^t^c^g^t^t-3' |
| | 17 | S-116 | 3'-$M_{15-6}$^a^a^aacagcaaaacag^c^a^a^$L_{4-18}$-5' |
| SEQ-239 | 17 | S-117 | 3'-$M_{15-6}$^a^a^aacagcaaaacag^c^a^a^g^g^$L_{4-18}$-5' |
| SEQ-240 | 13 | ODN2006 | 5'-t^c^g^t^c^g^t^t^t^t^g^t^c^g^t^t^t^t^g^t^c^g^t^t-3' |
| | 17 | S-117 | 3'-$M_{15-6}$^a^a^aacagcaaaacag^c^a^a^g^g^$L_{4-18}$-5' |
| SEQ-241 | 17 | S-118 | 3'-$M_{15-10}$^a^a^aacagcaaaacag^c^a^a^$L_{4-18}$-5' |
| SEQ-242 | 13 | ODN2006 | 5'-t^c^g^t^c^g^t^t^t^t^g^t^c^g^t^t^t^t^g^t^c^g^t^t-3' |
| | 17 | S-118 | 3'-$M_{15-10}$^a^a^aacagcaaaacag^c^a^a^$L_{4-18}$-5' |
| SEQ-243 | 17 | S-119 | 3'-$M_{15-10}$^a^a^aacagcaaaacag^c^a^a^g^g^$L_{4-18}$-5' |
| SEQ-244 | 13 | ODN2006 | 5'-t^c^g^t^c^g^t^t^t^t^g^t^c^g^t^t^t^t^g^t^c^g^t^t-3' |
| | 17 | S-119 | 3'-$M_{15-10}$^a^a^aacagcaaaacag^c^a^a^g^g^$L_{4-18}$-5' |
| SEQ-245 | 17 | S-120 | 3'-$M_{15-6}$^a^a^aacagcaaaacag^c^a^a^$L_{4-16}$-5' |
| SEQ-246 | 13 | ODN2006 | 5'-t^c^g^t^c^g^t^t^t^t^g^t^c^g^t^t^t^t^g^t^c^g^t^t-3' |
| | 17 | S-120 | 3'-$M_{15-6}$^a^a^aacagcaaaacag^c^a^a^$L_{4-16}$-5' |

TABLE 19

| No. | SEQ ID NO | ID | Sequence: CpG(5'⇒ 3') Complementary strand (3'⇒ 5') |
|---|---|---|---|
| SEQ-247 | 17 | S-121 | 3'-$M_{15-6}$^a^a^aacagcaaaacag^c^a^a^g^g^$L_{4-16}$-5' |
| SEQ-248 | 13 | ODN2006 | 5'-t^c^g^t^c^g^t^t^t^t^g^t^c^g^t^t^t^t^g^t^c^g^t^t-3' |
| | 17 | S-121 | 3'-$M_{15-6}$^a^a^aacagcaaaacag^c^a^a^g^g^$L_{4-16}$-5' |
| SEQ-249 | 17 | S-122 | 3'-$M_{15-10}$^a^a^aacagcaaaacag^c^a^a^$L_{4-16}$-5' |
| SEQ-250 | 13 | ODN2006 | 5'-t^c^g^t^c^g^t^t^t^t^g^t^c^g^t^t^t^t^g^t^c^g^t^t-3' |
| | 17 | S-122 | 3'-$M_{15-10}$^a^a^aacagcaaaacag^c^a^a^$L_{4-16}$-5' |
| SEQ-251 | 17 | S-123 | 3'-$M_{15-10}$^a^a^aacagcaaaacag^c^a^a^g^g^$L_{4-16}$-5' |
| SEQ-252 | 13 | ODN2006 | 5'-t^c^g^t^c^g^t^t^t^t^g^t^c^g^t^t^t^t^g^t^c^g^t^t-3' |
| | 17 | S-123 | 3'-$M_{15-10}$^a^a^aacagcaaaacag^c^a^a^g^g^$L_{4-16}$-5' |
| SEQ-253 | 26 | K3-CpG | 5'-a^t^c^g^a^c^t^c^t^c^g^a^g^c^g^t^t^c^t^c-3' |
| SEQ-254 | 27 | S-124 | 3'-t^g^agagctcgcaa^g^a^g^$L_{4-18}$-5' |
| SEQ-255 | 26 | K3-CpG | 5'-a^t^c^g^a^c^t^c^t^c^g^a^g^c^g^t^t^c^t^c-3' |
| | 27 | S-124 | 3'-t^g^agagctcgcaa^g^a^g^$L_{4-18}$-5' |
| SEQ-256 | 28 | D35-CpG | 5'-g^gtgcatcgatgcagggg^g^g-3' |
| SEQ-257 | 29 | S-125 | 3'-g^t^agctacgtccc^c^c^c^$L_{4-18}$-5' |
| SEQ-258 | 28 | D35-CpG | 5'-g^gtgcatcgatgcagggg^g^g-3' |
| | 29 | S-125 | 3'-g^t^agctacgtccc^c^c^c^$L_{4-18}$-5' |
| SEQ-259 | 25 | S-126 | 3'-$M_{22-10}$^a^g^cagcaaaacag^c^a^a-5' |
| SEQ-260 | 13 | ODN2006 | 5'-t^c^g^t^c^g^t^t^t^t^g^t^c^g^t^t^t^t^g^t^c^g^t^t-3' |
| | 25 | S-126 | 3'-$M_{22-10}$^a^g^cagcaaaacag^c^a^a-5' |
| SEQ-261 | 25 | S-127 | 3'-$M_{22-12}$^a^g^cagcaaaacag^c^a^a-5' |
| SEQ-262 | 13 | ODN2006 | 5'-t^c^g^t^c^g^t^t^t^t^g^t^c^g^t^t^t^t^g^t^c^g^t^t-3' |
| | 25 | S-127 | 3'-$M_{22-12}$^a^g^cagcaaaacag^c^a^a-5' |

TABLE 19-continued

| No. | SEQ ID NO | ID | Sequence: CpG(5'⇒ 3') Complementary strand (3'⇒ 5') |
|---|---|---|---|
| SEQ-261 | 25 | S-127 | 3'-$M_{22\text{-}12}$^a^g^cagcaaaacag^c^a^a-5' |
| SEQ-262 | 13 | ODN2006 | 5'-t^c^g^t^c^g^t^t^t^t^g^t^c^g^t^t^t^t^g^t^c^g^t^t-3' |
|  | 25 | S-127 | 3'-$M_{22\text{-}12}$^a^g^cagcaaaacag^c^a^a-5' |

TABLE 20

| No. | SEQ ID NO | ID | Sequence: CpG(5'⇒ 3') Complementary strand (3'⇒ 5') |
|---|---|---|---|
| SEQ-263 | 25 | S-128 | 3'-$M_{22\text{-}20}$^a^g^cagcaaaacag^c^a^a-5' |
| SEQ-264 | 13 | ODN2006 | 5'-t^c^g^t^c^g^t^t^t^t^g^t^c^g^t^t^t^t^g^t^c^g^t^t-3' |
|  | 25 | S-128 | 3'-$M_{22\text{-}20}$^a^g^cagcaaaacag^c^a^a-5' |
| SEQ-265 | 25 | S-129 | 3'-$M_{22\text{-}22}$^a^g^cagcaaaacag^c^a^a-5' |
| SEQ-266 | 13 | ODN2006 | 5'-t^c^g^t^c^g^t^t^t^t^g^t^c^g^t^t^t^t^g^t^c^g^t^t-3' |
|  | 25 | S-129 | 3'-$M_{22\text{-}22}$^a^g^cagcaaaacag^c^a^a-5' |
| SEQ-267 | 25 | S-130 | 3'-$M_{22\text{-}12}$^a^g^cagcaaaacag^c^a^a^$L_{8\text{-}6}$-5' |
| SEQ-268 | 13 | ODN2006 | 5'-t^c^g^t^c^g^t^t^t^t^g^t^c^g^t^t^t^t^g^t^c^g^t^t-3' |
|  | 25 | S-130 | 3'-$M_{22\text{-}12}$^a^g^cagcaaaacag^c^a^a^$L_{8\text{-}6}$-5' |
| SEQ-269 | 25 | S-131 | 3'-$M_{22\text{-}12}$^a^g^cagcaaaacag^c^a^a^$L_{8\text{-}10}$-5' |
| SEQ-270 | 13 | ODN2006 | 5'-t^c^g^t^c^g^t^t^t^t^g^t^c^g^t^t^t^t^g^t^c^g^t^t-3' |
|  | 25 | S-131 | 3'-$M_{22\text{-}12}$^a^g^cagcaaaacag^c^a^a^$L_{8\text{-}10}$-5' |
| SEQ-271 | 25 | S-132 | 3'-$M_{22\text{-}12}$^a^g^cagcaaaacag^c^a^a^$L_{8\text{-}14}$-5' |
| SEQ-272 | 13 | ODN2006 | 5'-t^c^g^t^c^g^t^t^t^t^g^t^c^g^t^t^t^t^g^t^c^g^t^t-3' |
|  | 25 | S-132 | 3'-$M_{22\text{-}12}$^a^g^cagcaaaacag^c^a^a^$L_{8\text{-}14}$-5' |
| SEQ-273 | 25 | S-133 | 3'-$M_{22\text{-}12}$^g^g^a^g^cagcaaaacag^c^a^a^$L_{8\text{-}6}$-5' |
| SEQ-274 | 13 | ODN2006 | 5'-t^c^g^t^c^g^t^t^t^t^g^t^c^g^t^t^t^t^g^t^c^g^t^t-3' |
|  | 25 | S-133 | 3'-$M_{22\text{-}12}$^g^g^a^g^cagcaaaacag^c^a^a^$L_{8\text{-}6}$-5' |
| SEQ-275 | 25 | S-134 | 3'-$M_{22\text{-}12}$^a^g^cagcaaaacag^c^a^a^g^g^$L_{8\text{-}6}$-5' |
| SEQ-276 | 13 | ODN2006 | 5'-t^c^g^t^c^g^t^t^t^t^g^t^c^g^t^t^t^t^g^t^c^g^t^t-3' |
|  | 25 | S-134 | 3'-$M_{22\text{-}12}$^g^g^a^g^cagcaaaacag^c^a^a^$L_{8\text{-}10}$-5' |
| SEQ-277 | 25 | S-135 | 3'-$M_{22\text{-}12}$^g^g^a^g^cagcaaaacag^c^a^a^$L_{8\text{-}10}$-5' |
| SEQ-278 | 13 | ODN2006 | 5'-t^c^g^t^c^g^t^t^t^t^g^t^c^g^t^t^t^t^g^t^c^g^t^t-3' |
|  | 25 | S-135 | 3'-$M_{22\text{-}12}$^g^g^a^g^cagcaaaacag^c^a^a^$L_{8\text{-}14\text{-}5'}$ |
| SEQ-279 | 18 | S-136 | 3'-a^a^cagcaaaacag^c^$A_{LNA}$^$A_{LNA}$-^g^g^$L_{8\text{-}13}$-5' |
| SEQ-280 | 13 | ODN2006 | 5'-t^c^g^t^c^g^t^t^t^t^g^t^c^g^t^t^t^t^g^t^c^g^t^t-3' |
|  | 18 | S-136 | 3'-a^a^cagcaaaacag^c^$A_{LNA}$^$A_{LNA}$-^g^g^$L_{4\text{-}13}$-5' |

TABLE 21

| No. | SEQ ID NO | ID | Sequence: CpG(5'⇒ 3') Complementary strand (3'⇒ 5') |
|---|---|---|---|
| SEQ-281 | 18 | S-137 | 3'-a^a^cagca$A_{LNA}A_{LNA\text{acag}}$^c^$A_{LNA}$^$A_{LNA}$g^g^$L_{4\text{-}18}$-5' |
| SEQ-282 | 13 | ODN2006 | 5'-t^c^g^t^c^g^t^t^t^t^g^t^c^g^t^t^t^t^g^t^c^g^t^t-3' |
|  | 18 | S-137 | 3'-a^a^cagca$A_{LNA}A_{LNA}$acag^c^$A_{LNA}$^$A_{LNA}$^g^g^$L_{4\text{-}18}$-5' |

TABLE 21-continued

| No. | SEQ ID NO | ID | Sequence: CpG(5'⇒ 3') Complementary strand (3'⇒ 5') |
|---|---|---|---|
| SEQ-283 | 18 | S-138 | 3'-a^A$_{LNA}$^cagcaA$_{LNA}$A$_{LNA}$acag^c^A$_{LNA}$ALNA^g^g^L$_{4-18}$-5' |
| SEQ-284 | 13 | ODN2006 | 5'-t^c^g^t^c^g^t^t^t^t^g^t^c^g^t^t^t^t^g^t^c^g^t^t-3' |
|  | 18 | S-138 | 3'-a^A$_{LNA}$^cagcaA$_{LNA}$A$_{LNA}$acag^c^A$_{LNA}$A$_{LNA}$^g^g^L$_{4-18}$-5' |
| SEQ-285 | 18 | S-139 | 3'-a^a^c^a^g^c^a^a^a^a^c^a^g^c^a^a^g^g^g^g^g^L$_{4-18}$-5' |
| SEQ-286 | 13 | ODN2006 | 5'-t^c^g^t^c^g^t^t^t^t^g^t^c^g^t^t^t^t^g^t^c^g^t^t-3' |
|  | 18 | S-139 | 3'-a^a^c^a^g^c^a^a^a^a^c^a^g^c^a^a^g^g^g^g^g^L$_{4-18}$-5' |
| SEQ-287 | 30 | S-140 | 3'-M$_{22-20}$^a^g^cagcaaaacagcaaa^a^c^a-5' |
| SEQ-288 | 13 | ODN2006 | 5'-t^c^g^t^c^g^t^t^t^t^g^t^c^g^t^t^t^t^g^t^c^g^t^t-3' |
|  | 30 | S-140 | 3'-M$_{22-20}$^a^g^cagcaaaacagcaaa^a^c^a-5' |
| SEQ-289 | 14 | S-141 | 3'-M$_{22-20}$^a^g^cagcaaaacagcaaaacag^c^a^a-5' |
| SEQ-290 | 13 | ODN2006 | 5'-t^c^g^t^c^g^t^t^t^t^g^t^c^g^t^t^t^t^g^t^c^g^t^t-3' |
|  | 14 | S-141 | 3'-M$_{22-20}$^a^g^cagcaaaacagcaaaacag^c^a^a-5' |
| SEQ-291 | 30 | S-142 | 3'-M$_{22-22}$^a^g^cagcaaaacagcaaa^a^c^a-5' |
| SEQ-292 | 13 | ODN2006 | 5'-t^c^g^t^c^g^t^t^t^t^g^t^c^g^t^t^t^t^g^t^c^g^t^t-3' |
|  | 30 | S-142 | 3'-M$_{22-22}$^a^g^cagcaaaacagcaaa^a^c^a-5' |
| SEQ-293 | 14 | S-143 | 3'-M$_{22-22}$^a^g^cagcaaaacagcaaaacag^c^a^a-5' |
| SEQ-294 | 13 | ODN2006 | 5'-t^c^g^t^c^g^t^t^t^t^g^t^c^g^t^t^t^t^g^t^c^g^t^t-3' |
|  | 14 | S-143 | 3'-M$_{22-22}$^a^g^cagcaaaacagcaaaacag^c^a^a-5' |
| SEQ-295 | 30 | S-144 | 3'-M$_{22-12}$^a^g^cagcaaaacagcaaa^a^c^a^L$_{8-6}$5' |
| SEQ-296 | 13 | ODN2006 | 5'-t^c^g^t^c^g^t^t^t^t^g^t^c^g^t^t^t^t^g^t^c^g^t^t-3' |
|  | 30 | S-144 | 3'-M$_{22-12}$^a^g^cagcaaaacagcaaa^a^c^a^L$_{8-6}$-5' |

TABLE 22

| No. | SEQ ID NO | ID | Sequence: CpG(5'⇒ 3') Complementary strand (3'⇒ 5') |
|---|---|---|---|
| SEQ-297 | 30 | S-145 | 3'-M$_{22-12}$^a^g^cagcaaaacagcaaa^a^c^a^L$_{8-10}$-5' |
| SEQ-298 | 13 | ODN2006 | 5'-t^c^g^t^c^g^t^t^t^t^g^t^c^g^t^t^t^t^g^t^c^g^t^t-3' |
|  | 30 | S-145 | 3'-M$_{22-12}$^a^g^cagcaaaacagcaaa^a^c^a^L$_{8-10}$-5' |
| SEQ-299 | 30 | S-146 | 3'-M$_{22-12}$^a^g^cagcaaaacagcaaa^a^c^a^L$_{8-14}$5' |
| SEQ-300 | 13 | ODN2006 | 5'-t^c^g^t^c^g^t^t^t^t^g^t^c^g^t^t^t^t^g^t^c^g^t^t-3' |
|  | 30 | S-146 | 3'-M$_{22-12}$^a^g^cagcaaaacagcaaa^a^c^a^L$_{8-14}$-5' |
| SEQ-301 | 30 | S-147 | 3'-M$_{22-12}$^g^g^a^g^cagcaaaacagcaaa^a^c^a^L$_{8-6}$-5' |
| SEQ-302 | 13 | ODN2006 | 5'-t^c^g^t^c^g^t^t^t^t^g^t^c^g^t^t^t^t^g^t^c^g^t^t-3' |
|  | 30 | S-147 | 3'-M$_{22-12}$^g^g^a^g^cagcaaaacagcaaa^a^c^a^L$_{8-6}$-5' |
| SEQ-303 | 30 | S-148 | 3'-M$_{22-12}$^g^g^a^g^cagcaaaacagcaaa^a^c^a^L$_{8-10}$-5' |
| SEQ-304 | 13 | ODN2006 | 5'-t^c^g^t^c^g^t^t^t^t^g^t^c^g^t^t^t^t^g^t^c^g^t^t-3' |
|  | 30 | S-148 | 3'-M$_{22-12}$^g^g^a^g^cagcaaaacagcaaa^a^c^a^L$_{8-10}$-5' |
| SEQ-305 | 30 | S-149 | 3'-M$_{22-12}$^g^g^a^g^cagcaaaacagcaaa^a^c^a^L$_{8-14}$-5' |

TABLE 22-continued

| No. | SEQ ID NO | ID | Sequence: CpG(5'⇒ 3') Complementary strand (3'⇒ 5') |
|---|---|---|---|
| SEQ-306 | 13 | ODN2006 | 5'-t^c^g^t^c^g^t^t^t^t^g^t^c^g^t^t^t^t^t^g^t^c^g^t^t-3' |
|  | 30 | S-149 | 3'-$M_{22-12}$^g^g^a^g^cagcaaaacagcaaa^a^c^a^$L_{8-14}$-5' |
| SEQ-307 | 14 | S-150 | 3'-$M_{22-12}$^a^g^cagcaaaacagcaaaacag^c^a^a^$L_{8-6}$-5' |
| SEQ-308 | 13 | ODN2006 | 5'-t^c^g^t^c^g^t^t^t^t^g^t^c^g^t^t^t^t^t^g^t^c^g^t^t-3' |
|  | 14 | S-150 | 3'-$M_{22-12}$^a^g^cagcaaaacagcaaaacag^c^a^a^$L_{8-6}$-5' |
| SEQ-309 | 14 | S-151 | 3'-$M_{22-12}$^a^g^cagcaaaacagcaaaacag^c^a^a^$L_{8-14}$-5' |
| SEQ-310 | 13 | ODN2006 | 5'-t^c^g^t^c^g^t^t^t^t^g^t^c^g^t^t^t^t^t^g^t^c^g^t^t-3' |
|  | 14 | S-151 | 3'-$M_{22-12}$^a^g^cagcaaaacagcaaaacag^c^a^a^$L_{8-14}$-5' |

TABLE 23

| No. | SEQ ID NO | ID | Sequence: CpG(5'⇒ 43') Complementary strand (3'⇒ 5') |
|---|---|---|---|
| SEQ-311 | 14 | S-152 | 3'-$M_{22-12}$^g^g^a^g^cagcaaaacagcaaaacag^c^a^a^$L_{8-6}$-5' |
| SEQ-312 | 13 | ODN2006 | 5'-t^c^g^t^c^g^t^t^t^t^g^t^c^g^t^t^t^t^t^g^t^c^g^t^t-3' |
|  | 14 | S-152 | 3'-$M_{22-12}$^g^g^a^g^cagcaaaacagcaaaacag^c^a^a^$L_{8-6}$-5' |
| SEQ-313 | 14 | S-153 | 3'-$M_{22-12}$^g^g^a^g^cagcaaaacagcaaaacag^c^a^a^$L_{8-10}$-5' |
| SEQ-314 | 13 | ODN2006 | 5'-t^c^g^t^c^g^t^t^t^t^g^t^c^g^t^t^t^t^t^g^t^c^g^t^t-3' |
|  | 14 | S-153 | 3'-$M_{22-12}$^g^g^a^g^cagcaaaacagcaaaacag^c^a^a^$L_{8-10}$-5' |
| SEQ-315 | 14 | S-154 | 3'-$M_{22-12}$^g^g^a^g^cagcaaaacagcaaaacag^c^a^a^$L_{8-14}$-5' |
| SEQ-316 | 13 | ODN2006 | 5'-t^c^g^t^c^g^t^t^t^t^g^t^c^g^t^t^t^t^t^g^t^c^g^t^t-3' |
|  | 14 | S-154 | 3'-$M_{22-12}$^g^g^a^g^cagcaaaacagcaaaacag^c^a^a^$L_{8-14}$-5' |
| SEQ-317 | 18 | S-155 | 3'-$M_{22-18}$^Bu^Bu^a^a^cagcaaaacag^c^a^a-5' |
| SEQ-318 | 13 | ODN2006 | 5'-t^c^g^t^c^g^t^t^t^t^g^t^c^g^t^t^t^t^t^g^t^c^g^t^t-3' |
|  | 18 | S-155 | 3'-$M_{22-18}$^Bu^Bu^a^a^cagcaaaacag^c^a^a-5' |
| SEQ-319 | 18 | S-156 | 3'-$M_{TEG-18}$^a^a^cagcaaaacag^c^a^a-5' |
| SEQ-320 | 13 | ODN2006 | 5'-t^c^g^t^c^g^t^t^t^t^g^t^c^g^t^t^t^t^t^g^t^c^g^t^t-3' |
|  | 18 | S-156 | 3'-$M_{TEG-18}$^a^a^cagcaaaacag^c^a^a-5' |
| SEQ-321 | 25 | S-157 | 3'-$M_{22-18}$^$A_{LNA}$^$G_{LNA}$^$5mC_{LNA}$agcaaaacag^$5mC_{LNA}$^$A_{LNA}$^$A_{LNA}$-5' |
| SEQ-322 | 13 | ODN2006 | 5'-t^c^g^t^c^g^t^t^t^t^g^t^c^g^t^t^t^t^t^g^t^c^g^t^t-3' |
|  | 25 | S-157 | 3'-$M_{22-18}$^$A_{LNA}$^$G_{LNA}$^$5mC_{LNA}$agcaaaacag^$5mC_{LNA}$^$A_{LNA}$^$A_{LNA}$-5' |
| SEQ-323 | 31 | S-158 | 3'-$M_{22-18}$^$A_{LNA}$^$G_{LNA}$^$5mC_{LNA}$agca^$A_{LNA}$^$A_{LNA}$^$A_{LNA}$-5' |
| SEQ-324 | 13 | ODN2006 | 5'-t^c^g^t^c^g^t^t^t^t^g^t^c^g^t^t^t^t^t^g^t^c^g^t^t-3' |
|  | 31 | S-158 | 3'-$M_{22-18}$^$A_{LNA}$^$G_{LNA}$^$5mC_{LNA}$agca^$A_{LNA}$^$A_{LNA}$^$A_{LNA}$-5' |

TABLE 24

| No. | SEQ ID NO | ID | Sequence: CpG(5'⇒ 3') Complementary strand (3'⇒ 5') |
|---|---|---|---|
| SEQ-325 | 30 | S-159 | 3'-$M_{22-14}$^a^g^cagcaaaacagcaaa^a^c^a^$L_{8-6}$-5' |
| SEQ-326 | 13 | ODN2006 | 5'-t^c^g^t^c^g^t^t^t^t^g^t^c^g^t^t^t^t^g^t^c^g^t^t-3' |
|  | 30 | S-159 | 3'-$M_{22-14}$^a^g^cagcaaaacagcaaa^a^c^a^$L_{8-6}$-5' |
| SEQ-327 | 30 | S-160 | 3'-$M_{22-14}$^a^g^cagcaaaacagcaaa^a^c^a^$L_{8-10}$-5' |
| SEQ-328 | 13 | ODN2006 | 5'-t^c^g^t^c^g^t^t^t^t^g^t^c^g^t^t^t^t^g^t^c^g^t^t-3' |
|  | 30 | S-160 | 3'-$M_{22-14}$^a^g^cagcaaaacagcaaa^a^c^a^$L_{8-10}$-5' |
| SEQ-329 | 30 | S-161 | 3'-$M_{22-14}$^a^g^cagcaaaacagcaaa^a^c^a^$L_{8-14}$-5' |
| SEQ-330 | 13 | ODN2006 | 5'-t^c^g^t^c^g^t^t^t^t^g^t^c^g^t^t^t^t^g^t^c^g^t^t-3' |
|  | 30 | S-161 | 3'-$M_{22-14}$^a^g^cagcaaaacagcaaa^a^c^a^$L_{8-14}$-5' |
| SEQ-331 | 30 | S-162 | 3'-$M_{22-14}$^g^g^a^g^cagcaaaacagcaaa^a^c^a^$L_{8-6}$-5' |
| SEQ-332 | 13 | ODN2006 | 5'-t^c^g^t^c^g^t^t^t^t^g^t^c^g^t^t^t^t^g^t^c^g^t^t-3' |
|  | 30 | S-162 | 3'-$M_{22-14}$^g^g^a^g^cagcaaaacagcaaa^a^c^a^$L_{8-6}$-5' |
| SEQ-333 | 30 | S-163 | 3'-$M_{22-14}$^g^g^a^g^cagcaaaacagcaaa^a^c^a^$L_{8-10}$-5' |
| SEQ-334 | 13 | ODN2006 | 5'-t^c^g^t^c^g^t^t^t^t^g^t^c^g^t^t^t^t^g^t^c^g^t^t-3' |
|  | 30 | S-163 | 3'-$M_{22-14}$^g^g^a^g^cagcaaaacagcaaa^a^c^a^$L_{8-10}$-5' |
| SEQ-335 | 30 | S-164 | 3'-$M_{22-14}$^g^g^a^g^cagcaaaacagcaaa^a^c^a^$L_{8-14}$-5' |
| SEQ-336 | 13 | ODN2006 | 5'-t^c^g^t^c^g^t^t^t^t^g^t^c^g^t^t^t^t^g^t^c^g^t^t-3' |
|  | 30 | S-164 | 3'-$M_{22-14}$^g^g^a^g^cagcaaaacagcaaa^a^c^a^$L_{8-14}$-5' |
| SEQ-337 | 25 | S-165 | 3'-a^$c_{OMe}$^ag$_{OMe}$ca$_{OMe}$aa$_{OMe}$ac$_{OMe}$ag$_{OMe}$^c^a$_{OMe}$^a^$L_{4-18}$-5' |
| SEQ-338 | 13 | ODN2006 | 5'-t^c^g^t^c^g^t^t^t^t^g^t^c^g^t^t^t^t^g^t^c^g^t^t-3' |
|  | 25 | S-165 | 3'-a^$c_{OMe}$^ag$_{OMe}$ca$_{OMe}$aa$_{OMe}$ac$_{OMe}$ag$_{OMe}$^c^a$_{OMe}$^a^$L_{4-18}$-5' |

TABLE 25

| No. | SEQ ID NO | ID | Sequence: CpG(5'⇒ 3') Complementary strand (3'⇒ 5') |
|---|---|---|---|
| SEQ-339 | 32 | ODN2216 | 5'-g^g^gggacgatcgtcg^g^g^g^g-3' |
| SEQ-340 | 33 | S-166 | 3'-$M_{22-18}$^c^c^ccctgctagca^g^c^c-5' |
| SEQ-341 | 32 | ODN2216 | 5'-g^g^gggacgatcgtcg^g^g^g^g-3' |
|  | 33 | S-166 | 3'-$M_{22-18}$^c^c^ccctgctagca^g^c^c-5' |
| SEQ-342 | 34 | ODN684 | 5'-t^c^g^a^c^g^t^t^c^g^t^c^g^t^t^c^g^t^c^g^t^t^c-3' |
| SEQ-343 | 35 | S-167 | 3'-$M_{22-18}$^a^g^ctgcaagcagc^a^a^g-5' |
| SEQ-344 | 34 | ODN684 | 5'-t^c^g^a^c^g^t^t^c^g^t^c^g^t^t^c^g^t^c^g^t^t^c-3' |
|  | 35 | S-167 | 3'-$M_{22-18}$^a^g^ctgcaagcagc^a^a^g-5' |
| SEQ-345 | 36 | D-LS01 | 5'-t^c^g^c^g^a^c^g^t^t^c^g^c^c^c^g^a^c^g^t^t^c^g^g^t^a-3' |
| SEQ-346 | 37 | S-168 | 3'-$M_{22-18}$^a^g^cgctgcaagcg^g^g^c-5' |
| SEQ-347 | 36 | D-LS01 | 5'-t^c^g^c^g^a^c^g^t^t^c^g^c^c^c^g^a^c^g^t^t^c^g^g^t^a-3' |
|  | 37 | S-16S | 3'-$M_{22-18}$^a^g^cgctgcaagcg^g^g^c-5' |
| SEQ-348 | 38 | D-LS03 | 5'-t^c^g^c^g^a^a^c^g^t^t^c^g^c^c^c^g^c^g^t^t^c^g^a^a^c^g^c^g-3' |
| SEQ-349 | 39 | S-169 | 3'-$M_{22-18}$^a^g^cgcttgcaagc^g^g^c-5' |

TABLE 25-continued

| No. | SEQ ID NO | ID | Sequence: CpG(5'⇒ 3') Complementary strand (3'⇒ 5') |
|---|---|---|---|
| SEQ-350 | 38 | D-LS03 | 5'-t^c^g^c^g^a^a^c^g^t^t^c^g^c^c^g^c^g^t^t^c^g^a^a^c^g^c^g^g-3' |
| | 39 | S-169 | 3'-M$_{22-18}$^a^g^cgcttgcaagc^g^g^c-5' |
| SEQ-351 | 40 | ODN2395 | 5'-t^c^g^t^c^g^t^t^t^t^c^g^g^c^g^c^g^c^g^c^c^g-3' |
| SEQ-352 | 41 | S-170 | 3'-M$_{22-18}$^a^g^cagcaaaagcc^g^c^g-5' |
| SEQ-353 | 40 | ODN2395 | 5'-t^c^g^t^c^g^t^t^t^t^c^g^g^c^g^c^g^c^g^c^c^g-3' |
| | 41 | S-170 | 3'-M$_{22-18}$^a^g^cagcaaaagcc^g^c^g-5' |
| SEQ-354 | 42 | ODNM362 | 5'-t^c^g^t^c^g^t^c^g^t^t^c^g^a^a^c^g^a^c^g^t^t^g^a^t-3' |
| SEQ-355 | 43 | S-171 | 3'-M$_{22-18}$^a^g^cagcagcaagc^t^t^g-5' |
| SEQ-356 | 42 | ODNM362 | 5'-t^c^g^t^c^g^t^c^g^t^t^c^g^a^a^c^g^a^c^g^t^t^g^a^t-3' |
| | 43 | S-171 | 3'-M$_{22-18}$^a^g^cagcagcaagc^t^t^g-5' |
| SEQ-357 | 44 | ODN2336 | 5'-g^g^ggacgacgtcgtgg^g^g^g^g^g-3' |
| SEQ-358 | 45 | S-172 | 3'-M$_{22-18}$^c^c^cctgctgcagc^a^c^c-5' |
| SEQ-359 | 44 | ODN2336 | 5'-g^g^ggacgacgtcgtgg^g^g^g^g^g-3' |
| | 45 | S-172 | 3'-M$_{22-18}$^c^c^cctgctgcagc^a^c^c-5' |

TABLE 26

| No. | SEQ ID NO | ID | Sequence: CpG(5'⇒ 3') Complementary strand (3'⇒ 5') |
|---|---|---|---|
| SEQ-360 | 25 | S-173 | 3'-M$_{22-6}$^a^g^cagcaaaacag^c^a^a-5' |
| SEQ-361 | 13 | ODN2006 | 5'-t^c^g^t^c^g^t^t^t^t^g^t^c^g^t^t^t^t^g^t^c^g^t^t-3' |
| | 25 | S-173 | 3'-M$_{22-6}$^a^g^cagcaaaacag^c^a^a-5' |
| SEQ-362 | 25 | S-174 | 3'-M$_{22-6}$^a^g^cagcaaaacag^c^a^a^L$_{8-10}$-5' |
| SEQ-363 | 13 | ODN2006 | 5'-t^c^g^t^c^g^t^t^t^t^g^t^c^g^t^t^t^t^g^t^c^g^t^t-3' |
| | 25 | S-174 | 3'-M$_{22-6}$^a^g^cagcaaaacag^c^a^a^L$_{8-10}$-5' |
| SEQ-364 | 25 | S-175 | 3'-M$_{22-6}$^a^g^cagcaaaacag^c^a^a^L$_{8-14}$-5' |
| SEQ-365 | 13 | ODN2006 | 5'-t^c^g^t^c^g^t^t^t^t^g^t^c^g^t^t^t^t^g^t^c^g^t^t-3' |
| | 25 | S-175 | 3'-M$_{22-6}$^a^g^cagcaaaacag^c^a^a^L$_{8-14}$-5' |
| SEQ-366 | 25 | S-176 | 3'-M$_{22-8}$^a^g^cagcaaaacag^c^a^a-5' |
| SEQ-367 | 13 | ODN2006 | 5'-t^c^g^t^c^g^t^t^t^t^g^t^c^g^t^t^t^t^g^t^c^g^t^t-3' |
| | 25 | S-176 | 3'-M$_{22-8}$^a^g^cagcaaaacag^c^a^a-5' |
| SEQ-368 | 25 | S-177 | 3'-M$_{22-8}$^a^g^cagcaaaacag^c^a^a^L$_{8-10}$-5' |
| SEQ-369 | 13 | ODN2006 | 5'-t^c^g^t^c^g^t^t^t^t^g^t^c^g^t^t^t^t^g^t^c^g^t^t-3' |
| | 25 | S-177 | 3'-M$_{22-8}$^a^g^cagcaaaacag^c^a^a^L$_{8-10}$-5' |
| SEQ-370 | 25 | S-178 | 3'-M$_{22-8}$^a^g^cagcaaaacag^c^a^a^L$_{8-14}$-5' |
| SEQ-371 | 13 | ODN2006 | 5'-t^c^g^t^c^g^t^t^t^t^g^t^c^g^t^t^t^t^g^t^c^g^t^t-3' |
| | 25 | S-178 | 3'-M$_{22-8}$^a^g^cagcaaaacag^c^a^a^L$_{8-14}$-5' |
| SEQ-372 | 14 | S-179 | 3'-M$_{22-14}$^a^g^cagcaaaacagcaaaacag^c^a^a^L$_{8-6}$-5' |
| SEQ-373 | 13 | ODN2006 | 5'-t^c^g^t^c^g^t^t^t^t^g^t^c^g^t^t^t^t^g^t^c^g^t^t-3' |
| | 14 | S-179 | 3'-M$_{22-14}$^a^g^cagcaaaacagcaaaacag^c^a^a^L$_{8-6}$-5' |
| SEQ-374 | 14 | S-180 | 3'-M$_{22-14}$^a^g^cagcaaaacagcaaaacag^c^a^a^L$_{8-10}$-5' |

TABLE 26-continued

| No. | SEQ ID NO | ID | Sequence: CpG(5'⇒ 3') Complementary strand (3'⇒ 5') |
|---|---|---|---|
| SEQ-375 | 13 | ODN2006 | 5'-t^c^g^t^c^g^t^t^t^t^g^t^c^g^t^t^t^t^t^g^t^c^g^t^t-3' |
| | 14 | S-180 | 3'-M$_{22-14}$^a^g^cagcaaaacagcaaaacag^c^a^a^L$_{8-10}$-5' |

TABLE 27

| No. | SEQ ID NO | ID | Sequence: CpG(5'⇒ 3') Complementary strand (3'⇒ 5') |
|---|---|---|---|
| SEQ-376 | 14 | S-181 | 3'-M$_{22-14}$^a^g^cagcaaaacagcaaaacag^c^a^a^L$_{8-14}$-5' |
| SEQ-377 | 13 | ODN2006 | 5'-t^c^g^t^c^g^t^t^t^t^g^t^c^g^t^t^t^t^t^g^t^c^g^t^t-3' |
| | 14 | S-181 | 3'-M$_{22-14}$^a^g^cagcaaaacagcaaaacag^c^a^a^L$_{8-14}$-5' |
| SEQ-378 | 14 | S-182 | 3'-M$_{22-14}$^g^g^a^g^cagcaaaacagcaaaacag^c^a^a^L$_{8-6}$-5' |
| SEQ-379 | 13 | ODN2006 | 5'-t^c^g^t^c^g^t^t^t^t^g^t^c^g^t^t^t^t^t^g^t^c^g^t^t-3' |
| | 14 | S-182 | 3'-M$_{22-14}$^g^g^a^g^cagcaaaacagcaaaacag^c^a^a^L$_{8-6}$-5' |
| SEQ-380 | 46 | 1018188 | 5'-t^g^a^c^t^g^t^g^a^a^c^g^t^t^c^g^a^g^a^t^g^a-3' |
| SEQ-381 | 47 | S-183 | 3'-M$_{22-18}$^a^c^tgacacttgca^a^g^c-5' |
| SEQ-382 | 46 | 1018ISS | 5'-t^g^a^c^t^g^t^g^a^a^c^g^t^t^c^g^a^g^a^t^g^a-3' |
| | 47 | S-183 | 3'-M$_{22-18}$^a^c^tgacacttgca^a^g^c-5' |
| SEQ-383 | 14 | S-184 | 3'-M$_{22-22}$^Bu^Bu^a^g^cagcaaaacagcaaaacag^c^a^a-5' |
| SEQ-384 | 13 | ODN2006 | 5'-t^c^g^t^c^g^t^t^t^t^g^t^c^g^t^t^t^t^t^g^t^c^g^t^t-3' |
| | 14 | S-184 | 3'-M$_{22-22}$^Bu^Bu^a^g^cagcaaaacagcaaaacag^c^a^a-5' |
| SEQ-385 | 14 | S-185 | 3'-M$_{22-22}$^g^g^g^g^g^a^g^cagcaaaacagcaaaacag^c^a^a-5' |
| SEQ-386 | 13 | ODN2006 | 5'-t^c^g^t^c^g^t^t^t^t^g^t^c^g^t^t^t^t^t^g^t^c^g^t^t-3' |
| | 14 | S-185 | 3'-M$_{22-22}$^g^g^g^g^g^a^g^cagcaaaacagcaaaacag^c^a^a-5' |
| SEQ-387 | 14 | S-186 | 3'-M$_{22-22}$^Bu^Bu^g^g^g^g^g^a^g^cagcaaaacagcaaaacag^c^a^a-5' |
| SEQ-386 | 13 | ODN2006 | 5'-t^c^g^t^c^g^t^t^t^t^g^t^c^g^t^t^t^t^t^g^t^c^g^t^t-3' |
| | 14 | S-186 | 3'-M$_{22-23}$^Bu^Bu^g^g^g^g^g^a^g^cagcaaaacagcaaaacag^c^a^a-5' |

In Tables 4 to 27, n (small letter) is DNA, $n_{OMe}$ is 2'-OMe-RNA, N (capital letter) is RNA, $N_F$ is 2'-deoxy-2'-F-RNA, $N_{LNA}$ is LNA and 5mC is 5-methylcytosine. ^ is —P(S)OH—, and the bond without any symbol is —P(O)OH—.

[III]

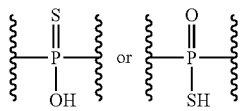

No symbol:

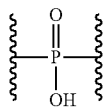

L is a compound introduced at the 5' end of oligonucleotide possibly comprising an oligonucleotide linker, and covalently binds with a hydroxyl group at the 5' end of oligonucleotide via the described bond. M is a compound introduced at the 3' end of oligonucleotide possibly comprising an oligonucleotide linker, and covalently binds with a hydroxyl group at the 3' end of oligonucleotide via the described bond. In $L_{x\text{-}n}$, x is a figure corresponding to the structure of Compound 4-n or Compound 10-n which is double strand or Compound 8-n which is single strand, and n is an integer of 6 to 28 corresponding to the carbon chain(s). In $M_{x\text{-}n}$, x is a figure corresponding to the structure of Compound 22-n, Compound 49-n or Compound 51-n which is double strand of Compound 15-n which is single strand, and n is an integer of 6 to 28 corresponding to the carbon chain(s).

In detail, $L_{x\text{-}n}$ is a group described below.

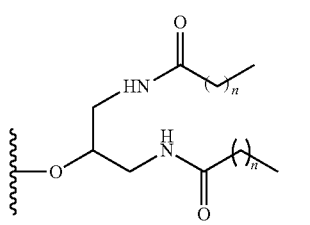
$L_{4\text{-}n}$

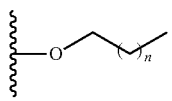
$L_{8\text{-}n}$

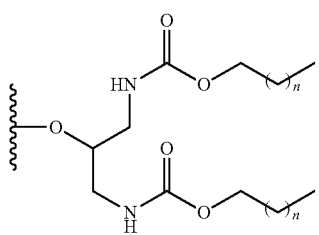
$L_{10\text{-}n}$ wherein n is an integer of 6 to 28.

$L_{4\text{-}n}$ is a group derived from Compound 4-n which is synthesized in 1-1) of the above A). $L_{8\text{-}n}$ is a group derived from Compound 8-n which is synthesized in 2) of the above A). $L_{10\text{-}n}$ is a group derived from Compound 10-n which is synthesized in 3) of the above A).

$L_{chol}$ or $L_{Toc}$ in Table is a group described below.

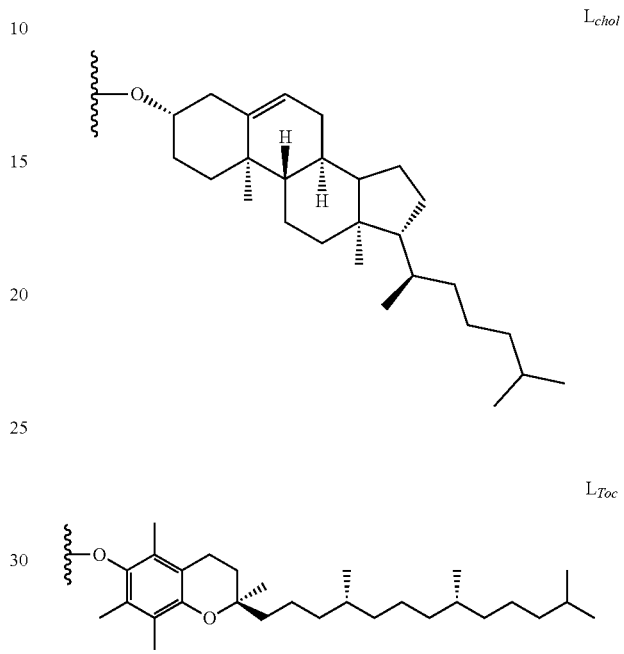

$L_{chol}$ is a group derived from Compound 26 which is synthesized in 8-1) of the above A). $L_{Toc}$ is a group derived from Compound 5'-Tocopherol-CE-Phosphoramidite which is purchased from Link Technologies Ltd.

$L_{farl}$ in Table is a group described below.

$L_{farl}$ is a group deriving from Compound 53 synthesized in 8-2) of the above A).

$M_{x\text{-}n}$ is a group described below.

$M_{15\text{-}n}$ $M_{22-n}$

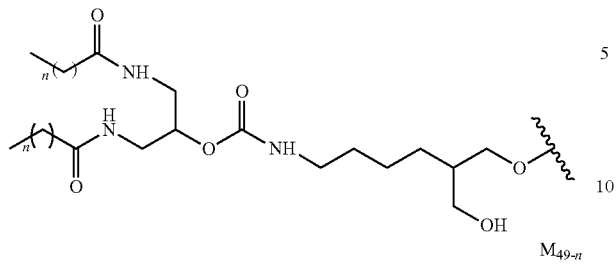

$M_{49-n}$

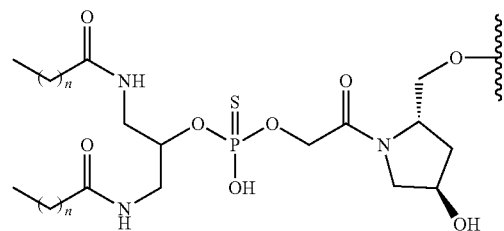

$M_{51-n}$

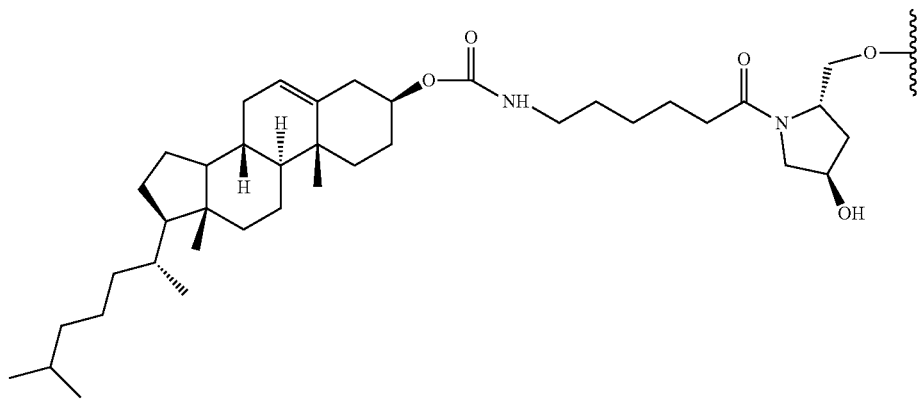

wherein n is an integer of 6 to 28.

$M_{15-n}$ is a group deriving from Compound 15-n synthesized in 4) of the above A), $M_{22-n}$ is a group deriving from Compound 22-n synthesized in 6) of the above A), $M_{49-n}$ is a group deriving from Compound 49-n synthesized in 11) of the above A), and $M_{51-n}$ is a group deriving from Compound 51-n synthesized in 13) of the above A).

$M_{chol}$ in Table is a group described below.

$M_{chol}$ is a group deriving from Compound 55 synthesized in 14) of the above A).

$M_{TEG-n}$ in Table is a group described below.

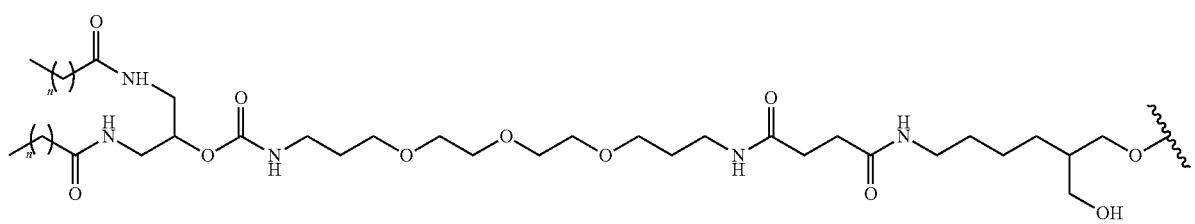

wherein n is an integer of 6 to 28.

$M_{TEG-n}$ is a group deriving from Compound 63-n synthesized in 15) of the above A).

$K_{22-n}$ in Table is a group described below.

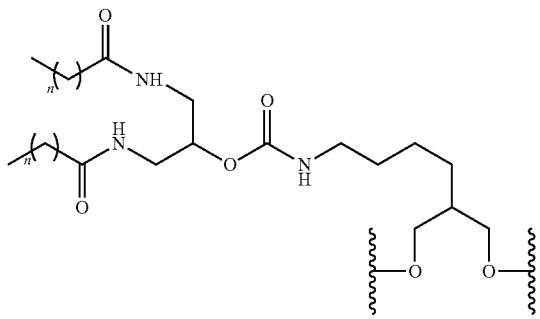

wherein n is an integer of 6 to 28.

$K_{22-n}$ is a group deriving from Compound 22-n synthesized in 6) of the above A).

The following linker (^Bu^Bu^ in Table) is used for S-155, S-184 or S-186.

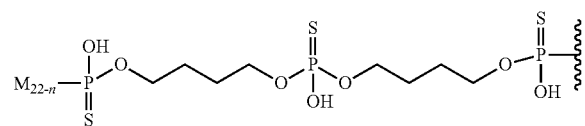

Example 2 Activity Evaluation of Lipid Binding Double-Stranded Oligonucleotides of the Present Invention Using the Reporter Assay (Materials and Methods)

HEK-Blue™ hTLR9 cells (Invivogen) used for the reporter assay were made by introducing human TLR9 gene and a reporter gene that secretory alkaline phosphatase gene bound to NF-kB-AP-1 binding region sequence in HEK293 cells, and are the cells stably expressing the both genes. $3.6 \times 10^4$ of the cells suspended in HEK-Blue™ Detection (Invitrogen) comprising substrates against the alkaline phosphatase were seeded on the 96 well plate, and 3 nM to 30 µM of a lipid binding double-stranded oligonucleotide of the present invention, the known CpG oligonucleotides (ODN2006, SEQ-49), or adjuvant based on design in Patent Document 1, i.e., ssCpG ODN introducing a lipid ligand (SEQ-142, 143 or 144) was added. After culturing in a 37° C., 5% $CO_2$ incubator for 16 hours, absorbency at 620 nm was measured using the culture supernatant developed a color. The result value was analyzed with TIBCO Spotfire software, and calculated the 50% effective concentration ($EC_{50}$) of each oligonucleotide.

(Result)

As previously described, it is known that the characteristity as an adjuvant was vanished when ssCpG ODN was administered as a double-stranded DNA (dsCpG ODN) by annealing the first and second strand (Non-patent Document 4). To examine that the adjuvant design of double-stranded nucleic acid shows an activity as a TLR9 agonist, activity evaluation of a double-stranded oligonucleotide was carried out by a reporter assay.

As shown in Table 28 and 29, ODN2006 (SEQ-49) which is a ssCpG ODN showed the activity as a TLR9 agonist, and the $EC_{50}$ value was about 467 nM (Experiment 1, Table 28) and about 245 nM (Experiment 2, Table 29). On the other hand, a lipid binding double-stranded oligonucleotide of the present invention comprising ODN2006 as a CpG oligonucleotide showed TLR9 agonist activity at a range of several tens to one thousand and several hundred nM. Most adjuvants of the present invention described in Table 28 and 29 had a tendency to enhance the activity compared to ODN2006. In addition, 16 sequences of SEQ-57, SEQ-59, SEQ-61, SEQ-63, SEQ-65, SEQ-111, SEQ-117, SEQ-135, SEQ-146, SEQ-226, SEQ-282, SEQ-284, SEQ-294, SEQ-324, SEQ-361 and SEQ-363 had a tendency to slightly lower the activity compared to ODN2006, but the difference was about 3 times. Therefore, it became clear that all lipid binding double-stranded oligonucleotides of the present invention have activity as a TLR9 agonist.

Furthermore, to examine that the modification form of SEQ-2 disclosed in Patent Document 1 applied for ODN2006 which is the human type CpG oligonucleotide sequence shows an activity as TLR9 agonist, activity evaluation was carried out in the same manner (SEQ-141, 142 or 143). SEQ-142, 143 or 144 could not induce the activation of TLR9 in the measured concentration range, and it was impossible to calculate the $EC_{50}$ values (n.d. in Table 28). That is, it is suggested that design (ssCpG ODN introducing a lipid ligand) disclosed in Patent Document 1 cannot be useful as an adjuvant of vaccine and/or vaccine itself because it showed the activity for ODN1826 (mouse type) but did not for ODN2006 (human type) as described in the example.

In contrast, it is suggested that a lipid binding double-stranded oligonucleotide of the present invention can be useful as adjuvant of vaccine and/or vaccine itself regardless of the sequence of the CpG oligonucleotides because it showed the activity for ODN2006 as well as ODN1826.

Experiment 1

TABLE 28

| No. | EC50 (nM) |
|---|---|
| SEQ-49 | 466.8 |
| SEQ-51 | 405.9 |
| SEQ-55 | 377.9 |
| SEQ-57 | 976.8 |
| SEQ-59 | 542.5 |
| SEQ-61 | 608.1 |
| SEQ-63 | 598.9 |
| SEQ-65 | 500.9 |
| SEQ-75 | 300.6 |
| SEQ-77 | 296.8 |
| SEQ-79 | 162.9 |
| SEQ-81 | 225.9 |
| SEQ-83 | 324.9 |
| SEQ-85 | 72.7 |
| SEQ-87 | 102.8 |
| SEQ-89 | 300.9 |
| SEQ-91 | 68.4 |
| SEQ-93 | 106.4 |
| SEQ-95 | 33.4 |
| SEQ-97 | 308.9 |
| SEQ-99 | 311.3 |
| SEQ-101 | 33.5 |
| SEQ-105 | 96.9 |
| SEQ-111 | 490.1 |
| SEQ-113 | 449.5 |
| SEQ-115 | 303.2 |
| SEQ-117 | 616.5 |
| SEQ-119 | 436.7 |

TABLE 28-continued

| No. | EC50 (nM) |
|---|---|
| SEQ-121 | 282.3 |
| SEQ-123 | 326.0 |
| SEQ-125 | 305.6 |
| SEQ-127 | 299.9 |
| SEQ-129 | 459.0 |
| SEQ-131 | 312.2 |
| SEQ-133 | 169.7 |
| SEQ-135 | 509.8 |
| SEQ-137 | 254.7 |
| SEQ-139 | 58.4 |
| SEQ-141 | 31.0 |
| SEQ-146 | 1128.2 |
| SEQ-148 | 376.6 |
| SEQ-150 | 309.9 |
| SEQ-142 | n.d. |
| SEQ-143 | n.d. |
| SEQ-144 | n.d. |

Experiment 2

TABLE 29

| No. | EC50 (nM) |
|---|---|
| SEQ-49 | 245.3 |
| SEQ-152 | 86.4 |
| SEQ-154 | 94.5 |
| SEQ-156 | 90.0 |
| SEQ-158 | 56.6 |
| SEQ-160 | 65.1 |
| SEQ-162 | 89.7 |
| SEQ-164 | 64.2 |
| SEQ-166 | 90.4 |
| SEQ-168 | 62.8 |
| SEQ-170 | 46.0 |
| SEQ-172 | 161.9 |
| SEQ-174 | 101.0 |
| SEQ-176 | 241.2 |
| SEQ-178 | 210.1 |
| SEQ-180 | 46.9 |
| SEQ-182 | 11.2 |
| SEQ-184 | 34.2 |
| SEQ-186 | 127.7 |
| SEQ-188 | 67.7 |
| SEQ-190 | 46.9 |
| SEQ-192 | 123.9 |
| SEQ-194 | 99.8 |
| SEQ-196 | 33.2 |
| SEQ-198 | 114.9 |
| SEQ-200 | 96.3 |
| SEQ-202 | 89.5 |
| SEQ-204 | 83.4 |
| SEQ-206 | 40.7 |
| SEQ-208 | 31.3 |
| SEQ-210 | 56.7 |
| SEQ-212 | 46.9 |
| SEQ-214 | 47.4 |
| SEQ-216 | 99.5 |
| SEQ-218 | 59.8 |
| SEQ-220 | 57.2 |
| SEQ-222 | 31.9 |
| SEQ-224 | 12.4 |
| SEQ-226 | 362.0 |
| SEQ-228 | 21.0 |
| SEQ-230 | 39.8 |
| SEQ-232 | 72.7 |
| SEQ-234 | 27.0 |
| SEQ-236 | 203.1 |
| SEQ-238 | 131.9 |
| SEQ-240 | 62.0 |
| SEQ-242 | 102.4 |
| SEQ-244 | 101.8 |
| SEQ-246 | 102.6 |
| SEQ-248 | 108.3 |

TABLE 29-continued

| No. | EC50 (nM) |
|---|---|
| SEQ-250 | 92.4 |
| SEQ-252 | 87.4 |
| SEQ-260 | 39.9 |
| SEQ-262 | 25.7 |
| SEQ-264 | 86.3 |
| SEQ-266 | 58.1 |
| SEQ-268 | 11.5 |
| SEQ-270 | 16.3 |
| SEQ-272 | 33.3 |
| SEQ-274 | 29.7 |
| SEQ-276 | 30.9 |
| SEQ-278 | 33.3 |
| SEQ-280 | 168.3 |
| SEQ-282 | 275.1 |
| SEQ-284 | 255.8 |
| SEQ-286 | 45.0 |
| SEQ-288 | 65.4 |
| SEQ-290 | 151.7 |
| SEQ-292 | 58.9 |
| SEQ-294 | 262.4 |
| SEQ-296 | 10.1 |
| SEQ-298 | 10.2 |
| SEQ-300 | 11.4 |
| SEQ-302 | 10.2 |
| SEQ-304 | 11.6 |
| SEQ-306 | 11.3 |
| SEQ-308 | 8.4 |
| SEQ-310 | 10.7 |
| SEQ-312 | 19.1 |
| SEQ-314 | 10.8 |
| SEQ-316 | 10.9 |
| SEQ-318 | 81.3 |
| SEQ-320 | 68.4 |
| SEQ-322 | 50.4 |
| SEQ-324 | 261.1 |
| SEQ-326 | 24.6 |
| SEQ-328 | 24.1 |
| SEQ-330 | 33.7 |
| SEQ-332 | 24.8 |
| SEQ-334 | 25.3 |
| SEQ-336 | 31.4 |
| SEQ-338 | 188.1 |
| SEQ-361 | 771.8 |
| SEQ-363 | 290.2 |
| SEQ-365 | 177.4 |
| SEQ-367 | 178.2 |
| SEQ-369 | 135.9 |
| SEQ-371 | 170.0 |
| SEQ-373 | 21.5 |
| SEQ-375 | 21.9 |
| SEQ-377 | 29.8 |
| SEQ-379 | 20.3 |

As shown in Table 30, even when the CpG oligonucleotides except for ODN2006 were used, most adjuvants of the present invention showed the tendency of activity enhancement compared to ssCpG ODN. It became clear that every lipid binding double-stranded oligonucleotide of the present invention shows activity as TLR9 agonist.

TABLE 30

| No. | EC50 (nM) |
|---|---|
| SEQ-253 (K3-CpG) | 2870.2 |
| SEQ-255 | 173.4 |
| SEQ-256 (D35-CpG) | 3421046.2 |
| SEQ-258 | 16328.8 |
| SEQ-339 (ODN2216) | 7244.7 |
| SEQ-341 | 7915.8 |
| SEQ-342 (ODN684) | 2339.9 |
| SEQ-344 | 111.4 |
| SEQ-345 (D-LS01) | 6280.7 |

TABLE 30-continued

| No. | EC50 (nM) |
|---|---|
| SEQ-347 | 10.7 |
| SEQ-351 (ODN2395) | 11569.8 |
| SEQ-353 | 1982.2 |
| SEQ-354 (ODN M362) | 16893838.1 |
| SEQ-356 | 292.6 |

Example 3 In Vivo Evaluation of Adjuvants of the Present Invention

A) Evaluation of CTL Inducibility
(Animals)
C57BL/6JJcl mice (6 to 8 weeks old) were purchased from CLEA Japan, Inc.
(Components of Vaccine 1)
OVA$_{257-264}$ peptide (SIINFEKL, SEQ ID NO: 22) which synthesized and purified by reversed phase HPLC and purchased from Sigma-Aldrich.
an adjuvant of the present invention or the well-known CpG ODN
(Components of Vaccine 2)
TRP2$_{180-188}$ peptide (SVYDFFVWL, SEQ ID NO: 23) which synthesized and purified by reversed phase HPLC and purchased from Sigma-Aldrich.
an adjuvant of the present invention or the well-known CpG ODN
(Components of Vaccine 3)
OVA$_{257-264}$ peptide or TRP2$_{180-188}$ peptide
Montanide ISA51 (SEPPIC)
(Preparation of Vaccine 1)
The specific immunity was induced by vaccinating a mouse twice at 7 days intervals. Each vaccine was that 100 μg of OVA peptide, and 1.57 or 4.71 nmol of an adjuvant of the present invention or well-known CpG ODN, were dissolved in 1×PBS. 100 μL of the vaccine was administered subcutaneous injection on the flank of a mouse.
(Preparation of Vaccine 2)
The specific immunity was induced by vaccinating a mouse twice at 7 days intervals. Each vaccine was that 100 μg of TRP2 peptide, and 1.57 or 4.71 nmol of an adjuvant of the present invention or well-known CpG ODN, were dissolved in 1×PBS. 100 μL of the vaccine was administered subcutaneous injection on the flank of a mouse.
(Preparation of Vaccine 3)
1:1 of 2 mg/ml of TRP2 peptide in PBS and Montanide (the above vaccine component 3) were mixed using a cylinder and pumping connector to form emulsion. 100 μL of the emulsion vaccine was administered subcutaneous injection on the flank of a mouse twice at 7 days intervals.
(Tetramer Staining)
On 7 days after second vaccination, the blood was collected, red blood cells was removed by BD Pharm Lyse (BD pharmingen), and the white blood cells were suspended in FACS buffer (1% fetal bovine serum, 2 mM PBS with EDTA). Anti-mouse CD16/32 monoclonal antibody (BioXcell) was added thereto, and Fc receptor blocking was carried out at 4° C. for 30 minutes. Next, PE labeled H-2Kb tetramer corresponding to the vaccine antigen (T-Select H-2Kb OVA Tetramer-SIINFEKL (SEQ ID NO: 22) or T-Select H-2Kb TRP-2 Tetramer-SVYDFFVWL (SEQ ID NO: 23); Both were purchased from Medical & Biological Laboratories Co., Ltd.) and Alexa 647 labeled anti-CD8 antibody (Medical & Biological Laboratories Co., Ltd.) were added thereto, and staining was carried out at room temperature for 45 minutes. Then, staining was carried out with DAPI (Invitrogen) and the cells were washed twice with FACS buffer. It was resuspended in FACS buffer and analyzed by FACS verse Flow Cytometer (BD bioscience) and FAC Suite software (BD bioscience). For analysis, after DAPI negative fraction was gated, white blood cells fraction were provided using forward and side-way scattering as indicators. In the white blood cells fraction, both positive cells of Alexa 647-CD8 and PE-H-2Kb Tetramer were defined as CTLs. CTL ratio in white blood cells was used for evaluation.

Calculation Method of the Indicator of CTL Inducibility
After calculation of the average CTL inducibility of each group per experiment, the ratio against average value of CTL inducibility of ssCpG ODN, ODN1826 (SEQ-1) or ODN2006 (SEQ-49) as a control was calculated.
In the case of an adjuvant comprising ODN1826

(Average of CTL inducibility of the adjuvant group)/
(Average of CTL inducibility of the ODN1826 group)=the ratio against average value In the case of an adjuvant comprising ODN2006

(Average of CTL inducibility of the adjuvant group)/
(Average of CTL inducibility of the ODN2006 group)=the ratio against average value CTL inducibility of each adjuvant was shown when CTL inducibility of ssCpG ODN was taken as 1, so the bigger value means the higher CTL inducibility.

B) Evaluation of Anti-Tumor Effect of TRP2 Peptide Vaccine Using an Adjuvant of the Present Invention
After immunization by TRP2 peptide vaccine, B16F10 cells (ATTC) which is mouse melanoma expressing TRP2 protein was subcutaneously transplanted to evaluate anti-tumor effect. In a similar method to Example 3 A), on the next day that tetramer-positive ratio in peripheral blood of mouse vaccinated twice every 7 days was observed, B16F10 cells ($1\times10^5$ cells/mouse) were subcutaneously transplanted in the right shoulder. The major and minor axes of the engrafted tumor were measured every 2 to 3 days, and the tumor volume was calculated by the formula:

(major axis×minor axis$^2$)/2

Calculation method for indicators of anti-tumor effect
For the adjuvant comprising ODN1826

100·(average tumor volume of adjuvant group)/(average tumor volume of ODN1826 group)

For the adjuvant comprising ODN2006

100·(average tumor volume of adjuvant group)/(average tumor volume of ODN2006 group)

The compound with bigger value has the stronger anti-tumor activity.
(Result Using ODN1826 as a CpG Oligonucleotide)
Result 1-A: Comparison of CTL Inducibility Between an Adjuvant of the Present Invention and the Known Adjuvants
When mice were immunized with TRP2 peptide and ODN1826 (SEQ-1), TRP2-specific CTL was induced. When dsCpG ODN (SEQ-4) was used, TRP2-specific CTL inducibility was lowered at 0.46 times compared to ODN1826. That is, double strands led to lower the CTL inducibility compared to a single-strand adjuvant. This suggested that when the CpG oligonucleotide is just made as a double-stranded form, the immunostimulatory activity is lowered as disclosed in Non-patent Document 4 and the like. On the other hand, when an adjuvant of the present invention, i.e., lipid binding double-stranded oligonucleotide adjuvant (SEQ-16) was used for immunization, the CTL inducibility was enhanced at 1.46 times compared to ODN1826. Therefore, it suggested that an adjuvant of the present invention has unexpected enhancement of activity. The results were shown in Table 31.

TABLE 31

| Peptide | Adjuvant | dose/head nmol | Ratio of average value of antigen-specific CTL |
|---|---|---|---|
| TRP2 | SEQ-1 | 1.57 | 1.00 |
| TRP2 | SEQ-4 | 1.57 | 0.46 |
| TRP2 | SEQ-16 | 1.57 | 1.46 |

Result 1-B: Comparison of Anti-Tumor Effect Between an Adjuvant of the Present Invention and the Known Adjuvants When mice were immunized with TRP2 peptide and ODN1826 (SEQ-1), they had little effect of inhibition on tumor progression of B16F10 cells. Furthermore, dsCpG ODN (SEQ-4) had little effect of inhibition on tumor progression of B16F10 cells. On the other hand, an adjuvant of the present invention (SEQ-16) showed the strong effect of inhibition, on tumor progression of B16F10 cells, 43% compared to ODN1826 on Day 14 after transplantation. The results were shown in FIG. 1.

Result 2-A, B: CTL Inducibility and Anti-Tumor Effect of Adjuvants of the Present Invention Comprising a Lipid Ligand with Different Number of Carbon Atoms The activity of an adjuvant of the present invention having a lipid comprising two acyl chains comprising 10 to 20 carbon atoms as a ligand was examined with OVA peptide. CTL inducibility and tumor inhibition rate of SEQ-12 (10 carbon atoms) was lowered compared to ODN1826 (SEQ-1). On the other hand, there is tendency to enhance CTL inducibility as the chain length is longer like SEQ-14 (14 carbon atoms), SEQ-6 (18 carbon atoms) and SEQ-16 (20 carbon atoms). In addition, tumor inhibition rate of SEQ-14 showed about 94% inhibition of the tumor growth compared to ODN1826 on. Day 14 after transplantation, and SEQ-6 and SEQ-16 perfectly inhibited the tumor growth on Day 14 after transplantation. The results were shown in Table 32.

TABLE 32

| Peptide | Adjuvant | dose/head nmol | Ratio of average value of antigen-specific CTL | Tumor inhibition rate (Day 14 after transplantation) |
|---|---|---|---|---|
| OVA | SEQ-1 | 1.57 | 1.00 | 0.00 |
| OVA | SEQ-12 | 1.57 | 0.42 | −62.88 |
| OVA | SEQ-14 | 1.57 | 0.85 | 93.94 |
| OVA | SEQ-6 | 1.57 | 0.77 | 100.00 |
| OVA | SEQ-16 | 1.57 | 2.32 | 100.00 |

Result 3-A: CTL Inducibility of Adjuvants of the Present Invention Introduced Lipids at the Both Ends The activity of an adjuvant of the present invention with a lipid comprising two acyl chains comprising 20 carbon atoms as a ligand and further comprising a single-strand lipid comprising 8 or 12 carbon atoms at 3' end of the CpG oligonucleotide (SEQ-46 or SEQ-48) was examined with TRP2 peptide. The both CTL inductivities were enhanced at about 2.8 times compared to ODN1826 (SEQ-1). The results were shown in Table 33.

TABLE 33

| Peptide | Adjuvant | dose/head nmol | Ratio of average value of antigen-specific CTL |
|---|---|---|---|
| TRP2 | SEQ-1 | 1.57 | 1.00 |
| TRP2 | SEQ-46 | 1.57 | 2.81 |
| TRP2 | SEQ-48 | 1.57 | 2.84 |

Result 3-B: Anticancer Effect of Adjuvants of the Present Invention Introduced Lipids at the Both Ends When mice were immunized with TRP2 peptide and an adjuvant of the present invention, SEQ-46 or SEQ-48, it showed the strong effect of inhibition on tumor progression of B16F10 cells, respectively 52% or 43% on Day 13 after transplantation compared to ODN1826 (SEQ-1). The results were shown in FIG. 2.

Result 4-A: CTL Inducibility of Adjuvants of the Present Invention with the Different Lengths of the Complementary Strand In a double-stranded oligonucleotide adjuvant design, it is necessary to release the CpG oligonucleotide, which is an active ingredient, in the lymph nodes. The speed to dissociate a double strand is proportionate to the heat stability, and the more complementary sites in the double strand structure are, the more stably the double strand exists. Then, the activity of adjuvants of the present invention whose chain length of complementary strand is different was examined with TRP2 peptide. The adjuvant whose the complementary strand is 10 mer for ODN1826 (20 mer), i.e., length of the complementary strand for the CpG oligonucleotide is 50% (SEQ-8) and the adjuvant whose complementary strand if 15 mer, i.e., length is 75% (SEQ-10) were used. Both SEQ-8 and SEQ-10 dominantly enhanced CTL inducibility compared to ODN1826 (SEQ-1) at about 1.2 and 2.5 times, respectively. The results were shown in Table 34.

TABLE 34

| Peptide | Adjuvant | dose/head nmol | Ratio of average value of antigen-specific CTL |
|---|---|---|---|
| TRP2 | SEQ-1 | 1.57 | 1.00 |
| TRP2 | SEQ-2 | 1.57 | 1.68 |
| TRP2 | SEQ-8 | 1.57 | 1.15 |
| TRP2 | SEQ-10 | 1.57 | 2.50 |

Result 4-B: Anticancer Effect of Adjuvants of the Present Invention with the Different Lengths of the Complementary Strand When mice were immunized with TRP2 peptide and ssCpG ODN introducing a lipid ligand in Patent Document 1 (SEQ-2), the tumor inhibition rate, was about 3.5% on Day 12 after transplantation compared to ODN1826 (SEQ-1), On the other hand, SEQ-8 which is an adjuvant of the present invention with 10 mer of complementary strand showed about 50% of the tumor inhibition rate compared to ODN1826 on Day 12 after transplantation. Furthermore, SEQ-10 which has 15 mer of complementary strand showed the strong effect of inhibition on tumor progression of B16F10 cells, about 76% compared to ODN1826 on Day 12 after transplantation. The results were shown in FIG. 3.

Result 5-A: CTL Inducibility of Adjuvants of the Present Invention with the Different Chain Length of Complementary Strand The activity of an adjuvant of the present invention whose chain length of complementary strand is from 10 to 20 mer against ODN1826 (20 mer), complementary strand is 50 to 100% against the CpG oligonucleotide was examined with TRP2 peptide. The adjuvant whose complementary strand is 14 mer (SEQ-28), 15 mer (SEQ-26), 17 mer (SEQ-22), 19 mer (SEQ-18) and 20 mer (SEQ-16) showed enhancement of CTL inducibility compared to ODN1826 (SEQ-1). Especially, adjuvant with 19 mer (SEQ-18). 17 mer (SEQ-22) and 15mer (SEQ-26) showed CTL inducibility at about 3 times compared to ODN1826 (SEQ-1). The results were shown in Table 35.

TABLE 35

| Peptide | Adjuvant | dose/head nmol | Ratio of average value of antigen-specific CTL |
|---|---|---|---|
| TRP2 | SEQ-1 | 1.57 | 1.00 |
| TRP2 | SEQ-16 | 1.57 | 1.63 |
| TRP2 | SEQ-18 | 1.57 | 3.40 |
| TRP2 | SEQ-22 | 1.57 | 2.69 |
| TRP2 | SEQ-26 | 1.57 | 2.82 |
| TRP2 | SEQ-28 | 1.57 | 2.21 |
| TRP2 | SEQ-32 | 1.57 | 1.10 |
| TRP2 | SEQ-36 | 1.57 | 1.07 |

Result 6-A: Comparison of CTL Inducibility with Montanide

The activities of ODN1826 (SEQ-1), ssCpG ODN introducing a lipid ligand (SEQ-2), an adjuvant of the present invention (SEQ-26) and Montanide which is an adjuvant used a lot in the clinical trials as an adjuvant of a peptide vaccine were compared with TRP2 peptide as antigen. SEQ-2 and SEQ-26 showed higher CTL inducibility than ODN1826. On the other hand, CTL inducibility of Montanide was lowered to one-seventh compared to ODN1826. The results were shown in Table 36.

TABLE 36

| Peptide | Adjuvant | dose/head nmol | Ratio of average value of antigen-specific CTL |
|---|---|---|---|
| TRP2 | SEQ-1 | 1.57 | 1.00 |
| TRP2 | SEQ-2 | 1.57 | 3.23 |
| TRP2 | SEQ-26 | 1.57 | 2.82 |
| TRP2 | Mondanide | 100 µL | 0.13 |

Result 6-B: Comparison of the Anti-Tumor Effect Against ssCpG ODN Introducing a Lipid Ligand When mice were immunized with TRP2 peptide and an adjuvant of the present invention, SEQ-26, it showed the very strong effect of inhibition on tumor progression of B16F10 cells, 76.8% on Day 12 after transplantation compared to ODN1826 (SEQ-1). The tumor inhibition rate of ssCpG ODN introducing a lipid ligand (SEQ-2) was 64.3% on Day 12 after transplantation compared to ODN1826. That is, an adjuvant of the present invention showed the stronger effect of inhibition on tumor progression of B16F10 cells than the adjuvant of SEQ-2, On the other hand, Montanide used as an adjuvant has no anti-tumor effect. The results were shown in FIG. 4.

Result 7-A: CTL Inducibility of Adjuvants of the Present Invention with the Different Kinds of Nucleic Acid Monomer in a Complementary Strand Activity of an adjuvant of the present invention whose nucleic acid monomers in the complementary strand were RNA, 2'-OMe-RNA or 2'-F-RNA was examined with TRP2 peptide. The adjuvant that all of the nucleic acid monomers were RNA (SEQ-40) or 2'-F-RNA (SEQ-42) did not show big enhancement of CTL inducibility compared to ODN1826 (SEQ-1). On the other hand, the adjuvant with 2'-OMe-RNA as a nucleic acid monomer (SEQ-38 and SEQ-44) showed enhancement of CTL inducibility at 2.9 or 2.4 times respectively compared to ODN1826. These results suggested that 2'-OMe-RNA is useful as nucleic acid monomer of an adjuvant of the present invention as well as DNA. The results were shown in Table 37.

TABLE 37

| Peptide | Adjuvant | dose/head nmol | Ratio of average value of antigen-specific CTL | Tumor inhibition rate (Day 14 after transplantation) |
|---|---|---|---|---|
| TRP2 | SEQ-1 | 1.57 | 1.00 | 0.00 |
| TRP2 | SEQ-38 | 1.57 | 2.85 | 86.19 |
| TRP2 | SEQ-40 | 1.57 | 1.24 | 3.73 |
| TRP2 | SEQ-42 | 1.57 | 0.99 | 57.38 |
| TRP2 | SEQ-44 | 1.57 | 2.39 | 57.51 |
| TRP2 | SEQ-2 | 1.57 | 3.11 | 72.64 |

Result 7-B: Anti-Tumor Effect of Adjuvants of the Present Invention with the Different Kinds of Nucleic Acid Monomer in a Complementary Strand When mice were immunized with TRP2 peptide and an adjuvant of the present invention with 2'OMe-RNA as nucleic acid monomers (SEQ-38), it showed the very strong effect of inhibition on tumor progression of B16F10 cells, about 86.2% on Day 14 after transplantation compared to ODN1826 (SEQ-1). The tumor inhibition rate of ssCpG ODN introducing a lipid ligand (SEQ-2) was about 72.6% on Day 14 after transplantation compared to ODN1826. That is, an adjuvant of the present invention showed the stronger effect of inhibition on tumor progression of B16F10 cells than the adjuvant of SEQ-2. In addition, the adjuvant whose chain length of SEQ-38 was shorten (SEQ-44) and the adjuvant with 2'-F-RNA as a nucleic acid monomer (SEQ-42) showed the effect of inhibition on tumor progression in B16F10 cells. On the other hand, the adjuvant with RNA as a nucleic acid monomer (SEQ-40) showed no effect of inhibition on tumor progression of B16F10 cells. The results were shown in Table 37 and FIG. 5.

(Result Using ODN2006 as a CpG Oligonucleotide)

Result 8-A: CTL Inducibility of Adjuvants of the Present Invention with the Different Chain Length of the Complementary Strand or a Linker The activities of ODN2006 (SEQ-49, 24 mer) and adjuvants of the present invention were compared with TRP2 peptide as antigen. The adjuvant whose chain length of the complementary strand is 24 mer, i.e., the length of the complementary strand against the CpG oligonucleotide is 100% (SEQ-51) and the adjuvant whose chain length of the complementary strand is 15 mer, i.e., the length of the complementary strand against the CpG oligonucleotide is 62.5% (SEQ-61) were used. Both of SEQ-51 and SEQ-61 showed high CTL inducibility at more than 5 times compared to ODN2006. Furthermore, the adjuvant with dTdT as a linker (SEQ-63) or dGdG (SEQ-65) was used. Both SEQ-63 and SEQ-65 showed very high CTL inducibility at about 10 times compared to ODN2006. The results were shown in Table 38.

TABLE 38

| Peptide | Adjuvant | dose/head nmol | Ratio of average value of antigen-specific CTL |
|---|---|---|---|
| TKP2 | SEQ-49 | 4.71 | 1.00 |
| TRP2 | SEQ-51 | 4.71 | 5.82 |
| TRP2 | SEQ-61 | 4.71 | 5.73 |

TABLE 38-continued

| Peptide | Adjuvant | dose/head nmol | Ratio of average value of antigen-specific CTL |
|---|---|---|---|
| TRP2 | SEQ-63 | 4.71 | 11.73 |
| TRP2 | SEQ-65 | 4.71 | 9.21 |

Result 8-B: Antitumor Effect of an Adjuvant of the Present Invention with the Different Chain Length of a Complementary Strand or a Linker When mice were immunized with TRP2 peptide and ODN2006 (SEQ-49), it showed little effect of inhibition on tumor progression of B16F10 cells. On the other hand, an, adjuvant of the present invention whose length of the complementary strand is 100% against the CpG oligonucleotide (SEQ-51) showed 20% of the effect of inhibition on tumor progression of B16F10 cells on Day 10 after transplantation compared to ODN2006. In addition, each the adjuvant whose length of the complementary strand is 62.5% against the CpG oligonucleotide (SEQ-61), and the adjuvant with dTdT as a linker (SEQ-63) or dGdG (SEQ-65) showed about 50% of the effect of inhibition on tumor progression of B16F10 cells on Day 10 after transplantation compared to ODN2006. The results were shown in FIG. 6.

Result 9-A: CTL Inducibility of Adjuvants of the Present Invention Whose Nucleic Acid Monomer in the Complementary Strand is 2'-OMe-RNA Activity of an adjuvant of the present invention whose nucleic acid monomer in the complementary strand is 2'-OMe-RNA was examined with TRP2. The chain length of the complementary strand is 24 mer, i.e., the adjuvant whose length of the complementary strand against the CpG oligonucleotides was 100% (SEQ-67) and, the adjuvant whose length of the complementary strand is 15 mer, i.e., the adjuvant whose length, of the complementary strand against the CpG oligonucleotide is 62.5% (SEQ-69) were used. SEQ-67 and SEQ-69 showed CTL inducibility at 1.4 or 1.2 times respectively compared to ODN2006 (SEQ-49). The results were shown in Table 39.

TABLE 39

| Peptide | Adjuvant | dose/head nmol | Ratio of average value of antigen-specific CTL |
|---|---|---|---|
| TRP2 | SEQ-49 | 4.71 | 1.00 |
| TRP2 | SEQ-67 | 4.71 | 1.39 |
| TRP2 | SEQ-69 | 4.71 | 1.21 |

Result 9-B: Anti-Tumor Effect of Adjuvants of the Present Invention Whose Nucleic Acid Monomer in the Complementary Strand is 2'-OMe-RNA When mice were immunized with TRP2 peptide and an adjuvant of the present, invention which has 2'-OMe-RNA as a nucleic acid monomer, adjuvant whose length of complementary strand against the CpG oligonucleotides is 100% (SEQ-67) showed very strong effect, of inhibition on tumor progression of B16F10 cells, about 75% on Day 10 after transplantation compared to ODN2006 (SEQ-49). The adjuvant whose length of the complementary strand against CpG oligonucleotides is 62.5% (SEQ-69) showed about 20% of the effect of inhibition on tumor progression of B16F10 cells on Day 10 after transplantation compared to ODN2006. The results were shown in FIG. 7.

These suggested that 2'-OMe-RNA was useful also for ODN2006 as nucleic acid monomer for an adjuvant of the present invention as well as DNA.

In similar methods, CTL inducibility or anti-tumor effect of adjuvants of the present invention was measured. Results are shown in Tables 40 to 68 and FIGS. 8 to 18 separately by experiments. For these experiments, TRP2 peptide was used and the dosage of the adjuvant, of the present invention was 4.71 nmol. NT in tables means "not tested"

TABLE 40

| Adjuvant | Ratio of average value of antigen-specific CTL |
|---|---|
| SEQ-49 | 1.00 |
| SEQ-59 | 5.34 |
| SEQ-57 | 4.28 |
| SEQ-55 | 3.02 |
| SEQ-53 | 2.86 |

TABLE 41

| Adjuvant | Ratio of average value of antigen-specific CTL | Tumor inhibition rate (Day 12 after transplantation) |
|---|---|---|
| SEQ-49 | 1.00 | 0.00 |
| SEQ-119 | 2.05 | 55.1 |
| SEQ-192 | 1.74 | 41.5 |

TABLE 42

| Adjuvant | Ratio of average value of antigen-specific CTL | Tumor inhibition rate (Day 12 after transplantation) |
|---|---|---|
| SEQ-49 | 1.00 | 0.00 |
| SEQ-121 | 3.99 | 56.8 |

TABLE 43

| Adjuvant | Ratio of average value of antigen-specific CTL | Tumor inhibition rate (Day 14 after transplantation) |
|---|---|---|
| SEQ-49 | 1.00 | 0.00 |
| SEQ-152 | 1.17 | 80.45 |
| SEQ-154 | 2.47 | NT |
| SEQ-158 | 3.06 | 100 |

TABLE 44

| Adjuvant | Ratio of average value of antigen-specific CTL |
|---|---|
| SEQ-49 | 1.00 |
| SEQ-182 | 2.24 |
| SEQ-184 | 2.38 |

TABLE 45

| Adjuvant | Ratio of average value of antigen-specific CTL | Tumor inhibition rate (Day 14 after transplantation) |
|---|---|---|
| SEQ-49 | 1.00 | 0.00 |
| SEQ-186 | 2.37 | NT |
| SEQ-188 | 1.49 | 51.03 |
| SEQ-190 | 1.95 | NT |
| SEQ-192 | 3.61 | 46.16 |

TABLE 45-continued

| Adjuvant | Ratio of average value of antigen-specific CTL | Tumor inhibition rate (Day 14 after transplantation) |
|---|---|---|
| SEQ-194 | 2.48 | 55.02 |
| SEQ-196 | 3.26 | NT |

TABLE 46

| Adjuvant | Ratio of average value of antigen-specific CTL | Tumor inhibition rate (Day 14 after transplantation) |
|---|---|---|
| SEQ-49 | 1.00 | 0.00 |
| SEQ-156 | 1.70 | NT |
| SEQ-160 | 3.65 | NT |
| SEQ-162 | 3.44 | NT |
| SEQ-164 | 4.88 | 53.69 |

TABLE 47

| Adjuvant | Ratio of average value of antigen-specific CTL |
|---|---|
| SEQ-49 | 1.00 |
| SEQ-166 | 2.57 |
| SEQ-168 | 1.96 |

TABLE 48

| Adjuvant | Ratio of average value of antigen-specific CTL | Tumor inhibition rate (Day 14 after transplantation) |
|---|---|---|
| SEQ-49 | 1.00 | 0.00 |
| SEQ-170 | 3.10 | 79.09 |
| SEQ-172 | 1.24 | NT |
| SEQ-174 | 1.78 | NT |

TABLE 49

| Adjuvant | Ratio of average value of antigen-specific CTL |
|---|---|
| SEQ-49 | 1.00 |
| SEQ-176 | 1.97 |
| SEQ-178 | 5.44 |
| SEQ-180 | 3.59 |
| SEQ-206 | 1.07 |
| SEQ-208 | 1.28 |
| SEQ-214 | 1.38 |
| SEQ-216 | 1.95 |

TABLE 50

| Adjuvant | Ratio of average value of antigen-specific CTL |
|---|---|
| SEQ-49 | 1.00 |
| SEQ-198 | 3.12 |
| SEQ-200 | 3.24 |
| SEQ-204 | 3.98 |

TABLE 51

| Adjuvant | Ratio of average value of antigen-specific CTL |
|---|---|
| SEQ-49 | 1.00 |
| SEQ-226 | 1.84 |
| SEQ-228 | 2.10 |
| SEQ-230 | 3.10 |
| SEQ-232 | 1.28 |
| SEQ-234 | 1.96 |

TABLE 52

| Adjuvant | Ratio of average value of antigen-specific CTL |
|---|---|
| SEQ-49 | 1.00 |
| SEQ-218 | 2.87 |
| SEQ-220 | 1.68 |
| SEQ-222 | 3.11 |
| SEQ-224 | 2.25 |

TABLE 53

| Adjuvant | Ratio of average value of antigen-specific CTL |
|---|---|
| SEQ-49 | 1.00 |
| SEQ-236 | 2.66 |

TABLE 54

| Adjuvant | Ratio of average value of antigen-specific CTL |
|---|---|
| SEQ-49 | 1.00 |
| SEQ-238 | 1.09 |
| SEQ-240 | 1.45 |
| SEQ-242 | 1.62 |
| SEQ-244 | 3.24 |

TABLE 55

| Adjuvant | Ratio of average value of antigen-specific CTL |
|---|---|
| SEQ-49 | 1.00 |
| SEQ-246 | 2.51 |
| SEQ-248 | 1.67 |
| SEQ-250 | 1.86 |
| SEQ-252 | 1.14 |

TABLE 56

| Adjuvant | Ratio of average value of antigen-specific CTL |
|---|---|
| SEQ-256 (D35-CpG) | 1.00 |
| SEQ-258 | 2.46 |

TABLE 57

| Adjuvant | Ratio of average value of antigen-specific CTL |
|---|---|
| SEQ-49 | 1.00 |
| SEQ-260 | 1.89 |

TABLE 57-continued

| Adjuvant | Ratio of average value of antigen-specific CTL |
|---|---|
| SEQ-262 | 1.45 |
| SEQ-264 | 3.44 |
| SEQ-266 | 2.51 |

TABLE 58

| Adjuvant | Ratio of average value of antigen-specific CTL |
|---|---|
| SEQ-49 | 1.00 |
| SEQ-268 | 2.09 |
| SEQ-270 | 2.31 |
| SEQ-272 | 1.77 |
| SEQ-274 | 4.03 |
| SEQ-276 | 3.77 |
| SEQ-278 | 2.58 |

TABLE 59

| Adjuvant | Ratio of average value of antigen-specific CTL |
|---|---|
| SEQ-49 | 1.00 |
| SEQ-280 | 5.27 |
| SEQ-282 | 2.82 |
| SEQ-284 | 5.57 |
| SEQ-286 | 2.40 |

TABLE 60

| Adjuvant | Ratio of average value of antigen-specific CTL |
|---|---|
| SEQ-49 | 1.00 |
| SEQ-288 | 4.22 |
| SEQ-290 | 2.80 |
| SEQ-292 | 4.63 |
| SEQ-294 | 5.30 |

TABLE 61

| Adjuvant | Ratio of average value of antigen-specific CTL |
|---|---|
| SEQ-49 | 1.00 |
| SEQ-296 | 2.43 |
| SEQ-298 | 2.08 |
| SEQ-300 | 3.48 |
| SEQ-302 | 2.58 |
| SEQ-304 | 2.42 |
| SEQ-306 | 3.04 |

TABLE 62

| Adjuvant | Ratio of average value of antigen-specific CTL |
|---|---|
| SEQ-49 | 1.00 |
| SEQ-308 | 2.52 |
| SEQ-310 | 4.91 |
| SEQ-312 | 1.75 |
| SEQ-314 | 2.58 |
| SEQ-316 | 1.30 |

TABLE 63

| Adjuvant | Ratio of average value of antigen-specific CTL |
|---|---|
| SEQ-49 | 1.00 |
| SEQ-318 | 4.19 |
| SEQ-320 | 3.81 |
| SEQ-322 | 2.15 |
| SEQ-324 | 1.92 |

TABLE 64

| Adjuvant | Ratio of average value of antigen specific CTL |
|---|---|
| SEQ-49 | 1.00 |
| SEQ-326 | 4.27 |
| SEQ-328 | 2.93 |
| SEQ-330 | 2.53 |
| SEQ-332 | 2.98 |
| SEQ-334 | 1.66 |
| SEQ-336 | 3.62 |
| SEQ-338 | 1.72 |

TABLE 65

| Adjuvant | Ratio of average value of antigen-specific CTL |
|---|---|
| SEQ-339(ODN2216) | 1.00 |
| SEQ-341 | 1.25 |
| SEQ-342(ODN684) | 1.00 |
| SEQ-344 | 1.20 |
| SEQ-345(D-LS01) | 1.00 |
| SEQ-347 | 2.73 |

TABLE 66

| Adjuvant | Ratio of average value of antigen-specific CTL |
|---|---|
| SEQ-354(ODN M362) | 1.00 |
| SEQ-356 | 1.91 |

TABLE 67

| Adjuvant | Ratio of average value of antigen-specific CTL |
|---|---|
| SEQ-49 | 1.00 |
| SEQ-373 | 2.21 |
| SEQ-375 | 2.58 |
| SEQ-377 | 1.57 |

TABLE 68

| Adjuvant | Ratio of average value of antigen-specific CTL |
|---|---|
| SEQ-49 | 1.00 |
| SEQ-361 | 1.09 |
| SEQ-365 | 2.04 |
| SEQ-369 | 1.70 |
| SEQ-371 | 1.11 |

Example 4

Antigen-specific CTL inducibility and anti-tumor effect of ODN2006 (SEQ-49) and SEQ-121 in the absence of a tumor antigen peptide were evaluated. In similar methods of A) and B) of Example 3, the effect of vaccine without a tumor antigen peptide was verified. Both of the antigen-specific CTL values of SEQ-49 and SEQ-121 were undetectable. On the other hand, SEQ-121 showed 85.3% of the effect of inhibition on tumor progression of B16F10 cells on Day 12 after transplantation compared to ODN2006. From these results, SEQ-121 was expected to apply to therapeutic vaccine with anti-tumor effect even it is a single agent (Table 69, FIG. 14).

TABLE 69

| Adjuvant | Ratio of average value of antigen-specific CTL | Tumor inhibition rate (Day 12 after transplantation) |
| --- | --- | --- |
| SEQ-49 | Undetectable | 0.00 |
| SEQ-121 | Undetectable | 85.3 |

Example 5 Irritation Test in a Single Dose of Adjuvants of the Present Invention A) Subcutaneous Irritation Test in a Single Dose Subcutaneous irritation of a compound of the present invention was evaluated by gross examination and histopathological examination about the skin at necropsy one day, one and four week(s) after subcutaneous administration in a single dose.

The compound of the present invention was subcutaneously administered to the center of back between the shoulder blades of rats. At necropsy one day, one or four week(s) after administration (isoflurane anesthesia, euthanasia by bleeding), skin at the administration site was collected, grossly observed and fixed in 10% neutral buffered formalin solution. The fixed skin was cut out, embedded and put in a thin slice by the usual methods, and Hematoxylin-eosin (HE) stained sections were made. The pathological observers were observed the HE stained sections by an optical microscope, and recorded the histopathological findings. The changes in pathological findings were evaluated in four grades of Minimal; ±, Mild; +, Moderate; 2+ and Marked; 3+. When any grade was not appropriate for the finding, it was recorded as Positive.

(Result)

To verify the safety of adjuvants of the present invention as a medicine, the subcutaneous irritation was compared to that of Montanide used in clinical trials as an adjuvant, Amph1826 (SEQ-2) or ODN2006 (SEQ-49) which is the well-known adjuvant.

Montanide is an adjuvant consisting of mineral oil and surfactant, and used in clinical trials as an adjuvant of peptide vaccine by preparation of emulsion with aqueous formulation. Although it is an adjuvant with excellent safety profile about systemic safety concerns, there is a problem about the occurrence of skin induration caused by remaining emulsion in the administration site. In this experiment, the administration site reaction of the double-stranded oligonucleotide was compared to that of Montanide, and it was examined whether it could be an adjuvant with week local irritation.

Rat subcutaneous irritation tests in a single dose were carried out for Montanide, SEQ-2, SEQ-49 or an adjuvant of the present invention (SEQ-61, SEQ-119, SEQ-121, SEQ-170, SEQ-192 or SEQ-216). Montanide was administered at 1 mL/site in emulsion of Montanide:saline (1:1). SEQ-2, SEQ-49 or an adjuvant of the present invention was dissolved in phosphate buffered saline and administered at 4.71, 15.7 or 47.1 nmol/1 mL/site, respectively.

As a result, it became clear that Montanide was not absorbed/decomposed/eliminated because white accumulation or white nodules was grossly observed under the skin and cyst-like structures was histologically confirmed one day, one and four week(s) after administration. Montanide remaining under the skin continued eliciting inflammation from one day to four weeks after administration. One day after administration, neutrophil infiltration and edema were observed. One week after administration, neutrophil infiltration and edema continued, but the inflammation became slightly chronic to observe as granulomatous inflammation. Four weeks after administration, thick fibrous capsule encapsulated Montanide was formed. Inflammation was slightly reduced compared to one week after administration, but even four weeks after administration, the animals with continuous neutrophil infiltration or edema were observed.

In the case of SEQ-2, inflammation cellular infiltration, edema and crust were observed one day and one week after administration. Even four weeks after administration, skin inflammation was not recovered, and granulomatous inflammation by continuous activation of monocyte/macrophage system was observed.

In the case of SEQ-49, and SEQ-61, SEQ-119, SEQ-121, SEQ-170, SEQ-192 and SEQ-216, which is an adjuvant of the present invention, acute inflammation, mainly neutrophil infiltration, was observed under the skin one day after administration. One week after administration, inflammation, mainly lymphocyte and macrophage, was observed from subcutaneous to dermis tissue, and four weeks after administration, inflammation was almost recovered. Regarding SEQ-119, SEQ-121 and SEQ-170, subcutaneous irritation evaluation four weeks after administration was not carried out, but when their subcutaneous irritation one day and one week after administration were compared to those of SEQ-119, SEQ-121, SEQ-170 and SEQ-61, the irritation were equal to or weaker than SEQ-61. These suggested that regarding SEQ-119, SEQ-121 and SEQ-170, inflammation was almost completely recovered four weeks after administration.

Tables 70 to 72 showed the results one day after administration, Tables 73 to 75 showed the results one week after administration, and Tables 76 and 77 showed the results four weeks after administration. The notes in the tables are as below.
1) Values after findings are numbers of the observed animals.
2) Values after findings are scores. The scores were calculated the total, provided that grades of each individual were put as Minimal; 1, Mild; 2 and Moderate; 3.

The above showed that compared between adjuvants of the present invention and Montanide, adjuvants of the present invention did not cause the accumulation of the compounds under the skin (low risk of induration), necrosis or neutrophil infiltration was not occurred even one week after administration, and inflammation was almost completely recovered four weeks after administration. Therefore, it was concluded that subcutaneous irritation of the adjuvants of the present invention was weaker than that of Montanide. Also, compared between adjuvants of the present invention and Amph1826 (SEQ-2), inflammation caused by adjuvants of the present invention was almost completely recovered four weeks after administration, but on the other hand skin inflammation caused by SEQ-2 was not recovered, and granulomatous inflammation by continuous activation of monocyte/macrophage system was observed even four weeks after administration. Therefore, it was concluded that subcutaneous irritation of the adjuvants of the present invention was weaker than that of SEQ-2. Subcutaneous irritation of adjuvants of the present invention was no significant difference from that of ODN2006 (SEQ-49).

TABLE 70

| | | | | Montanide | SEQ-49 | | | SEQ-61 | | |
|---|---|---|---|---|---|---|---|---|---|---|
| | | | | | Dose (nmol/site) | | | | | |
| | | | | — | 4.71 | 15.7 | 47.1 | 4.71 | 15.7 | 47.1 |
| | Number of animals | | | 3 | 3 | 3 | 3 | 3 | 3 | 3 |
| | Number of deaths/imminent dissections | | | 0/0 | 0/0 | 0/0 | 0/0 | 0/0 | 0/0 | 0/0 |
| Pathology | Administration site | Gross[1] | Subcutaneous: White accumulation | 3 | 0 | 0 | 0 | 0 | 0 | 0 |
| | | | Subcutaneous: Red spots, Erythema | 0 | 0 | 0 | 1 | 0 | 0 | 0 |
| | | Histo-pathological | Subcutaneous: Neutrophilic infiltration[2] | 3 | 6 | 6 | 6 | 5 | 6 | 6 |
| | | | Subcutaneous: Edema[2] | 3 | 4 | 5 | 5 | 2 | 3 | 5 |
| | | | Subcutaneous: Bleeding[2] | 2 | 2 | 1 | 2 | 1 | 0 | 1 |
| | | | Subcutaneous: Cyst-like structure[1] | 3 | 0 | 0 | 0 | 0 | 0 | 0 |
| | | | Muscle layer: Neutrophilic infiltration[2] | 0 | 4 | 6 | 5 | 4 | 5 | 5 |
| | | | Muscle layer: Edema[2] | 0 | 2 | 1 | 0 | 3 | 2 | 3 |

TABLE 71

| | | | | | SEQ-192 | | | SEQ-216 | | | SEQ-2 | | |
|---|---|---|---|---|---|---|---|---|---|---|---|---|---|
| | | | | | Dose (nmol/site) | | | | | | | | |
| | | | | | 4.71 | 15.7 | 47.1 | 4.71 | 15.7 | 47.1 | 4.71 | 15.7 | 47.1 |
| | Number of animals | | | | 3 | 3 | 3 | 3 | 3 | 3 | 3 | 3 | 3 |
| | Number of deaths/imminent dissections | | | | 0/0 | 0/0 | 0/0 | 0/0 | 0/0 | 0/0 | 0/0 | 0/0 | 0/0 |
| Pathology | Administration site | Histo-pathological[2] | Subcutaneous tissue | Inflammatory cell infiltration[2] | 6 | 5 | 5 | 6 | 6 | 5 | 7 | 6 | 6 |
| | | | | Edema[2] | 7 | 6 | 4 | 5 | 7 | 4 | 3 | 5 | 6 |
| | | | | Bleeding[2] | 2 | 1 | 1 | 3 | 1 | 1 | 0 | 3 | 3 |
| | | | | Necrosis[2] | 1 | 0 | 1 | 1 | 0 | 0 | 1 | 1 | 1 |
| | | | | Cyst-like structure[1] | 2 | 1 | 2 | 2 | 3 | 0 | 1 | 2 | 1 |
| | | | Dermis | Inflammatory cell infiltration[2] | 6 | 6 | 6 | 7 | 7 | 6 | 5 | 9 | 6 |
| | | | Muscle layer | Inflammatory cell infiltration[2] | 2 | 3 | 4 | 3 | 6 | 2 | 4 | 7 | 6 |
| | | | | Edema[2] | 1 | 2 | 3 | 2 | 2 | 1 | 1 | 3 | 4 |
| | | | | Necrosis[2] | 0 | 0 | 0 | 0 | 0 | 1 | 0 | 0 | 0 |

TABLE 72

| | | | | | SEQ-121 | | | SEQ-170 | | | SEQ-119 | | |
|---|---|---|---|---|---|---|---|---|---|---|---|---|---|
| | | | | | Dose (nmol/site) | | | | | | | | |
| | | | | | 4.71 | 15.7 | 47.1 | 4.71 | 15.7 | 47.1 | 4.71 | 15.7 | 47.1 |
| | Number of animals | | | | 3 | 3 | 3 | 3 | 3 | 3 | 3 | 3 | 3 |
| | Number of deaths/imminent dissections | | | | 0/0 | 0/0 | 0/0 | 0/0 | 0/0 | 0/0 | 0/0 | 0/0 | 0/0 |
| Pathology | Administration site | Gross[1] | | Turbidity | 0 | 0 | 0 | 1 | 1 | 0 | 1 | 0 | 2 |
| | | | | Erythema | 0 | 0 | 0 | 1 | 2 | 2 | 0 | 0 | 0 |
| | | Histo-pathological[2] | Subcutaneous tissue | Inflammatory cell infiltration[2] | 5 | 5 | 6 | 3 | 6 | 8 | 3 | 4 | 6 |
| | | | | Edema[2] | 9 | 8 | 5 | 6 | 5 | 7 | 5 | 5 | 6 |

TABLE 72-continued

| | | | Compound name | | | | | | | |
|---|---|---|---|---|---|---|---|---|---|---|
| | | | SEQ-121 | | | SEQ-170 | | | SEQ-119 | | |
| | | | | | | Dose (nmol/site) | | | | | |
| | | | 4.71 | 15.7 | 47.1 | 4.71 | 15.7 | 47.1 | 4.71 | 15.7 | 47.1 |
| | Dermis | Inflammatory cell infiltration[2] | 1 | 4 | 6 | 1 | 0 | 5 | 1 | 2 | 6 |
| | Muscle layer | Inflammatory cell infiltration[2] | 2 | 5 | 6 | 3 | 5 | 6 | 1 | 2 | 4 |

TABLE 73

| | | | | Compound name | | | | | |
|---|---|---|---|---|---|---|---|---|---|
| | | | | Montanide | SEQ-49 | | | SEQ-61 | | |
| | | | | | | | Dose (nmol/site) | | | |
| | | | | — | 4.71 | 15.7 | 47.1 | 4.71 | 15.7 | 47.1 |
| | Number of animals | | | 3 | 3 | 3 | 3 | 3 | 3 | 3 |
| | Number of deaths/imminent dissections | | | 0/0 | 0/0 | 0/0 | 0/0 | 0/0 | 0/0 | 0/0 |
| Pathology | Administration site | Gross[1] | Subcutaneous: White nudules | 3 | 0 | 0 | 0 | 0 | 0 | 0 |
| | | | Epidermis: Crust | 0 | 1 | 1 | 0 | 1 | 0 | 0 |
| | | Hepathological | Subcutaneous: Necrosis[2] | 2 | 0 | 0 | 0 | 0 | 0 | 0 |
| | | | Subcutaneous: Neutrophilic infiltration[2] | 6 | 0 | 0 | 0 | 0 | 0 | 0 |
| | | | Subcutaneous: Monocyte infiltration[2] | 0 | 3 | 6 | 8 | 2 | 3 | 7 |
| | | | Subcutaneous: Granulomatous inflammation[2] | 7 | 0 | 0 | 0 | 0 | 0 | 0 |
| | | | Subcutaneous: Edema[2] | 5 | 4 | 6 | 5 | 4 | 5 | 6 |
| | | | Subcutaneous: Cyst-like structure[1] | 3 | 0 | 0 | 0 | 0 | 0 | 0 |

TABLE 74

| | | | | Compound name | | | | | | | |
|---|---|---|---|---|---|---|---|---|---|---|---|
| | | | | SEQ-192 | | | SEQ-216 | | | SEQ-2 | | |
| | | | | | | | Dose (nmol/site) | | | | | |
| | | | | 4.71 | 15.7 | 47.1 | 4.71 | 15.7 | 47.1 | 4.71 | 15.7 | 47.1 |
| | Number of animals | | | 3 | 3 | 3 | 3 | 3 | 3 | 3 | 3 | 3 |
| | Number of deaths/imminent dissections | | | 0/0 | 0/0 | 0/0 | 0/0 | 0/0 | 0/0 | 0/0 | 0/0 | 0/0 |
| Pathology | Administration site | Gross[1] | White matter accumulation | 0 | 0 | 0 | 0 | 0 | 0 | 0 | 0 | 0 |
| | | | Dark red spots | 0 | 0 | 0 | 0 | 0 | 1 | 0 | 0 | 0 |
| | | | Edema | 0 | 0 | 0 | 0 | 1 | 0 | 0 | 1 | 1 |
| | | | Crust | 0 | 1 | 1 | 0 | 1 | 2 | 0 | 0 | 0 |
| | Histo-pathological[2] | Subcutaneous | Granulomatous inflammation[2] | 0 | 0 | 0 | 0 | 0 | 0 | 0 | 0 | 0 |
| | | | Inflammatory cell infiltration[2] | 4 | 6 | 7 | 3 | 6 | 5 | | 8 | 8 |
| | | | Edema[2] | 3 | 3 | 2 | 1 | 2 | 2 | 3 | 4 | 3 |
| | | | Necrosis[2] | 0 | 1 | 3 | 0 | 0 | 2 | 0 | 0 | 0 |
| | | | Cyst-like structure[1] | 0 | 1 | 2 | 2 | 2 | 1 | 1 | 1 | 3 |
| | | Dermis | Inflammatory cell infiltration[2] | 2 | 5 | 7 | 0 | 5 | 8 | 4 | 6 | 9 |
| | | Muscle layer | Inflammatory cell infiltration[2] | 0 | 5 | 3 | 0 | 4 | 4 | 0 | 4 | 6 |

TABLE 75

| | | | | | SEQ-121 | | | SEQ-170 | | | SEQ-119 | | |
|---|---|---|---|---|---|---|---|---|---|---|---|---|---|
| | | | | | | | | Compound name | | | | | |
| | | | | | | | | Dose (nmol/site) | | | | | |
| | | | | | 4.71 | 15.7 | 47.1 | 4.71 | 15.7 | 47.1 | 4.71 | 15.7 | 47.1 |
| | Number of animals | | | | 3 | 3 | 3 | 3 | 3 | 3 | 3 | 3 | 3 |
| | Number of deaths/imminent dissections | | | | 0/0 | 0/0 | 0/0 | 0/0 | 0/0 | 0/0 | 0/0 | 0/0 | 0/0 |
| Pathology | Administration site | Gross[1] | | Turbidity | 0 | 0 | 0 | 1 | 1 | 0 | 1 | 0 | 2 |
| | | | | Erythema | 0 | 0 | 0 | 1 | 2 | 2 | 0 | 0 | 0 |
| | | Histo-pathological[2] | Subcutaneous | Inflammatory cell infiltration[2] | 5 | 5 | 6 | 3 | 6 | 8 | 3 | 4 | 6 |
| | | | Dermis | Inflammatory cell infiltration[2] | 1 | 4 | 6 | 1 | 0 | 5 | 1 | 2 | 6 |
| | | | Muscle layer | Inflammatory cell infiltration[2] | 2 | 5 | 6 | 3 | 5 | 6 | 1 | 2 | 4 |

TABLE 76

| | | | | | Montanide | SEQ-49 | | | SEQ-61 | | |
|---|---|---|---|---|---|---|---|---|---|---|---|
| | | | | | | | Compound name | | | | |
| | | | | | | | Dose (nmol/site) | | | | |
| | | | | | — | 4.71 | 15.7 | 47.1 | 4.71 | 15.7 | 47.1 |
| | Number of animals | | | | 3 | 3 | 3 | 3 | 3 | 3 | 3 |
| | Number of deaths/imminent dissections | | | | 0/0 | 0/0 | 0/0 | 0/0 | 0/0 | 0/0 | 0/0 |
| Pathology | Administration site | Gross[1] | | Subcutaneous: White nudules | 3 | 0 | 0 | 0 | 0 | 0 | 0 |
| | | Histo-pathological | | Muscle layer: Monocyte infiltration[2] | 0 | 0 | 0 | 0 | 0 | 0 | 1 |
| | | | | Subcutaneous: Neutrophilic infiltration[2] | 3 | 0 | 0 | 0 | 0 | 0 | 0 |
| | | | | Subcutaneous: Granulomatous infiltration[2] | 6 | 0 | 0 | 0 | 0 | 0 | 0 |
| | | | | Subcutaneous: Edema[2] | 1 | 0 | 0 | 0 | 0 | 0 | 0 |
| | | | | Subcutaneous: Cyst-like structure accompanied with formulation of fibrous capsule[1] | 3 | 0 | 0 | 0 | 0 | 0 | 0 |

TABLE 77

| | | | | | SEQ-192 | | | SEQ-216 | | | SEQ-2 | | |
|---|---|---|---|---|---|---|---|---|---|---|---|---|---|
| | | | | | | | | Compound name | | | | | |
| | | | | | | | | Dose (nmol/site) | | | | | |
| | | | | | 4.71 | 15.7 | 47.1 | 4.71 | 15.7 | 47.1 | 4.71 | 15.7 | 47.1 |
| | Number of animals | | | | 3 | 3 | 3 | 3 | 3 | 3 | 3 | 3 | 3 |
| | Number of deaths/imminent dissections | | | | 0/0 | 0/0 | 0/0 | 0/0 | 0/0 | 0/0 | 0/0 | 0/0 | 0/0 |
| Pathology | Administration site | Gross[1] | | White matter accumulation | 0 | 0 | 0 | 0 | 0 | 0 | 0 | 0 | 0 |
| | | | | Crust | 0 | 0 | 0 | 0 | 1 | 1 | 0 | 0 | 0 |
| | | Histo-pathological[2] | Subcutaneous | Granulomatous inflammation[2] | 0 | 0 | 0 | 0 | 0 | 0 | 4 | 5 | 7 |
| | | | | Inflammatory cell infiltration[2] | 0 | 0 | 0 | 0 | 0 | 0 | 0 | 0 | 0 |
| | | | | Edema[2] | 0 | 0 | 0 | 0 | 1 | 0 | 0 | 0 | 0 |
| | | | | Fibrosis[2] | | | | | | | | | |
| | | | | Cyst-like structure[1] | 0 | 0 | 0 | 0 | 0 | 0 | 0 | 0 | 0 |
| | | | Dermis | Inflammatory cell infiltration[2] | 0 | 1 | 0 | 0 | 1 | 0 | 0 | 4 | 7 |

B) Intradermal Irritation Test in a Single Dose

Subcutaneous irritation of adjuvants of the present invention of the present invention is evaluated by gross examination and histopathological examination about the skin at necropsy one day, one and four week(s) after subcutaneous administration in a single dose.

An adjuvant of the present invention is subcutaneously administered to skin of back of rats. The following procedure is carried out in a similar method to A) of Example 5.

Example 6 Evaluation of Inducibility of Antibody Production of the Adjuvant of the Present Invention in Immunization by *Pseudomonas aeruginosa* PCRV Antigen Vaccine When antigen and adjuvant are administered as an infectious disease vaccine and induced antibody production from B lymphocyte in the immunized animal, effect of prevention and treatment for infectious disease is expected. Therefore, in expectation of apply for an infectious disease vaccine of this adjuvant, and antibody production from B lymphocyte was evaluated. PCRV antigen which is *Pseudomonas aeruginosa* was used for the examination as an antigen. It has been already reported that *Pseudomonas aeruginosa* PCRV antigen have a vaccine effect (Moriyama et al., Infect. Immun., September 2001, vol. 69, no. 9, 5908-5910), and therefore effect of inducibility of antibody production by the adjuvant was evaluated compared to PCRV antigen administration group. Freund's adjuvant was used for a control group. Freund's adjuvant is an adjuvant that *Tubercle bacillus* killed by heating is mixed in oil consisting of paraffin oil and mannide monooleate, and known as an adjuvant strongly inducing antibody production in non-clinical studies. Freund's adjuvant shows strong effect in non-clinical studies, but the use in clinical trials has been prohibited because of concern of side effects (The European Agency for the Evaluation of Medical Products Evaluation of Medicines for Human Use, 25 Mar. 2004, Internet (URL: http://www.ema.europa.eu/docs/en_GB/document_library/Scientific_guideline/2009/11/WC500015469.pdf))

Perv nucleotide sequence (SEQ ID NO: 48) derived from *Pseudomonas aeruginosa* Strain PAO1 was cloned at NdeI-XhoI site in pET21a vector, and *Escherichia coli* strain BL21 (DE3) was transformed with the prepared plasmid. Strain perV-BL21 (DE3) was cultured in 500 mL of LB/Ampicillin liquid medium at 37° C., and 200 µL of 0.1 M IPTG was added when OD600 became 0.5 to induce expression of recombinant PCRV protein. After culturing at 16° C. for 18 hours, bacteria was separated by a centrifuge, and 15 ml of Buffer A (50 mM Tris-HCl (pH8.0), 0.2M NaCl) comprising 0.5% lysozyme (SIGMA Corporation) was added. After putting at 4° C. for 30 minutes, ultrasonic treatment was carried out. After centrifugation at 12,000 rpm for 10 minutes, soluble fraction was obtained. 1 mL of Ni-NTA agarose gel (QIAGEN) was added to Polyprep column (BIO-RAD Laboratories, Inc) and equilibrated with 10 mL of Buffer A. Soluble fraction was added to the column and passed. The column was washed with 20 mL of Buffer A+20 mM imidazole and eluted with 1 mL of Buffer A+250 mM imidazole. Superdex 200 16/60 GL column was connected to AKTA Explorer (GE Healthcare), and equilibrated with 1.5 CV of Buffer A. The fraction eluted with imidazole was purified by gel filtration and recombinant PCRV protein C-end HIS (SEQ ID NO: 49) was purified. The resulting recombinant PCRV protein was measured the concentration with BCA assay kit (PIERCE) and kept at −80° C.

70 µg of recombinant PCRV protein and 33 nmol of an adjuvant of the present invention were mixed with saline to be 0.7 mL. To each 5 mice of 5 weeks old female A/J mice (Japan SLC, Inc.), 0.1 mL of immunogen was intradermally injected on Day 0, 7 and 27. As a control, only recombinant PCRV protein was used for immunization in a similar method. Regarding Freund's adjuvant, 100 µg of recombinant PCRV protein was mixed with saline to be 0.5 mL, and emulsion was prepared with the same amount of Complete Freund's adjuvant (Difco Laboratories). 0.1 mL was intradermally injected on Day 7 as initial immunization. On Day 27, Incomplete Freund's adjuvant (Difco Laboratories) was used for immunization in a similar method. On Day 33, blood was collect using a heparin from tail vein of mice, and centrifuged at 6,000 rpm for 15 minutes. The supernatant was collected as an antiserum and kept at −40° C.

Antibody titer was measured as blow. Recombinant PCRV protein was mixed with PBS (pH7.4) (Invitrogen) to be 1 µg/mL, and 20 µL/well of the solution was added to Nunc Maxisorp 384 well plate (Thermo). The plate was sealed with a plate seal and incubation was carried out at 4° C. over night. After washing twice with 90 µL/well of Washing Buffer (9 g/L NaCl, 0.5 g/L Proclin 150, 0.1 g/L Tween-20), 60 µL/well of 1×Assay Buffer (Invitrogen) was added. The plate was sealed with a plate seal and blocking was carried out at room temperature for 2 hours. After removing the liquid by tapping, antiserum was diluted with 1×Assay Buffer at $10^3$ to $10^7$ times and 20 µL/well of the solution was added. The plate was sealed with a plate seal and incubation was carried out at 4° C. over night. After washing three times with Washing Buffer, GOAT Anti-mouse IgG Fc-HRP (JacksonImmunoResearch) was diluted at 20,000 with 1×Assay Buffer and 20 µL/well of the solution was added. The plate was sealed with a plate seal and incubation was carried out at room temperature for 2 hours. After washing three times with Washing Buffer, 20 µL/well of TMB substrate (Dako) was added and incubation was carried out at room temperature for 30 minutes. 20 µL/well of 0.5 N sulfuric acid (Nacalai) was added, and absorbance at 450 nm was measured with a plate reader. The dilution ratio when absorbance at 450 nm is 1.0 was calculated and put as an antibody titer. The results were shown in FIG. 15.

The antibody titers were $3.0 \times 10^6$ for SEQ-121 which is the highest, $2.5 \times 10^6$ for Freund's adjuvant, $7.1 \times 10^5$ for SEQ-61 and $5.3 \times 10^5$ for ODN2006 (SEQ-49) in order. The antibody titer for only PCRV protein was $1.3 \times 10^5$. These results suggested that the adjuvants of the present invention have strong immunostimulatory activity against B cells. Especially, antibody titer for SEQ-121 showed higher inducibility of antibody production than ODN2006 and almost same with antibody titer for Freund's adjuvant. Then, it was suggested that adjuvants of the present invention are excellent as an adjuvant for vaccine against infectious diseases. From these results, the adjuvants of the present invention are expected to apply for a vaccine against infectious diseases.

INDUSTRIAL APPLICABILITY

As it is clear from the above examples, lipid binding double-stranded oligonucleotides of the present invention show the excellent immunostimulatory activity. Therefore, they are very useful especially as an adjuvant to enhance the effect of vaccine.

The invention claimed is:

1. A double-stranded oligonucleotide, wherein
a first strand consists of a CpG oligonucleotide consisting of 8 to 50 nucleotides,
a second strand of the double-stranded oligonucleotide is 8 to 60 nucleotides and capable of hybridizing with the first strand,
wherein the second strand is not an oligonucleotide all of which nucleosides consist of an RNA nucleoside,
wherein the length of the second strand is 50% or more of that of the first strand, and
wherein a lipid comprising C12 to C30 hydrocarbon chain(s) is bound to the second strand through a linker.

2. The double-stranded oligonucleotide of claim 1, wherein the oligonucleotide of the second strand is an oligonucleotide consisting of DNA nucleosides and/or nucleoside derivatives.

3. The double-stranded oligonucleotide of claim 2, wherein the nucleoside derivative is a nucleoside having a substituent at the 2' position of the sugar and/or a nucleoside having a bridge structure between the 4' and 2' positions of the sugar.

4. The double-stranded oligonucleotide of claim 3, wherein the bridge structure between the 4' and 2' positions of the sugar is 4'-($CH_2$)m-O-2', wherein m is an integer of 1 to 4.

5. The double-stranded oligonucleotide of claim 1, wherein the lipid is a diacyl lipid.

6. The double-stranded oligonucleotide of claim 1, wherein the lipid binds at the 3' end and/or 5' end of the second strand.

7. The double-stranded oligonucleotide of claim 1, wherein the linker is an oligonucleotide linker.

8. The double-stranded oligonucleotide of claim 7, wherein the linker is -($dX^1$)u-, wherein $X^1$ is each independently, A, G, C or T, and u is an integer of 1 to 8.

9. A method for treating a cancer or an infectious disease, comprising administering the double-stranded oligonucleotide of claim 1 to a subject in need thereof.

10. The method of claim 9, wherein the double-stranded oligonucleotide is administered in combination with an antigen.

11. The double-stranded oligonucleotide of claim 5, wherein the diacyl lipid is

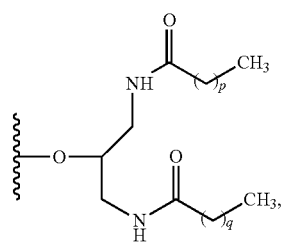

-continued

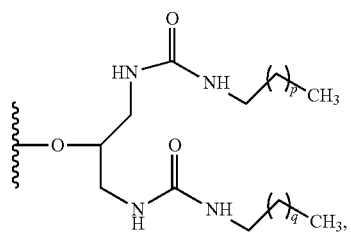

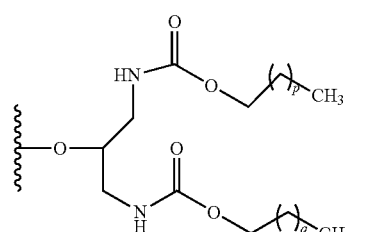

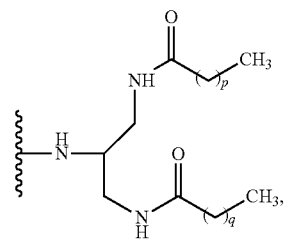

wherein p and q are each independently an integer of 10 to 28.

12. The double-stranded oligonucleotide of claim 1, wherein the first strand has the sequence set forth in SEQ ID NO:13.

13. A double-stranded oligonucleotide having a first strand and a second strand, wherein the first strand is represented by the formula:

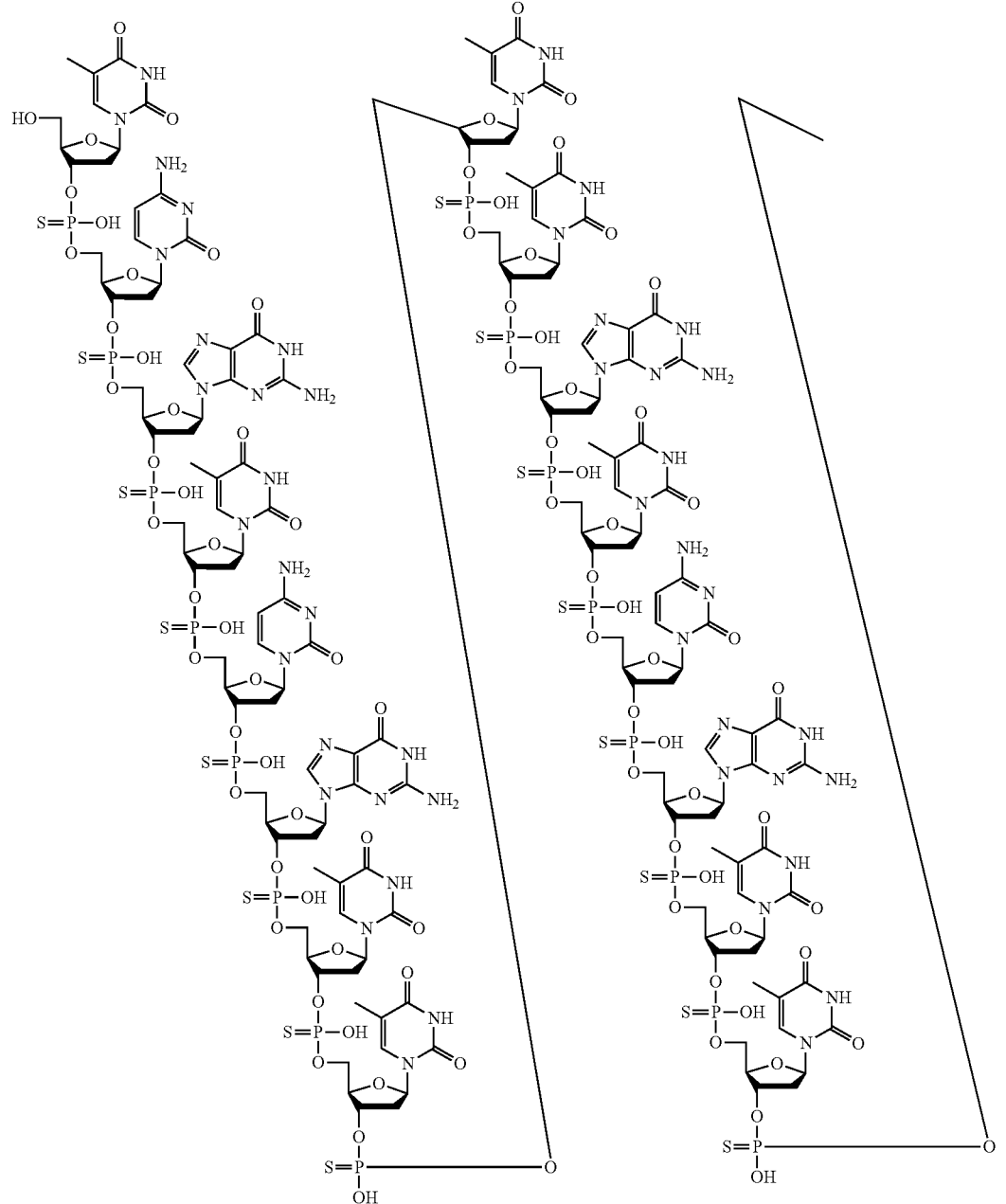
(ODN2006)
(SEQ. ID. NO.: 13)

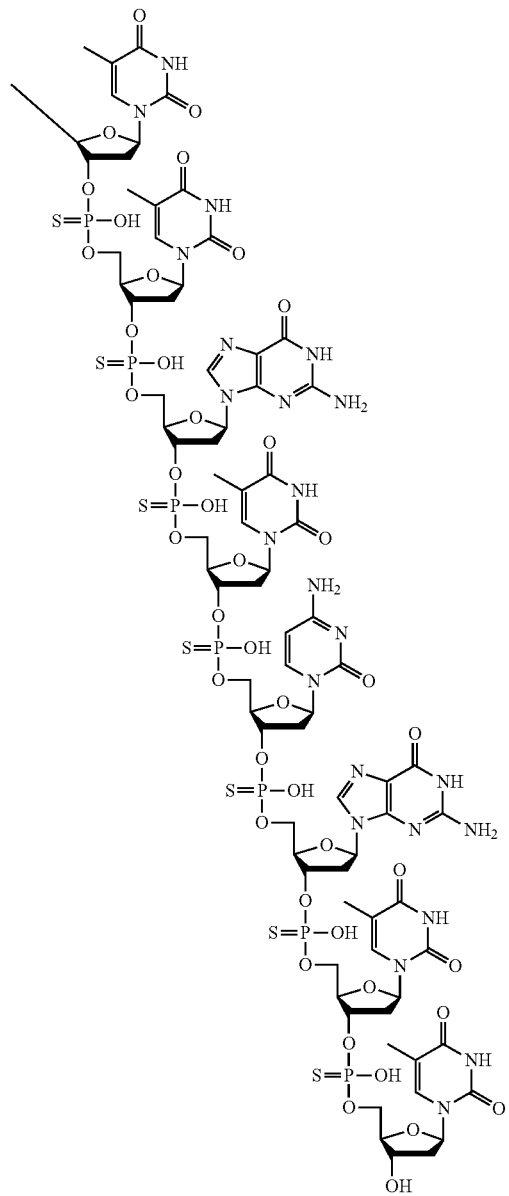 [SMILES: Cc1cn([C@H]2C[C@@H](OP(O)(=S)OC[C@H]3O[C@@H](n4cc(C)c(=O)[nH]c4=O)C[C@H]3OP(O)(=S)OC[C@H]3O[C@@H](n4cnc5c(=O)[nH]c(N)nc54)C[C@H]3OP(O)(=S)OC[C@H]3O[C@@H](n4cc(C)c(=O)[nH]c4=O)C[C@H]3OP(O)(=S)OC[C@H]3O[C@@H](n4ccc(N)nc4=O)C[C@H]3OP(O)(=S)OC[C@H]3O[C@@H](n4cnc5c(=O)[nH]c(N)nc54)C[C@H]3OP(O)(=S)OC[C@H]3O[C@@H](n4cc(C)c(=O)[nH]c4=O)C[C@H]3OP(O)(=S)OC[C@H]3O[C@@H](n4cc(C)c(=O)[nH]c4=O)C[C@H]3O)[C@@H](C)O2)c(=O)[nH]c1=O]
and wherein the second strand is represented by the formula:
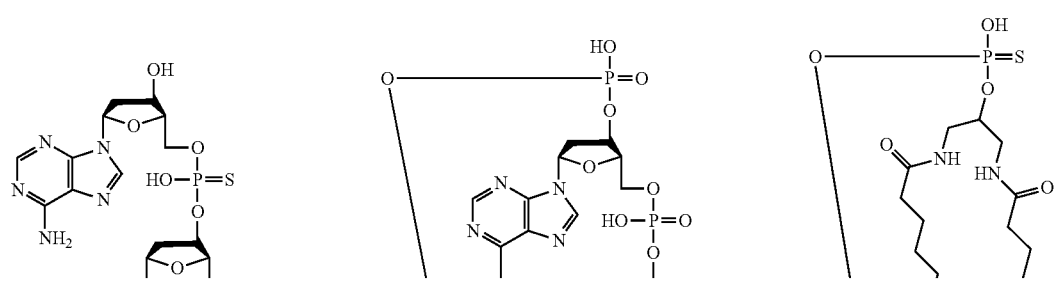
(S-28)

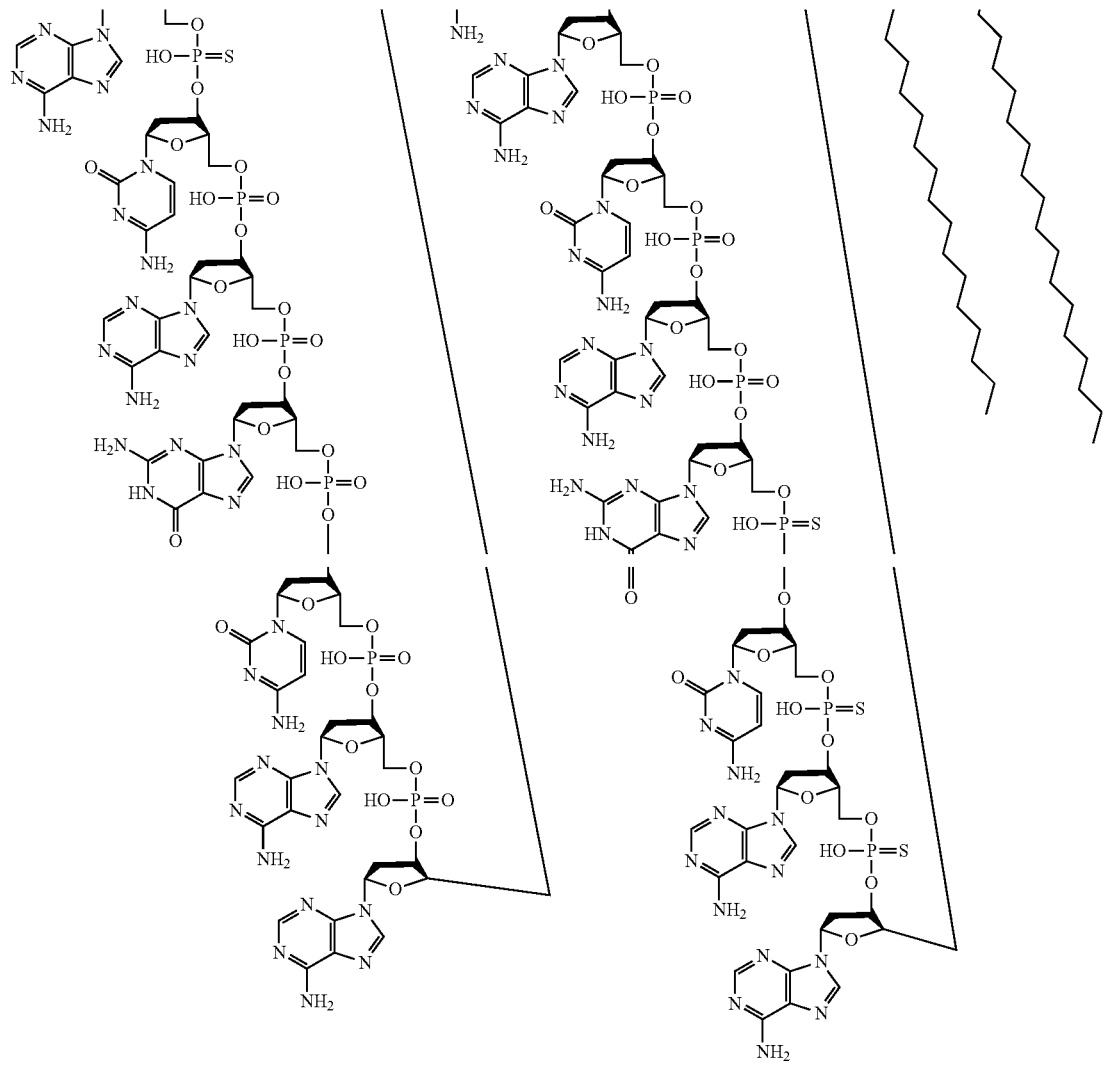
(SEQ. ID. NO.:18);

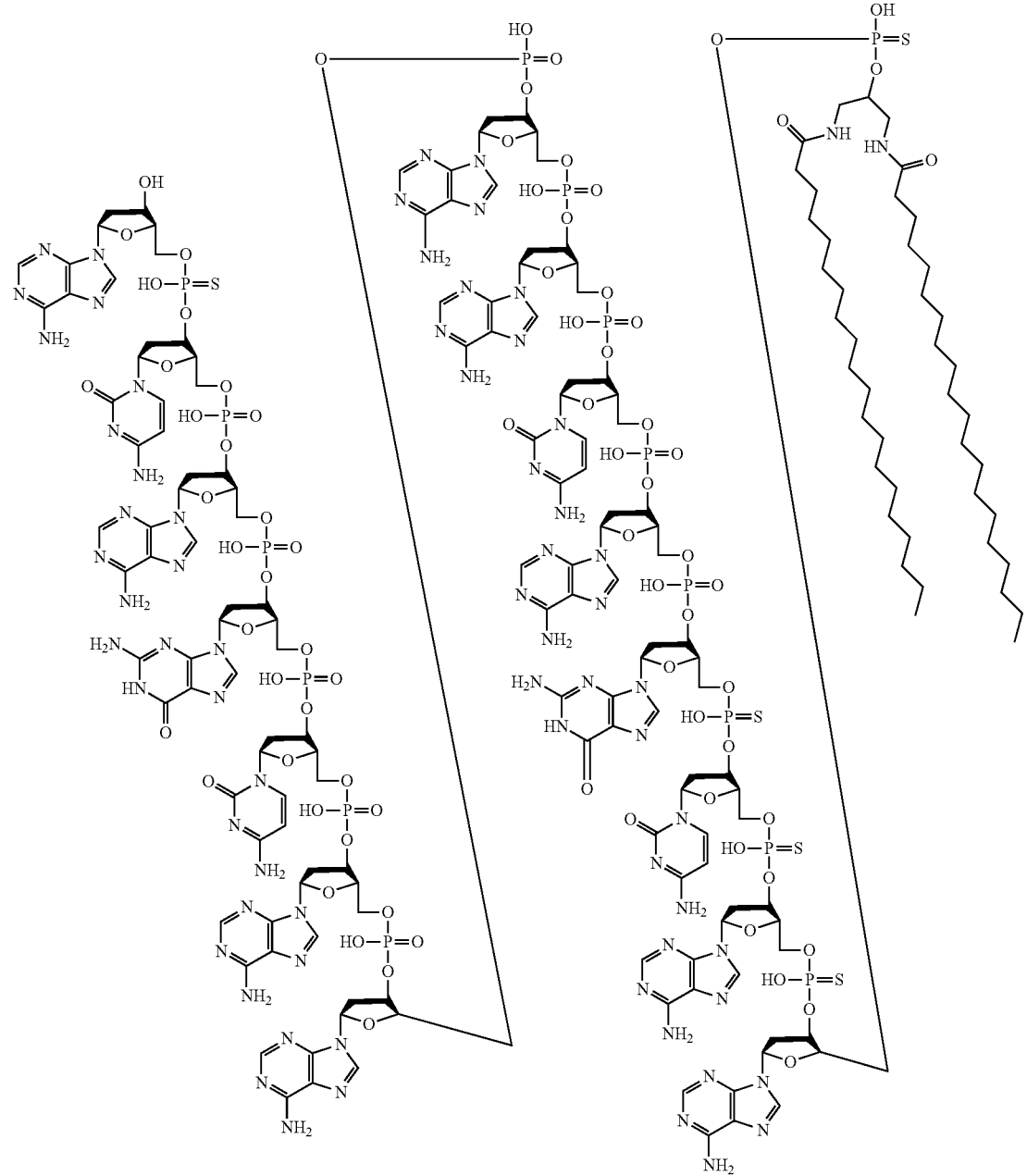
(SEQ. ID. NO.:19);

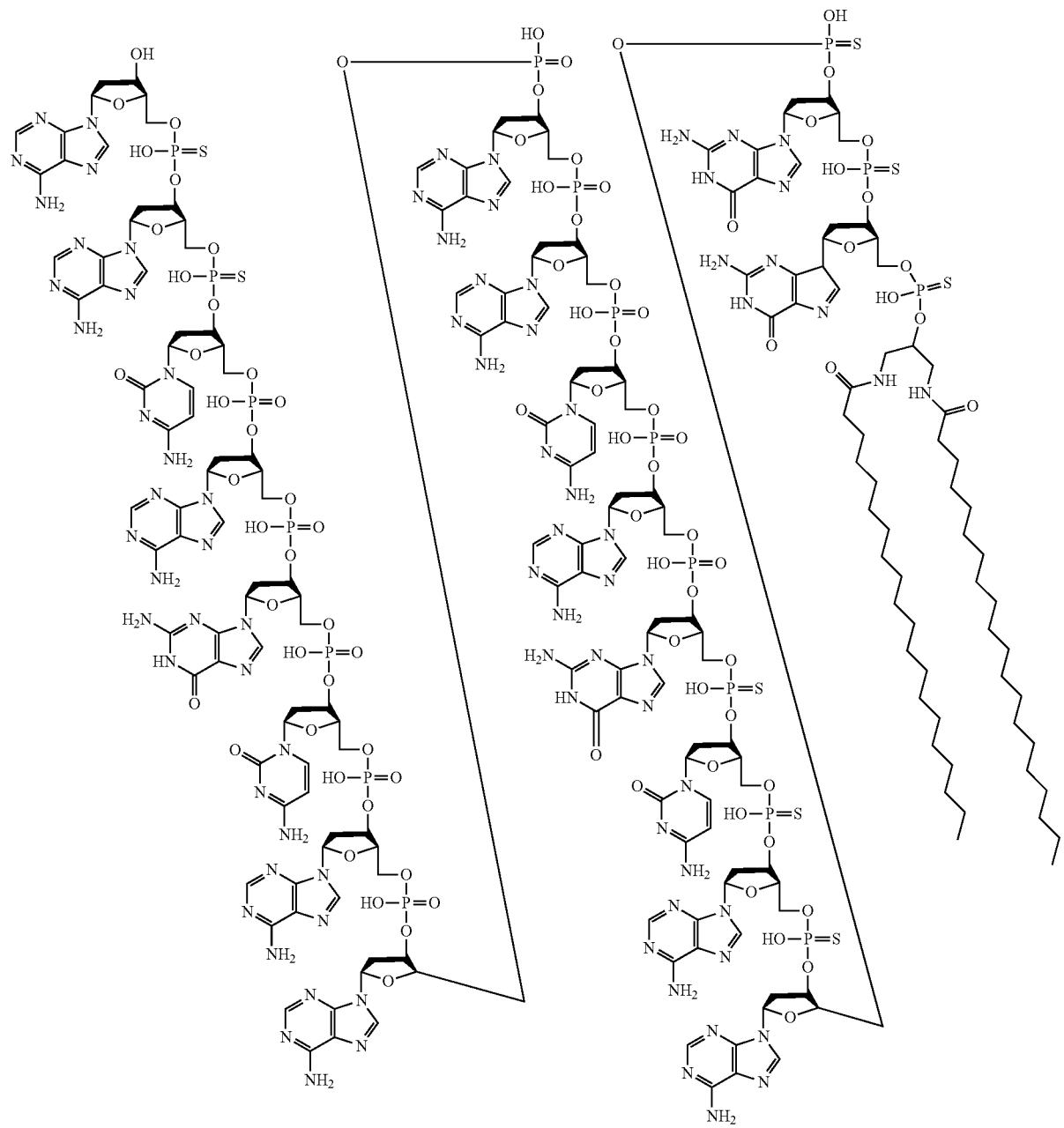
(S-58)
(SEQ. ID. NO.: 18);

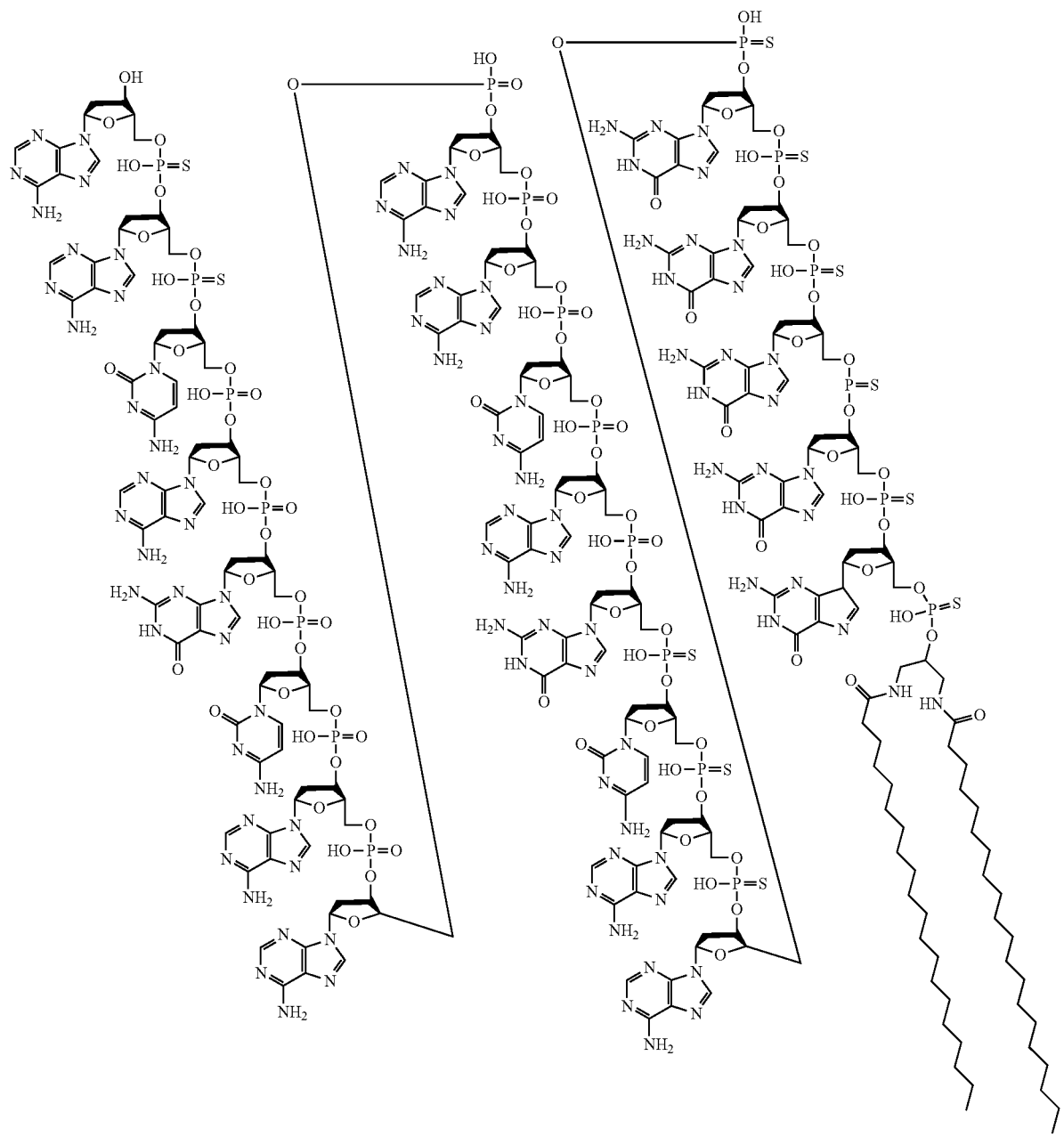
(SEQ. ID. NO.: 18);

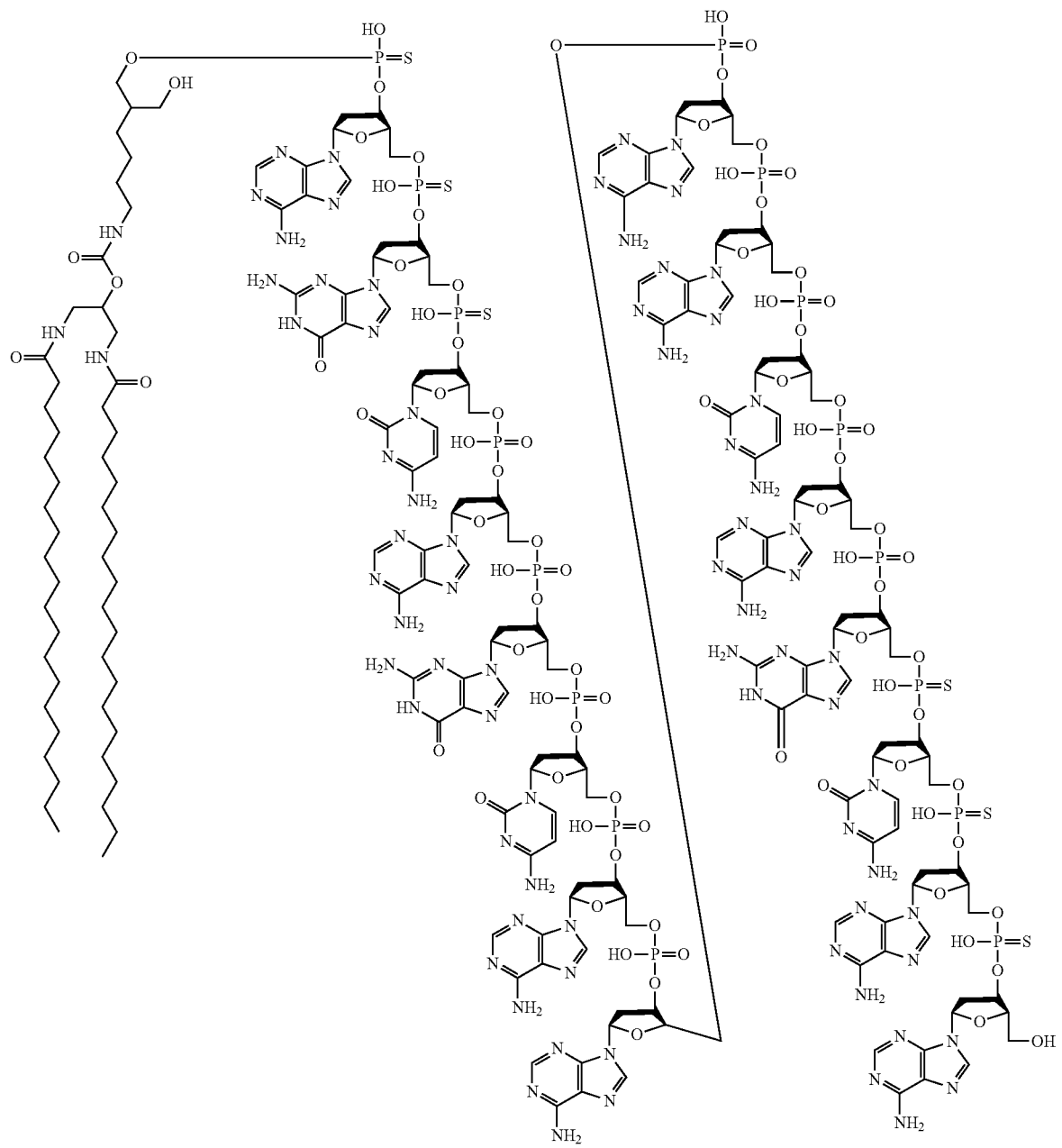
(S-80)
(SEQ. ID. NO.: 25);

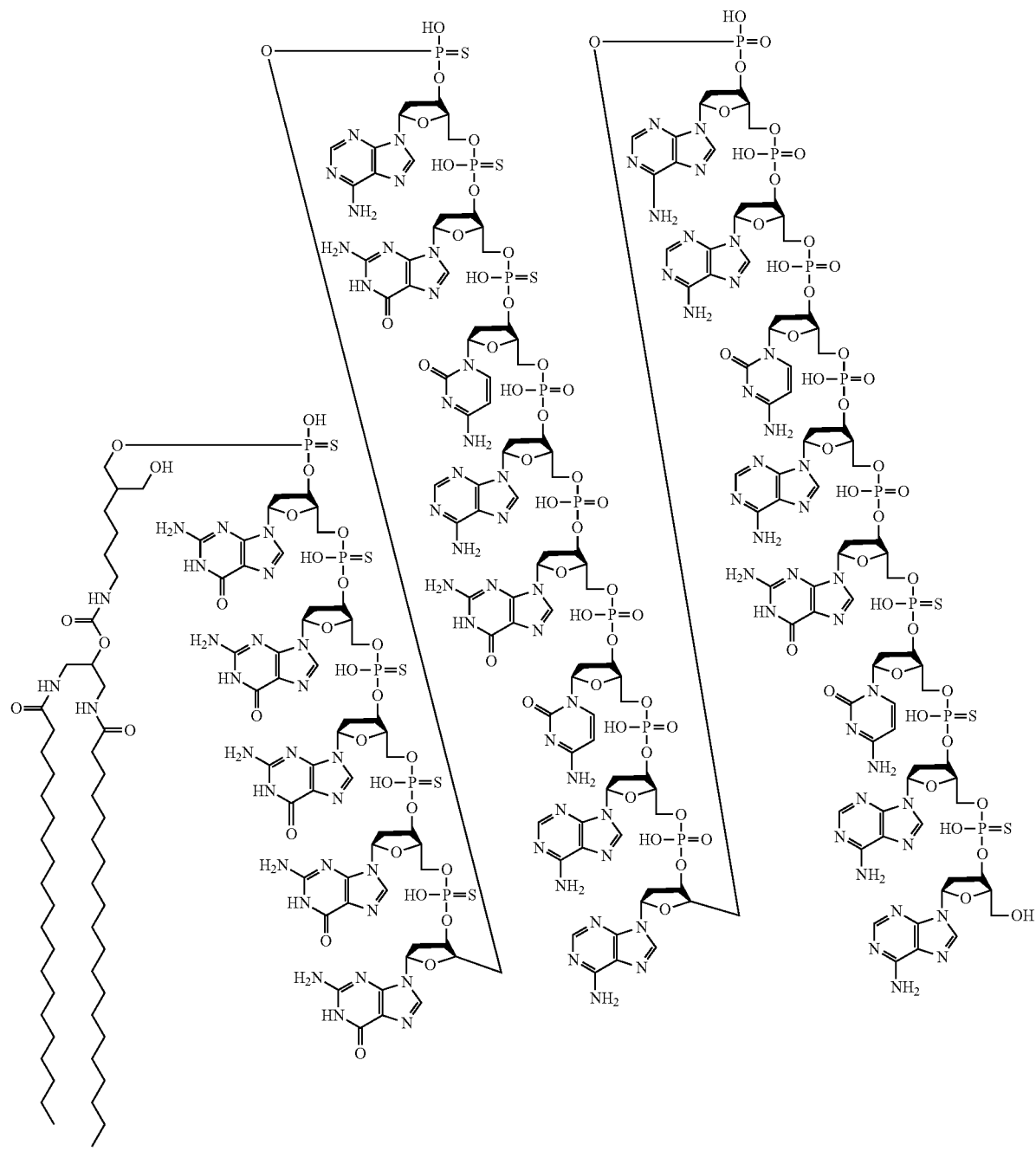
(S-82)
(SEQ. ID. NO.: 25);

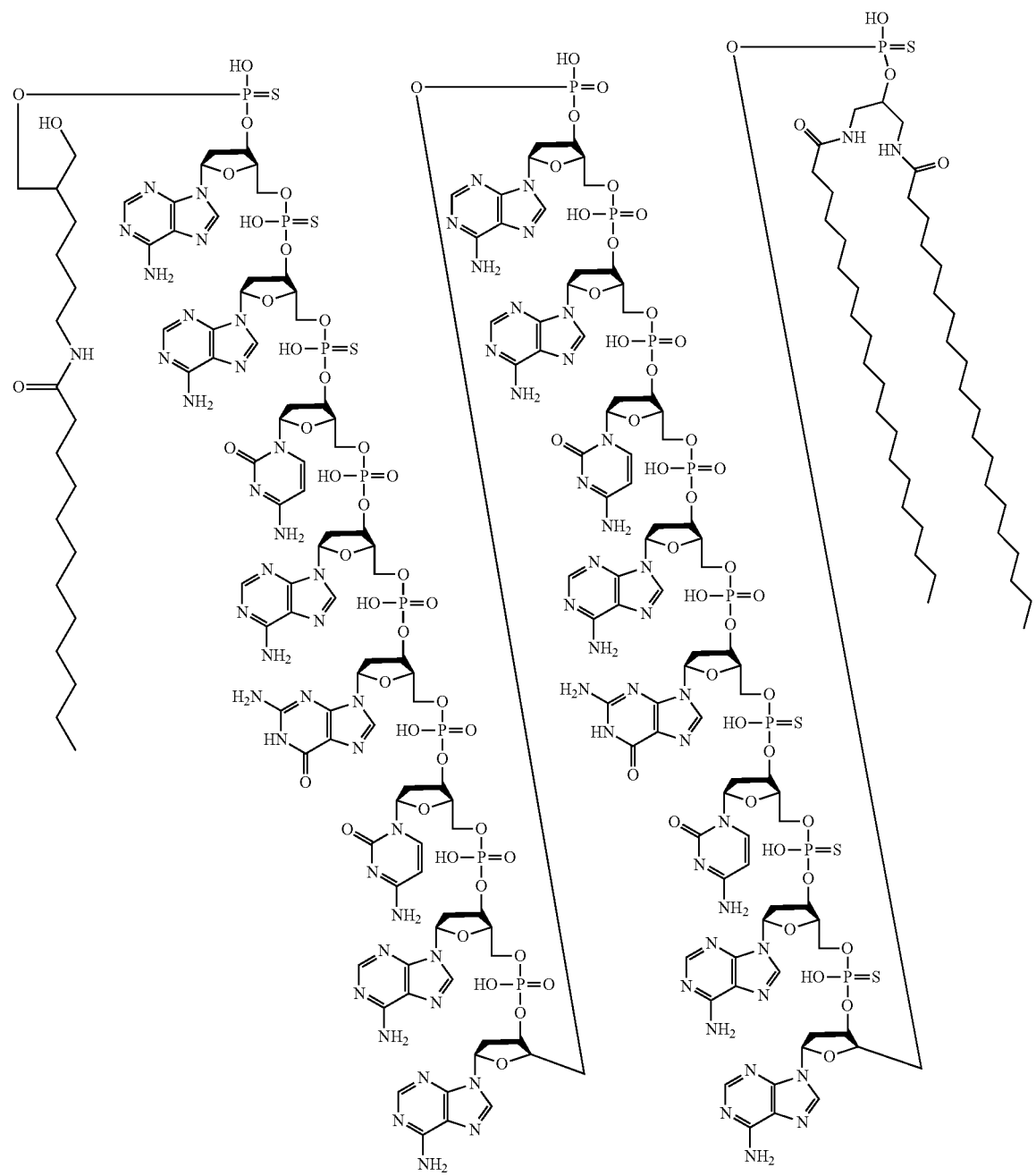
(SEQ. ID. NO.: 18);

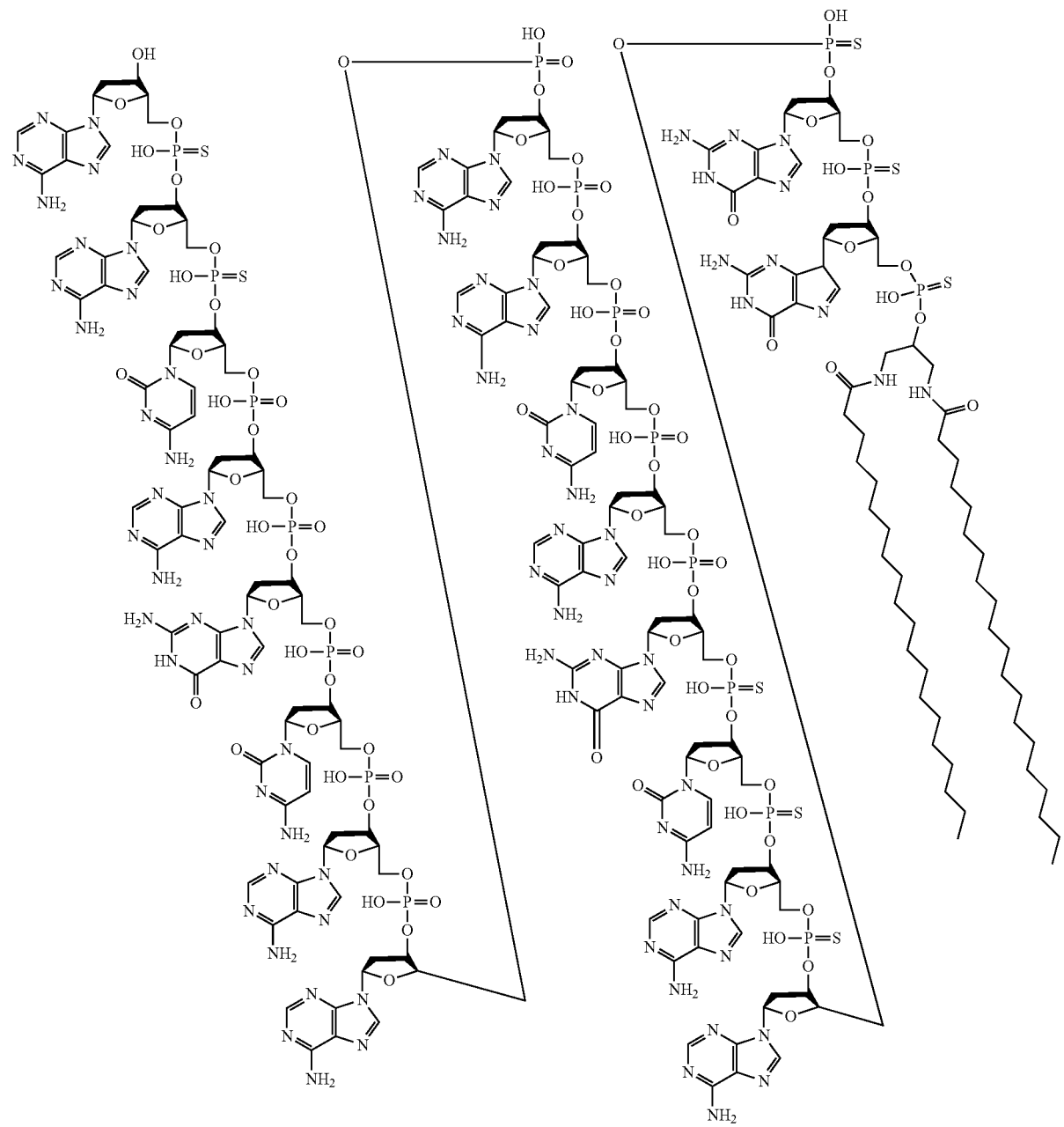
(SEQ. ID. NO.: 18);
(S-136)

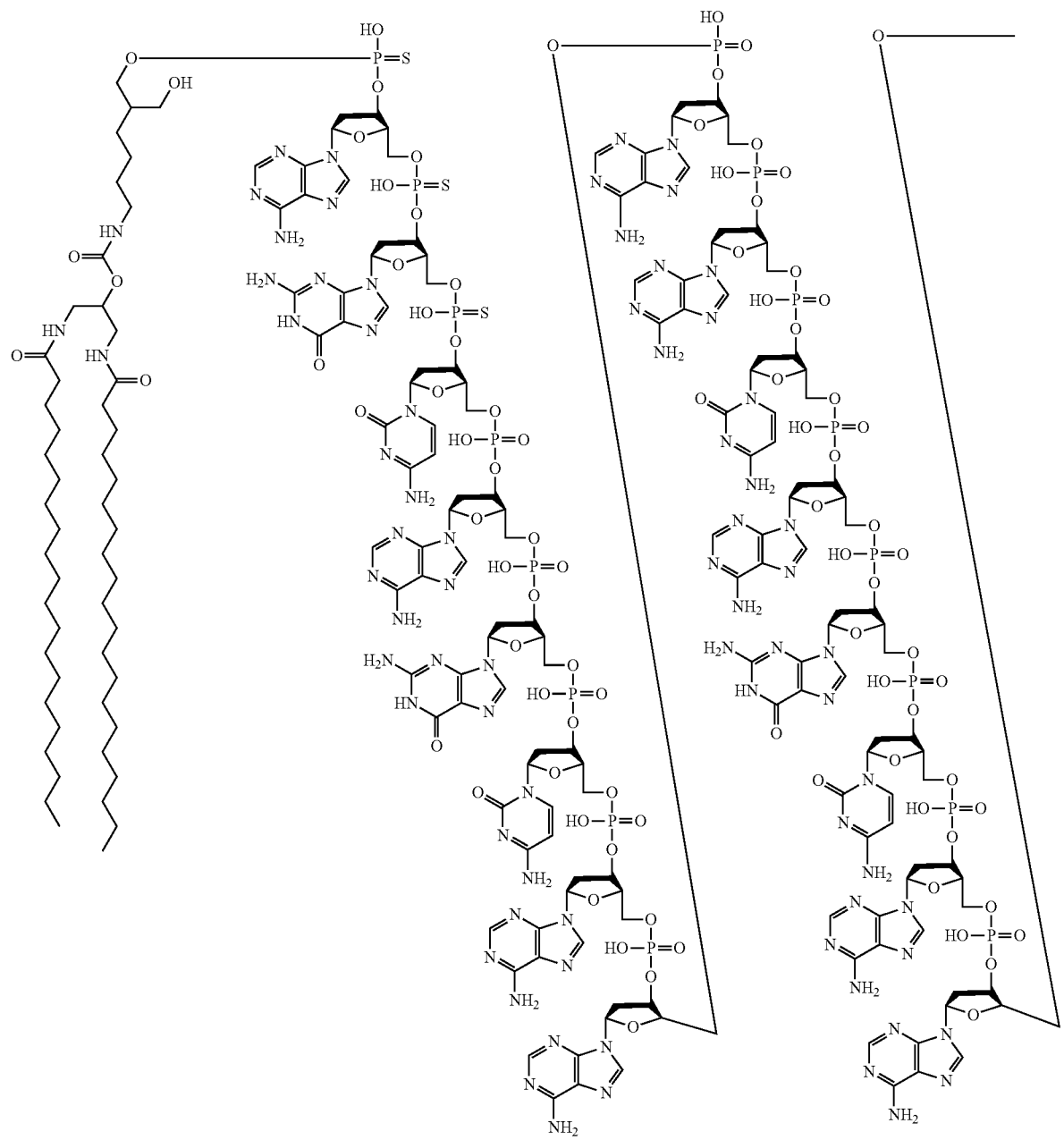
(SEQ. ID. NO.: 14);

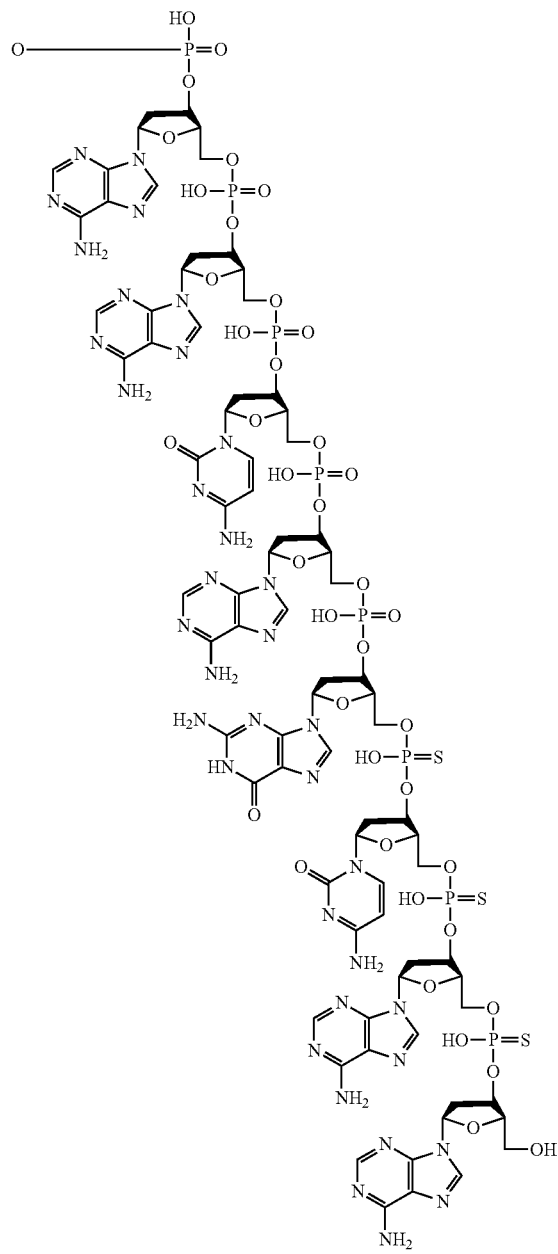 [SMILES: Nc1ccn([C@H]2C[C@@H](OP(=O)(O)OC[C@H]3O[C@@H](n4cnc5c(N)ncnc54)C[C@H]3OP(=O)(O)OC[C@H]3O[C@@H](n4cnc5c(N)ncnc54)C[C@H]3OP(=O)(O)O)[C@@H](COP(=O)(O)O[C@@H]3C[C@H](n4cnc5c(N)ncnc54)O[C@@H]3COP(=O)(O)O[C@@H]3C[C@H](n4cnc5c(=O)[nH]c(N)nc54)O[C@@H]3COP(O)(=S)O[C@@H]3C[C@H](n4ccc(N)nc4=O)O[C@@H]3COP(O)(=S)O[C@@H]3C[C@H](n4cnc5c(N)ncnc54)O[C@@H]3COP(O)(=S)O[C@@H]3C[C@H](n4cnc5c(N)ncnc54)O[C@@H]3CO)O2)c(=O)n1]

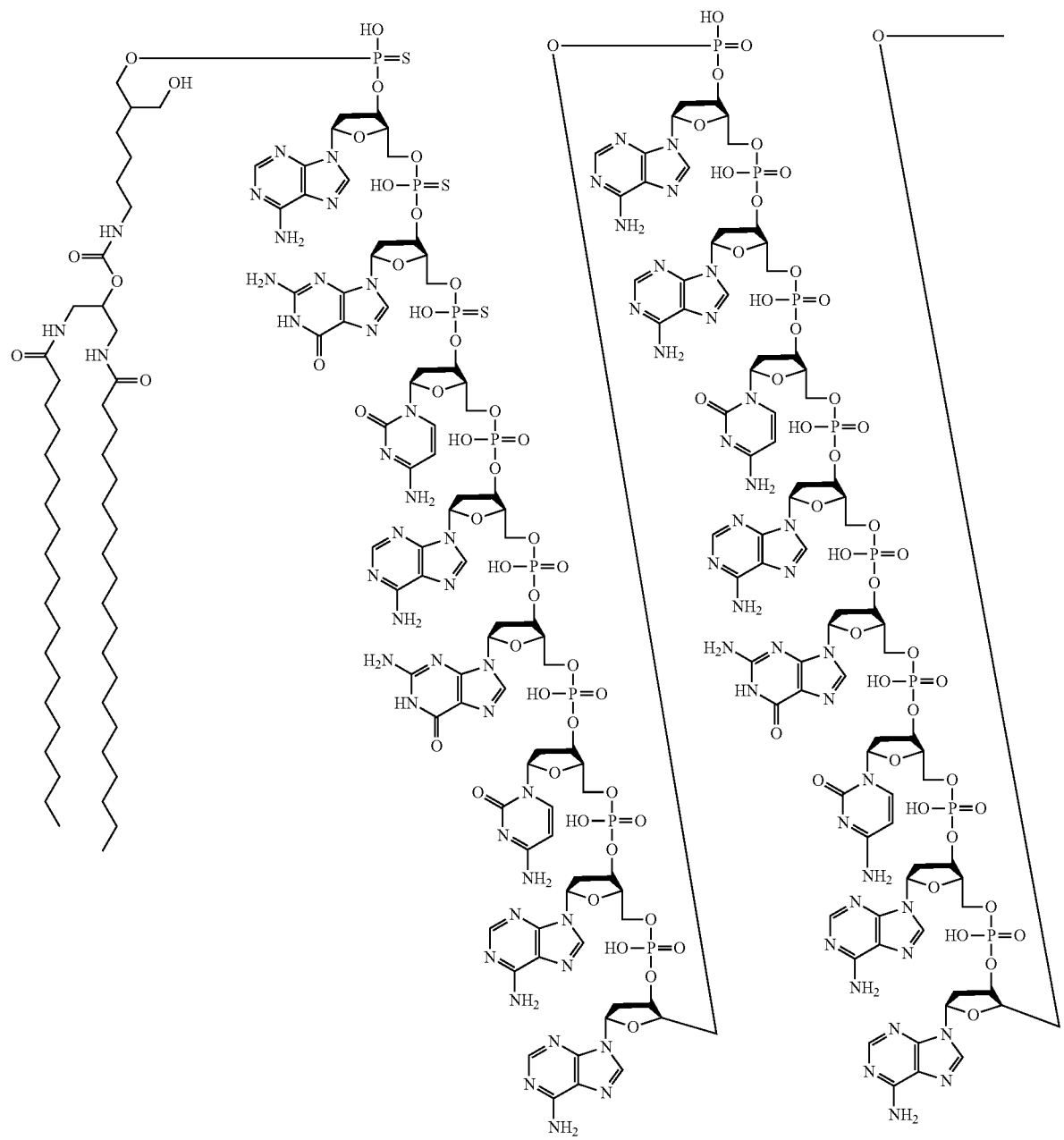
(S-143)
(SEQ. ID. NO.: 14);

-continued
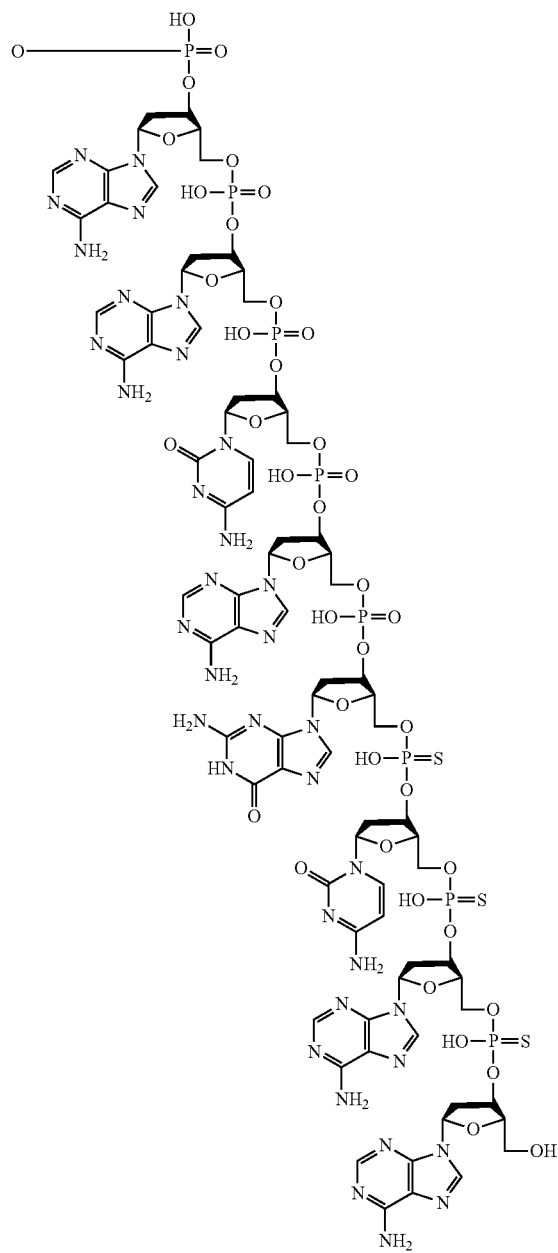 [SMILES: Nc1ccn([C@H]2C[C@@H](OP(=O)(O)OC[C@H]3O[C@@H](n4cnc5c(N)ncnc54)C[C@H]3OP(=O)(O)OC[C@H]3O[C@@H](n4cnc5c(N)ncnc54)C[C@H]3OP(=O)(O)O)[C@@H](COP(=O)(O)O[C@@H]3C[C@H](n4cnc5c(N)ncnc54)O[C@@H]3COP(=O)(O)O[C@@H]3C[C@H](n4cnc5c(=O)[nH]c(N)nc54)O[C@@H]3COP(O)(=S)O[C@@H]3C[C@H](n4ccc(N)nc4=O)O[C@@H]3COP(O)(=S)O[C@@H]3C[C@H](n4cnc5c(N)ncnc54)O[C@@H]3COP(O)(=S)O[C@@H]3C[C@H](n4cnc5c(N)ncnc54)O[C@@H]3CO)O2)c(=O)n1]

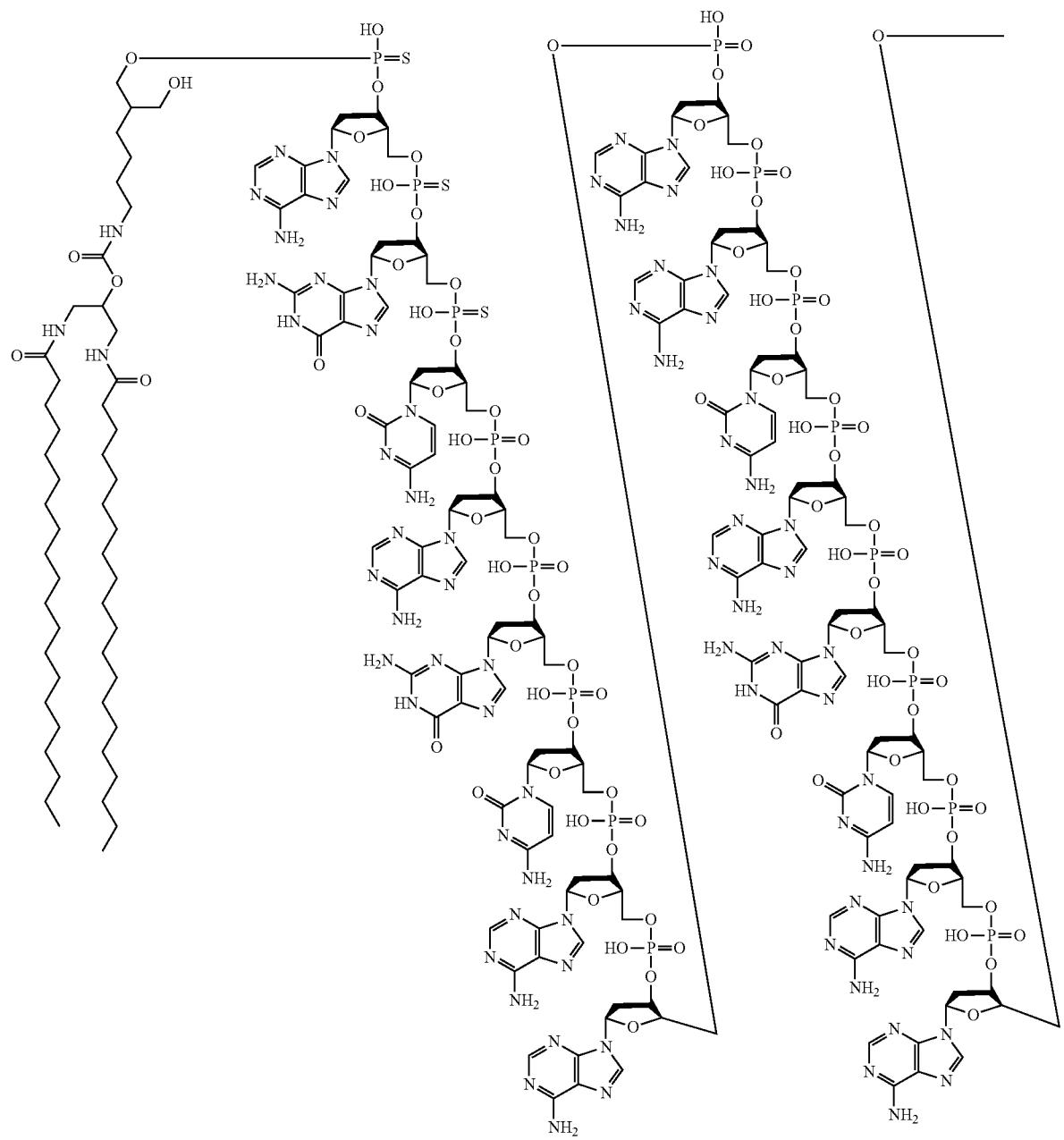
(S-151)
(SEQ. ID. NO.: 14); or

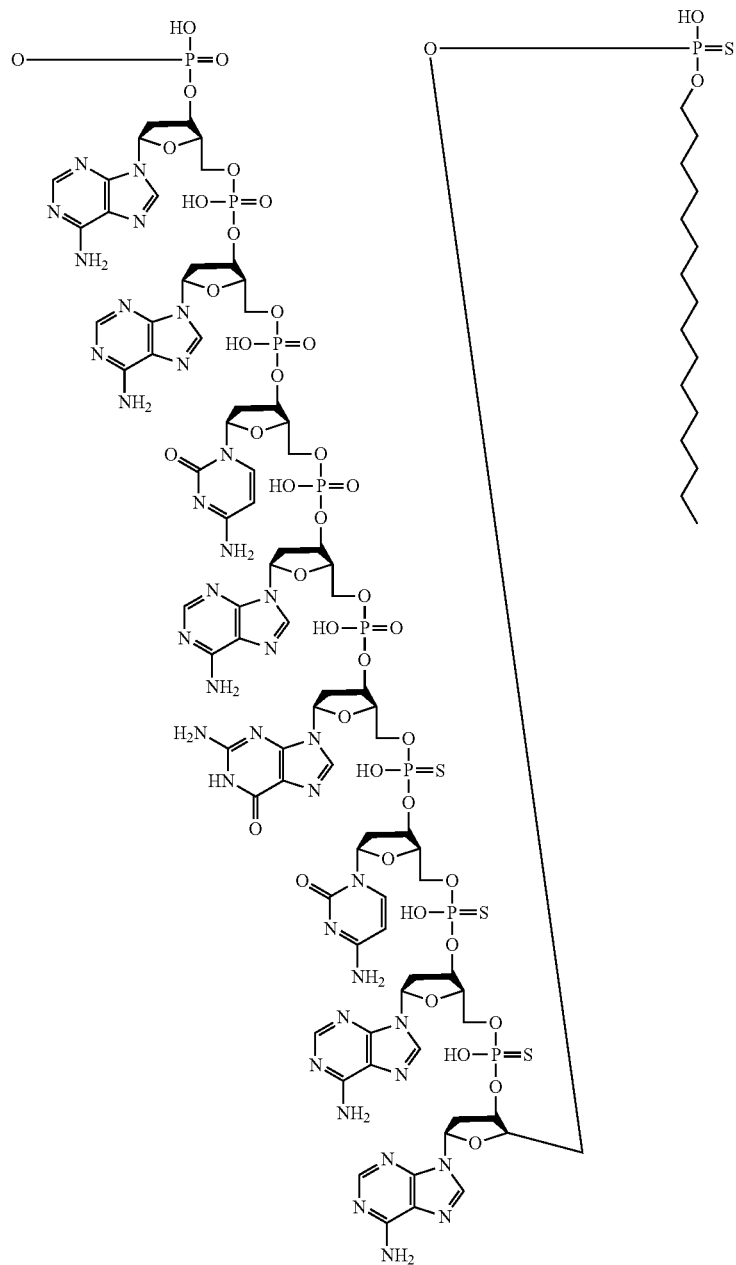 [SMILES: CCCCCCCCCCCCCCCCOP(O)(=S)OC[C@H]1O[C@@H](n2cnc3c(N)ncnc32)C[C@H]1OP(O)(=S)OC[C@H]1O[C@@H](n2cnc3c(N)ncnc32)C[C@H]1OP(O)(=S)OC[C@H]1O[C@@H](n2ccc(N)nc2=O)C[C@H]1OP(O)(=S)OC[C@H]1O[C@@H](n2cnc3c(=O)[nH]c(N)nc32)C[C@H]1OP(=O)(O)OC[C@H]1O[C@@H](n2cnc3c(N)ncnc32)C[C@H]1OP(=O)(O)OC[C@H]1O[C@@H](n2ccc(N)nc2=O)C[C@H]1OP(=O)(O)OC[C@H]1O[C@@H](n2cnc3c(N)ncnc32)C[C@H]1OP(=O)(O)OC[C@H]1O[C@@H](n2cnc3c(N)ncnc32)C[C@H]1OP(=O)(O)O]

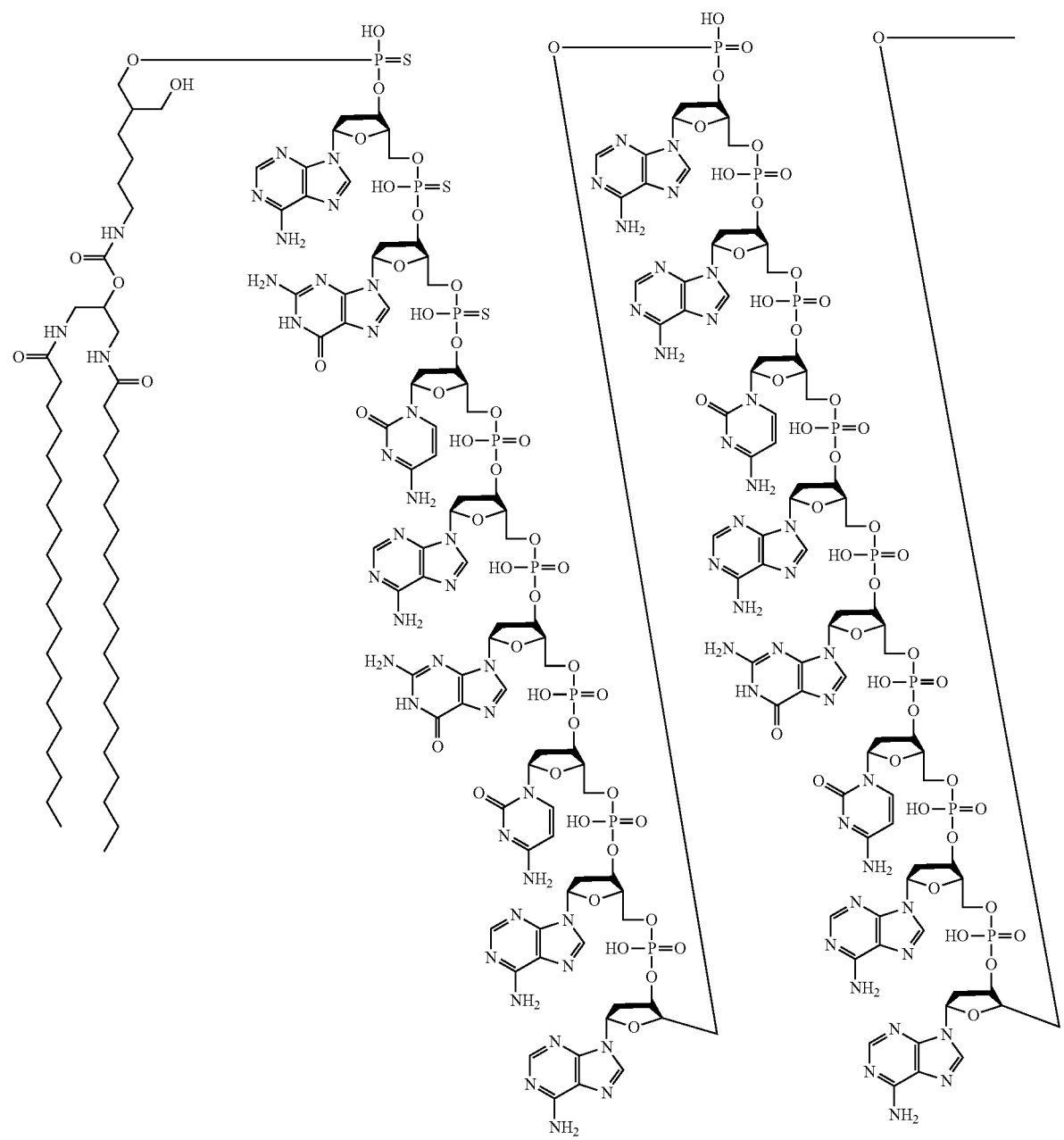
(S-179)
(SEQ. ID. NO.: 14).

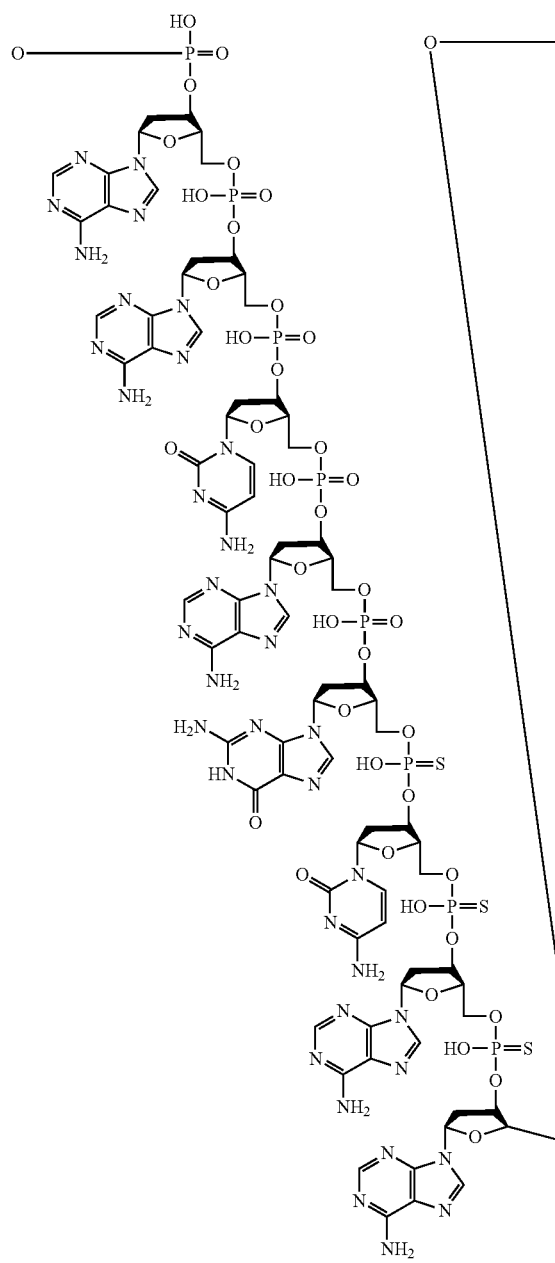

-continued

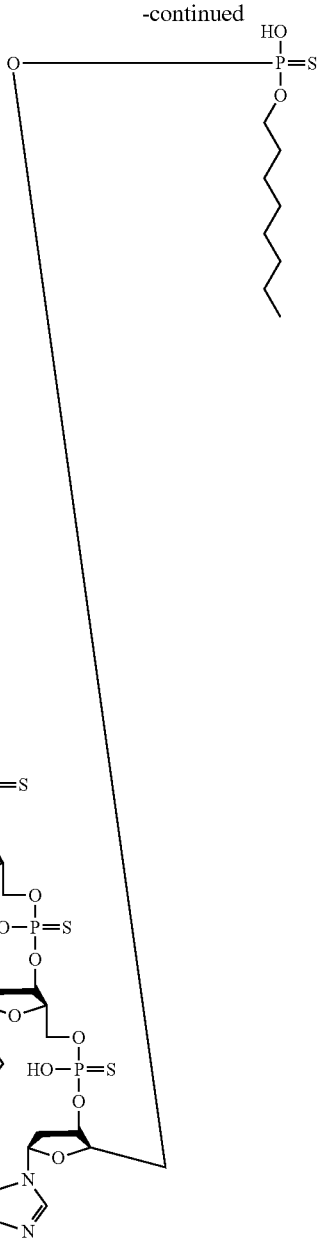

14. A method for treating a cancer or an infectious disease, comprising administering the double-stranded oligonucleotide of claim 11 to a subject in need thereof.

15. The method of claim 14, wherein the double-stranded oligonucleotide is administered in combination with an antigen.

16. A method for treating a cancer or an infectious disease, comprising administering the double-stranded oligonucleotide of claim 12 to a subject in need thereof.

17. The method of claim 16, wherein the double-stranded oligonucleotide is administered in combination with an antigen.

18. A method for treating a cancer or an infectious disease, comprising administering the double-stranded oligonucleotide of claim 13 to a subject in need thereof.

19. The method of claim 18, wherein the double-stranded oligonucleotide is administered in combination with an antigen.

* * * * *

SEQUENCE LISTING

<160> NUMBER OF SEQ ID NOS: 52

<210> SEQ ID NO 1
<211> LENGTH: 20
<212> TYPE: DNA
<213> ORGANISM: Artificial Sequence
<220> FEATURE:
<223> OTHER INFORMATION: Synthetic: CpG oligonucleotide

<400> SEQUENCE: 1
tccatgacgt tcctgacgtt                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic: oligonucleotide

<400> SEQUENCE: 2
aacgtcagga acgtcatgga                                               20

<210> SEQ ID NO 3
<211> LENGTH: 10
<212> TYPE: DNA
<213> ORGANISM: Artificial Sequence
<220> FEATURE:
<223> OTHER INFORMATION: Synthetic: oligonucleotide

<400> SEQUENCE: 3
aacgtcagga                                                          10

<210> SEQ ID NO 4
<211> LENGTH: 15
<212> TYPE: DNA
<213> ORGANISM: Artificial Sequence
<220> FEATURE:
<223> OTHER INFORMATION: Synthetic: oligonucleotide

<400> SEQUENCE: 4
aacgtcagga acgtc                                                    15

<210> SEQ ID NO 5
<211> LENGTH: 19
<212> TYPE: DNA
<213> ORGANISM: Artificial Sequence
<220> FEATURE:
<223> OTHER INFORMATION: Synthetic: oligonucleotide

<400> SEQUENCE: 5
aacgtcagga acgtcatgg                                                19

<210> SEQ ID NO 6
<211> LENGTH: 18
<212> TYPE: DNA
<213> ORGANISM: Artificial Sequence
<220> FEATURE:
<223> OTHER INFORMATION: Synthetic: oligonucleotide

<400> SEQUENCE: 6
aacgtcagga acgtcatg                                                 18

<210> SEQ ID NO 7
<211> LENGTH: 17
<212> TYPE: DNA
<213> ORGANISM: Artificial Sequence

```
<220> FEATURE:
<223> OTHER INFORMATION: Synthetic: oligonucleotide

<400> SEQUENCE: 7
aacgtcagga acgtcat                                                    17

<210> SEQ ID NO 8
<211> LENGTH: 16
<212> TYPE: DNA
<213> ORGANISM: Artificial Sequence
<220> FEATURE:
<223> OTHER INFORMATION: Synthetic: oligonucleotide

<400> SEQUENCE: 8
aacgtcagga acgtca                                                     16

<210> SEQ ID NO 9
<211> LENGTH: 14
<212> TYPE: DNA
<213> ORGANISM: Artificial Sequence
<220> FEATURE:
<223> OTHER INFORMATION: Synthetic: oligonucleotide

<400> SEQUENCE: 9
aacgtcagga acgt                                                       14

<210> SEQ ID NO 10
<211> LENGTH: 13
<212> TYPE: DNA
<213> ORGANISM: Artificial Sequence
<220> FEATURE:
<223> OTHER INFORMATION: Synthetic: oligonucleotide

<400> SEQUENCE: 10
aacgtcagga acg                                                        13

<210> SEQ ID NO 11
<211> LENGTH: 12
<212> TYPE: DNA
<213> ORGANISM: Artificial Sequence
<220> FEATURE:
<223> OTHER INFORMATION: Synthetic: oligonucleotide

<400> SEQUENCE: 11
aacgtcagga ac                                                         12

<210> SEQ ID NO 12
<211> LENGTH: 11
<212> TYPE: DNA
<213> ORGANISM: Artificial Sequence
<220> FEATURE:
<223> OTHER INFORMATION: Synthetic: oligonucleotide

<400> SEQUENCE: 12
aacgtcagga a                                                          11

<210> SEQ ID NO 13
<211> LENGTH: 24
<212> TYPE: DNA
<213> ORGANISM: Artificial Sequence
<220> FEATURE:
<223> OTHER INFORMATION: Synthetic: CpG oligonucleotide

<400> SEQUENCE: 13
tcgtcgtttt gtcgttttgt cgtt                                            24
```

-continued

```
<210> SEQ ID NO 14
<211> LENGTH: 24
<212> TYPE: DNA
<213> ORGANISM: Artificial Sequence
<220> FEATURE:
<223> OTHER INFORMATION: Synthetic: oligonucleotide

<400> SEQUENCE: 14
aacgacaaaa cgacaaaacg acga                                          24

<210> SEQ ID NO 15
<211> LENGTH: 22
<212> TYPE: DNA
<213> ORGANISM: Artificial Sequence
<220> FEATURE:
<223> OTHER INFORMATION: Synthetic: oligonucleotide

<400> SEQUENCE: 15
aacgacaaaa cgacaaaacg ac                                            22

<210> SEQ ID NO 16
<211> LENGTH: 20
<212> TYPE: DNA
<213> ORGANISM: Artificial Sequence
<220> FEATURE:
<223> OTHER INFORMATION: Synthetic: oligonucleotide

<400> SEQUENCE: 16
aacgacaaaa cgacaaaacg                                               20

<210> SEQ ID NO 17
<211> LENGTH: 18
<212> TYPE: DNA
<213> ORGANISM: Artificial Sequence
<220> FEATURE:
<223> OTHER INFORMATION: Synthetic: oligonucleotide

<400> SEQUENCE: 17
aacgacaaaa cgacaaaa                                                 18

<210> SEQ ID NO 18
<211> LENGTH: 16
<212> TYPE: DNA
<213> ORGANISM: Artificial Sequence
<220> FEATURE:
<223> OTHER INFORMATION: Synthetic: oligonucleotide

<400> SEQUENCE: 18
aacgacaaaa cgacaa                                                   16

<210> SEQ ID NO 19
<211> LENGTH: 15
<212> TYPE: DNA
<213> ORGANISM: Artificial Sequence
<220> FEATURE:
<223> OTHER INFORMATION: Synthetic: oligonucleotide

<400> SEQUENCE: 19
aacgacaaaa cgaca                                                    15

<210> SEQ ID NO 20
<211> LENGTH: 15
<212> TYPE: DNA
<213> ORGANISM: Artificial Sequence
<220> FEATURE:
<223> OTHER INFORMATION: Synthetic: oligonucleotide
```

```
<400> SEQUENCE: 20
acgacaaaac gacga                                                    15

<210> SEQ ID NO 21
<211> LENGTH: 15
<212> TYPE: DNA
<213> ORGANISM: Artificial Sequence
<220> FEATURE:
<223> OTHER INFORMATION: Synthetic: oligonucleotide

<400> SEQUENCE: 21
caaaacgaca aaacg                                                    15

<210> SEQ ID NO 22
<211> LENGTH: 8
<212> TYPE: PRT
<213> ORGANISM: Artificial Sequence
<220> FEATURE:
<223> OTHER INFORMATION: Synthetic: OVA Peptide

<400> SEQUENCE: 22

Ser Ile Ile Asn Phe Glu Lys Leu
1               5

<210> SEQ ID NO 23
<211> LENGTH: 10
<212> TYPE: PRT
<213> ORGANISM: Artificial Sequence
<220> FEATURE:
<223> OTHER INFORMATION: Synthetic: TRP2 peptide

<400> SEQUENCE: 23

Cys Ser Val Tyr Asp Phe Phe Val Trp Leu
1               5                   10

<210> SEQ ID NO 24
<211> LENGTH: 17
<212> TYPE: DNA
<213> ORGANISM: Artificial Sequence
<220> FEATURE:
<223> OTHER INFORMATION: Synthetic: oligonucleotide

<400> SEQUENCE: 24
aacgacaaaa cgacaaa                                                  17

<210> SEQ ID NO 25
<211> LENGTH: 16
<212> TYPE: DNA
<213> ORGANISM: Artificial Sequence
<220> FEATURE:
<223> OTHER INFORMATION: Synthetic: oligonucleotide

<400> SEQUENCE: 25
aacgacaaaa cgacga                                                   16

<210> SEQ ID NO 26
<211> LENGTH: 20
<212> TYPE: DNA
<213> ORGANISM: Artificial Sequence
<220> FEATURE:
<223> OTHER INFORMATION: Synthetic: CpG oligonucleotide

<400> SEQUENCE: 26
atcgactctc gagcgttctc                                               20
```

<210> SEQ ID NO 27
<211> LENGTH: 16
<212> TYPE: DNA
<213> ORGANISM: Artificial Sequence
<220> FEATURE:
<223> OTHER INFORMATION: Synthetic: oligonucleotide

<400> SEQUENCE: 27
gagaacgctc gagagt                                                         16

<210> SEQ ID NO 28
<211> LENGTH: 20
<212> TYPE: DNA
<213> ORGANISM: Artificial Sequence
<220> FEATURE:
<223> OTHER INFORMATION: Synthetic: CpG oligonucleotide

<400> SEQUENCE: 28
ggtgcatcga tgcagggggg                                                     20

<210> SEQ ID NO 29
<211> LENGTH: 16
<212> TYPE: DNA
<213> ORGANISM: Artificial Sequence
<220> FEATURE:
<223> OTHER INFORMATION: Synthetic: oligonucleotide

<400> SEQUENCE: 29
cccccctgca tcgatg                                                         16

<210> SEQ ID NO 30
<211> LENGTH: 20
<212> TYPE: DNA
<213> ORGANISM: Artificial Sequence
<220> FEATURE:
<223> OTHER INFORMATION: Synthetic: oligonucleotide

<400> SEQUENCE: 30
acaaaacgac aaaacgacga                                                     20

<210> SEQ ID NO 31
<211> LENGTH: 10
<212> TYPE: DNA
<213> ORGANISM: Artificial Sequence
<220> FEATURE:
<223> OTHER INFORMATION: Synthetic: oligonucleotide

<400> SEQUENCE: 31
aaaacgacga                                                                10

<210> SEQ ID NO 32
<211> LENGTH: 20
<212> TYPE: DNA
<213> ORGANISM: Artificial Sequence
<220> FEATURE:
<223> OTHER INFORMATION: Synthetic: CpG oligonucleotide

<400> SEQUENCE: 32
gggggacgat cgtcgggggg                                                     20

<210> SEQ ID NO 33
<211> LENGTH: 16
<212> TYPE: DNA
<213> ORGANISM: Artificial Sequence
<220> FEATURE:
<223> OTHER INFORMATION: Synthetic: oligonucleotide

```
<400> SEQUENCE: 33
ccgacgatcg tccccc                                              16

<210> SEQ ID NO 34
<211> LENGTH: 23
<212> TYPE: DNA
<213> ORGANISM: Artificial Sequence
<220> FEATURE:
<223> OTHER INFORMATION: Synthetic: CpG oligonucleotide

<400> SEQUENCE: 34
tcgacgttcg tcgttcgtcg ttc                                      23

<210> SEQ ID NO 35
<211> LENGTH: 16
<212> TYPE: DNA
<213> ORGANISM: Artificial Sequence
<220> FEATURE:
<223> OTHER INFORMATION: Synthetic: oligonucleotide

<400> SEQUENCE: 35
gaacgacgaa cgtcga                                              16

<210> SEQ ID NO 36
<211> LENGTH: 26
<212> TYPE: DNA
<213> ORGANISM: Artificial Sequence
<220> FEATURE:
<223> OTHER INFORMATION: Synthetic: CpG oligonucleotide

<400> SEQUENCE: 36
tcgcgacgtt cgcccgacgt tcggta                                   26

<210> SEQ ID NO 37
<211> LENGTH: 16
<212> TYPE: DNA
<213> ORGANISM: Artificial Sequence
<220> FEATURE:
<223> OTHER INFORMATION: Synthetic: oligonucleotide

<400> SEQUENCE: 37
cgggcgaacg tcgcga                                              16

<210> SEQ ID NO 38
<211> LENGTH: 29
<212> TYPE: DNA
<213> ORGANISM: Artificial Sequence
<220> FEATURE:
<223> OTHER INFORMATION: Synthetic: CpG oligonucleotide

<400> SEQUENCE: 38
tcgcgaacgt tcgccgcgtt cgaacgcgg                                29

<210> SEQ ID NO 39
<211> LENGTH: 16
<212> TYPE: DNA
<213> ORGANISM: Artificial Sequence
<220> FEATURE:
<223> OTHER INFORMATION: Synthetic: oligonucleotide

<400> SEQUENCE: 39
cggcgaacgt tcgcga                                              16

<210> SEQ ID NO 40
```

```
<211> LENGTH: 22
<212> TYPE: DNA
<213> ORGANISM: Artificial Sequence
<220> FEATURE:
<223> OTHER INFORMATION: Synthetic: CpG oligonucleotide

<400> SEQUENCE: 40
tcgtcgtttt cggcgcgcgc cg                                          22

<210> SEQ ID NO 41
<211> LENGTH: 16
<212> TYPE: DNA
<213> ORGANISM: Artificial Sequence
<220> FEATURE:
<223> OTHER INFORMATION: Synthetic: oligonucleotide

<400> SEQUENCE: 41
gcgccgaaaa cgacga                                                 16

<210> SEQ ID NO 42
<211> LENGTH: 25
<212> TYPE: DNA
<213> ORGANISM: Artificial Sequence
<220> FEATURE:
<223> OTHER INFORMATION: Synthetic: CpG oligonucleotide

<400> SEQUENCE: 42
tcgtcgtcgt tcgaacgacg ttgat                                       25

<210> SEQ ID NO 43
<211> LENGTH: 16
<212> TYPE: DNA
<213> ORGANISM: Artificial Sequence
<220> FEATURE:
<223> OTHER INFORMATION: Synthetic: oligonucleotide

<400> SEQUENCE: 43
gttcgaacga cgacga                                                 16

<210> SEQ ID NO 44
<211> LENGTH: 21
<212> TYPE: DNA
<213> ORGANISM: Artificial Sequence
<220> FEATURE:
<223> OTHER INFORMATION: Synthetic: CpG oligonucleotide

<400> SEQUENCE: 44
ggggacgacg tcgtgggggg g                                           21

<210> SEQ ID NO 45
<211> LENGTH: 16
<212> TYPE: DNA
<213> ORGANISM: Artificial Sequence
<220> FEATURE:
<223> OTHER INFORMATION: Synthetic: oligonucleotide

<400> SEQUENCE: 45
ccacgacgtc gtcccc                                                 16

<210> SEQ ID NO 46
<211> LENGTH: 22
<212> TYPE: DNA
<213> ORGANISM: Artificial Sequence
<220> FEATURE:
<223> OTHER INFORMATION: Synthetic: CpG oligonucleotide

<400> SEQUENCE: 46
```

```
tgactgtgaa cgttcgagat ga                                          22
```

<210> SEQ ID NO 47
<211> LENGTH: 16
<212> TYPE: DNA
<213> ORGANISM: Artificial Sequence
<220> FEATURE:
<223> OTHER INFORMATION: Synthetic: oligonucleotide

<400> SEQUENCE: 47

```
cgaacgttca cagtca                                                 16
```

<210> SEQ ID NO 48
<211> LENGTH: 882
<212> TYPE: DNA
<213> ORGANISM: Pseudomonas aeruginosa

<400> SEQUENCE: 48

```
atggaagtca gaaaccttaa tgccgctcgc gagctgttcc tggacgagct cctggccgcg    60
tcggcggcgc ctgccagtgc cgagcaggag gaactgctgg ccctgttgcg cagcgagcgg   120
atcgtgctgg cccacgccgg ccagccgctg agcgaggcgc aagtgctcaa ggcgctcgcc   180
tggttgctcg cggccaatcc gtccgcgcct ccggggcagg gcctcgaggt actccgcgaa   240
gtcctgcagg cacgtcggca gcccggtgcg cagtgggatc tgcgcgagtt cctggtgtcg   300
gcctatttca gcctgcacgg cgtctcgac gaggatgtca tcggtgtcta caaggatgtc   360
ctgcagaccc aggacggcaa gcgcaaggcg ctgctcgacg agctcaaggc gctgaccgcg   420
gagttgaagg tctacagcgt gatccagtcg cagatcaacg ccgcgctgtc ggccaagcag   480
ggcatcagga tcgacgctgg cggtatcgat ctggtcgacc ccacgctata tggctatgcc   540
gtcggcgatc ccaggtggaa ggacagcccc gagtatcgcg tgctgagcaa tctggatacc   600
ttcagcggca agctgtcgat caaggatttt tcagcggct cgccgaagca gagcggggag   660
ctcaagggcc tcagcgatga gtacccctt gagaaggaca caacccggt cggcaatttc   720
gccaccacgg tgagcgaccg ctcgcgtccg ctgaacgaca aggtcaacga gaagaccacc   780
ctgctcaacg acaccagctc ccgctacaac tcggcggtcg aggcgctcaa ccgcttcatc   840
cagaaatacg acagcgtcct gcgcgacatt ctcagcgcga tc                     882
```

<210> SEQ ID NO 49
<211> LENGTH: 302
<212> TYPE: PRT
<213> ORGANISM: Artificial sequence
<220> FEATURE:
<223> OTHER INFORMATION: Synthetic: PcrV Recombinant Protein (C-His tag)

<400> SEQUENCE: 49

```
Met Glu Val Arg Asn Leu Asn Ala Ala Arg Glu Leu Phe Leu Asp Glu
1               5                   10                  15

Leu Leu Ala Ala Ser Ala Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65                  70                  75                  80
```

```
Val Leu Gln Ala Arg Gln Pro Gly Ala Gln Trp Asp Leu Arg Glu
                 85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
        115                 120                 125

Lys Ala Leu Leu Asp Glu Leu Lys Ala Leu Thr Ala Glu Leu Lys Val
    130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
        195                 200                 205

Asp Phe Leu Ser Gly Ser Pro Lys Gln Ser Gly Glu Leu Lys Gly Leu
    210                 215                 220

Ser Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
        275                 280                 285

Asp Ile Leu Ser Ala Ile Leu Glu His His His His His His
    290                 295                 300

<210> SEQ ID NO 50
<211> LENGTH: 23
<212> TYPE: RNA
<213> ORGANISM: Artificial Sequence
<220> FEATURE:
<223> OTHER INFORMATION: Synthetic: oligonucleotide

<400> SEQUENCE: 50
aacguucagg aacguucauu gga                                           23

<210> SEQ ID NO 51
<211> LENGTH: 20
<212> TYPE: RNA
<213> ORGANISM: Artificial Sequence
<220> FEATURE:
<223> OTHER INFORMATION: Synthetic: oligonucleotide

<400> SEQUENCE: 51
aacgucagga acgucaugga                                               20

<210> SEQ ID NO 52
<211> LENGTH: 17
<212> TYPE: RNA
<213> ORGANISM: Artificial Sequence
<220> FEATURE:
<223> OTHER INFORMATION: Synthetic: oligonucleotide

<400> SEQUENCE: 52
aacguucagg aacguuc                                                  17
```